US009884075B2

(12) United States Patent
Bethune et al.

(10) Patent No.: US 9,884,075 B2
(45) Date of Patent: Feb. 6, 2018

(54) DOMAIN-SWAP T CELL RECEPTORS

(71) Applicant: California Institute of Technology, Pasadena, CA (US)

(72) Inventors: Michael T. Bethune, Pasadena, CA (US); Marvin H. Gee, Stanford, CA (US); David Baltimore, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 203 days.

(21) Appl. No.: 14/597,908

(22) Filed: Jan. 15, 2015

(65) Prior Publication Data

US 2015/0197771 A1 Jul. 16, 2015

Related U.S. Application Data

(60) Provisional application No. 61/928,142, filed on Jan. 16, 2014.

(51) Int. Cl.

| | |
|---|---|
| ***A61K 48/00*** | (2006.01) |
| ***A61K 35/26*** | (2015.01) |
| ***A61K 35/28*** | (2015.01) |
| ***A61K 35/16*** | (2015.01) |
| ***A61K 35/17*** | (2015.01) |
| ***C07K 14/725*** | (2006.01) |

(52) U.S. Cl.
CPC .......... *A61K 35/17* (2013.01); *C07K 14/7051* (2013.01)

(58) Field of Classification Search
None
See application file for complete search history.

(56) References Cited

U.S. PATENT DOCUMENTS

| | | | |
|---|---|---|---|
| 7,446,190 | B2 | 11/2008 | Sadelain et al. |
| 2011/0014659 | A1 | 1/2011 | Balazs et al. |
| 2012/0232133 | A1 | 9/2012 | Balazs et al. |
| 2013/0316366 | A1 | 11/2013 | Yu et al. |

OTHER PUBLICATIONS

Backstrom et al. (Immunity, 1996, 5:437-447).*
Ciccarese et al. (Genetics, 1997, 145:409-419).*
Kim et al. (PLOS One, 2011, 6:318556, pp. 1-8).*
Bethune et al., 2016, eLife, 5:319095, pp. 1-24; supplemental figures.*
Call, M. E. & Wucherpfennig, K.W. The T cell receptor: critical role of the membrane environment in receptor assembly and function. Annual Review of Immunology 23, 101-125, 2005.
Bonifacino, J. S., et al. Pre-Golgi degradation of newly synthesized T-cell antigen receptor chains: intrinsic sensitivity and the role of subunit assembly. The Journal of Cell Biology 109, 73-83, 1989.
Kuhns, M. S., et al. Disruption of extracellular interactions impairs T cell receptor-CD3 complex stability and signaling. Immunity 26, 357-369, 2007.
Xu, C., et al. A membrane-proximal tetracysteine motif contributes to assembly of CD3deltaepsilon and CD3gammaepsilon dimers with the T cell receptor. Journal of Biological Chemistry 281, 36977-36984, 2006.
Park, T. S., et al. Treating cancer with genetically engineered T cells. Trends in Biotechnology 29, 550-557, 2011.
Johnson, L. A., et al. Gene therapy with human and mouse T-cell receptors mediates cancer regression and targets normal tissues expressing cognate antigen. Blood 114, 535-546, 2009.
Morgan, R. A., et al. Cancer regression in patients after transfer of genetically engineered lymphocytes. Science 314, 126-129, 2006.
Jorritsma, A., et al. Selecting highly affine and well-expressed TCRs for gene therapy of melanoma. Blood 110, 3564-3572, 2007.
Van Loenen, M. M., et al. Mixed T cell receptor dimers harbor potentially harmful neoreactivity. Proc. Natl. Acad. Sci. U.S.A. 107, 10972-10977, 2010.
Bendle, G. M., et al. Lethal graft-versus-host disease in mouse models of T cell receptor gene therapy. Nature Medicine 16, 565-570, 2010.
Govers, C., et al. T cell receptor gene therapy: strategies for optimizing transgenic TCR pairing. Trends in Molecular Medicine 16, 77-87, 2010.
Okamoto, S., et al. Improved expression and reactivity of transduced tumor-specific TCRs in human lymphocytes by specific silencing of endogenous TCR. Cancer Research 69, 9003-9011, 2009.
Thomas, S., et al. Targeting the Wilms tumor antigen 1 by TCR gene transfer: TCR variants improve tetramer binding but not the function of gene modified human T cells. J Immunol. 179, 5803-5810, 2007.
Davis, J. L., et al. Development of human anti-murine T-cell receptor antibodies in both responding and nonresponding patients enrolled in TCR gene therapy trials. Clinical Cancer Research : An Official Journal of the American Association for Cancer Research 16, 5852-5861, 2010.
Johnson, L. A., et al. Gene transfer of tumor-reactive TCR confers both high avidity and tumor reactivity to nonreactive peripheral blood mononuclear cells and tumor-infiltrating lymphocytes. J Immunol. 177, 6548-6559, 2006.
Holler, P. D., et al. TCRs with high affinity for foreign pMHC show self-reactivity. Nat. Immunol. 4, 55-62, 2003.
Robbins, P. F., et al. Single and dual amino acid substitutions in TCR CDRs can enhance antigen-specific T cell functions. J Immunol. 180, 6116-6131, 2008.
Schmid, D. A., et al. Evidence for a TCR affinity threshold delimiting maximal CD8 T cell function. J Immunol. 184, 4936-4946, 2010.
Kuhns, M. S., et al. Evidence for a functional sidedness to the alphabetaTCR. Proc. Natl. Acad. Sci. U. S. A. 107, 5094-5099, 2010.
Alexopoulou et al. The CMV early enhancer/chicken β actin (CAG) promoter can be used to drive transgene expression during the differentiation of murine embryonic stem cells into vascular progenitors. BMC Cell Biology 9:2, 2008.

(Continued)

*Primary Examiner* — Julie Wu
(74) *Attorney, Agent, or Firm* — Fenwick & West LLP

(57) ABSTRACT

Disclosed herein are genetically engineered T cell receptors, and methods, vectors, and genetically engineered T cells related to genetically engineered T cell receptors.

27 Claims, 27 Drawing Sheets

(56) References Cited

OTHER PUBLICATIONS

Brisson et al. Expression of a bacterial gene in plants by using a viral vector. Nature 310, 511-514, 1984.
Gurley et al. Upstream Sequences Required for Efficient Expression of a Soybean Heat Shock Gene. Mol. Cell. Biol. 6, 559-565, 1986.
Green and Sambrook, Molecular Cloning: A Laboratory Manual, Fourth Ed., Cold Spring Harbor Laboratory Press, Cold Spring Harbor, N. Y. 2012.
Kessels, et al. Generation of T Cell Help through a MHC Class I-Restricted TCR. The Journal of Immunology. 177, 976-982, 2006.
Van Der Veken, et al. αβ T Cell Receptor Transfer to γδ T Cells Generates Functional Effector Cells without Mixed TCR Dimers in Vivo. The Journal of Immunology. 182, 164-170, 2009.
Tran et al. Cancer Immunotherapy Based on Mutation-Specific CD4+ T Cells in a Patient with Epithelial Cancer. Science, vol. 344, p. 641-645, May 9, 2014.

* cited by examiner

Wild-type F5 TCR in pMTB1281

```
1     MATGSRTSLL LAFGLLCLPW LQEASAQQKE VEQNSGPLSV PEGAIASLNC TYSDRGSQSF
61    FWYRQYSGKS PELIMFIYSN GDKEDGRFTA QLNKASQYVS LLIRDSQPSD SATYLCAVNF
121   GGGKLIFGQG TELSVKPNIQ NPDPAVYQLR DSKSSDKSVC LFTDFDSQTN VSQSKDSDVY
181   ITDKTVLDMR SMDFKSNSAV AWSNKSDFAC ANAFNNSIIP EDTFFPSPES SCDVKLVEKS
241   FETDTNLNFQ NLSVIGFRIL LLKVAGFNLL MTLRLWSSRA KRSGSGAPVK QTLNFDLLKL
301   AGDVESNPGP MATGSRTSLL LAFGLLCLPC LQEGSAGITQ APTSQILAAG RRMTLRCTQD
361   MRHNAMYWYR QDLGLGLRLI HYSNTAGTTG KGEVPDGYSV SRANTDDFPL TLASAVPSQT
421   SVYFCASSLS FGTEAFFGQG TRLTVVEDLN KVFPPEVAVF EPSEAEISHT QKATLVCLAT
481   GFFPDHVELS WWVNGKEVHS GVSTDPQPLK EQPALNDSRY CLSSRLRVSA TFWQNPRNHF
541   RCQVQFYGLS ENDEWTQDRA KPVTQIVSAE AWGRADCGFT SVSYQQGVLS ATILYEILLG
601   KATLYAVLVS ALVLMAMVKR KDFRAKRGSG ATNFSLLKQA GDVEENPGPM GAGATGRAMD
661   GPRLLLLLLL GVSLGGAKEQ KLISEEDLEI PGRWITRSTP PEGSDSTAPS TQEPEAPPEQ
721   DLIASTVAGV VTTVMGSSQP VVTRGTTDNL IPVYCSILAA VVVGLVAYIA FKR-
(SEQ ID NO: 56)
```

| Amino acids of SEQ ID NO: 56 | Sequence description |
|---|---|
| 1-26 | HGH signal sequence 1 |
| 27-138 | F5 TCR alpha variable Ig domain |
| 139-231 | TCR alpha constant Ig domain |
| 232-250 | TCR alpha connecting peptide |
| 251-273 | TCR alpha transmembrane domain |
| 274-278 | TCR alpha cytoplasmic domain |
| 279-310 | Viral 2A ribosomal-skipping sequence |
| 311-336 | HGH signal sequence 2 |
| 337-448 | F5 TCR beta variable Ig domain |
| 449-576 | TCR beta constant Ig domain |
| 577-592 | TCR beta connecting peptide |
| 593-614 | TCR beta transmembrane domain |
| 615-623 | TCR beta cytoplasmic domain |
| 624-649 | Viral 2A ribosomal-skipping sequence |
| 650-678 | LNGFR signal sequence |
| 679-688 | Myc epitope |
| 689-773 | LNGFR truncated extracellular and transmembrane domain |

FIG. 9A

Domain-swap F5 TCR VC-swap, BA orientation in pMTB1282

1 MATGSRTSLL LAFGLLCLPW LQEASAGITQ APTSQILAAG RRMTLRCTQD MRHNAMYWYR

61 QDLGLGLRLI HYSNTAGTTG KGEVPDGYSV SRANTDDFPL TLASAVPSQT SVYFCASSLS

121 FGTEAFFGQG TRLTVVEDLN KVFPPEVAVF EPSEAEISHT QKATLVCLAT GFFPDHVELS

181 WWVNGKEVHS GVSTDPQPLK EQPALNDSRY CLSSRLRVSA TFWQNPRNHF RCQVQFYGLS

241 ENDEWTQDRA KPVTQIVSAE AWGRADCDVK LVEKSFETDT NLNFQNLSVI GFRILLLKVA

301 GFNLLMTLRL WSSRAKRSGS GAPVKQTLNF DLLKLAGDVE SNPGPMATGS RTSLLLAFGL

361 LCLPCLQEGS AQQKEVEQNS GPLSVPEGAI ASLNCTYSDR GSQSFFWYRQ YSGKSPELIM

421 FIYSNGDKED GRFTAQLNKA SQYVSLLIRD SQPSDSATYL CAVNFGGGKL IFGQGTELSV

481 KPNIQNPDPA VYQLRDSKSS DKSVCLFTDF DSQTNVSQSK DSDVYITDKT VLDMRSMDFK

541 SNSAVAWSNK SDFACANAFN NSIIPEDTFF PSPESSCGFT SVSYQQGVLS ATILYEILLG

601 KATLYAVLVS ALVLMAMVKR KDFRAKRGSG ATNFSLLKQA GDVEENPGPM GAGATGRAMD

661 GPRLLLLLLL GVSLGGAKEQ KLISEEDLEI PGRWITRSTP PEGSDSTAPS TQEPEAPPEQ

721 DLIASTVAGV VTTVMGSSQP VVTRGTTDNL IPVYCSILAA VVVGLVAYIA FKR~
(SEQ ID NO: 57)

| Amino acids of SEQ ID NO: 57 | Sequence description |
|---|---|
| 1-26 | HGH signal sequence 1 |
| 27-138 | F5 TCR beta variable Ig domain |
| 139-266 | TCR beta constant Ig domain |
| 267-285 | TCR alpha connecting peptide |
| 286-308 | TCR alpha transmembrane domain |
| 309-313 | TCR alpha cytoplasmic domain |
| 314-345 | Viral 2A ribosomal-skipping sequence |
| 346-371 | HGH signal sequence 2 |
| 372-483 | F5 TCR alpha variable Ig domain |
| 484-576 | TCR alpha constant Ig domain |
| 577-592 | TCR beta connecting peptide |
| 593-614 | TCR beta transmembrane domain |
| 615-623 | TCR beta cytoplasmic domain |
| 624-649 | Viral 2A ribosomal-skipping sequence |
| 650-678 | LNGFR signal sequence |
| 679-688 | Myc epitope |
| 689-773 | LNGFR truncated extracellular and transmembrane domain |

FIG. 9B

Domain-swap F5 TCR VCcp-swap, BA orientation in pMTB1284

```
1     MATGSRTSLL LAFGLLCLPW LQEASAGITQ APTSQILAAG RRMTLRCTQD MRHNAMYWYR

61    QDLGLGLRLI HYSNTAGTTG KGEVPDGYSV SRANTDDFPL TLASAVPSQT SVYFCASSLS

121   FGTEAFFGQG TRLTVVEDLN KVFPPEVAVF EPSEAEISHT QKATLVCLAT GFFPDHVELS

181   WWVNGKEVHS GVSTDPQPLK EQPALNDSRY CLSSRLRVSA TFWQNPRNHF RCQVQFYGLS

241   ENDEWTQDRA KPVTQIVSAE AWGRADCGFT SVSYQQGVLS ATNLSVIGFR ILLLKVAGFN

301   LLMTLRLWSS RAKRSGSGAP VKQTLNFDLL KLAGDVESNP GPMATGSRTS LLLAFGLLCL

361   PCLQEGSAQQ KEVEQNSGPL SVPEGAIASL NCTYSDRGSQ SFFWYRQYSG KSPELIMFIY

421   SNGDKEDGRF TAQLNKASQY VSLLIRDSQP SDSATYLCAV NFGGGKLIFG QGTELSVKPN

481   IQNPDPAVYQ LRDSKSSDKS VCLFTDFDSQ TNVSQSKDSD VYITDKTVLD MRSMDFKSNS

541   AVAWSNKSDF ACANAFNNSI IPEDTFFPSP ESSCDVKLVE KSFETDTNLN FQILYEILLG

601   KATLYAVLVS ALVLMAMVKR KDFRAKRGSG ATNFSLLKQA GDVEENPGPM GAGATGRAMD

661   GPRLLLLLLL GVSLGGAKEQ KLISEEDLEI PGRWITRSTP PEGSDSTAPS TQEPEAPPEQ

721   DLIASTVAGV VTTVMGSSQP VVTRGTTDNL IPVYCSILAA VVVGLVAYIA FKR-
(SEQ ID NO: 59)
```

| Amino acids of SEQ ID NO: 59 | Sequence description |
|---|---|
| 1-26 | HGH signal sequence 1 |
| 27-138 | F5 TCR beta variable Ig domain |
| 139-266 | TCR beta constant Ig domain |
| 267-282 | TCR beta connecting peptide |
| 283-305 | TCR alpha transmembrane domain |
| 306-310 | TCR alpha cytoplasmic domain |
| 311-342 | Viral 2A ribosomal-skipping sequence |
| 343-368 | HGH signal sequence 2 |
| 369-480 | F5 TCR alpha variable Ig domain |
| 481-573 | TCR alpha constant Ig domain |
| 574-592 | TCR alpha connecting peptide |
| 593-614 | TCR beta transmembrane domain |
| 615-623 | TCR beta cytoplasmic domain |
| 624-649 | Viral 2A ribosomal-skipping sequence |
| 650-678 | LNGFR signal sequence |
| 679-688 | Myc epitope |
| 689-773 | LNGFR truncated extracellular and transmembrane domain |

FIG. 9C

Domain-swap F5 TCR AlphaDelta+BetaGamma in pMTB1301

```
1     MATGSRTSLL LAFGLLCLPW LQEASAQQKE VEQNSGPLSV PEGAIASLNC TYSDRGSQSF
61    FWYRQYSGKS PELIMFIYSN GDKEDGRFTA QLNKASQYVS LLIRDSQPSD SATYLCAVNF
121   GGGKLIFGQG TELSVKPNIQ NPDPAVYQLR DSKSSDKSVC LFTDFDSQTN VSQSKDSDVY
181   ITDKTVLDMR SMDFKSNSAV AWSNKSDFAC ANAFNNSIIP EDTFFPSPES SDSTDHVKPK
241   ETENTKQPSK SCHKPKAIVH TEKVNMMSLT VLGLRMLFAK TVAVNFLLTA RLWSSRAKRS
301   GSGAPVKQTL NFDLLKLAGD VESNPGPMAT GSRTSLLLAF GLLCLPCLQE GSAGITQAPT
361   SQILAAGRRM TLRCTQDMRH NAMYWYRQDL GLGLRLIHYS NTAGTTGKGE VPDGYSVSRA
421   NTDDFPLTLA SAVPSQTSVY FCASSLSFGT EAFFGQGTRL TVVEDLNKVF PPEVAVFEPS
481   EAEISHTQKA TLVCLATGFF PDHVELSWWV NGKEVHSGVS TDPQPLKEQP ALNDSRYCLS
541   SRLRVSATFW QNPRNHFRCQ VQFYGLSEND EWTQDRAKPV TQIVSAEAWG RADDVITMDP
601   KDNCSKDAND TLLLQLTNTS AYYMYLLLLL KSVVYFAIIT CCLLMAMVKR KDFRAKRGSG
661   ATNFSLLKQA GDVEENPGPM GAGATGRAMD GPRLLLLLLL GVSLGGAKEQ KLISEEDLEI
721   PGRWITRSTP PEGSDSTAPS TQEPEAPPEQ DLIASTVAGV VTTVMGSSQP VVTRGTTDNL
781   IPVYCSILAA VVVGLVAYIA FKR-
(SEQ ID NO: 61)
```

| Amino acids of SEQ ID NO: 61 | Sequence description |
|---|---|
| 1-26 | HGH signal sequence 1 |
| 27-138 | F5 TCR alpha variable Ig domain |
| 139-231 | TCR alpha constant Ig domain |
| 232-268 | TCR delta connecting peptide |
| 269-290 | TCR delta transmembrane domain |
| 291-295 | TCR alpha cytoplasmic domain |
| 296-327 | Viral 2A ribosomal-skipping sequence |
| 328-353 | HGH signal sequence 2 |
| 354-465 | F5 TCR beta variable Ig domain |
| 466-593 | TCR beta constant Ig domain |
| 594-623 | TCR gamma C1a connecting peptide |
| 624-644 | TCR gamma C1a transmembrane domain |
| 645-653 | TCR beta cytoplasmic domain |
| 654-679 | Viral 2A ribosomal-skipping sequence |
| 680-708 | LNGFR signal sequence |
| 709-718 | Myc epitope |
| 719-803 | LNGFR truncated extracellular and transmembrane domain |

FIG. 9D

Domain-swap F5 TCR AlphaGamma+BetaDelta in pMTB1302

1 MATGSRTSLL LAFGLLCLPW LQEASAQQKE VEQNSGPLSV PEGAIASLNC TYSDRGSQSF

61 FWYRQYSGKS PELIMFIYSN GDKEDGRFTA QLNKASQYVS LLIRDSQPSD SATYLCAVNF

121 GGGKLIFGQG TELSVKPNIQ NPDPAVYQLR DSKSSDKSVC LFTDFDSQTN VSQSKDSDVY

181 ITDKTVLDMR SMDFKSNSAV AWSNKSDFAC ANAFNNSIIP EDTFFPSPES SDVITMDPKD

241 NCSKDANDTL LLQLTNTSAY YMYLLLLLKS VVYFAIITCC LLRLWSSRAK RSGSGAPVKQ

301 TLNFDLLKLA GDVESNPGPM ATGSRTSLLL AFGLLCLPCL QEGSAGITQA PTSQILAAGR

361 RMTLRCTQDM RHNAMYWYRQ DLGLGLRLIH YSNTAGTTGK GEVPDGYSVS RANTDDFPLT

421 LASAVPSQTS VYFCASSLSF GTEAFFGQGT RLTVVEDLNK VFPPEVAVFE PSEAEISHTQ

481 KATLVCLATG FFPDHVELSW WVNGKEVHSG VSTDPQPLKE QPALNDSRYC LSSRLRVSAT

541 FWQNPRNHFR CQVQFYGLSE NDEWTQDRAK PVTQIVSAEA WGRADDSTDH VKPKETENTK

601 QPSKSCHKPK AIVHTEKVNM MSLTVLGLRM LFAKTVAVNF LLTAMAMVKR KDFRAKRGSG

661 ATNFSLLKQA GDVEENPGPM GAGATGRAMD GPRLLLLLLL GVSLGGAKEQ KLISEEDLEI

721 PGRWITRSTP PEGSDSTAPS TQEPEAPPEQ DLIASTVAGV VTTVMGSSQP VVTRGTTDNL

781 IPVYCSILAA VVVGLVAYIA FKR-
(SEQ ID NO: 62)

| Amino acids of SEQ ID NO: 62 | Sequence description |
|---|---|
| 1-26 | HGH signal sequence 1 |
| 27-138 | F5 TCR alpha variable Ig domain |
| 139-231 | TCR alpha constant Ig domain |
| 232-261 | TCR gamma C1a connecting peptide |
| 262-282 | TCR gamma C1a transmembrane domain |
| 283-287 | TCR alpha cytoplasmic domain |
| 288-319 | Viral 2A ribosomal-skipping sequence |
| 320-345 | HGH signal sequence 2 |
| 346-457 | F5 TCR beta variable Ig domain |
| 458-585 | TCR beta constant Ig domain |
| 586-622 | TCR delta connecting peptide |
| 623-644 | TCR delta transmembrane domain |
| 645-653 | TCR beta cytoplasmic domain |
| 654-679 | Viral 2A ribosomal-skipping sequence |
| 680-708 | LNGFR signal sequence |
| 709-718 | Myc epitope |
| 719-803 | LNGFR truncated extracellular and transmembrane domain |

FIG. 9E

DOMAIN-SWAP T CELL RECEPTORS

RELATED APPLICATIONS

This application claims the benefit of U.S. Provisional application 61/928,142, filed on Jan. 16, 2014 which is hereby incorporated by reference in its entirety.

STATEMENT REGARDING FEDERALLY SPONSORED R&D

This invention was made with government support under CA132681 awarded by the National Institute of Health. The government has certain rights in the invention.

SEQUENCE LISTING IN ELECTRONIC FORMAT

The present application is being filed along with a Sequence Listing in electronic format. The Sequence Listing is provided as a file entitled CALTE_104A_SEQLIST.TXT which is 202,964 bytes in size, created on Jan. 14, 2015 and last modified on Jan. 15, 2015, and updated by a file entitled CALTE_104A_SEQLIST_REPLACEMENT.TXT which is 203,050 bytes in size, created on Feb. 19, 2015 and last modified on Feb. 25, 2015.

FIELD

Some embodiments herein relate to genetically modified T cells, for example T cells comprising modified T cell receptors.

BACKGROUND

T cells are cells of the immune system. T cells express T cell receptors (TCRs) on their surface. The TCRs can recognize antigens and induce the T cell to generate an immune response against the recognized antigens. There are two main kinds of T cells namely, CD4 and CD8 T cells that typically generate an immune response. A small fraction of T cells, called regulatory T cells (Tregs), are typically involved in regulating the CD4 and CD8 T cell immune responses. Typically, CD4 T cells recognize antigens that are presented on antigen presenting cells in the context of an MHC Class II molecule. In contrast, CD8 T cells typically recognize antigens that are presented on antigen presenting cells in the context of an MHC Class I molecule.

Adaptive immunity to cancers and pathogens can be mediated by T cells, lymphocytes that are capable of identifying and killing cellular targets with exquisite specificity. This specificity is typically determined by the TCR, which is a heterodimer of two polypeptide chains. A typical wild-type (WT) TCR can be expressed on the surface of a T cell either as an alpha chain-beta chain heterodimer or as a gamma chain-delta chain heterodimer. During typical T cell development, the gene that encodes each polypeptide chain is uniquely rearranged by genetic recombination such that the sequence of each encoded polypeptide is unique for a given T cell. Each T cell typically expresses only one alpha and one beta, or one gamma and one delta chain.

Each TCR polypeptide chain comprises a variable domain, which confers specificity on the T cell, and several invariant domains including a constant domain, a connecting peptide, a transmembrane domain, and a short cytoplasmic tail. To achieve functional form, the TCR heterodimer typically recruits six additional chains which comprise the CD3 dimers gamma-epsilon, delta-epsilon and zeta-zeta. These additional chains can facilitate assembly and export of the TCR heterodimer to the T cell surface, as well as enable signal transduction upon engagement of a TCR heterodimer by its target antigen (Call et al., Ann. Rev. Immunol. 23: 101-125 (2005)).

Most T cells (~90%) express TCRs that comprise an alpha chain and a beta chain. A smaller fraction (~5-10%) of T cells express TCRs that comprise a gamma chain and a delta chain. Typically, a TCR heterodimer is assembled following recruitment of six additional polypeptide chains that form three CD3 dimers. The CD3 dimers are involved in expression of the heterodimeric TCR on the T cell surface. The CD3 dimers are also involved in signaling by TCRs following antigen recognition.

It has been observed that TCR heterodimers that are not properly assembled with the CD3 dimers prior to export are degraded (Bonifacino et al., J. Cell Biol. 109: 73-83 (1989)). Without being limited by any theory, the amino acid residues that are identified as involved in recruiting the CD3 dimers are present within the invariant domains of both chains of a TCR heterodimer (Call et al., Ann. Rev. Immunol. 23: 101-125 (2005); Kuhns et al., Immunity 26: 357-369 (2007); Xu et al., J. Biol. Chem. 281: 36977-36984 (2006)).

SUMMARY

In some embodiments, a method of making a T cell that expresses a domain-swap T cell receptor (DS-TCR) is provided. The method can comprise contacting a T cell with a first nucleic acid that encodes a first domain-swap chain in which the first domain-swap chain comprises a first chain transmembrane domain, a second chain variable domain and a second chain constant domain, but does not comprise a first chain variable domain and does not comprise a first chain constant domain. The method can comprise contacting the T cell with a second nucleic acid that encodes a second domain-swap chain, in which the second domain-swap chain comprises a second chain transmembrane domain, a first chain variable domain and a first chain constant domain, but does not comprise a second chain variable domain and does not comprise a second chain constant domain. The first chain variable domain can comprise an alpha or a gamma chain variable domain and the first chain constant domain can comprise an alpha or a gamma chain constant domain and the first chain transmembrane domain can comprise an alpha or a gamma chain transmembrane domain and the second chain variable domain can comprise a beta or a delta chain variable domain and the second chain constant domain can comprise a beta or a delta chain constant domain and the second chain transmembrane domain can comprises a beta or a delta chain transmembrane domain; or the first chain variable domain can comprise an alpha or a delta chain variable domain and the first chain constant domain can comprise an alpha or a delta chain constant domain and the first chain transmembrane domain can comprise an alpha or a delta chain transmembrane domain and the second chain variable domain can comprise a beta or a gamma chain variable domain and the second chain constant domain can comprise a beta or a gamma chain constant domain and the second chain transmembrane domain can comprise a beta or a gamma chain transmembrane domain. As such, the method can comprise configuring the T cell to express a DS-TCR comprising the first domain-swap chain and the second domain-swap chain. In some embodiments, the first domain-swap chain further comprises a second chain connecting peptide and the second domain-swap chain can further comprises a first chain connecting peptide, in which the first chain connecting peptide comprises an alpha or gamma chain connecting peptide and the second chain connecting peptide comprises a beta or delta chain connecting peptide, or in which the first chain connecting peptide comprises an alpha or delta chain connecting peptide and the second chain connecting peptide comprises a beta or gamma chain connecting peptide. In some embodiments, the first chain variable domain comprises an alpha chain variable domain and the first chain constant domain comprises an alpha chain constant domain and the first chain transmembrane domain comprises a beta chain transmembrane domain and the second chain variable domain comprises a beta chain variable domain and the second chain constant domain can comprise a beta chain constant domain and the second chain transmembrane domain comprises an alpha chain transmembrane domain. In some embodiments, the first chain variable domain comprises a gamma chain variable domain and the first chain constant domain comprises a gamma chain constant domain and the first chain transmembrane domain comprises a gamma chain transmembrane domain and the second chain variable domain comprises a delta chain variable domain and the second chain constant domain comprises a delta chain constant domain and the second chain transmembrane domain comprises a delta chain transmembrane domain. In some embodiments, the first chain variable domain comprises an alpha chain variable domain and the first chain constant domain comprises an alpha chain constant domain and the first chain transmembrane domain comprises a gamma chain transmembrane domain and the second chain variable domain comprises a beta chain variable domain and the second chain constant domain comprises a beta chain constant domain and the second chain transmembrane domain comprises a delta chain transmembrane domain. In some embodiments, the first chain variable domain comprises an alpha chain variable domain and the first chain constant domain comprises an alpha chain constant domain and the first chain transmembrane domain comprises a delta chain transmembrane domain and the second chain variable domain comprises a beta chain variable domain and the second chain constant domain comprises a beta chain constant domain and the second chain transmembrane domain comprises a gamma chain transmembrane domain.

In some embodiments, an expression vector is provided. The expression vector can comprise a first nucleic acid that encodes a first domain-swap chain comprising a first chain transmembrane domain, a second chain variable domain and a second chain constant domain. The expression vector can comprise a second nucleic acid that encodes a second domain-swap chain comprising a second chain transmembrane domain, a first chain variable domain and a first chain constant domain. The first chain variable domain can comprise an alpha or a gamma chain variable domain and the first chain constant domain can comprise an alpha or a gamma chain constant domain and the first chain transmembrane domain can comprise an alpha or a gamma chain transmembrane domain and the second chain variable domain can comprise a beta or a delta chain variable domain and the second chain constant domain can comprise a beta or a delta chain constant domain and the second chain transmembrane domain can comprise a beta or a delta chain transmembrane domain; or the first chain variable domain can comprise an alpha or a delta chain variable domain and the first chain constant domain can comprise an alpha or a delta chain constant domain and the first chain transmembrane domain can comprise an alpha or a delta chain transmembrane domain and the second chain variable domain can comprise a beta or a gamma chain variable domain and the second chain constant domain can comprise a beta or a gamma chain constant domain and the second chain transmembrane domain can comprise a beta or a gamma chain transmembrane domain. In some embodiments, the first domain-swap chain further comprises a second chain connecting peptide but not a first chain connecting peptide, and the second domain-swap chain further comprises a first chain connecting peptide but not a second chain connecting peptide, in which the first chain connecting peptide comprises an alpha or gamma chain connecting peptide and the second chain connecting peptide comprises a beta or delta chain connecting peptide; or the first chain connecting peptide comprises an alpha or delta chain connecting peptide and the second chain connecting peptide comprises a beta or gamma chain connecting peptide. In some embodiments, the first nucleic acid and the second nucleic acid are part of the same expression vector and the expression vector further comprises a 2A peptide-encoding sequence flanked by the first nucleic acid and the second nucleic acid in which the first nucleic acid and the second nucleic acid are driven by a single promoter. In some embodiments, the first nucleic acid and the second nucleic acid are part of separate expression vectors. Optionally, the first nucleic acid and the second nucleic acid can be driven by their own separate promoters. Optionally, the first nucleic acid and the second nucleic acid can be part of a single expression vector and driven by their own separate promoters. In some embodiments, the expression vector comprises a lentiviral vector, retroviral vector, adenoviral vector, or adeno-associated viral vector.

In some embodiments, a genetically engineered T cell is provided. The genetically engineered T cell can comprise a first nucleic acid that encodes a first domain-swap chain comprising a first chain transmembrane domain, a second chain variable domain and a second chain constant domain. The genetically engineered T cell can comprise a second nucleic acid that encodes a second domain-swap chain comprising a second chain transmembrane domain, a first chain variable domain and a first chain constant domain. The first chain variable domain can comprise an alpha or a gamma chain variable domain and the first chain constant domain can comprise an alpha or a gamma chain constant domain and the first chain transmembrane domain can comprise an alpha or a gamma chain transmembrane domain and the second chain variable domain can comprise a beta or a delta chain variable domain and the second chain constant domain can comprise a beta or a delta chain constant domain and the second chain transmembrane domain can comprise a beta or a delta chain transmembrane domain; or the first chain variable domain can comprise an alpha or a delta chain variable domain and the first chain constant domain can comprise an alpha or a delta chain constant domain and the first chain transmembrane domain can comprise an alpha or a delta chain transmembrane domain and the second chain variable domain can comprise a beta or a gamma chain variable domain and the second chain constant domain can comprise a beta or a gamma chain constant domain and the second chain transmembrane domain can comprise a beta or a gamma chain transmembrane domain. As such, the T cell can be configured to express a DS_TCR comprising the first domain-swap chain and the second domain-swap chain. In some embodiments, the first domain-swap chain further comprises a second chain connecting peptide and the second domain-swap chain further comprises a first chain connecting peptide, in which the first chain connecting peptide comprises an alpha or gamma chain connecting peptide and the second chain connecting peptide comprises a beta or delta chain connecting peptide; or in which the first chain connecting peptide comprises an alpha or delta chain connecting peptide and the second chain connecting peptide comprises a beta or gamma chain connecting peptide. In some embodiments, the genetically engineered T cell is configured to express the first domain-swap chain as a first polypeptide and the second domain-swap chain as a second polypeptide, in which the first domain-swap chain and second domain-swap chain are separate molecules. In some embodiments, expression of an endogenous TCR is repressed or eliminated in the genetically engineered T cell.

In some embodiments, a method of inducing an immune response in a subject is provided. The method can comprise configuring an isolated T cell to express a first domain-swap chain that comprises a first chain transmembrane domain, a second chain variable domain, and a second chain constant domain, but does not comprise a first chain variable domain and does not comprise a first chain constant domain. The method can comprise configuring the isolated T cell to express a second domain-swap chain that comprises a second chain transmembrane domain, a first chain variable domain, and a first chain constant domain, but does not comprise a second chain variable domain and does not comprise a second chain constant domain. The first chain variable domain can comprise an alpha or a gamma chain variable domain and the first chain constant domain can comprise an alpha or a gamma chain constant domain and the first chain transmembrane domain can comprise an alpha or a gamma chain transmembrane domain and the second chain variable domain can comprise a beta or a delta chain variable domain and the second chain constant domain can comprise a beta or a delta chain constant domain and the second chain transmembrane domain can comprise a beta or a delta chain transmembrane domain; or the first chain variable domain can comprise an alpha or a delta chain variable domain and the first chain constant domain can comprise an alpha or a delta chain constant domain and the first chain transmembrane domain can comprise an alpha or a delta chain transmembrane domain and the second chain variable domain can comprise a beta or a gamma chain variable domain and the second chain constant domain can comprise a beta or a gamma chain constant domain and the second chain transmembrane domain can comprise a beta or a gamma chain transmembrane domain. As such, the genetically engineered T cell configured to express a domain-swap T cell receptor (DS-TCR) comprising the first domain-swap chain and the second domain-swap chain can be administered to the subject. In some embodiments, the first domain-swap chain further comprises a second chain connecting peptide and the second domain-swap chain can further comprise a first chain connecting peptide, in which the first chain connecting peptide comprises an alpha or gamma chain connecting peptide and the second chain connecting peptide comprises a beta or delta chain connecting peptide; or in which the first chain connecting peptide comprises an alpha or delta chain connecting peptide and the second chain connecting peptide comprises a beta or gamma chain connecting peptide. In some embodiments, the isolated T cell is autologous to the subject. In some embodiments, the isolated T cell is allogeneic to the subject. In some embodiments, the T cell comprises a CD4 T cell. In some embodiments, the T cell comprises a CD8 T cell. In some embodiments, the T cell comprises a regulatory T cell (Treg). In some embodiments, the T cell is co-administered with a second genetically-engineered T cell population. In some embodiments, the T cell is administered in a single dose. In some embodiments, the T cell is administered in in multiple doses. In some embodiments, the subject has at least one of a tumor, a cancer, an infectious disease, an autoimmune disease and is in need of treatment therefor. In some embodiments, the subject has diminished or ineffective or exhausted T cells and is in need of treatment therefor. In some embodiments, the T cell is induced to express a plurality of DS-TCR against an array of antigens. In some embodiments, the T cell can be administered to the subject via at least one of intramuscular injection, intravaginal injection, intravenous injection, intraperitoneal injection, subcutaneous injection, epicutaneous administration, intradermal administration, or nasal administration. In some embodiments, the administered T cell is further be monitored over time. In some embodiments, the method can be repeated as desired.

BRIEF DESCRIPTION OF THE DRAWINGS

FIG. 2C top panel is a graph showing expression of TCR configurations on the surface of CD3+ 293T cells as determined by binding of a cognate peptide-WIC tetramer in accordance with some embodiments herein. Beneath the graph, each TCR configuration is shown schematically, including WT TCR, a mispaired TCR configuration, and a correctly paired DS-TCR. It is noted that the indicated mispaired TCRs in this schematic comprise a domain swap performed on either the alpha chain or the beta chain, but not both chains.

FIG. 9A is the sequence and annotation of the DS-TCR configuration with SEQ ID NO: 56.

FIG. 9B is the sequence and annotation of the DS-TCR configuration with SEQ ID NO: 57.

FIG. 9C is the sequence and annotation of the DS-TCR configuration with SEQ ID NO: 59.

FIG. 9D is the sequence and annotation of the DS-TCR configuration with SEQ ID NO: 61.

FIG. 9E is the sequence and annotation of the DS-TCR configuration with SEQ ID NO: 62.

DETAILED DESCRIPTION

Figure 1A:
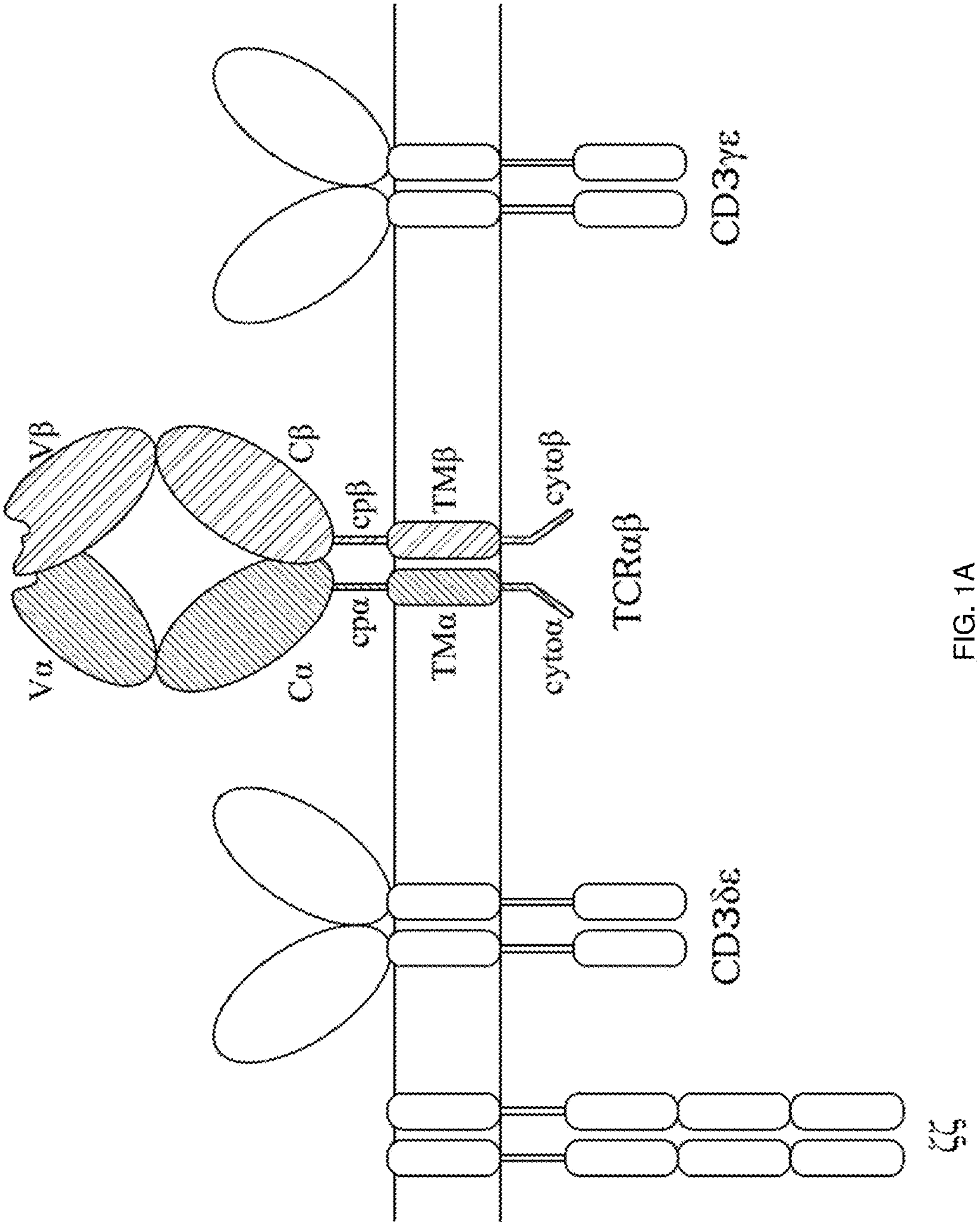
FIG. 1A is a schematic diagram showing a T Cell Receptor (TCR) complex which comprises a TCR heterodimer and additional CD3 dimers in accordance with some embodiments herein. The TCR in this schematic comprises an alpha chain and a beta chain.

Various embodiments herein relate generally to domain-swap T cell receptors (DS-TCRs).

T cell receptors (TCRs) are expressed on the surface of T cells and are involved in the recognition of antigens. Each TCR comprises a heterodimer of two polypeptide chains. Some endogenous TCRs comprise a pairing of an alpha chain and a beta chain. Some endogenous TCRs comprise a pairing of a gamma chain and a delta chain. Each polypeptide chain of a typical TCR comprises a variant region comprising a variable domain, and an invariant region comprising a constant domain, a connecting peptide, a transmembrane domain and a short cytoplasmic tail.

In accordance with some embodiments herein, the DS-TCR comprises a first polypeptide chain and a second polypeptide chain whose variant and invariant regions comprise domains from a repertoire of sequences homologous to the domain sequences of the endogenous alpha, beta, gamma and/or delta chains. In some embodiments, reference is made to the nucleic acid sequences that encode the first and second polypeptide chains of a DS-TCR. In some embodiments, reference is made to the first and second polypeptide chains of a DS-TCR. Depending on the context, it will be evident to the skilled artisan whether reference is made to nucleic acids encoding the polypeptide chains of a DS-TCR or to the polypeptide chains of a DS-TCR. In some embodiments, DS-TCRs minimize or avoid mispairing with other T cell receptor chains such as endogenous (WT) T cell receptor chains. In some embodiments, a T cell is isolated from a subject (e.g., a cancer patient) and genetically engineered to express a DS-TCR. In some embodiments, the endogenous TCR expression is reduced or eliminated such that the DS-TCR is the predominant TCR or the only TCR expressed on the surface of T cell. In some embodiments, the DS-TCR-expressing T cell is administered to a subject as a treatment (e.g., preventive, prophylactic, or therapeutic). In some embodiments, the DS-TCR expressing T cell stimulates immunity in a subject (e.g., a cancer patient).

Domain-Swap T cell Receptors (DS-TCRs)

Some embodiments herein provide a strategy for preventing TCR mispairing that exploits our understanding of TCR biogenesis. Without being limited by any theory, functional surface expression of the TCR complex typically involves the recruitment of accessory CD3 proteins by invariant domains of the two polypeptide chains of the TCR. Disruption of the TCR-CD3 interactions can ablate both surface expression and signaling of the TCR complex. Accordingly, it can be useful to prevent mispairing of introduced and endogenous chains entirely, thereby eliminating the risk of autoimmunity and maximizing surface expression of the therapeutic TCR heterodimer. Additionally, it can be useful for modifications made to the introduced TCR chains to minimize or avoid foreign sequences, at least in that it is contemplated that the absence of foreign sequences can minimize immunogenicity and avoid development of antibodies against the introduced TCRs. It is noted that DS-TCR's in accordance with some embodiments herein can minimize or prevent mispairing, while also comprising host organism sequences (e.g. fully human TCR's for a human host) so as to minimize immunogenicity against the DS-TCR.

A number of suitable DS-TCR configurations are provided in accordance with some embodiments herein. Without being limited by any theory, DS-TCR's can be useful for minimizing mispairing, while maintaining TCR function, for example to minimize mispairing between an endogenous TCR chain and a chain of a genetically modified TCR, and/or to minimize mispairing between chains of two different genetically modified TCR's.

Figure 1B:
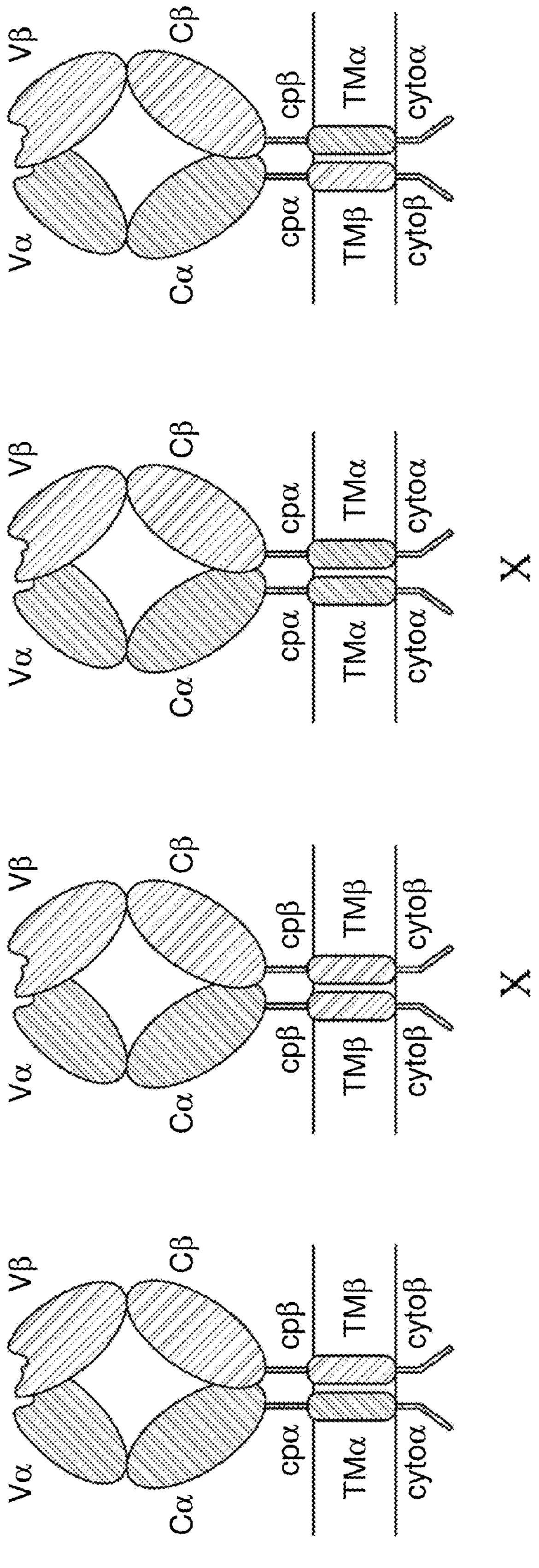
FIG. 1B is a schematic showing an endogenous (WT) TCR, TCRs resulting from mispairing between a domain-swap chain and a WT chain, and a DS-TCR with correctly paired domain-swap chains in accordance with some embodiments herein.

DS-TCR chains can comprise various domains, including the variable domain (V), constant domain (C), connecting peptide (CP), transmembrane domain (TM), and cytoplasmic tail (CT) (see, e.g. FIG. 1 for a schematic diagram of a WT TCR). A number of configurations for the chains of a DS-TCR in accordance with some embodiments herein are set forth in Alternatives 1-32 in Table 1, herein. It is contemplated that synthetic versions and variants of any or all of the indicated domains can be useful in DS-TCR's in accordance with some embodiments herein. As such, unless stated otherwise, V, C, CP, TM, and CT domains are contemplated to encompass naturally-occurring and synthetic versions of the indicated domains. In some embodiments, the DS-TCR comprises synthetic variants of naturally occurring human domains. In some embodiments, the DS-TCR comprises synthetic variants of naturally occurring murine domains. In some embodiments, the DS-TCR is a chimera of synthetic variants of naturally occurring human domains and murine domains.

In accordance with some embodiments herein, DS-TCR can be entirely of one organism. Optionally, the DS-TCR can be chimeric, comprising a combination of domains from two different organisms (for example, human and murine). For example, chimeric TCRs are described in U.S. Pat. No. 7,446,190, which is hereby incorporated by reference in its entirety. Without being limited by any theory, it is contemplated that fully human and/or chimeric DS-TCRs are less likely to be immunogenic in a human host than murine DS-TCRs. In some embodiments, a chimeric DS-TCR is provided. In some embodiments, the domains of the DS-TCR are fully human. In some embodiments, the domains of the DS-TCR are fully murine. In some embodiments, the DS-TCR is a chimera of human domains and murine domains.

TABLE 1

DS-TCR alternatives

| Alternative # | Chain | Domain: Variable | Constant | Connecting peptide | Transmembrane | Cytoplasmic tail |
|---|---|---|---|---|---|---|
| 1 | 1st | Alpha | Alpha | Beta | Beta | Beta |
| | 2nd | Beta | Beta | Alpha | Alpha | Alpha |
| 2 | 1st | Alpha | Alpha | Alpha | Beta | Beta |
| | 2nd | Beta | Beta | Beta | Alpha | Alpha |
| 3 | 1st | Gamma | Gamma | Delta | Delta | Delta |
| | 2nd | Delta | Delta | Gamma | Gamma | Gamma |
| 4 | 1st | Gamma | Gamma | Gamma | Delta | Delta |
| | 2nd | Delta | Delta | Delta | Gamma | Gamma |
| 5 | 1st | Alpha | Alpha | Gamma | Gamma | Gamma |
| | 2nd | Gamma | Gamma | Alpha | Alpha | Alpha |
| 6 | 1st | Alpha | Alpha | Alpha | Gamma | Gamma |
| | 2nd | Gamma | Gamma | Gamma | Alpha | Alpha |
| 7 | 1st | Alpha | Alpha | Delta | Delta | Delta |
| | 2nd | Delta | Delta | Alpha | Alpha | Alpha |
| 8 | 1st | Alpha | Alpha | Alpha | Delta | Delta |
| | 2nd | Delta | Delta | Delta | Alpha | Alpha |
| 9 | 1st | Beta | Beta | Gamma | Gamma | Gamma |
| | 2nd | Gamma | Gamma | Beta | Beta | Beta |
| 10 | 1st | Beta | Beta | Beta | Gamma | Gamma |
| | 2nd | Gamma | Gamma | Gamma | Beta | Beta |
| 11 | 1st | Beta | Beta | Delta | Delta | Delta |
| | 2nd | Delta | Delta | Beta | Beta | Beta |
| 12 | 1st | Beta | Beta | Beta | Delta | Delta |
| | 2nd | Delta | Delta | Delta | Beta | Beta |
| 13 | 1st | Alpha | Alpha | Gamma | Gamma | Alpha |
| | 2nd | Beta | Beta | Delta | Delta | Beta |
| 14 | 1st | Alpha | Alpha | Delta | Delta | Alpha |
| | 2nd | Beta | Beta | Gamma | Gamma | Beta |
| 15 | 1st | Gamma | Gamma | Alpha | Alpha | Gamma |
| | 2nd | Delta | Delta | Beta | Beta | Delta |
| 16 | 1st | Gamma | Gamma | Beta | Beta | Gamma |
| | 2nd | Delta | Delta | Alpha | Alpha | Delta |
| 17 | 1st | Alpha | Alpha | Alpha | Alpha | Beta |
| | 2nd | Beta | Beta | Beta | Beta | Alpha |
| 18 | 1st | Gamma | Gamma | Gamma | Gamma | Delta |
| | 2nd | Delta | Delta | Delta | Delta | Gamma |
| 19 | 1st | Alpha | Alpha | Alpha | Alpha | Gamma |
| | 2nd | Gamma | Gamma | Gamma | Gamma | Alpha |
| 20 | 1st | Alpha | Alpha | Alpha | Alpha | Delta |
| | 2nd | Delta | Delta | Delta | Delta | Alpha |
| 21 | 1st | Beta | Beta | Beta | Beta | Gamma |
| | 2nd | Gamma | Gamma | Gamma | Gamma | Beta |
| 22 | 1st | Beta | Beta | Beta | Beta | Delta |
| | 2nd | Delta | Delta | Delta | Delta | Beta |
| 23 | 1st | Alpha | Beta | Beta | Beta | Beta |
| | 2nd | Beta | Alpha | Alpha | Alpha | Alpha |
| 24 | 1st | Gamma | Delta | Delta | Delta | Delta |
| | 2nd | Delta | Gamma | Gamma | Gamma | Gamma |
| 25 | 1st | Alpha | Gamma | Gamma | Gamma | Gamma |
| | 2nd | Gamma | Alpha | Alpha | Alpha | Alpha |

TABLE 1-continued

| DS-TCR alternatives | | | | | | |
|---|---|---|---|---|---|---|
| Alter- | | Domain | | | | |
| native # | Chain | Vari-able | Con-stant | Connecting peptide | Trans-membrane | Cytoplas-mic tail |
| 26 | 1st | Alpha | Delta | Delta | Delta | Delta |
| | 2nd | Delta | Alpha | Alpha | Alpha | Alpha |
| 27 | 1st | Beta | Gamma | Gamma | Gamma | Gamma |
| | 2nd | Gamma | Beta | Beta | Beta | Beta |
| 28 | 1st | Beta | Delta | Delta | Delta | Delta |
| | 2nd | Delta | Beta | Beta | Beta | Beta |
| 29 | 1st | Alpha | Gamma | Gamma | Gamma | Alpha |
| | 2nd | Beta | Delta | Delta | Delta | Beta |
| 30 | 1st | Alpha | Delta | Delta | Delta | Alpha |
| | 2nd | Beta | Gamma | Gamma | Gamma | Beta |
| 31 | 1st | Gamma | Alpha | Alpha | Alpha | Gamma |
| | 2nd | Delta | Beta | Beta | Beta | Delta |
| 32 | 1st | Gamma | Beta | Beta | Beta | Gamma |
| | 2nd | Delta | Alpha | Alpha | Alpha | Delta |

In accordance with Alternative 1, the DS-TCR comprises two polypeptide chains: in the first chain, the variable domain and constant domain of the alpha chain, and the connecting peptide, transmembrane domain and cytoplasmic tail of the beta chain, and reciprocally, in the second chain, the variable domain and constant domain of the beta chain, and the connecting peptide, transmembrane domain and cytoplasmic tail of the alpha chain. Schematically, this can be diagrammed as: first chain: $V_{alpha}$-$C_{alpha}$-$CP_{beta}$-$TM_{beta}$-$CT_{beta}$; second chain: $V_{beta}$-$C_{beta}$-$CP_{alpha}$-$TM_{alpha}$-$CT_{alpha}$.

In accordance with Alternative 2, the DS-TCR comprises two polypeptide chains: in the first chain, the variable domain, constant domain and connecting peptide of the alpha chain and the transmembrane domain and cytoplasmic tail of the beta chain, and reciprocally, in the second chain, the variable domain, constant domain and connecting peptide of the beta chain combined with the transmembrane domain and cytoplasmic tail of the alpha chain. Schematically, this can be diagrammed as: first chain: $V_{alpha}$-$C_{alpha}$-$CP_{alpha}$-$TM_{beta}$-$CT_{beta}$; second chain: $V_{beta}$-$C_{beta}$-$CP_{beta}$-$TM_{alpha}$-$CT_{alpha}$.

In accordance with Alternative 3, the DS-TCR comprises two polypeptide chains: in the first chain, the variable domain and constant domain of the gamma chain and the connecting peptide, transmembrane domain and cytoplasmic tail of the delta chain, and reciprocally, in the second chain, the variable domain and constant domain of the delta chain and the connecting peptide, transmembrane domain and cytoplasmic tail of the gamma chain. Schematically, this can be diagrammed as: first chain: $V_{gamma}$-$C_{gamma}$-$CP_{delta}$-$TM_{delta}$-$CT_{delta}$; second chain: $V_{delta}$-$C_{delta}$-$CP_{gamma}$-$TM_{gamma}$-$CT_{gamma}$.

In accordance with Alternative 4, the DS-TCR comprises two polypeptide chains: in the first chain, the variable domain, constant domain and connecting peptide of the gamma chain and the transmembrane domain and cytoplasmic tail of the delta chain, and reciprocally, in the second chain, the variable domain, constant domain and connecting peptide of the delta chain and the transmembrane domain and cytoplasmic tail of the gamma chain. Schematically, this can be diagrammed as: first chain: $V_{gamma}$-$C_{gama}$-$CP_{gama}$-$TM_{delta}$-$CT_{delta}$; second chain: $V_{delta}$-$C_{delta}$-$CP_{delta}$-$TM_{gamma}$-$CT_{gamma}$.

A number of other suitable DS-TCR Alternatives in accordance with some embodiments herein are listed in Table 1.

In some embodiments, the DS-TCR is in accordance with any of Alternatives 1-32. In some embodiments, the DS-TCR is in accordance with any of Alternatives 1-4. In some embodiments, the DS-TCR is in accordance with any of Alternatives 1-16. In some embodiments, the DS-TCR is in accordance with any of Alternatives 5-16. In some embodiments, the DS-TCR is in accordance with any of Alternatives 1-22. In some embodiments, the DS-TCR is in accordance with any of Alternatives 17-22. In some embodiments, the DS-TCR is in accordance with any of Alternatives 17-32. In some embodiments, the DS-TCR is in accordance with any of Alternatives 23-32.

Nucleic Acids

A number of nucleic acid arrangements encoding the first and second domain swap chains are suitable in accordance with some embodiments herein In some embodiments (and in accordance with Alternative 1), a first nucleic acid encodes the first domain-swap chain comprising the variable domain and constant domain of the alpha chain combined with the connecting peptide, transmembrane domain and cytoplasmic tail of the beta chain, and reciprocally, a second nucleic acid encodes the second domain-swap chain comprising the variable domain and constant domain of the beta chain combined with the connecting peptide, transmembrane domain and cytoplasmic tail of the alpha chain.

In some embodiments (and in accordance with Alternative 2), a first nucleic acid encodes the first domain-swap chain comprising the variable domain, constant domain and connecting peptide of the alpha chain combined with the transmembrane domain and cytoplasmic tail of the beta chain, and reciprocally, a second nucleic acid encodes the second domain-swap chain comprising the variable domain, constant domain and connecting peptide of the beta chain combined with the transmembrane domain and cytoplasmic tail of the alpha chain.

In some embodiments (and in accordance with Alternative 3), a first nucleic acid encodes the first domain-swap chain comprising the variable domain and constant domain of the gamma chain combined with the connecting peptide, transmembrane domain and cytoplasmic tail of the delta chain, and reciprocally, a second nucleic acid encodes the second domain-swap chain comprising the variable domain and constant domain of the delta chain combined with the connecting peptide, transmembrane domain and cytoplasmic tail of the gamma chain.

In some embodiments (and in accordance with Alternative 4), a first nucleic acid encodes the first domain-swap chain comprising the variable domain, constant domain and connecting peptide of the gamma chain combined with the transmembrane domain and cytoplasmic tail of the delta chain, and reciprocally, a second nucleic acid encodes the second domain-swap chain comprising the variable domain, constant domain and connecting peptide of the delta chain combined with the transmembrane domain and cytoplasmic tail of the gamma chain.

In some embodiments, a first nucleic acid encodes the first domain-swap chain and a second nucleic acid encodes the second domain-swap chain in accordance with Alternatives 5-16. In some embodiments, a first nucleic acid encodes the first domain-swap chain and a second nucleic acid encodes the second domain-swap chain in accordance with Alternatives 17-22. In some embodiments, a first nucleic acid encodes the first domain-swap chain and a second nucleic acid encodes the second domain-swap chain in accordance with Alternatives 23-32.

In some embodiments, a first nucleic acid encodes the first domain-swap chain and a second nucleic acid encodes the second domain-swap chain in accordance with any of Alternatives 1-32. In some embodiments, a first nucleic acid encodes the first domain-swap chain and a second nucleic acid encodes the second domain-swap chain in accordance with any of Alternatives 1-4. In some embodiments, a first nucleic acid encodes the first domain-swap chain and a second nucleic acid encodes the second domain-swap chain in accordance with any of Alternatives 1-16. In some embodiments, a first nucleic acid encodes the first domain-swap chain and a second nucleic acid encodes the second domain-swap chain in accordance with any of Alternatives 5-16. In some embodiments, a first nucleic acid encodes the first domain-swap chain and a second nucleic acid encodes the second domain-swap chain in accordance with any of Alternatives 1-22. In some embodiments, a first nucleic acid encodes the first domain-swap chain and a second nucleic acid encodes the second domain-swap chain in accordance with any of Alternatives 17-22. In some embodiments, a first nucleic acid encodes the first domain-swap chain and a second nucleic acid encodes the second domain-swap chain in accordance with any of Alternatives 17-32. In some embodiments, a first nucleic acid encodes the first domain-swap chain and a second nucleic acid encodes the second domain-swap chain in accordance with any of Alternatives 23-32.

In some embodiments, the first nucleic acid and second nucleic acid are part of the same construct (e.g. a vector). Optionally, the first and second nucleic acid can be under the control of different promoters. Optionally, the first and second nucleic acid can be under the control of the same promoter.

Optionally, the first and second nucleic acid can be separated by a 2A polypeptide-encoding polynucleotide sequence. Examples of 2A polypeptide-encoding polynucleotide sequences and their corresponding encoded polypeptide sequence are described in U.S. Pat. Application Publication US 2013/0316366 A1 which is hereby incorporated by reference in its entirety. In some embodiments, a 2A polynucleotide sequence encoding a 2A polypeptide can be selected from Table 2. The corresponding encoded polypeptide sequence for each polynucleotide sequence is listed in Table 3.

TABLE 2

2A polynucleotide sequences

| SEQ ID NO: | 2A Polypeptide | Polypeptide sequence | Corresponding Polypeptide SEQ ID NO (TABLE 3): |
|---|---|---|---|
| 1 | F2A | CAGCTGTTGAATTTTGACCTTCTTAAGCTTG<br>CGGGAGACGTCGAGTCCAACCCCGGGCCC | 19 |
| 2 | F2A(-I) | CTGTTGAATTTTGACCTTCTTAAGCTTGCGG<br>GAGACGTCGAGTCCAACCCCGGGCCC | 20 |
| 3 | F2A(-2) | TTGAATTTTGACCTTCTTAAGCTTGCGGGAG<br>ACGTCGAGTCCAACCCCGGGCCC | 21 |
| 4 | F2A(-3) | AATTTTGACCTTCTTAAGCTTGCGGGAGACG<br>TCGAGTCCAACCCCGGGCCC | 22 |
| 5 | F2A(-4) | TTTGACCTTCTTAAGCTTGCGGGAGAACGTC<br>GAGTCCAACCCCGGGCCC | 23 |
| 6 | F2A(-5) | GACCTTCTTAAGCTTGCGGGAGACGTCGAGT<br>CCAACCCCGGGCCC | 24 |
| 7 | F2A(-6) | CTTCTTAAGCTTGCGGGAGACGTCGAGTCCA<br>ACCCCGGGCCC | 25 |
| 8 | F2A(-7) | CTTAAGCTTGCGGGAGACGTCGAGTCCAACC<br>CCGGGCCC | 26 |
| 9 | F2A(3) | CAGCTGTTGAATTTTGACCTTCTTAAGCTTG<br>CGGGAGACGTCCAGTCCAACCCCGGGCCC | 27 |
| 10 | F2A(11) | CAGCTGTTGAATTTTGACCTTCTTAAGCTTG<br>CGGGAGACGTCGAGATTAACCCCGGGCCC | 28 |
| 11 | F2A(14) | CAGCTGTTGAATTTTGACCTTCTTAAGCTTG<br>CGGGAGACGTCGAGTCCGAGCCCGGGCCC | 29 |
| 12 | F2A(19) | CAGCTGTTGAATTTTGACCTTCTTAAGCTTG<br>CGGGAGACGTCGAGTCCAACCCCGCGCCC | 30 |
| 13 | I2A(0) | ACGAGGGCGGAGATTGAGGATGAATTGATTC<br>GTCGAGGAATTGAATCAAATCCTGGGCCC | 31 |
| 14 | I2A(I) | ACGAGGGCGGAGATTGAGGATGAATTGATTC<br>GTGCAGGAATTGAATCAAATCCTGGACCC | 32 |
| 15 | I2A(I) | ACGAGGGCGGAGATTGAGGATGAATTGATTC<br>GTCGAGGAATTGAATCAAATCCTGGACCC | 33 |

TABLE 2-continued 2A polynucleotide sequences

| SEQ ID NO: | 2A Polypeptide | Polypeptide sequence | Corresponding Polypeptide SEQ ID NO (TABLE 3): |
|---|---|---|---|
| 16 | I2A(3) | ACGAGGGCGGAGATTGAGGATGAATTGATTC GTCGAGGAATTGAATCAAATCCTGCGCCC | 34 |
| 17 | Furin-GSG-F2A | AGGGCAAAACGTTCGGGTTCGGGTGCGGCCA GTAAAGCAGACATTAAACTTTGATTTGTCGA AACTTGCAGGTGATGTAGAGTCAAATCCAGG TCCA | 35 |
| 18 | Furin-GSG-P2A | AGAGCCAAAAGAGGCTCCGGAGCCACTAACT TCTCCCTGTTGAAACAGGCTGGCGATGTTGA AGAAAACCCCGGTCCT | 36 |

TABLE 3

2A polypeptide sequences encoded by the 2A polynucleotide sequences of Table 2

| SEQ ID NO: | 2A Polypeptide | Mutation Type | Amino Acid Sequence |
|---|---|---|---|
| 19 | F2A | None | QLLNFDLLKLAGDVESNPGP |
| 20 | F2A(-I) | 1aa N-terminal deletion | LLNFDLLKLAGDVESNPGP |
| 21 | F2A(-2) | 2aa N-terminal deletion | LNFDLLKLAGDVESNPGP |
| 22 | F2A(-3) | 3 aa N-terminal deletion | NFDLLKLAGDVESNPGP |
| 23 | F2A(-4) | 4aa N-terminal deletion | FDLLKLAGDVESNPGP |
| 24 | F2A(-5) | 5 aa N-terminal deletion | DLLKLAGDVESNPGP |
| 25 | F2A(-6) | 6aa N-terminal deletion | LLKLAGDVESNPGP |
| 26 | F2A(-7) | 7aa N-terminal deletion | LKLAGDVESNPGP |
| 27 | F2A(3) | Point mutation | QLLNFDLLKLAGDVQSNPGP |
| 28 | F2A(11) | Point mutation | QLLNFDLLKLAGDVEINPGP |
| 29 | F2A(14) | Point mutation | QLLNFDLLKLAGDVESEPGP |
| 30 | F2A(19) | Point mutation | QLLNFDLLKLAGDVESNPAP |
| 31 | I2A(0) | Wild-type | TRAEIEDELIRRGIESNPGP |
| 32 | I2A(I) | Point mutation | TRAEIEDELIRAGIESNPGP |
| 33 | I2A(2) | Alternative codon | TRAEIEDELIRRGIESNPGP |
| 34 | I2A(3) | Point mutation | TRAEIEDELIRRGIESNPAP |
| 35 | Furin-GSG-F2A | RAKR = furin cleavage sequence; GSG = GlySerGly linker; APVK . . . NPGP = F2A sequence | RAKRSGSGAPVKQTLNFDLL KLAGDVESNPGP |
| 36 | Furin-GSG-P2A | RAKR = furin cleavage sequence; GSG = GlySerGly linker; ATNF . . . NPGP = P2A sequence | RAKRGSGATNFSLLKQAGDV EENPGP |

In some embodiments, the first and second nucleic acid can be separated by an internal ribosome entry site (IRES). In some embodiments, the first nucleic acid and second nucleic acid are part of different constructs. Optionally, the different constructs can both be administered to the same T cell, for example simultaneously, or separately.

Vectors

A number of vectors such as expression vectors are suitable for comprising nucleic acids encoding one or both chains of a DS-TCR in accordance with some embodiments herein.

Exemplary suitable vectors include, but are not limited to, lentiviral vectors, adenoviral vectors, adeno-associated viral (AAV) vectors, and/or retroviral vectors. A suitable vector can be selected depending on a number of factors, for example, the cell type to be genetically engineered, construct to be expressed, patient characteristics, disease indication. Optionally, the vector is further modified and/or optimized for a particular use or set of uses.

In some embodiments, the first nucleic acid and second nucleic acid are present on separate expression vectors. Each vector can comprise a promoter positioned to drive expression of the first or second nucleic acid. In some embodiments, the first nucleic acid and second nucleic acid are present on the same expression vector. The first and second nucleic acid can be under the control of separate promoters, for example a first promoter positioned to drive expression of the first nucleic acid, and a second promoter positioned to drive expression of the second nucleic acid. In some embodiments, the first nucleic acid and second nucleic acid are present on the same expression vector. Optionally, the two nucleic acids can flank a nucleotide sequence that can mediate separation and/or the separate expression of the polypeptides encoded by the two nucleic acids. As such, the expression of both nucleic acids can be driven by one promoter. In some embodiments, the nucleotide sequence that can mediate separation and/or the separate expression encodes a 2A peptide (e.g. a 2A polynucleotide sequence of Table 2 encoding a 2A peptide of Table 3). In some embodiments, the nucleotide sequence that can mediate separation and/or the separate expression encodes a protease target site such as a furin cleavage site. In some embodiments, the nucleotide sequence that can mediate separation and/or the separate expression encodes a 2A peptide with a protease target site furin cleavage site. In some embodiments, the nucleotide sequence encodes an internal ribosome entry site (IRES). In some embodiments, the nucleotide sequence encodes a protease target site.

Recombinant adeno-associated viruses (AAVs) are provided and may be capable of expressing one or more proteins of interest in an appropriate environment, for example, in a cell, a tissue, an organ, or a subject transfected with the recombinant AAVs. Also disclosed herein are the methods for making and using the recombinant AAVs. For example, the recombinant AAVs can be used to produce a protein of interest, for example one or more chains of a DS-TCR, in vivo, ex vivo, or in vitro. In some embodiments, the expression of the protein of interest can be used to diagnose, prevent, or treat one or more diseases or disorders, such as to reduce or inhibit the risk of viral infections.

In some embodiments, an AAV comprises a 5' inverted terminal repeat (ITR) of AAV and a 3' AAV ITR, a promoter, a restriction site downstream of the promoter to allow insertion of a polynucleotide encoding one or more chains of a DS-TCR, and a posttranscriptional regulatory element downstream of the restriction site, where the promoter, the restriction site and the posttranscription regulatory element are located downstream of the 5' AAV ITR and upstream of the 3' AAV ITR.

Various vectors encoding example DS-TCRs in accordance with some embodiments herein are shown in Table 4. In some embodiments, a vector comprises a vector backbone of any of the constructs shown in Table 4, and nucleic acids encoding a DS-TCR of interest (e.g. a DS-TCR in accordance with any one of Alternatives 1-32, Alternatives 1-4, Alternatives 1-16, Alternatives 5-16, Alternatives 1-22, Alternatives 17-22, Alternatives 17-32, or Alternatives 23-32). Various features of the constructs of Table 4 are noted in Tables 5-14.

TABLE 4

Example constructs encoding DS-TCRs

| ID | Description | SEQ ID NO: |
|---|---|---|
| pMTB1184 | pMX_2A OT1 TCR | 37 |
| pMTB1185 | pMX_2A OT1 TCR VCswapBAorientation | 38 |
| pMTB1186 | pMX_2A OT1 TCR VCswapABorientation | 39 |
| pMTB1281 | pCCLc_MND_F5TCR-Myc271 | 40 |
| pMTB1282 | pCCLc_MND_F5TCR VCswap(BA)-Myc271 | 41 |
| pMTB1283 | pCCLc_MND_F5TCR VCswap(AB)-Myc271 | 42 |
| pMTB1284 | pCCLc_MND_F5TCR VCcpswap(BA)-Myc271 | 43 |
| pMTB1285 | pCCLc_MND_F5TCR VCcpswap(AB)-Myc271 | 44 |
| pMTB1301 | pCCLc_MND_F5TCR_alpha_cpTMdelta_beta_cpTMgamma-Myc271 | 45 |
| pMTB1302 | pCCLc_MND_F5TCR_alpha_cpTMgamma_beta_cpTMdelta-Myc271 | 46 |

TABLE 5

Annotation of features in pMTB1184 (SEQ ID NO: 37)

| Feature | Location | Annotation |
|---|---|---|
| CDS | 844 . . . 1895 | GagPol\polyprotein |
| LTR | 7 . . . 599 | 5'\LTR |
| LTR | complement (3780 . . . 4372) | 3'\LTR |
| misc_feature | 1060 . . . 1069 | approx\packaging\signal |
| misc_feature | 2322 . . . 2693 | Mouse\TCR\Cbeta |
| misc_feature | 2694 . . . 2741 | Mouse\TCR\connecting\peptide\beta |
| misc_feature | 2742 . . . 2807 | Mouse\TCR\transmembrane\domain\beta |
| misc_feature | 2808 . . . 2834 | Mouse\TCR\cyto\beta |
| misc_feature | 2835 . . . 2903 | GlySer\linked\2A\sequence |
| misc_feature | 3321 . . . 3587 | Mouse\TCR\Calpha |
| misc_feature | 3588 . . . 3647 | Mouse\TCR\connecting\peptide\alpha |
| misc_feature | 3648 . . . 3713 | Mouse\TCR\transmembrane\domain\alpha |
| misc_feature | 3714 . . . 3728 | Mouse\TCR\cyto\alpha |
| misc_feature | 3729 . . . 3731 | STOP |
| misc_feature | 3749 . . . 3784 | PPT |
| misc_feature | 524 . . . 598 | aprox\U5 |
| primer_bind | 601 . . . 618 | PBS |
| repeat_region | 456 . . . 523 | aprox\R |
| sig_peptide | 1896 . . . 1982 | Leader\sequence\2 |
| sig_peptide | 2904 . . . 2987 | Leader\sequence\1 |
| V_region | 1983 . . . 2321 | OTI\Vbeta |
| V_segment | 2967 . . . 3320 | OTI\Valpha |

TABLE 6

Annotation of features in pMTB1185 (SEQ ID NO: 38)

| Feature | Location | Annotation |
|---|---|---|
| LTR | complement (3780 . . . 4372) | 3'\LTR |
| LTR | 7 . . . 599 | 5'\LTR |
| primer_bind | 601 . . . 618 | PBS |
| misc_feature | 3749 . . . 3784 | PPT |
| misc_feature | 1060 . . . 1069 | approx\packaging\signal |
| misc_feature | 524 . . . 598 | aprox\U5 |

TABLE 6-continued

Annotation of features in pMTB1185 (SEQ ID NO: 38)

| Feature | Location | Annotation |
|---|---|---|
| repeat_region | 456 . . . 523 | aprox\R |
| CDS | 844 . . . 1895 | GagPol\polyprotein |
| misc_feature | 3729 . . . 3731 | STOP |
| misc_feature | 2835 . . . 2903 | GlySer\linked\2A\sequence |
| sig_peptide | 2904 . . . 2987 | Leader\sequence\1 |
| V_segment | 2967 . . . 3320 | OTI\Valpha |
| misc_feature | 3321 . . . 3587 | Mouse\TCR\Calpha |
| V_region | 1983 . . . 2321 | OTI\Vbeta |
| misc_feature | 2322 . . . 2693 | Mouse\TCR\Cbeta |
| sig_peptide | 1896 . . . 1982 | Leader\sequence\2 |
| misc_feature | 3588 . . . 3635 | Mouse\TCR\connecting\peptide\beta |
| misc_feature | 3636 . . . 3701 | Mouse\TCR\transmembrane\domain\beta |
| misc_feature | 3702 . . . 3728 | Mouse\TCR\cyto\beta |
| misc_feature | 2694 . . . 2753 | Mouse\TCR\connecting\peptide\alpha |
| misc_feature | 2754 . . . 2819 | Mouse\TCR\transmembrane\domain\alpha |
| misc_feature | 2820 . . . 2834 | Mouse\TCR\cyto\alpha |

TABLE 7

Annotation of features in pMTB1186 (SEQ ID NO: 39)

| Feature | Location | Annotation |
|---|---|---|
| LTR | complement (3780 . . . 4372) | 3'\LTR |
| LTR | 7 . . . 599 | 5'\LTR |
| primer_bind | 601 . . . 618 | PBS |
| misc_feature | 3749 . . . 3784 | PPT |
| misc_feature | 1060 . . . 1069 | approx\packaging\signal |
| misc_feature | 524 . . . 598 | aprox\U5 |
| repeat_region | 456 . . . 523 | aprox\R |
| CDS | 844 . . . 1895 | GagPol\polyprotein |
| misc_feature | 3729 . . . 3731 | STOP |
| misc_feature | 2721 . . . 2789 | GlySer\linked\2A\sequence |
| misc_feature | 3588 . . . 3647 | Mouse\TCR\connecting\peptide\alpha |
| misc_feature | 3648 . . . 3713 | Mouse\TCR\transmembrane\domain\alpha |
| misc_feature | 3714 . . . 3728 | Mouse\TCR\cyto\alpha |
| misc_feature | 2580 . . . 2627 | Mouse\TCR\connecting\peptide\beta |
| misc_feature | 2628 . . . 2693 | Mouse\TCR\transmembrane\domain\beta |
| misc_feature | 2694 . . . 2720 | Mouse\TCR\cyto\beta |
| V_region | 2877 . . . 3215 | OTI\Vbeta |
| misc_feature | 3216 . . . 3587 | Mouse\TCR\Cbeta |
| sig_peptide | 2790 . . . 2876 | Leader\sequence\2 |
| sig_peptide | 1896 . . . 1979 | Leader\sequence\1 |
| V_segment | 1959 . . . 2312 | OTI\Valpha |
| misc_feature | 2313 . . . 2579 | Mouse\TCR\Calpha |

TABLE 8

Annotation of features in pMTB1281 (SEQ ID NO: 40)

| Feature | Location | Annotation |
|---|---|---|
| misc_feature | 4469 . . . 4648 | cPPT |
| misc_feature | 3725 . . . 3924 | RRE |
| misc_feature | 4660 . . . 5194 | MNDU3 |
| misc_feature | 3123 . . . 3260 | Psi |
| misc_feature | 7661 . . . 7713 | U3 |
| misc_feature | 2987 . . . 3070 | U5 |
| misc_feature | 7810 . . . 7893 | U5(1) |
| misc_feature | 2891 . . . 2986 | R |
| misc_feature | 7714 . . . 7809 | R(1) |
| misc_feature | 2362 . . . 2890 | CMV |
| primer_bind | 2175 . . . 2194 | T3 |
| misc_feature | 6066 . . . 6161 | F2Aopt |
| misc_feature | 5925 . . . 5984 | Alpha\connecting\peptide |
| misc_feature | 5790 . . . 5819 | Pep3a |

TABLE 8-continued

Annotation of features in pMTB1281 (SEQ ID NO: 40)

| Feature | Location | Annotation |
|---|---|---|
| CDS | 5646 . . . 6065 | TCR-Alpha-Constant |
| primer_bind | complement (8323 . . . 8340) | M13-fwd |
| sig_peptide | 6162 . . . 6239 | HGH\SS\2 |
| misc_feature | 5985 . . . 6050 | Alpha\Transmembrane\Domain |
| misc_feature | 5877 . . . 5912 | Pep4a |
| CDS | 6576 . . . 7100 | TCR-Beta\Constant |
| primer_bind | 2137 . . . 2157 | M13-rev |
| sig_peptide | 5232 . . . 5309 | HGH\SS |
| misc_feature | 6051 . . . 6065 | Alpha\Cytoplasmic\tail |
| misc_feature | 6876 . . . 6917 | Pep1b |
| primer_bind | complement (8294 . . . 8314) | T7 |
| mutation | 6941 . . . 6941 | G->A |
| misc_feature | 6515 . . . 6526 | N\region\addition |
| misc_feature | 6876 . . . 6917 | FG-Loop |
| rep_origin | 1087 . . . 1769 | ColE1\origin |
| V_region | 5310 . . . 5588 | TRAV12-2*01 |
| misc_feature | 6960 . . . 7007 | Beta\connecting\peptide |
| rep_origin | 8501 . . . 8807 | F1\ori |
| J_segment | 5592 . . . 5645 | TRAJ23*01 |
| misc_feature | 7008 . . . 7073 | Beta\Transmembrane\Domain |
| rep_origin | 8484 . . . 8939 | M13\origin |
| V_region | 6240 . . . 6514 | TRBV6-4*01 |
| misc_feature | 7074 . . . 7100 | Beta\Cytoplasmic\tail |
| CDS | 8411 . . . 8479 | LacZ\alpha |
| J_segment | 6527 . . . 6575 | TRBJ1-1*01 |
| misc_feature | 6240 . . . 6575 | F5\TCR\Vb |
| misc_binding | 2109 . . . 2131 | LacO |
| misc_feature | 5589 . . . 5594 | N\region\addition(1) |
| misc_feature | 5646 . . . 5675 | Pep1a |
| misc_feature | 6576 . . . 6959 | F5\TCR\Cb |
| CDS | 330 . . . 989 | AmpR |
| misc_feature | 5310 . . . 5645 | F5\TCR\Va |
| misc_feature | 5727 . . . 5768 | Pep2a |
| misc_feature | 5646 . . . 5924 | F5\TCR\Ca |
| misc_feature | 7551 . . . 7553 | STOP |
| misc_feature | 7113 . . . 7121 | GSG\linker |
| misc_feature | 7122 . . . 7178 | P2A |
| CDS | 7179 . . . 7550 | delta\LNGFR(CD271)_tm-cMyc |
| misc_feature | 7266 . . . 7295 | cMyc\tag |
| misc_feature | 7179 . . . 7265 | Signal\sequence\for\CD271 |
| misc_feature | 7101 . . . 7112 | Furin\cleavage\sequence |

TABLE 9

Annotation of features in pMTB1282 (SEQ ID NO: 41)

| Feature | Location | Annotation |
|---|---|---|
| misc_feature | 4469 . . . 4648 | cPPT |
| misc_feature | 3725 . . . 3924 | RRE |
| misc_feature | 4660 . . . 5194 | MNDU3 |
| misc_feature | 3123 . . . 3260 | Psi |
| misc_feature | 7661 . . . 7713 | U3 |
| misc_feature | 2987 . . . 3070 | U5 |
| misc_feature | 7810 . . . 7893 | U5(1) |
| misc_feature | 2891 . . . 2986 | R |
| misc_feature | 7714 . . . 7809 | R(1) |
| misc_feature | 2362 . . . 2890 | CMV |
| primer_bind | 2175 . . . 2194 | T3 |
| primer_bind | complement (8323 . . . 8340) | M13-fwd |
| primer_bind | 2137 . . . 2157 | M13-rev |
| primer_bind | complement (8294 . . . 8314) | T7 |
| rep_origin | 1087 . . . 1769 | ColE1\origin |
| rep_origin | 8501 . . . 8807 | F1\ori |
| rep_origin | 8484 . . . 8939 | M13\origin |
| CDS | 8411 . . . 8479 | LacZ\alpha |
| misc_binding | 2109 . . . 2131 | LacO |
| CDS | 330 . . . 989 | AmpR |
| misc_feature | 7551 . . . 7553 | STOP |

TABLE 9-continued

| Annotation of features in pMTB1282 (SEQ ID NO: 41) | | |
|---|---|---|
| Feature | Location | Annotation |
| misc__feature | 7113 . . . 7121 | GSG\linker |
| misc__feature | 7122 . . . 7178 | P2A |
| CDS | 7179 . . . 7550 | delta\LNGFR(CD271)__tm-cMyc |
| misc__feature | 7266 . . . 7295 | cMyc\tag |
| misc__feature | 7179 . . . 7265 | Signal\sequence\for\CD271 |
| misc__feature | 7101 . . . 7112 | Furin\cleavage\sequence |
| misc__feature | 6171 . . . 6266 | F2Aopt |
| sig__peptide | 6267 . . . 6344 | HGH\SS\2 |
| sig__peptide | 5232 . . . 5309 | HGH\SS |
| misc__feature | 6030 . . . 6089 | Alpha\connecting\peptide |
| misc__feature | 6090 . . . 6155 | Alpha\Transmembrane\Domain |
| misc__feature | 6156 . . . 6170 | Alpha\Cytoplasmic\tail |
| misc__feature | 6960 . . . 7007 | Beta\connecting\peptide |
| misc__feature | 7008 . . . 7073 | Beta\Transmembrane\Domain |
| misc__feature | 7074 . . . 7100 | Beta\Cytoplasmic\tail |
| V__region | 6345 . . . 6623 | TRAV12-2*01 |
| J__segment | 6627 . . . 6680 | TRAJ23*01 |
| misc__feature | 6624 . . . 6629 | N\region\addition |
| misc__feature | 6345 . . . 6680 | F5\TCR\Va |
| V__region | 5310 . . . 5584 | TRBV6-4*01 |
| J__segment | 5597 . . . 5645 | TRBJ1-1*01 |
| misc__feature | 5585 . . . 5596 | N\region\addition |
| misc__feature | 5310 . . . 5645 | F5\TCR\Vb |
| misc__feature | 6681 . . . 6959 | F5\TCR\Ca |
| mutation | 6011 . . . 6011 | G->A |
| misc__feature | 5646 . . . 6029 | F5\TCR\Cb |

TABLE 10

| Annotation of features in pMTB1283 (SEQ ID NO: 42) | | |
|---|---|---|
| Feature | Location | Annotation |
| misc__feature | 4469 . . . 4648 | cPPT |
| misc__feature | 3725 . . . 3924 | RRE |
| misc__feature | 4660 . . . 5194 | MNDU3 |
| misc__feature | 3123 . . . 3260 | Psi |
| misc__feature | 7661 . . . 7713 | U3 |
| misc__feature | 2987 . . . 3070 | U5 |
| misc__feature | 7810 . . . 7893 | U5(1) |
| misc__feature | 2891 . . . 2986 | R |
| misc__feature | 7714 . . . 7809 | label = R(1) |
| misc__feature | 2362 . . . 2890 | CMV |
| primer__bind | 2175 . . . 2194 | T3 |
| primer__bind | complement (8323 . . . 8340) | M13-fwd |
| primer__bind | 2137 . . . 2157 | M13-rev |
| primer__bind | complement (8294 . . . 8314) | T7 |
| rep__origin | 1087 . . . 1769 | ColE1\origin |
| rep__origin | 8501 . . . 8807 | F1\ori |
| rep__origin | 8484 . . . 8939 | M13\origin |
| CDS | 8411 . . . 8479 | LacZ\alpha |
| misc__binding | 2109 . . . 2131 | LacO |
| CDS | 330 . . . 989 | AmpR |
| misc__feature | 7551 . . . 7553 | STOP |
| misc__feature | 7113 . . . 7121 | GSG\linker |
| misc__feature | 7122 . . . 7178 | P2A |
| CDS | 7179 . . . 7550 | delta\LNGFR(CD271)__tm-cMyc |
| misc__feature | 7266 . . . 7295 | cMyc\tag |
| misc__feature | 7179 . . . 7265 | Signal\sequence\for\CD271 |
| misc__feature | 7101 . . . 7112 | Furin\cleavage\sequence |
| misc__feature | 6066 . . . 6161 | F2Aopt |
| sig__peptide | 6162 . . . 6239 | HGH\SS\2 |
| sig__peptide | 5232 . . . 5309 | HGH\SS |
| misc__feature | 6960 . . . 7019 | Alpha\connecting\peptide |
| misc__feature | 7020 . . . 7085 | Alpha\Transmembrane\Domain |
| misc__feature | 7086 . . . 7100 | Alpha\Cytoplasmic\tail |
| V__region | 6240 . . . 6514 | TRBV6-4*01 |
| J__segment | 6527 . . . 6575 | TRBJ1-1*01 |
| misc__feature | 6515 . . . 6526 | N\region\addition |
| misc__feature | 6240 . . . 6575 | F5\TCR\Vb |
| misc__feature | 6576 . . . 6959 | F5\TCR\Cb |

TABLE 10-continued

| Annotation of features in pMTB1283 (SEQ ID NO: 42) | | |
|---|---|---|
| Feature | Location | Annotation |
| misc__feature | 5925 . . . 5972 | Beta\connecting\peptide |
| misc__feature | 5973 . . . 6038 | Beta\Transmembrane\Domain |
| misc__feature | 6039 . . . 6065 | Beta\Cytoplasmic\tail |
| V__region | 5310 . . . 5588 | TRAV12-2*01 |
| J__segment | 5592 . . . 5645 | TRAJ23*01 |
| misc__feature | 5589 . . . 5594 | N\region\addition |
| misc__feature | 5310 . . . 5645 | F5\TCR\Va |
| misc__feature | 5646 . . . 5924 | F5\TCR\Ca |

TABLE 11

| Annotation of features in pMTB1284 (SEQ ID NO: 43) | | |
|---|---|---|
| Feature | Location | Annotation |
| misc__feature | 4469 . . . 4648 | cPPT |
| misc__feature | 3725 . . . 3924 | RRE |
| misc__feature | 4660 . . . 5194 | MNDU3 |
| misc__feature | 3123 . . . 3260 | Psi |
| misc__feature | 7661 . . . 7713 | U3 |
| misc__feature | 2987 . . . 3070 | U5 |
| misc__feature | 7810 . . . 7893 | U5(1) |
| misc__feature | 2891 . . . 2986 | R |
| misc__feature | 7714 . . . 7809 | R(1) |
| misc__feature | 2362 . . . 2890 | CMV |
| primer__bind | 2175 . . . 2194 | T3 |
| primer__bind | complement (8323 . . . 8340) | M13-fwd |
| primer__bind | 2137 . . . 2157 | M13-rev |
| primer__bind | complement (8294 . . . 8314) | T7 |
| rep__origin | 1087 . . . 1769 | ColE1\origin |
| rep__origin | 8501 . . . 8807 | F1\ori |
| rep__origin | 8484 . . . 8939 | M13\origin |
| CDS | 8411 . . . 8479 | LacZ\alpha |
| misc__binding | 2109 . . . 2131 | LacO |
| CDS | 330 . . . 989 | AmpR |
| misc__feature | 7551 . . . 7553 | STOP |
| misc__feature | 7113 . . . 7121 | GSG\linker |
| misc__feature | 7122 . . . 7178 | P2A |
| CDS | 7179 . . . 7550 | delta\LNGFR(CD271)__tm-cMyc |
| misc__feature | 7266 . . . 7295 | cMyc\tag |
| misc__feature | 7179 . . . 7265 | Signal\sequence\for\CD271 |
| misc__feature | 7101 . . . 7112 | Furin\cleavage\sequence |
| misc__feature | 6162 . . . 6257 | F2Aopt |
| sig__peptide | 6258 . . . 6335 | HGH\SS\2 |
| sig__peptide | 5232 . . . 5309 | HGH\SS |
| misc__feature | 6078 . . . 6146 | Alpha\Transmembrane\Domain\(a1\joint) |
| misc__feature | 6147 . . . 6161 | Alpha\Cytoplasmic\tail |
| misc__feature | 7008 . . . 7073 | Beta\Transmembrane\Domain\(b4\joint) |
| misc__feature | 7074 . . . 7100 | Beta\Cytoplasmic\tail |
| V__region | 6336 . . . 6614 | TRAV12-2*01 |
| J__segment | 6618 . . . 6671 | TRAJ23*01 |
| misc__feature | 6615 . . . 6620 | N\region\addition |
| misc__feature | 6336 . . . 6671 | F5\TCR\Va |
| V__region | 5310 . . . 5584 | TRBV6-4*01 |
| J__segment | 5597 . . . 5645 | TRBJ1-1*01 |
| misc__feature | 5585 . . . 5596 | N\region\addition |
| misc__feature | 5310 . . . 5645 | F5\TCR\Vb |
| misc__feature | 6672 . . . 6950 | F5\TCR\Ca |
| mutation | 6011 . . . 6011 | G->A |
| misc__feature | 5646 . . . 6029 | F5\TCR\Cb |
| misc__feature | 6951 . . . 7007 | Alpha\connecting\peptide\(a1\joint) |
| misc__feature | 6030 . . . 6077 | Beta\connecting\peptide\(b4\joint) |

TABLE 12

| Annotation of features in pMTB1285 (SEQ ID NO: 44) | | |
|---|---|---|
| Feature | Location | Annotation |
| misc__feature | 4469 . . . 4648 | cPPT |
| misc__feature | 3725 . . . 3924 | RRE |
| misc__feature | 4660 . . . 5194 | MNDU3 |
| misc__feature | 3123 . . . 3260 | Psi |
| misc__feature | 7661 . . . 7713 | U3 |
| misc__feature | 2987 . . . 3070 | U5 |
| misc__feature | 7810 . . . 7893 | U5(1) |
| misc__feature | 2891 . . . 2986 | R |
| misc__feature | 7714 . . . 7809 | R(1) |
| misc__feature | 2362 . . . 2890 | CMV |
| primer__bind | 2175 . . . 2194 | T3 |
| primer__bind | complement (8323 . . . 8340) | M13-fwd |
| primer__bind | 2137 . . . 2157 | M13-rev |
| primer__bind | complement (8294 . . . 8314) | T7 |
| rep__origin | 1087 . . . 1769 | ColE1\origin |
| rep__origin | 8501 . . . 8807 | F1\ori |
| rep__origin | 8484 . . . 8939 | M13\origin |
| CDS | 8411 . . . 8479 | LacZ\alpha |
| misc__binding | 2109 . . . 2131 | LacO |
| CDS | 330 . . . 989 | AmpR |
| misc__feature | 7551 . . . 7553 | STOP |
| misc__feature | 7113 . . . 7121 | GSG\linker |
| misc__feature | 7122 . . . 7178 | P2A |
| CDS | 7179 . . . 7550 | delta\LNGFR(CD271)__tm-cMyc |
| misc__feature | 7266 . . . 7295 | cMyc\tag |
| misc__feature | 7179 . . . 7265 | Signal\sequence\for\CD271 |
| misc__feature | 7101 . . . 7112 | Furin\cleavage\sequence |
| misc__feature | 6075 . . . 6170 | F2Aopt |
| misc__feature | 7017 . . . 7085 | Alpha\Transmembrane\Domain\(a1\joint) |
| misc__feature | 7086 . . . 7100 | Alpha\Cytoplasmic\tail |
| V__region | 6249 . . . 6523 | TRBV6-4*01 |
| J__segment | 6536 . . . 6584 | TRBJ1-1*01 |
| misc__feature | 6524 . . . 6535 | N\region\addition |
| misc__feature | 6249 . . . 6584 | F5\TCR\Vb |
| mutation | 6950 . . . 6950 | G->A |
| misc__feature | 6585 . . . 6968 | F5\TCR\Cb |
| misc__feature | 6969 . . . 7016 | Beta\connecting\peptide\(b4\joint) |
| misc__feature | 5982 . . . 6047 | Beta\Transmembrane\Domain\(b4\joint) |
| misc__feature | 6048 . . . 6074 | Beta\Cytoplasmic\tail |
| V__region | 5310 . . . 5588 | TRAV12-2*01 |
| J__segment | 5592 . . . 5645 | TRAJ23*01 |
| misc__feature | 5589 . . . 5594 | N\region\addition |
| misc__feature | 5310 . . . 5645 | F5\TCR\Va |
| misc__feature | 5646 . . . 5924 | F5\TCR\Ca |
| misc__feature | 5925 . . . 5981 | Alpha\connecting\peptide\(a1\joint) |
| sig__peptide | 6171 . . . 6248 | HGH\SS\2 |
| sig__peptide | 5232 . . . 5309 | HGH\SS |

TABLE 13

| Annotation of features in pMTB1301 (SEQ ID NO: 45) | | |
|---|---|---|
| Feature | Location | Annotation |
| misc__feature | 4469 . . . 4648 | cPPT |
| misc__feature | 3725 . . . 3924 | RRE |
| misc__feature | 4660 . . . 5194 | MNDU3 |
| misc__feature | 3123 . . . 3260 | Psi |
| misc__feature | 7751 . . . 7803 | U3 |
| misc__feature | 2987 . . . 3070 | U5 |
| misc__feature | 7900 . . . 7983 | U5(1) |
| misc__feature | 2891 . . . 2986 | R |
| misc__feature | 7804 . . . 7899 | R(1) |
| misc__feature | 2362 . . . 2890 | CMV |
| primer__bind | 2175 . . . 2194 | T3 |
| primer__bind | complement (8413 . . . 8430) | M13-fwd |
| primer__bind | 2137 . . . 2157 | M13-rev |

TABLE 13-continued

| Annotation of features in pMTB1301 (SEQ ID NO: 45) | | |
|---|---|---|
| Feature | Location | Annotation |
| primer__bind | complement (8384 . . . 8404) | T7 |
| rep__origin | 1087 . . . 1769 | ColE1\origin |
| rep__origin | 8591 . . . 8897 | F1\ori |
| rep__origin | 8574 . . . 9029 | M13\origin |
| CDS | 8501 . . . 8569 | LacZ\alpha |
| misc__binding | 2109 . . . 2131 | LacO |
| CDS | 330 . . . 989 | AmpR |
| misc__feature | 7641 . . . 7643 | STOP |
| misc__feature | 7203 . . . 7211 | GSG\linker |
| misc__feature | 7212 . . . 7268 | P2A |
| CDS | 7269 . . . 7640 | delta\LNGFR(CD271)__tm-cMyc |
| misc__feature | 7356 . . . 7385 | cMyc\tag |
| misc__feature | 7269 . . . 7355 | Signal\sequence\for\CD271 |
| misc__feature | 7191 . . . 7202 | Furin\cleavage\sequence |
| misc__feature | 6117 . . . 6212 | F2Aopt |
| sig__peptide | 6213 . . . 6290 | HGH\SS\2 |
| sig__peptide | 5232 . . . 5309 | HGH\SS |
| mutation | 6992 . . . 6992 | G->A |
| V__region | 5310 . . . 5588 | TRAV12-2*01 |
| J__segment | 5592 . . . 5645 | TRAJ23*01 |
| V__region | 6291 . . . 6565 | TRBV6-4*01 |
| J__segment | 6578 . . . 6623 | TRBJ1-1*01 |
| misc__feature | 5589 . . . 5594 | N\region\addition |
| misc__feature | 5310 . . . 5645 | F5\TCR\Va |
| misc__feature | 6102 . . . 6116 | Alpha\Cytoplasmic\tail |
| misc__feature | 6566 . . . 6577 | N\region\addition |
| misc__feature | 7164 . . . 7190 | Beta\Cytoplasmic\tail |
| misc__feature | 6291 . . . 6626 | F5\TCR\Vb |
| misc__feature | 5646 . . . 5924 | F5\TCR\Ca |
| misc__feature | 6627 . . . 7010 | F5\TCR\Cb |
| misc__feature | 5925 . . . 6035 | Delta\connecting\peptide |
| misc__feature | 7011 . . . 7100 | GammaC1a\connecting\peptide |
| misc__feature | 6036 . . . 6101 | Delta\transmembrane\domain |
| misc__feature | 7101 . . . 7163 | GammaC1a\transmembrane\domain |

TABLE 14

| Annotation of features in pMTB1302 (SEQ ID NO: 46) | | |
|---|---|---|
| Feature | Location | Annotation |
| misc__feature | 4469 . . . 4648 | cPPT |
| misc__feature | 3725 . . . 3924 | RRE |
| misc__feature | 4660 . . . 5194 | MNDU3 |
| misc__feature | 3123 . . . 3260 | Psi |
| misc__feature | 7751 . . . 7803 | U3 |
| misc__feature | 2987 . . . 3070 | U5 |
| misc__feature | 7900 . . . 7983 | U5(1) |
| misc__feature | 2891 . . . 2986 | R |
| misc__feature | 7804 . . . 7899 | R(1) |
| misc__feature | 2362 . . . 2890 | CMV |
| primer__bind | 2175 . . . 2194 | T3 |
| primer__bind | complement (8413 . . . 8430) | M13-fwd |
| primer__bind | 2137 . . . 2157 | M13-rev |
| primer__bind | complement (8384 . . . 8404) | T7 |
| rep__origin | 1087 . . . 1769 | ColE1\origin |
| rep__origin | 8591 . . . 8897 | F1\ori |
| rep__origin | 8574 . . . 9029 | M13\origin |
| CDS | 8501 . . . 8569 | LacZ\alpha |
| misc__binding | 2109 . . . 2131 | LacO |
| CDS | 330 . . . 989 | AmpR |
| misc__feature | 7641 . . . 7643 | STOP |
| misc__feature | 7203 . . . 7211 | GSG\linker |
| misc__feature | 7212 . . . 7268 | P2A |
| CDS | 7269 . . . 7640 | delta\LNGFR(CD271)__tm-cMyc |
| misc__feature | 7356 . . . 7385 | cMyc\tag |
| misc__feature | 7269 . . . 7355 | Signal\sequence\for\CD271 |
| misc__feature | 7191 . . . 7202 | Furin\cleavage\sequence |
| misc__feature | 6093 . . . 6188 | F2Aopt |
| sig__peptide | 6189 . . . 6266 | HGH\SS\2 |

TABLE 14-continued

| Annotation of features in pMTB1302 (SEQ ID NO: 46) | | |
|---|---|---|
| Feature | Location | Annotation |
| sig_peptide | 5232 . . . 5309 | HGH\SS |
| CDS | 6603 . . . 7190 | TCR-Beta\Constant |
| mutation | 6968 . . . 6968 | G->A |
| CDS | 5646 . . . 6092 | TCR-Alpha-Constant |
| V_region | 5310 . . . 5588 | TRAV12-2*01 |
| J_segment | 5592 . . . 5645 | TRAJ23*01 |
| V_region | 6267 . . . 6541 | TRBV6-4*01 |
| J_segment | 6554 . . . 6602 | TRBJ1-1*01 |
| misc_feature | 5589 . . . 5594 | N\region\addition |
| misc_feature | 5310 . . . 5645 | F5\TCR\Va |
| misc_feature | 6078 . . . 6092 | Alpha\Cytoplasmic\tail |
| misc_feature | 6542 . . . 6553 | N\region\addition |
| misc_feature | 7164 . . . 7190 | Beta\Cytoplasmic\tail |
| misc_feature | 6267 . . . 6602 | F5\TCR\Vb |
| misc_feature | 5925 . . . 6014 | GammaC1a\connecting\peptide |
| misc_feature | 6987 . . . 7097 | Delta\connecting\peptide |
| misc_feature | 6015 . . . 6077 | GammaC1a\transmembrane\domain |
| misc_feature | 7098 . . . 7163 | Delta\transmembrane\domain |

Promoters

A number of promoters are suitable for driving expression of the first and/or second nucleic acid in accordance with some embodiments herein. The promoter can be naturally-occurring or non-naturally occurring. Examples of promoters, include, but are not limited to, viral promoters, plant promoters and mammalian promoters. In some embodiments, the promoter drives expression in a particular cell type or combination of cell types. In some embodiments, the promoter drives expression in a particular cell lineage, for example a T cell lineage. In some embodiments, the promoter drives expression in a particular tissue type or combination of tissue types. In some embodiments, the promoter is inducible. In some embodiments, the promoter is inducible via a hormone, drug, small molecule, or stimulus, such as heat or electromagnetic radiation.

Examples of viral promoters include, but are not limited to cytomegalovirus (CMV) immediate early promoter, CAG promoter (which is a combination of the CMV early enhancer element and chicken beta-actin promoter, described in Alexopoulou et al. BMC Cell Biology 9:2, (2008)), simian virus 40 (SV40) promoter, the 35S RNA and 19S RNA promoters of cauliflower mosaic virus (CaMV) described in Brisson et al., Nature 1984, 310:511-514, the coat protein promoter to tobacco mosaic virus (TMV), and any variants thereof. Examples of plant promoters include, but are not limited to, heat shock promoters, such as soybean hsp17.5-E or hsp17.3-B described in Gurley et al., Mol. Cell. Biol. 1986, 6:559-565, and any variants thereof. Examples of mammalian promoters include, but are not limited to, human elongation factor 1alpha-subunit (EF1-1alpha) promoter, human ubiquitin C (UCB) promoter, murine phosphoglycerate kinase-1 (PGK) promoter, and any variants thereof.

In some embodiments, a cell-type specific promoter can be used (e.g., CD4 vs CD8 vs Treg), depending on the type of cell to be genetically engineered. In some embodiments, a promiscuous promoter can be used.

Markers

In some embodiments, a vector provided herein includes a gene for a selectable marker that is effective in a eukaryotic cell. This selectable marker gene can encode a factor necessary for the survival or growth of a T cell contacted with the vector in a selective culture medium. T cells not contacted with the vector containing the selectable marker will not survive in the selective culture medium. Typical selectable marker genes encode proteins that confer resistance to an antibiotic or toxin (e.g., neomycin, methotrexate, gentamycin, zeocin) or complement auxotrophic deficiencies.

T Cells

In some embodiments, the DS-TCR is expressed in a CD4 T cell. In some embodiments, the DS-TCR is expressed in a CD8 T cell. In some embodiments, the DS-TCR is expressed in a Treg T cell. In some embodiments the DS-TCR is expressed in two or more types of T cell, for example CD4 and CD8, CD4 and Treg, CD8 and Treg, or CD4 and CD8 and Treg. In some embodiments, the DS-TCR is expressed in a T cell of a cell line, for example Jurkat T cells. In some embodiments, the DS-TCR is expressed in an autologous T cell of a subject. In some embodiments, the DS-TCR is expressed in an allogeneic T cell of a donor who is different from the subject.

Methods of Making T Cells Expressing DS-TCRs

In accordance with some embodiments herein, methods of making T cells expressing DS-TCRs are provided. T cells can be isolated from a subject or a donor. Optionally, T cells can be provided from a cell line. T cells can be genetically engineered to express a DS-TCR. T cells can be genetically modified using any of a number of approaches known to the skilled artisan. The T cells can be contacted with/transfected with an expression vector or collection of expression vectors encoding a DS-TCR as described herein. In some embodiments, two expression vectors, one vector encoding a first chain of a DS-TCR and one vector encoding a second chain of a DS-TCR, are contacted with the isolated T cells. In some embodiments, the expression vector carries both the first and second nucleic acids and therefore only one expression vector is contacted with the isolated T cells. The vectors express DS-TCR in accordance with any of the DS-TCR configurations described herein (Table 1).

Optionally, following contact with a single vector or two vectors, a T cell is placed in a selective culture medium. In some embodiments, the vector comprises a selectable marker gene which encodes a protein that confers resistance to an antibiotic or toxin present in the selective culture medium. Optionally, the selectable marker gene encodes a protein that complements an auxotrophic deficiency and enables the T cell to survive in a selective culture medium. Optionally, a selection step can be performed wherein T cells contacted with/transfected with a DS-TCR expression vector are sorted by flow cytometry to select for T cells that express the DS-TCR and separate them from the T cells that do not express the DS-TCR. Optionally, sorting by flow cytometry is used to select for T cells expressing relatively high levels of DS-TCR. Optionally, the expression of endogenous TCR is knocked down or eliminated in the transfected T cell. Optionally, the effect of knockdown or elimination of endogenous TCR is measured, for example, by determining messenger RNA levels and/or polypeptide levels of endogenous TCR. Suitable approaches for preparing nucleic acid expression vectors and transforming mammalian cells such as T cells are described in Green and Sambrook, *Molecular Cloning: A Laboratory Manual* (Fourth ed., Cold Spring Harbor Laboratory Press, Cold Spring Harbor, N.Y. 2012), which is hereby incorporated by reference in its entirety.

In some embodiments, the expression of an endogenous TCR is repressed or eliminated prior to sorting by flow cytometry of DS-TCR-expressing T cell and prior to administering a DS-TCR-expressing T cell to a subject. In some embodiments the method of repressing or eliminating an endogenous TCR comprises RNA interference (RNAi), using siRNA or antisense RNA, blocking translation using miRNA, or generating a TCR knockout by gene deletion using homologous recombination, zinc finger nucleases, CRISPR, or TALEN.

Optionally, the genetically modified T cells are subsequently used, for example, to induce an immune response in a subject with a cancer or an infectious disease. Optionally, genetically modified T cells are preserved for later use, for example cryogenically preserved. For example, allogeneic T cells may be preserved in a bank for later use is a suitable subject.

In some embodiments, the genetically modified T cell comprises a first nucleic acid encoding the first domain swap chain and a second nucleic acid encoding the second domain swap chain of any of the DS-TCRs of any of Alternatives 1-32. In some embodiments, the first nucleic acid and the second nucleic acid encode the first domain swap chain and the second domain swap chain of any of a DS-TCR of any of Alternatives 1-4. In some embodiments, the first nucleic acid and the second nucleic acid encode the first domain swap chain and the second domain swap chain of any of Alternatives 5-16. In some embodiments, the first nucleic acid and the second nucleic acid encode the first domain swap chain and the second domain swap chain of any of Alternatives 1-16. In some embodiments, the first nucleic acid and the second nucleic acid encode the first domain swap chain and the second domain swap chain of any of Alternatives 17-22. In some embodiments, the first nucleic acid and the second nucleic acid encode the first domain swap chain and the second domain swap chain of any of Alternatives 1-22. In some embodiments, the first nucleic acid and the second nucleic acid encode the first domain swap chain and the second domain swap chain of any of Alternatives 23-32.

In some embodiments, a CD4 T cell comprises any of the DS-TCR configurations of Alternatives 1-4. In some embodiments, a CD4 T cell comprises any of the DS-TCR configurations of Alternatives 5-16. In some embodiments, a CD4 T cell comprises any of the DS-TCR configurations of Alternatives 17-22. Optionally, the CD4 T cell comprises nucleic acid encoding the DS-TCR, for example a first nucleic acid encoding the first chain of the DS-TCR, and a second nucleic acid encoding the second chain. Optionally, the nucleic acids can be integrated into the genome of the CD4 T cell. Optionally, the nucleic acids can be on a stably-replicated extragenomic construct of the CD4 T cell.

In some embodiments, a CD8 T cell comprises any of the DS-TCR configurations of Alternatives 1-4. In some embodiments, a CD8 T cell comprises any of the DS-TCR configurations of Alternatives 5-16. In some embodiments, a CD8 T cell comprises any of the DS-TCR configurations of Alternatives 17-22. Optionally, the CD8 T cell comprises nucleic acid encoding the DS-TCR, for example a first nucleic acid encoding the first chain of the DS-TCR, and a second nucleic acid encoding the second chain. Optionally, the nucleic acids can be integrated into the genome of the CD8 T cell. Optionally, the nucleic acids can be on a stably-replicated extragenomic construct of the CD8 T cell.

In some embodiments, a Treg T cell comprises any of the DS-TCR configurations of Alternatives 1-4. In some embodiments, a Treg T cell comprises any of the DS-TCR configurations of Alternatives 5-16. In some embodiments, a Treg T cell comprises any of the DS-TCR configurations of Alternatives 17-22. Optionally, the Treg T cell comprises nucleic acid encoding the DS-TCR, for example a first nucleic acid encoding the first chain of the DS-TCR, and a second nucleic acid encoding the second chain. Optionally, the nucleic acids can be integrated into the genome of the Treg T cell. Optionally, the nucleic acids can be on a stably-replicated extragenomic construct of the Treg T cell.

Methods of Inducing an Immune Response

In accordance with some embodiments herein, methods of inducing an immune response in a subject in need thereof are provided. A T cell comprising nucleic acids encoding any of the DS-TCR configurations discussed herein, for example, any of Alternatives 1-4, 5-16, 17-22, and/or 23-32 can be administered to the subject. Optionally, the T cell expresses any of the DS-TCR configurations described herein, for example, any of Alternatives 1-4, 5-16, 17-22, and/or 23-32. Optionally, the T cell encodes any of the DS-TCR configurations described herein, for example, any of Alternatives 1-4, 5-16, 17-22, and/or 23-32, and can be subsequently induced to express them.

The DS-TCR expressing T cell can be administered to a subject. Optionally, the subject is in need of inducing an immune response. For example, the subject can be either susceptible to or have a tumor or cancer, infectious disease, parasitic disease or autoimmune disease. The subject is in need of a preventive treatment, prophylactic treatment, or therapeutic treatment.

In some embodiments, the T cell is isolated and administered to the same subject such that the administered DS-TCR-expressing T cell is autologous. In some embodiments, the T cell is isolated from one subject and administered to a different subject such that the administered DS-TCR-expressing T cell is allogeneic.

It has been observed that co-administration of two or more types of T cells can induce a more robust immune response than administration of a single type of T cell. As such, in some embodiments, two or more populations of different types of T cells, each encoding a DS-TCR are administered to the subject, for example, two, three, four, five, six, seven, eight, nine, or ten, different populations of T cell, each encoding a DS-TCR. In some embodiments, a first genetically engineered CD4 T cell encoding a DS-TCR is co-administered with a second genetically engineered CD8 T cell encoding a DS-TCR. In some embodiments, a first genetically engineered CD4 T cell encoding a DS-TCR is co-administered with a second genetically engineered Treg cell encoding a DS-TCR. In some embodiments, a first genetically engineered CD8 T cell encoding a DS-TCR is co-administered with a second genetically engineered Treg T cell encoding a DS-TCR. In some embodiments, a first genetically engineered T cell encoding a DS-TCR is co-administered with a second T cell encoding an endogenous TCR. Optionally, two or more of the populations of co-administered T cells are administered simultaneously. Optionally, two or more of the populations of co-administered T cells are administered at different times.

Without being limited by any theory, it is contemplated that co-administration of the two genetically engineered T cells can boost the immune response.

In some embodiments, the T cells are isolated once, configured to express DS-TCR and administered in a single administration. A therapeutically effective amount can be administered.

In some embodiments, the T cells are isolated once, configured to express DS-TCR and administered in multiple administrations. For example, the T cells can be isolated multiple times and administered in multiple administrations. The DS-TCR expressing T cell can be a CD4, CD8, or regulatory T cell. Optionally, at least 2 administrations are performed, for example 2, 3, 4, 5, 6, 7, 8, 9, 10, 15, 20, 30, 40, or 50, including ranges between any two of the listed values.

In some embodiments a vector encoding a DS-TCR is administered directly to a subject. The vector can provide nucleic acids encoding the chains of a DS-TCR to a T cell in the subject, so as to provide a DS-TCR in vivo.

The effective amount T cells administered in accordance with some embodiments herein can depend on a variety of factors, for example characteristics of the subject, the type of disease state being treated, characteristics of the DS-TCR, activity levels of the DS-TCR-expressing T cell, and/or the level of immune response desired. Optionally, the amount of T cells administered is determined by the skilled artisan. In some embodiments, at least about 10 DS-TCR-expressing T cells are administered to the subject, for example, at least about 10, $10^2$, $10^3$, $10^4$, $10^5$, $10^6$, $10^7$, $10^8$, $10^9$, or $10^{10}$ T cells, including ranges between any two of the listed values.

In some embodiments, the DS-TCR-expressing T cell is administered via intramuscular injection, intravaginal injection, intravenous injection, intraperitoneal injection, subcutaneous injection, epicutaneous administration, intradermal administration, or nasal administration.

In some embodiments, The DS-TCR is generated against a multitude of antigens (e.g., two or more tumor antigens).

In some embodiments, the subject is monitored for the induction of immune responses by the administered DS-TCR-expressing T cells against the clinical condition for which the therapeutic DS-TCR-expressing T cells are administered. Optionally, the administered DS-TCR-expressing T cell is monitored by determining levels over time, rate of attrition, surface expression of DS-TCR, cytokine secretion. Optionally, the condition of the subject is monitored over time for remission of tumor or cancer, clearance or suppression of an infectious disease agent, alleviation of an autoimmune condition, or the lack of development of a tumor or cancer, the prevention of infection by an infectious agent or the prevention of development of autoimmune symptoms.

Inducing an immune response can be useful for a clinical intervention made in response to a disease, disorder or physiological condition manifested by a patient or to which a patient may be susceptible. The aim of treatment can include, but is not limited to, the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Subjects in need of treatment include those already affected by a disease or disorder or undesired physiological condition as well as those in which the disease or disorder or undesired physiological condition is to be prevented.

Additional Embodiments

Given that the TCR is typically the sole determinant of T cell specificity, transfer into a T cell of genes encoding the two polypeptide chains of a TCR that is specific for a particular antigen (e.g., a tumor antigen) can redirect the T cell to target that tumor antigen. Upon adoptive transfer into patients such engineered T cells have been shown to mediate potent anti-tumor cytotoxicity without the significant bystander toxicity observed with anti-tumor chemotherapy (Park et al., Trends Biotechnol. 29: 550-557 (2011)). This therapeutic approach, termed TCR gene therapy, can be useful for treatment of cancers, for example, blood cancers (Johnson et al., Blood 114: 535-546 (2009)), and has demonstrated up to a 30% objective response rate in clinical trials targeting melanoma (Morgan et al., Science 314: 126-129 (2006)).

However, in conventional T cell therapy, there is a potential for the introduced TCR polypeptide chains to mispair with the endogenous chains. For example, the introduced alpha chain can mispair with the endogenous beta chain and, reciprocally, the introduced beta chain can mispair with the endogenous alpha chain. Mispairing between TCR chains reduces the level of correctly paired, tumor-reactive TCR heterodimers expressed on the T cell surface, a key determinant of therapeutic efficacy (Jorritsma, A. et al., Blood 110: 3564-3572 (2007)). Moreover, mispairing can give rise to self-reactive TCR heterodimers that mediate autoimmunity (van Loenen et al., Proc. Natl. Acad. Sci. 107: 10972-10977 (2010)). Indeed, TCR chain mispairing causes a lethal graft-versus-host disease in up to 90% of mice when a protocol closely mimicking human clinical trials is followed (Bendle et al., Nat. Med. 16: 565-570 (2010)).

It can also be useful for modifications to be restricted to the invariant TCR domains, such that they can be generalized to any TCR of therapeutic interest without further optimization. It is noted that DS-TCR's in accordance with some embodiments herein involve modification to invariant TCR domains, while providing a platform that can be generalized to a plurality of TCR's of interest.

It is contemplated that DS-TCRs in accordance with some embodiments herein will improve the safety and efficacy of TCR gene therapies under clinical investigation for a broad array of cancers as well as pathogens. As the approach can be readily extended to any TCR of interest, it is contemplated that DS-TCR's in accordance with some embodiments herein can have broad application to human health and commercial potential.

Example 1

Figure 2A:
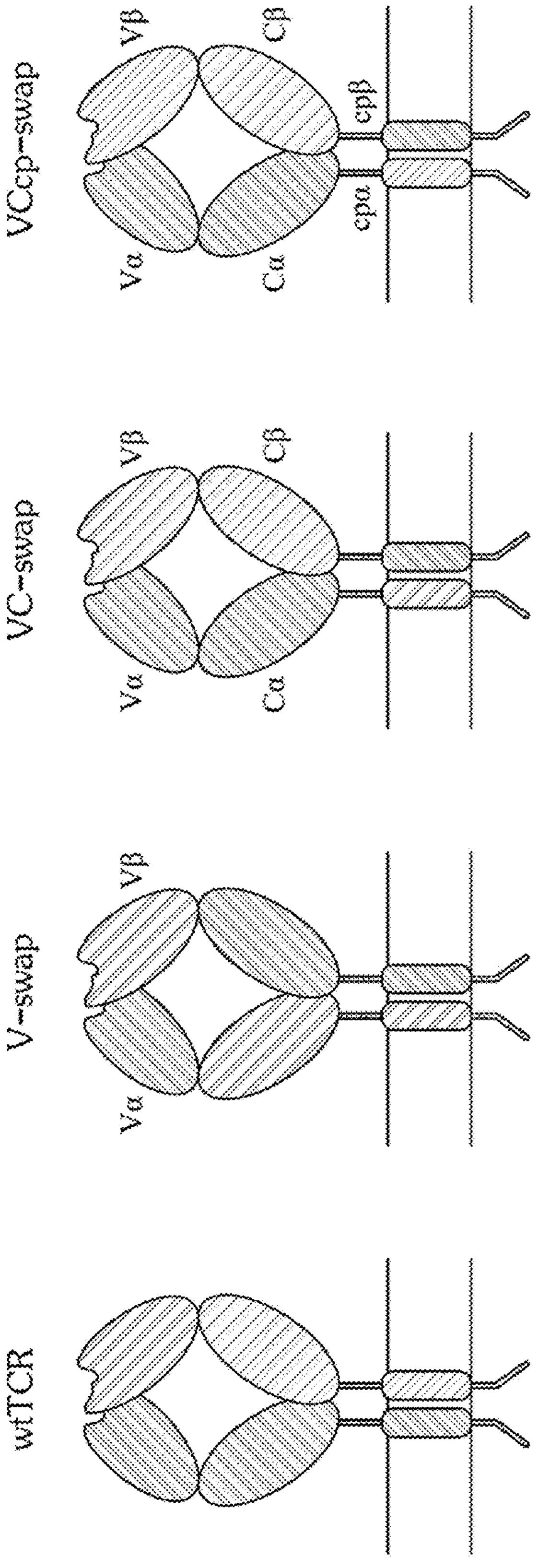
FIG. 2A is a schematic diagram showing an endogenous TCR and three different DS-TCR configurations comprising either a variable domain swap configuration, or a variable domain and constant domain swap configuration, or a variable domain, constant domain and connecting peptide swap configuration in accordance with some embodiments herein. To achieve the three domain swap configurations, domain swap was performed on both the alpha chain and the beta chain of the TCR.
Figure 2B:
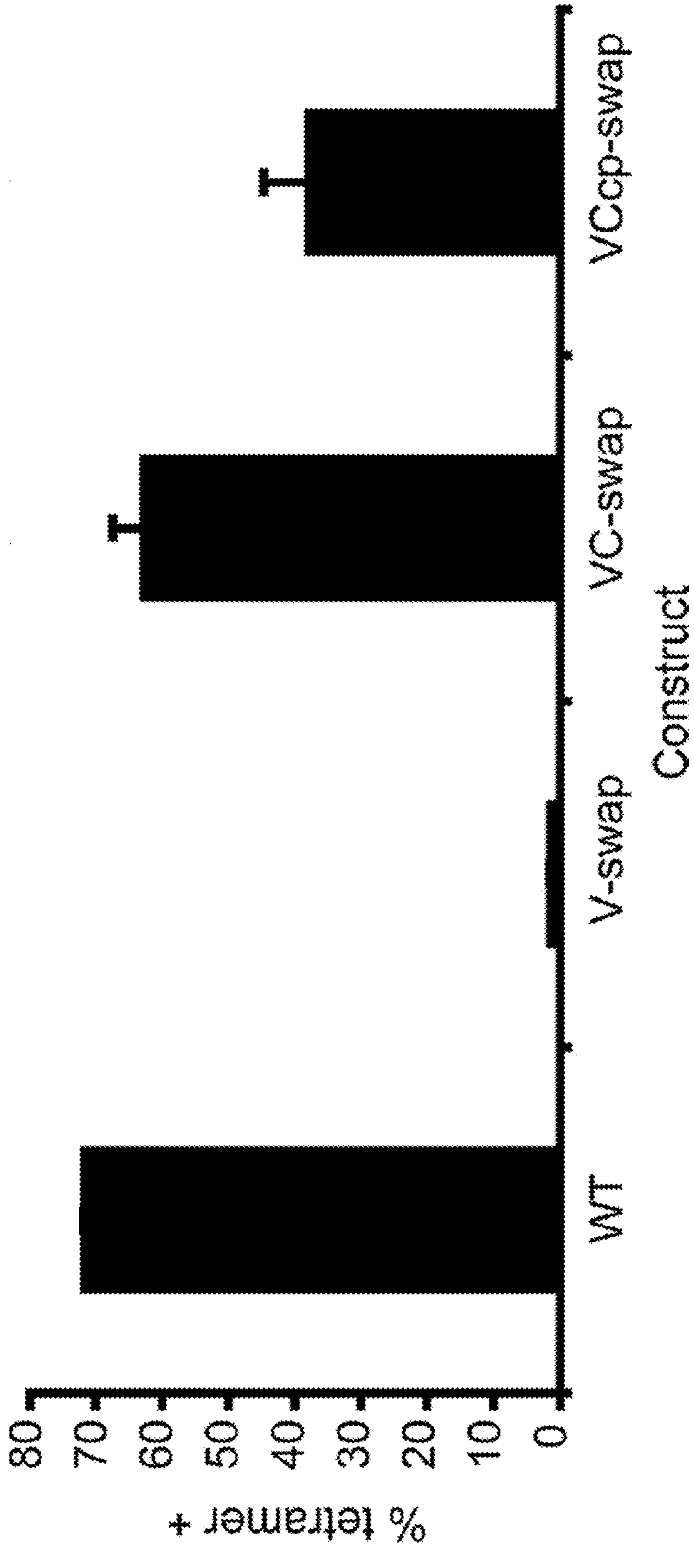
FIG. 2B is a graph showing expression of WT and various DS-TCR configurations of FIG. 2A on the surface of CD3+ 293T cells as determined by binding of a cognate peptide-WIC tetramer in accordance with some embodiments herein. Plot shows mean+/−standard deviation (std. dev.) from triplicate measurements in one representative experiment of at least three independent experiments.

To prevent mispairing between the first and second chains of the TCR, the invariant domains between the TCR first and second chains were swapped in a complementary manner. Guided by the crystal structure of human TCR comprising an alpha chain and a beta chain, three DS-TCRs were designed in which the alpha and beta sequences were swapped at various inter-domain junctions as illustrated in FIG. 2A. It is noted that some embodiments herein, for example the DCS-TCR of Alternatives 1-3 correspond to the DS-TCRs that were constructed. Correctly paired DS-TCRs retain all domains necessary to recruit CD3 and express on the cell surface, whereas mispaired TCRs comprising one DS-TCR chain and one endogenous (WT) TCR chain did not recruit CD3, and are apparently degraded. Vectors encoding either the indicated DS-TCRs or endogenous WT TCR (human F5 TCR15) were contacted with/transfected into CD3+ 293T cells, and surface expression of the TCR was assessed by flow cytometry by staining with a fluorescent cognate peptide-MHC tetramer. Expression of TCR from vector encoding Alternative 23 (schematically diagrammed as: first chain: $V_{alpha}$-$C_{beta}$-$CP_{beta}$-$TM_{beta}$-$CT_{beta}$; second chain: $V_{beta}$-$C_{alpha}$-$CP_{alpha}$-$TM_{alpha}$-$CT_{alpha}$) (Table 1) was not detectable on the cell surface, but expression of TCR from vectors encoding Alternative 1 (schematically diagrammed as: first chain: $V_{alpha}$-$C_{alpha}$-$CP_{beta}$-$TM_{beta}$-$CT_{beta}$; second chain: $V_{beta}$-$C_{beta}$-$CP_{alpha}$-$TM_{alpha}$-$CT_{alpha}$) (Table 1) and Alternative 2 (schematically diagrammed as: first chain: $V_{alpha}$-$C_{alpha}$-$CP_{alpha}$-$TM_{beta}$-$CT_{beta}$; second chain: $V_{beta}$-$C_{beta}$-$CP_{beta}$-$TM_{alpha}$-$CT_{alpha}$) (Table 1) was comparable to expression of TCR from vector encoding WT TCR (FIG. 2B). Thus, in accordance with some of the embodiments described herein, correctly paired DS-TCRs are expressed on the T cell surface.

Example 2

Figure 2C:
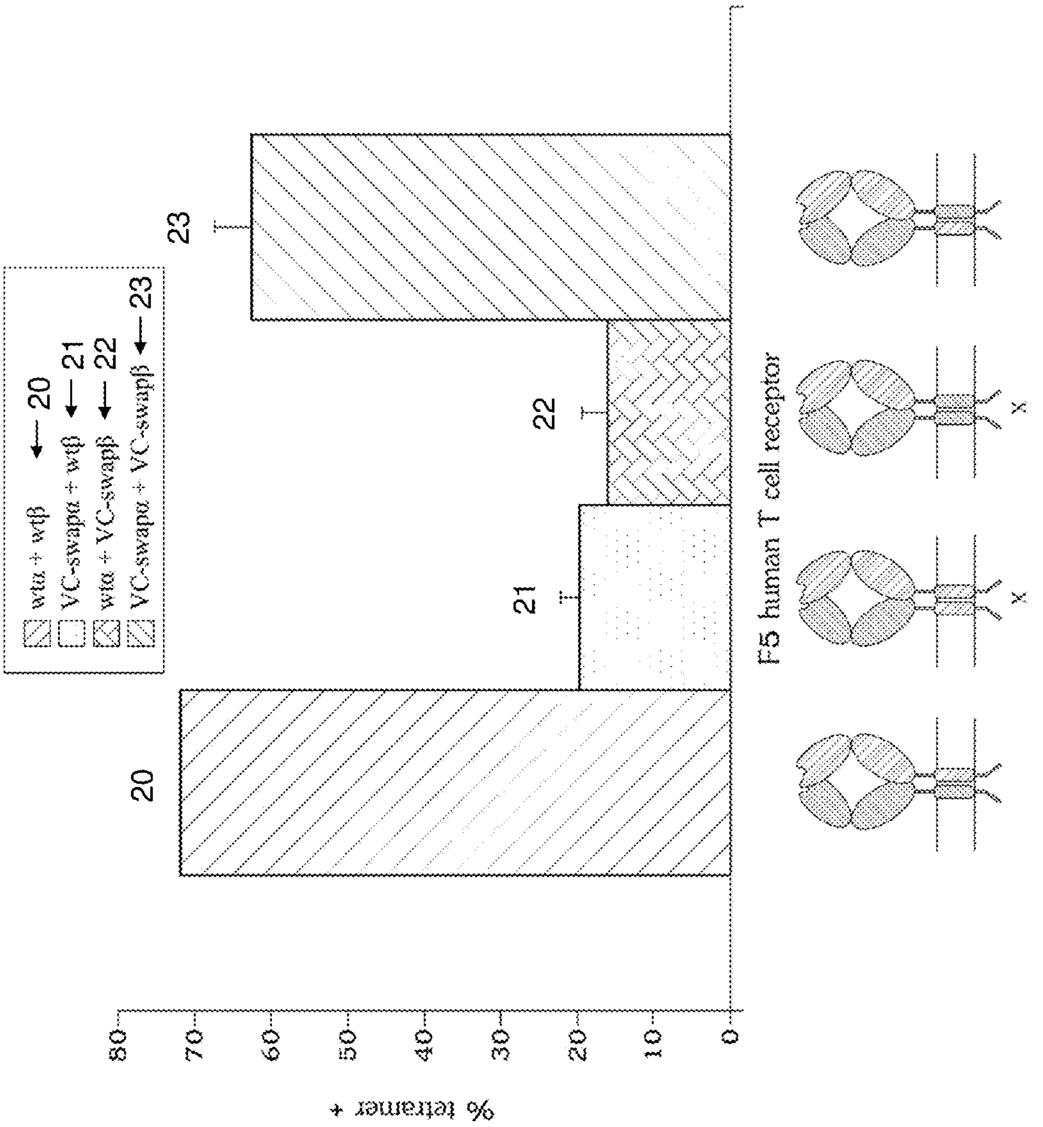

To simulate mispairing with WT TCR chains, expression constructs were made in which only the alpha or beta chain was domain-swapped, but not both. These constructs were then tested for surface expression in CD3+ 293T by flow cytometry as described in Example 1. Compared to fully WT or DS-TCRs, surface expression of mispaired TCRs was significantly reduced (FIG. 2C). This significantly reduced expression was not due to lower transfection efficiency. Thus, preliminary results with some of the embodiments described herein suggest that domain-swapping significantly mitigates mispairing. It is contemplated in accordance with some embodiments herein that the residual level of mispaired TCR expression observed on the surface could be due to very high, non-physiological levels of expression of TCR and CD3 chains in light of the observation that some TCR is exported to the surface even when one CD3 chain is omitted. Without being limited by any theory, it is further contemplated that domain swap TCRs in accordance with some of the embodiments herein can to prevent mispairing through at least three mechanisms: 1) DS-TCR chains will mispair with WT TCR chains inefficiently due to juxtaposition of non-pairing domains (i.e. neither alpha nor beta self-associate); 2) Mispaired TCRs will lack domains necessary to recruit CD3 and will be degraded; and 3) Mispaired TCR complexes that express on the surface without recruiting CD3 will have impaired signaling capacity. Thus, in accordance with some embodiments herein, significantly higher expression levels of DS-TCRs were achieved as compared to TCRs with mispaired chains (FIG. 2C).

Example 3

Figure 3A:
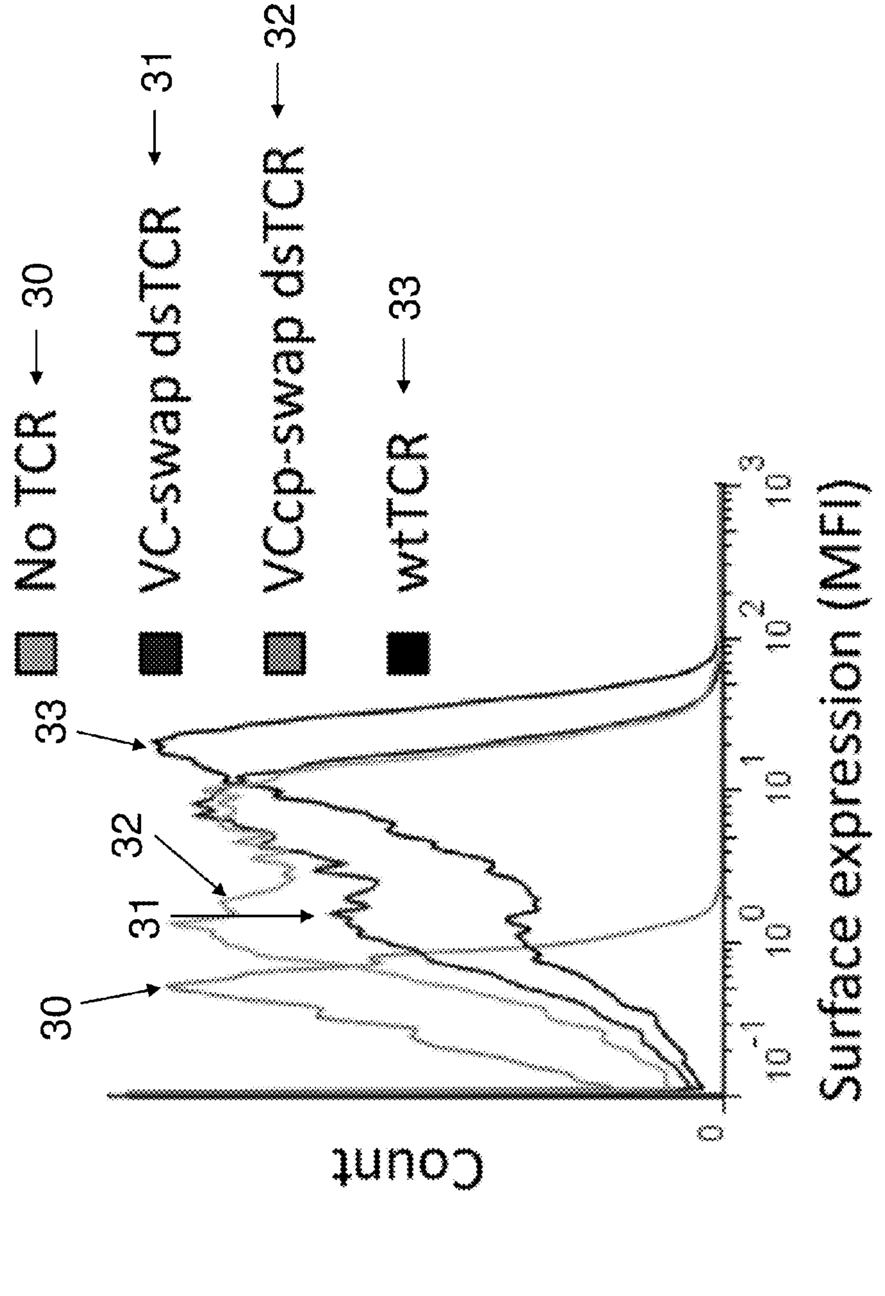
FIG. 3A is a graph comparing the intensity of expression of WT TCR and two domain swap TCR configurations on the surface of Jurkat T cells in accordance with some embodiments herein. The TCR configurations shown comprise variable domain and constant domain swap configuration, and variable domain, constant domain and connecting peptide domain swap configuration as detected by binding of a cognate peptide-WIC tetramer.

To determine whether DS-TCRs are expressed on the surface of T cells, we produced retroviral vectors encoding the DS-TCR and used these to infect Jurkat T cells, again using flow cytometry to assess surface expression. At levels similar to the parental WT TCR, DS-TCRs compete for endogenous CD3, express on the cell surface, and retain specificity for cognate peptide-WIC ligand (FIG. 3A).

Example 4

Figure 3B:
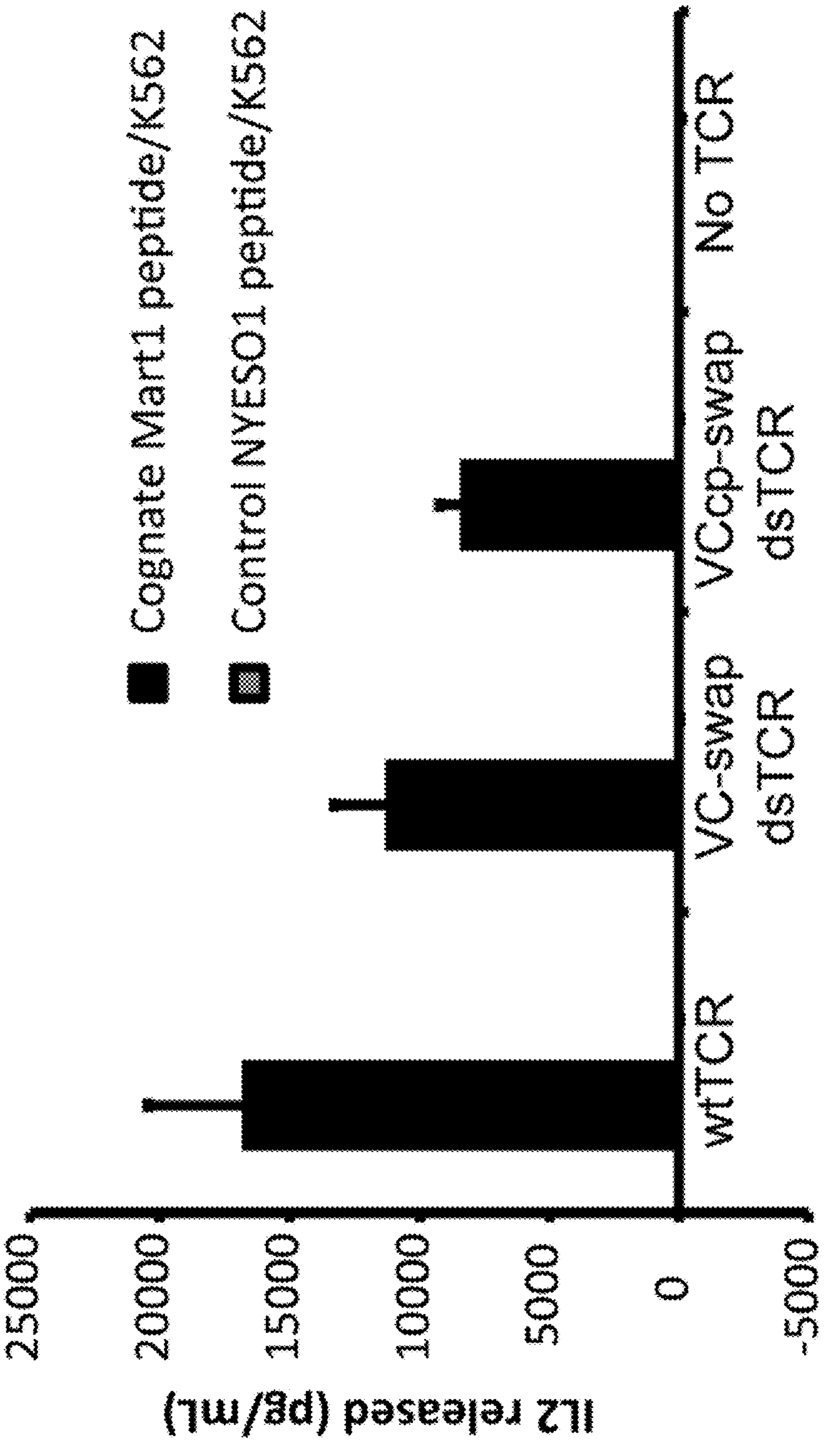
FIG. 3B is a graph comparing the amount of the cytokine IL-2 produced by Jurkat T cells expressing various TCR configurations in accordance with some embodiments herein. Plot shows mean+/−std. dev. from triplicate measurements in one representative experiment of at least three independent experiments.

To determine whether DS-TCRs are functional, DS-TCR-transduced Jurkat cells were coincubated with K562 cells that express cognate peptide-WIC. After two days, supernatant was collected and tested by ELISA for IL-2 secretion as an indicator of antigen-specific activation. DS-TCR-transduced Jurkat cells produced IL-2 in an antigen-specific, WIC-restricted manner, indicating these constructs are indeed functional (FIG. 3B).

Example 5

Figure 3C:
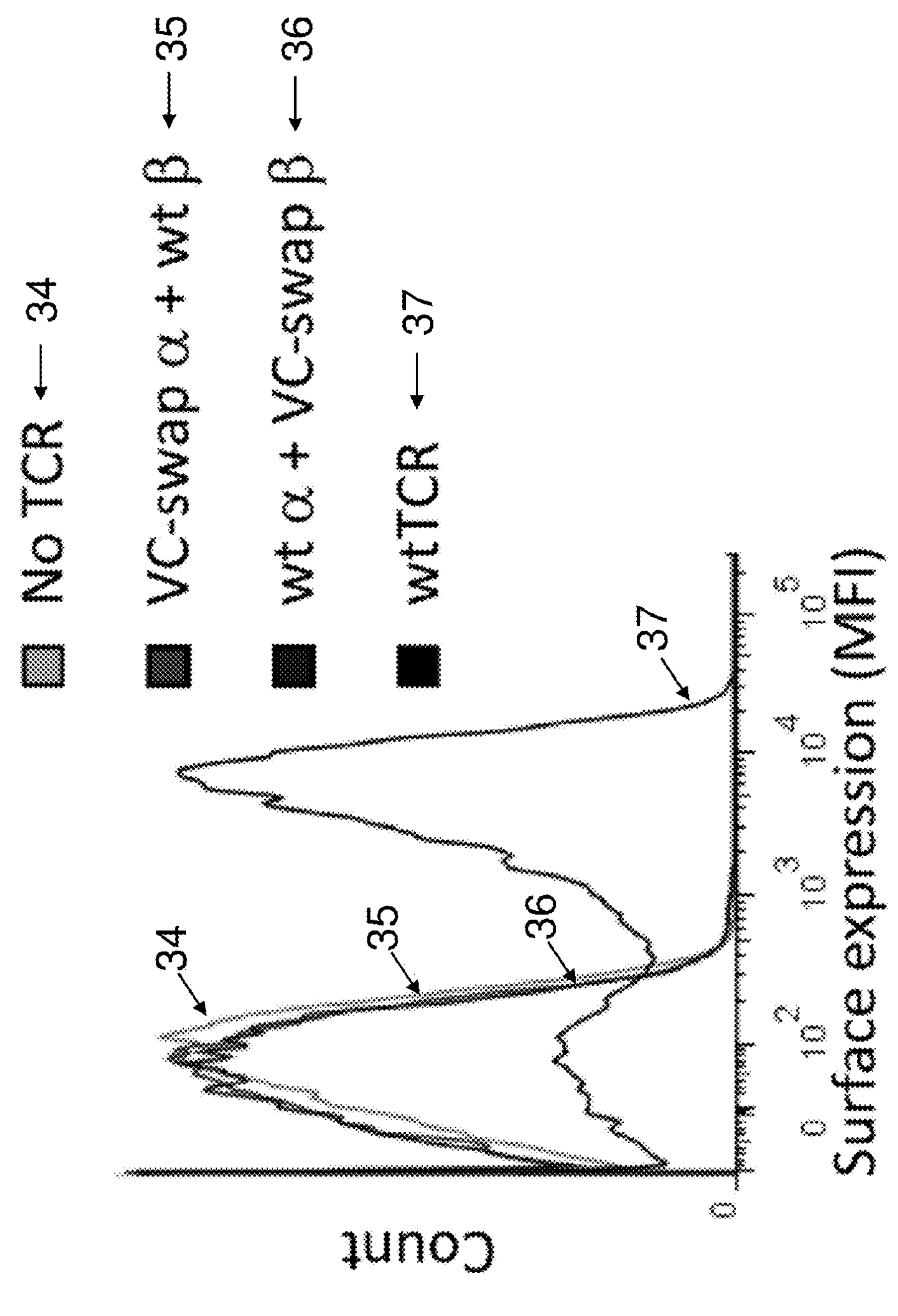
FIG. 3C is a graph showing lack of expression of mispaired TCR configurations in contrast to WT TCR configuration on the surface of Jurkat T cells as determined by binding of a cognate peptide-WIC tetramer. Similar to FIG. 2C, the mispaired TCRs in this schematic herein result from domain swap performed on either the alpha chain or the beta chain but not both in accordance with some embodiments.

In contrast to Example 2, mispaired constructs comprising one DS-TCR chain and one WT TCR chain were not detectable on the surface of transduced Jurkats and did not produce IL-2 when stimulated (FIG. 3C and data not shown). Together these results demonstrate the feasibility of domain swapping: DS-TCR alpha and beta chains pair together to form antigen-specific, functional heterodimers but do not mispair with WT TCR chains.

Example 6

Figure 4A:
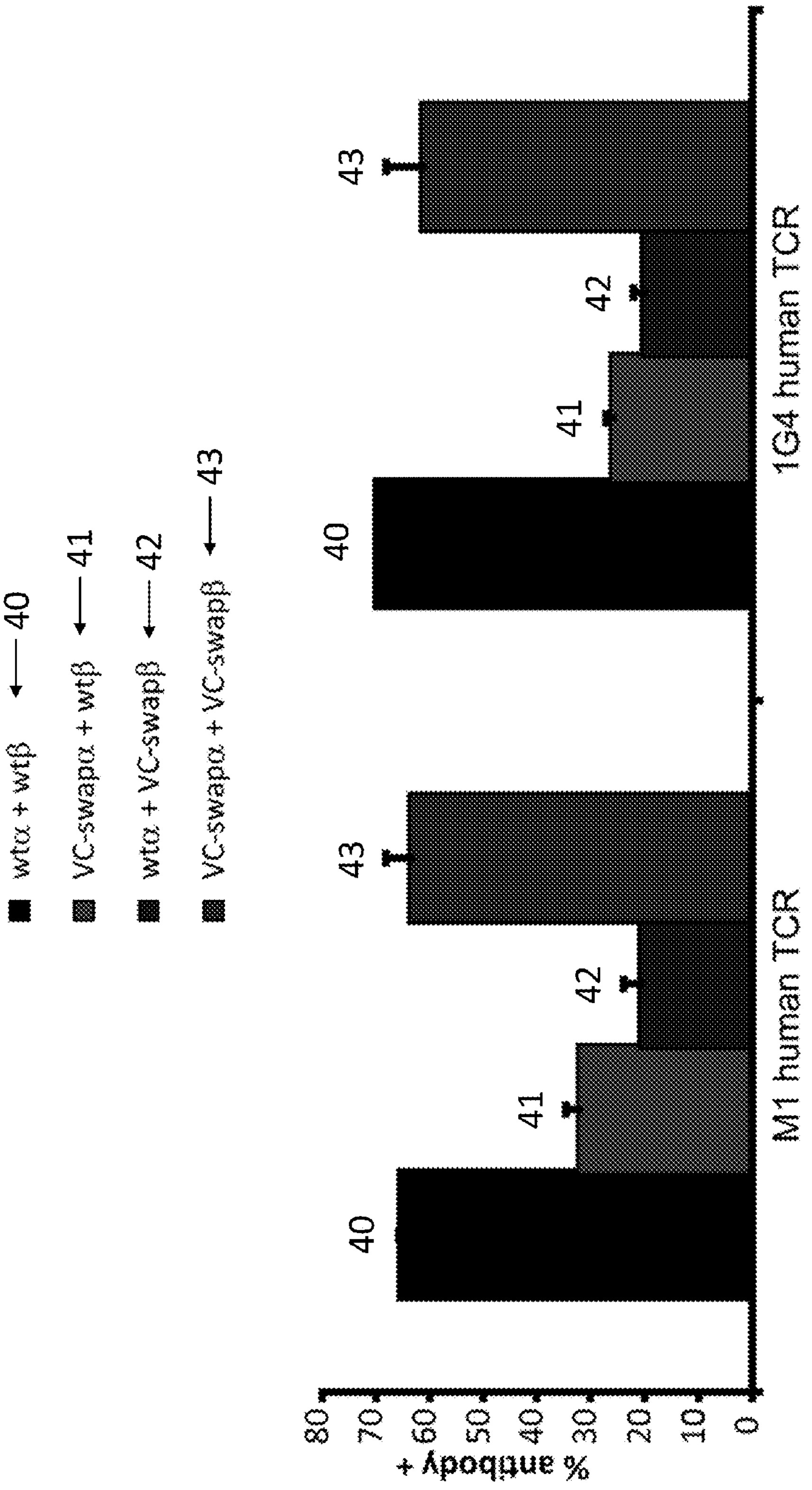
FIG. 4A is a graph showing expression on the surface of CD3+ 293T cells as determined by binding of a cognate peptide-WIC tetramer of TCR configurations in accordance with some embodiments herein. Data are shown for domain swap configurations of two human TCRs in addition to those of FIG. 2C, namely, M1 human TCR and 1G4 human TCR as determined by binding of the cognate peptide-WIC tetramer for each TCR. Plot shows mean+/−std. dev. from triplicate measurements in one representative experiment of at least three independent experiments.
Figure 4B:
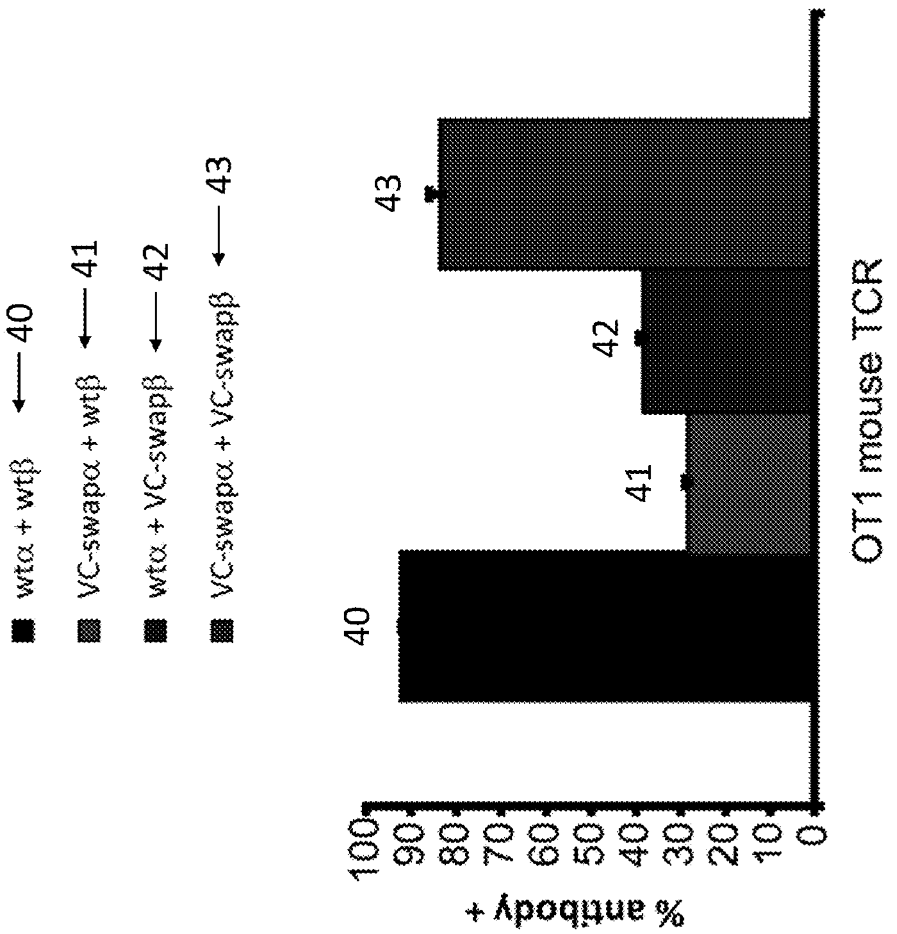
FIG. 4B is a graph showing expression on the surface of CD3+ 293T cells as determined by binding of a cognate peptide-WIC tetramer of TCR configurations in accordance with some embodiments herein. Data are shown for cell surface expression for the domain swap configurations of the ovalbumin-specific OT1 mouse TCR as determined by binding of the cognate peptide-WIC tetramer. Plot shows mean+/−std. dev. from triplicate measurements in one representative experiment of at least two independent experiments.

The DS-TCR configurations and techniques in accordance with some embodiments herein may be applied to any new TCR of clinical interest with minimal additional optimization. We constructed DS-TCR variants of two additional human TCRs and for the ovalbumin-specific OT1 mouse TCR. Using the transfection assay from Example 1 using CD+ 293T cells, we confirmed for all of these TCRs that the domain-swap derivatives do indeed express on the cell surface and mitigate mispairing (FIG. 4). These data demonstrate generality of the domain-swapping approach, suggesting application of this approach to other human TCRs of clinical interest is feasible. Moreover, the OT1 mouse DS-TCR we constructed enables preclinical characterization of the function and safety of this approach in the context of a fully functional immune system.

Example 7

Figure 5A:
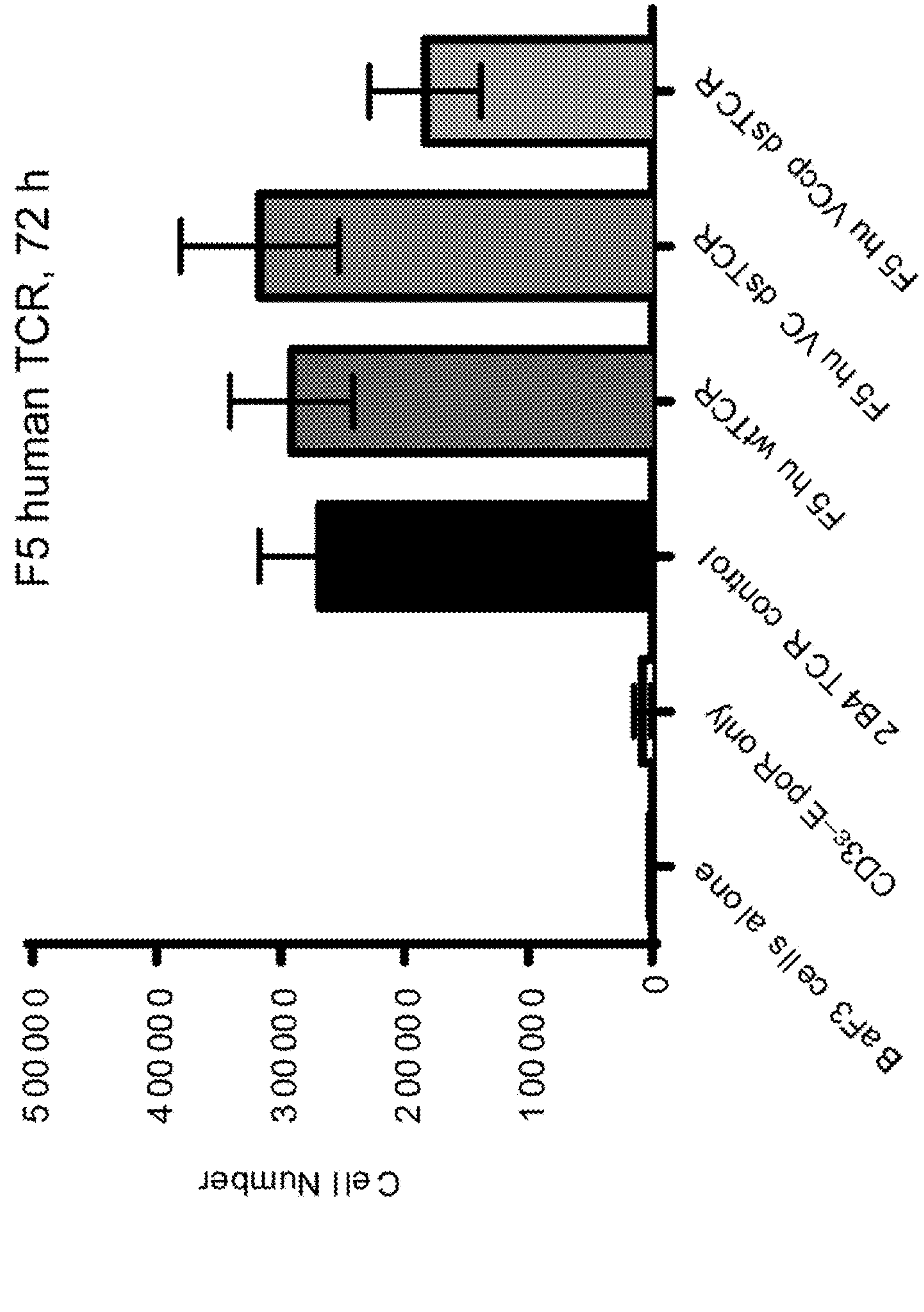
FIG. 5A is a graph showing recruitment of CD3 chains in the same orientation as WT TCRs by domain-swap TCRs as determined by proliferation of BaF3 cells expressing CD3epsilon-EpoR and domain-swapped versions of the human F5 TCR. Plot shows mean+/−std. dev. from triplicate measurements in one representative experiment of three independent experiments.
Figure 5B:
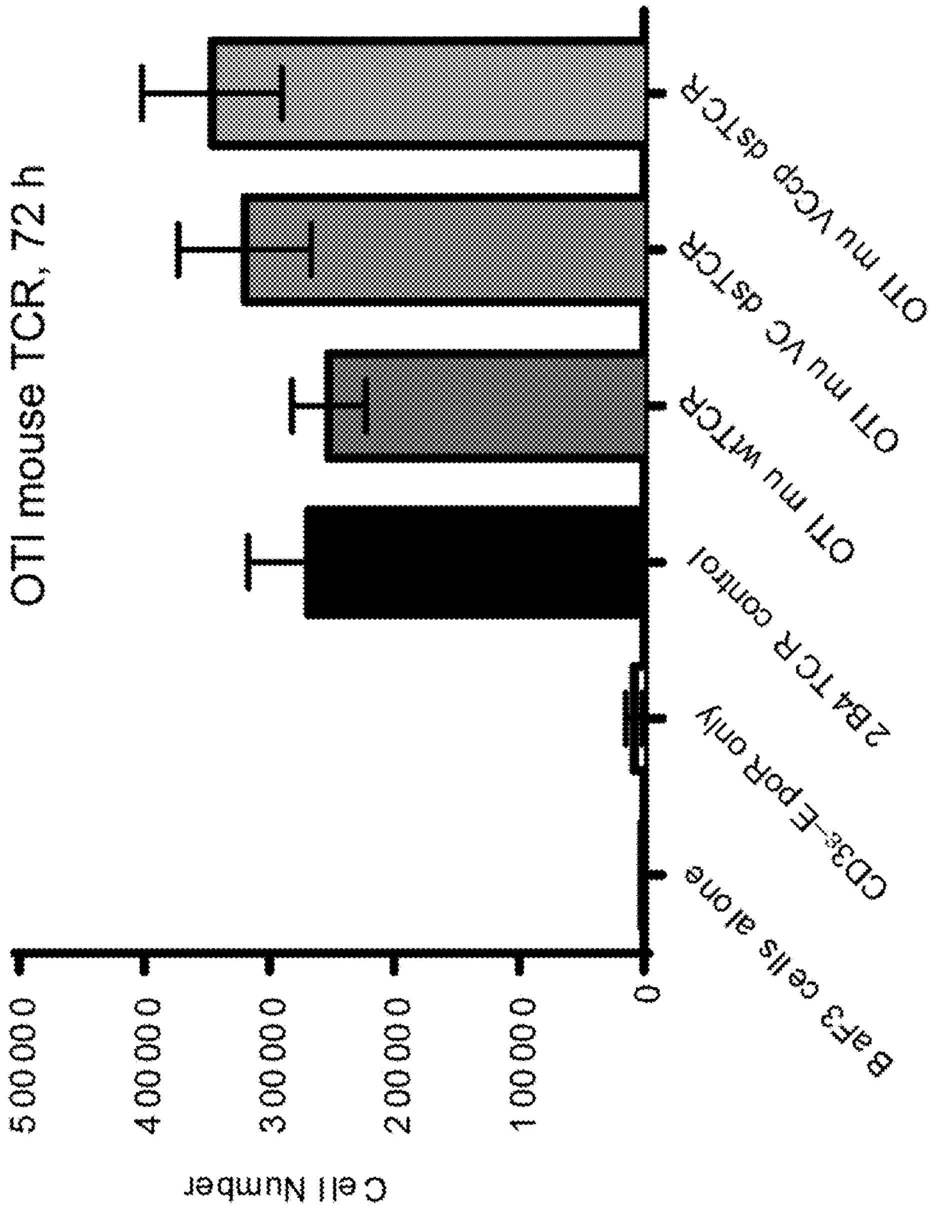
FIG. 5B is a graph showing recruitment of CD3 chains in the same orientation as WT TCRs by domain-swap TCRs as determined by proliferation of BaF3 cells expressing with CD3epsilon-EpoR and domain-swapped versions of the mouse OTI TCR. Plot shows mean+/−std. dev. from triplicate measurements in one representative experiment of three independent experiments.
Figure 6A:
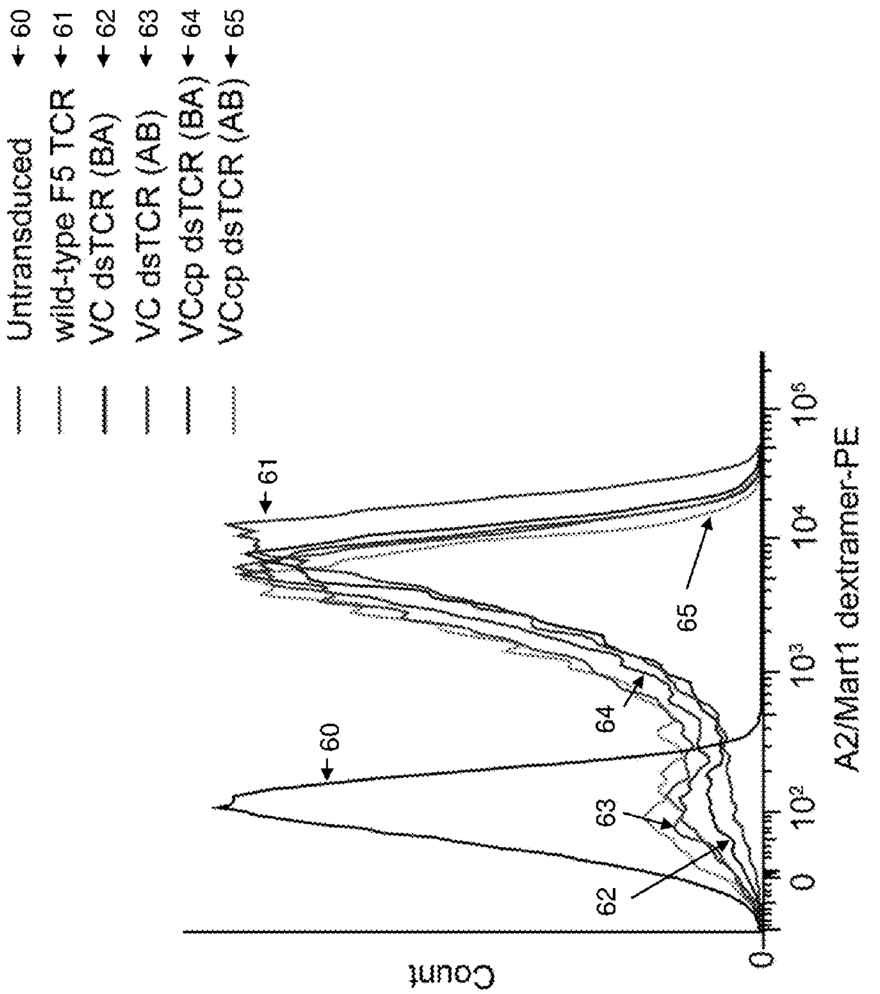
FIG. 6A is a graph showing comparable surface expression of DS-TCRs and WT TCRs, and absence of misparing between DS-TCRs and WT TCRs, as determined by flow cytometry-based detection of A2/Mart1 dextramer staining of Jurkat T cells expressing either WT or DS-TCRs derived from A2-restricted, Mart1(ELAGIGILTV)-specific F5 TCR.
Figure 6B:
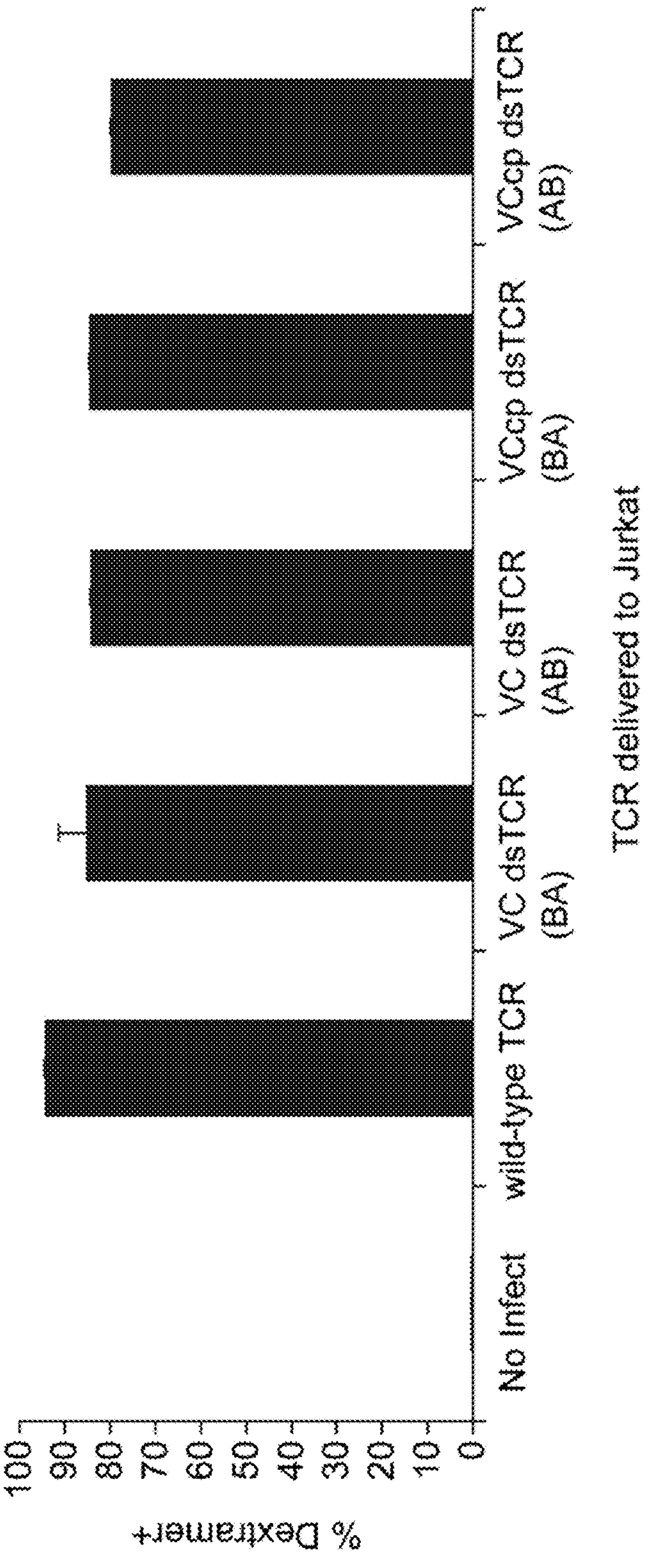
FIG. 6B is a graph showing the percent dextramer positive events quantified from FIG. 6A. Plot shows mean+/−std. dev. from triplicate measurements in one representative experiment of three independent experiments.
Figure 6C:
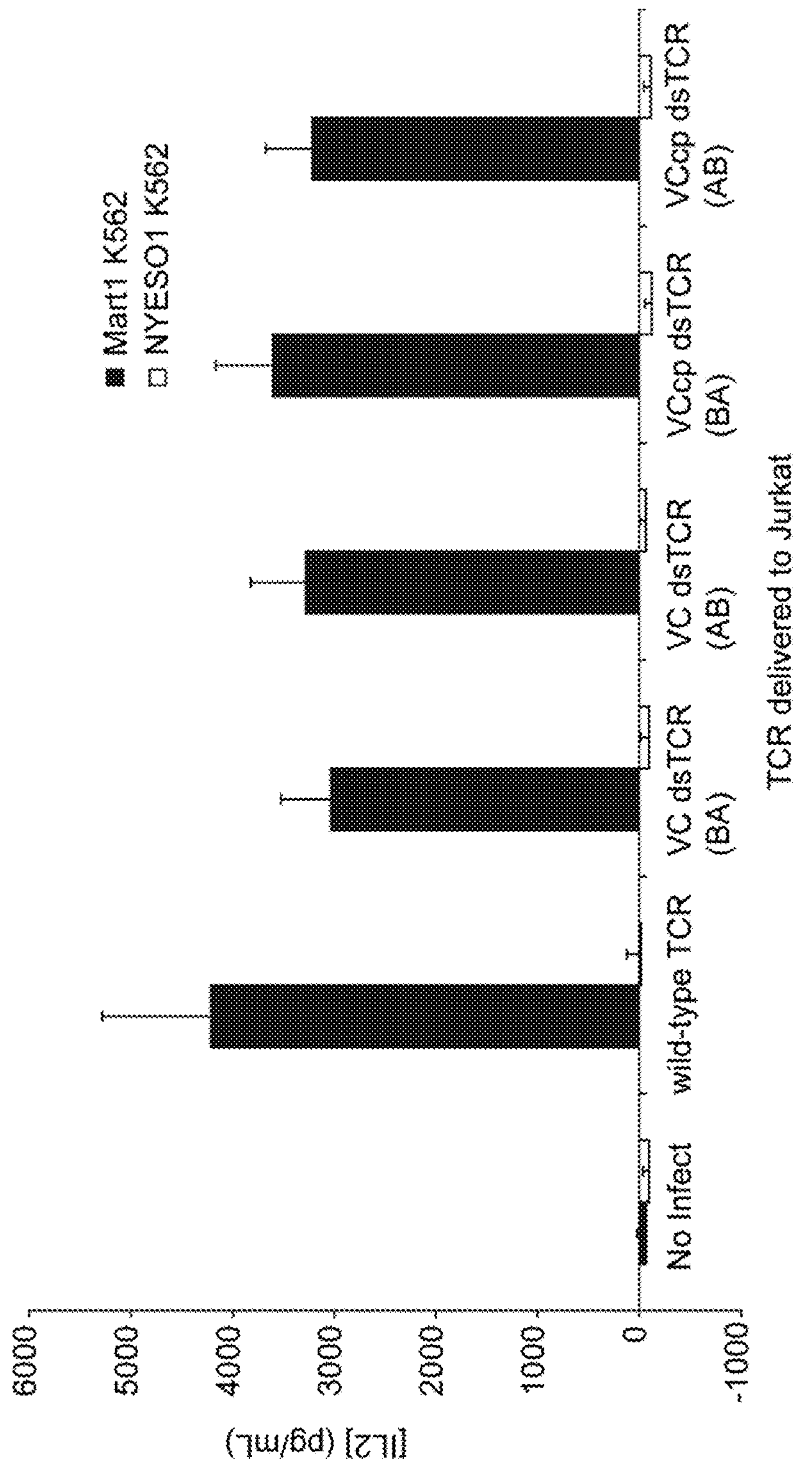
FIG. 6C is a graph showing comparable function of DS-TCRs and WT TCRs as determined by antigen-specific IL-2 release following coincubation of Jurkat T cells expressing either WT or DS-TCR with K562 cells engineered to present cognate A2/Mart1 or control A2/NY-ESO-1. Plot shows mean+/−std. dev. from triplicate measurements in one representative experiment of three independent experiments.
Figure 6D:
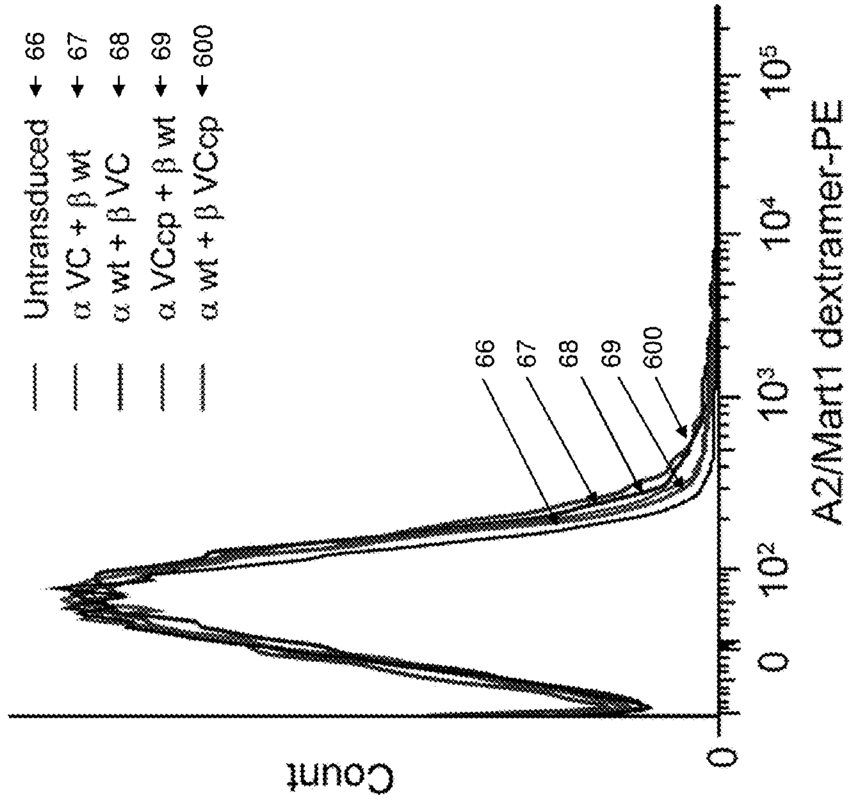
FIG. 6D is a graph showing lack of detection of A2/Mart1 dextramer staining of TCRs by flow cytometry on the surface of Jurkat T cells expressing simulated mispaired F5 TCRs comprising one domain-swap chain and one WT chain.

Recruitment of CD3 chains is typically mediated by the constant domains of the TCR heterodimer, predominantly the transmembrane domains. In light of the swap in the orientation of the constant domains, a BaF3 cell-based assay was used to determine whether the domain-swapped TCRs recruit CD3 chains in a similar or different orientation as the WT TCR. The assay is described in detail in Kuhns et al. accessible on the world wide web at www.ncbi.nlm.nih.gov/pubmed/20202921 (Kuhns et al., Proc. Natl. Acad. Sci. 107: 5094-5099 (2010)). BaF3 cells do not grow in the absence of IL3 unless provided a surrogate input. EpoR expressed on the BaF3 surface can provide this input only if its cytoplasmic domains are dimerized. An expression vector, generated previously, was used which encodes all CD3 chains, including a CD3epsilon chain fused to the cytoplasmic domain of EpoR (Kuhns et al., Proc. Natl. Acad. Sci. 107: 5094-5099 (2010)). This expression vector, when introduced into BaF3 by itself, does not rescue growth (FIG. 5A). However, when a TCR alpha/beta (or gamma/delta) heterodimer is co-delivered with the CD3epsilon-EpoR fusion, the TCR assembles CD3 chains, bringing the two CD3-epsilon chains in the complex into proximity and inducing BaF3 cells to grow (FIG. 5A). The results suggest that CD3 chains are recruited by domain-swap human TCRs in a similar orientation and to a similar extent as by WT F5 human TCRs (FIG. 5A). As with human DS-TCR, CD3 chains are also recruited by murine DS-TCRs in a similar orientation and to a similar extent as by WT OTI murine TCRs (FIG. 5B)

Example 8

Figure 7A:
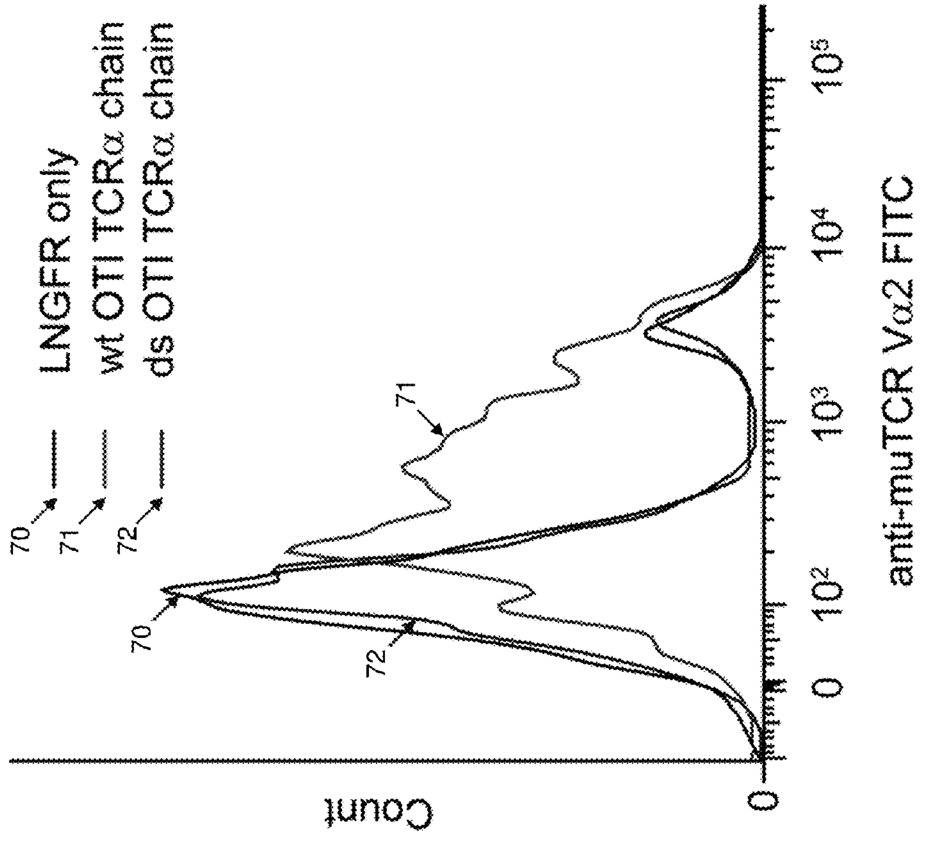
FIG. 7A is a graph showing lack of surface expression of surface-expressed OTI alpha chain following expression of domain-swapped alpha chain only but not WT alpha chain only due to mispairing of introduced domain-swap alpha chain with endogenous TCR beta chain.
Figure 7B:
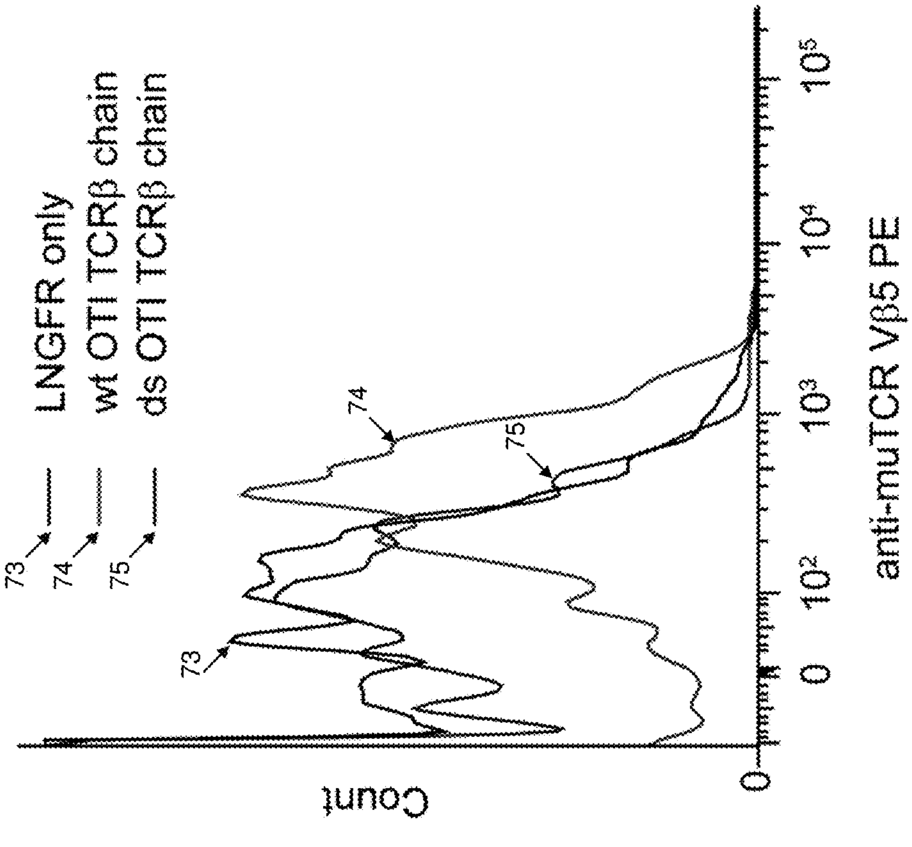
FIG. 7B is a graph showing lack of surface expression of surface-expressed OTI beta chain following expression of domain-swapped beta chain only but not WT beta chain only due to mispairing of introduced domain-swap beta chain with endogenous TCR alpha chain.
Figure 7C:
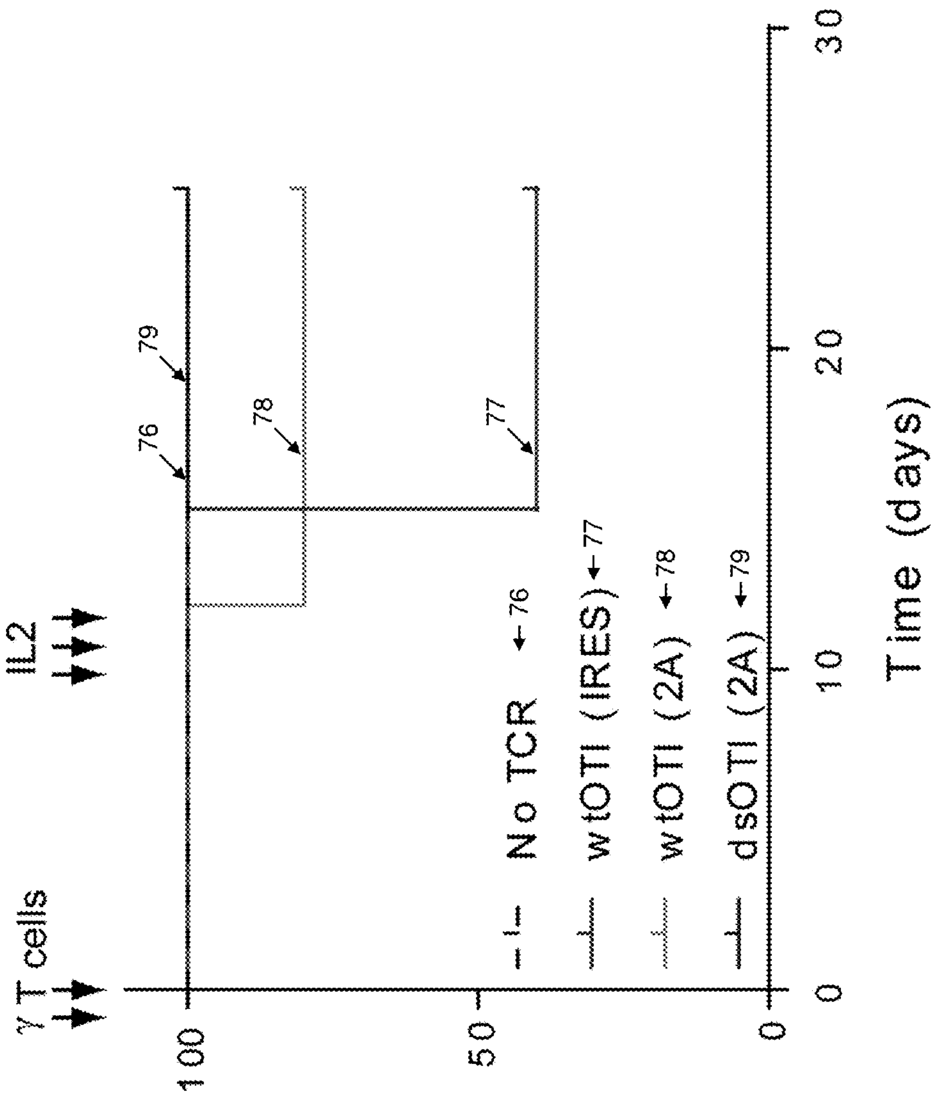
FIG. 7C is a Kaplan-Meier survival curve showing frequency and rate of deaths of mice due to TCR gene transfer-induced graft-vs-host disease. Data are from one experiment with five mice in each group. Repeat experiments are underway and results will be aggregated.
Figure 8A:
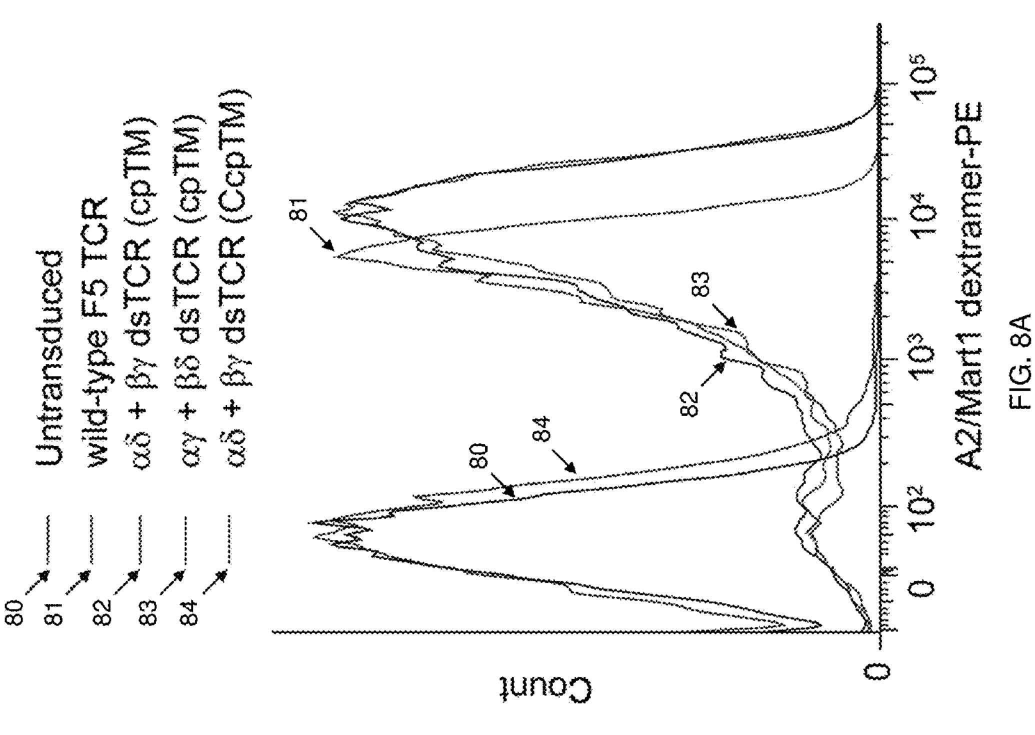
FIG. 8A is a graph showing flow cytometry analysis of A2/Mart1 dextramer staining of Jurkat T cells expressing either WT F5 TCR or chimeric F5-derived TCRs. Incorporation of only connecting peptide and transmembrane domain from gamma/delta chain into alpha/beta chain retains (perhaps improves) function of DS-TCR. Incorporation of constant domain along with connecting peptide and transmembrane domain from delta chain into alpha chain and constant domain along with connecting peptide and transmembrane domain from gamma chain into beta chain renders DS-TCR non-functional.
Figure 8B:
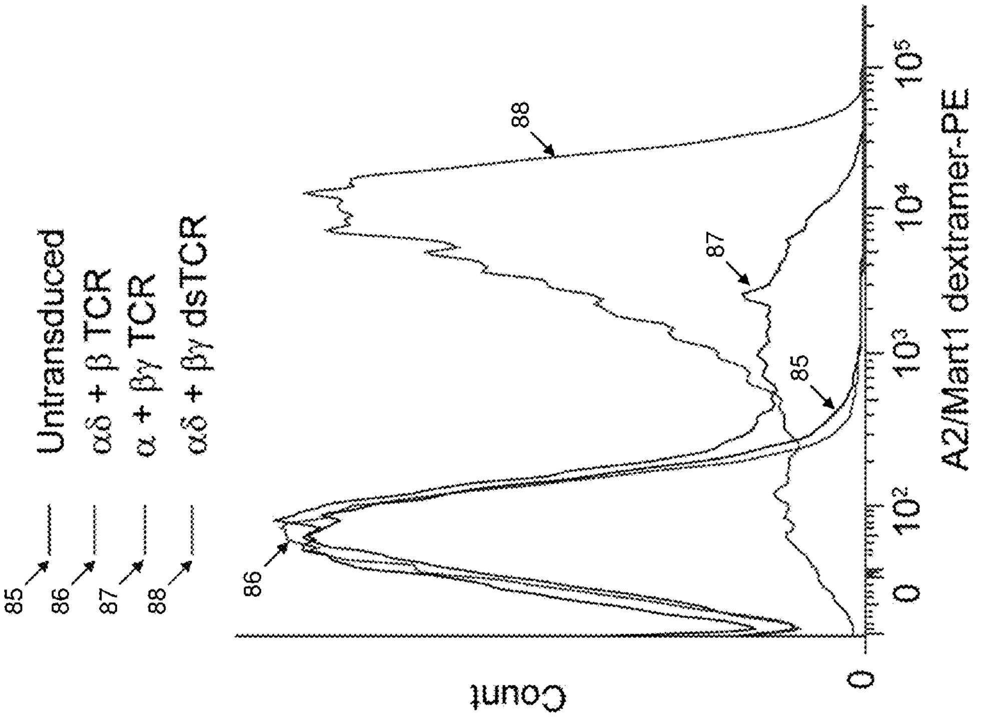
FIG. 8B is a graph showing detection by flow cytometry of A2/Mart1 dextramer staining of F5 DS-TCR on the surface of Jurkat T cells expressing both alpha-delta and beta-gamma or but not on the surface of T cells expressing one domain-swap chain and one WT chain.
Figure 8C:
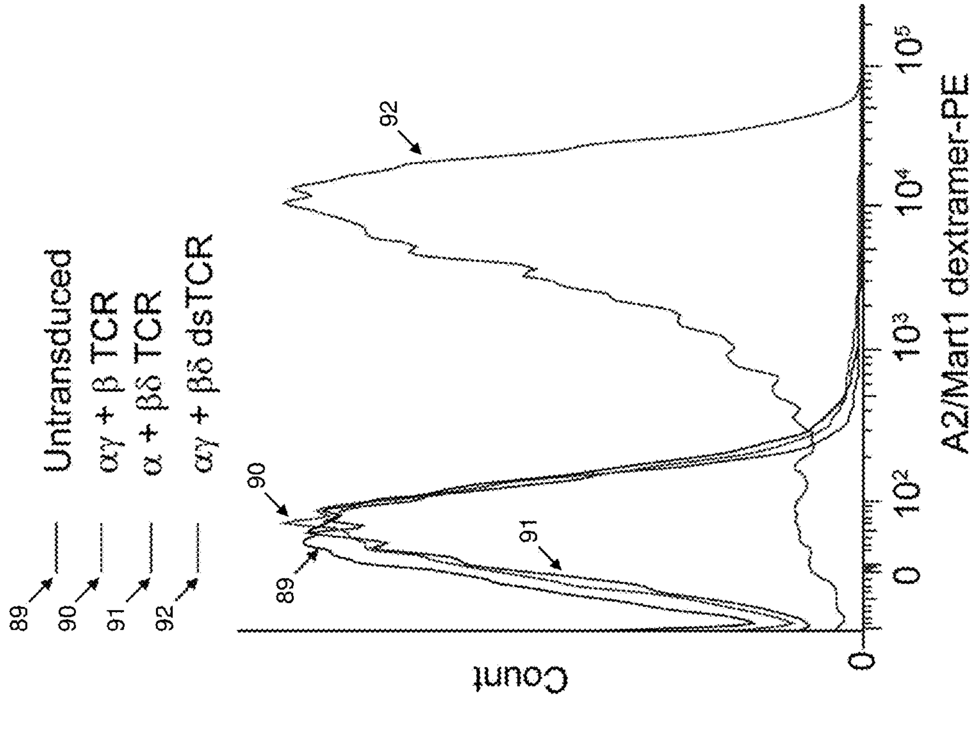
FIG. 8C is a graph showing detection by flow cytometry of A2/Mart1 dextramer staining of F5 DS-TCR on the surface of Jurkat T cells expressing both alpha-gamma and beta-delta or but not on the surface of T cells expressing one domain-swap chain and one WT chain.

To assess whether or not DS-TCRs precipitate TCR gene transfer-induced graft-vs-host disease, mice, for example, C57BL/6J mice from Jackson Laboratories, were gamma-irradiated on day −1 with a sub-lethal dose of 500 Rad. On Day 0, mice were retro-orbitally injected with 1×10e6 T cells that were transduced with LNGFR only or LNGFR plus either WT or domain-swapped OTI TCR. On Days 10, 11, and 12, mice were injected twice daily with 7.2×10e5 U IL-2. Cachexia was the primary indicator used to assess graft-vs-host disease. Mice were weighed once daily starting on Day 10 and were euthanized when weight loss exceeded 15% of initial weight. Results (FIG. 7C) suggest that the DS-TCRs do not cause gene transfer-induced graft-vs-host disease in mice. The assay is described in detail in Bendle et al. accessible on the world wide web at www.ncbi.nlm.nih.gov/pubmed/20400962. (Bendle et al., Nat. Med. 16: 565-570 (2010)).

Example 9

A number of expression constructs were used to express DS-TCRs in accordance with some embodiments herein. Example constructs, which were used in Examples 1-8 are shown in Table 4.

Example 10

In accordance with some embodiments herein, a human subject is selected. The subject has prostate cancer, and has an elevated level of a biomarker, for example, the prostate-specific antigen (PSA) in the subject's serum. The endogenous CD8 T cell TCR repertoire does not target a dominant antigen of this cancer. CD8 T cells are isolated from the subject. A DS-TCR specific for a dominant antigen of the cancer is selected. The DS-TCR is designed with a first domain swap chain configuration $V_{alpha}$-$C_{alpha}$-$CP_{beta}$-$TM_{beta}$-$CT_{beta}$ and a second domain swap chain configuration $V_{beta}$-$C_{beta}$-$CP_{alpha}$-$TM_{alpha}$-$CT_{alpha}$. The isolated CD8 T cell is transfected with a lentivirus comprising two nucleic acid sequences which encode the two domain swap chains of the DS-TCR. The two nucleic acid sequences flank a 2A nucleotide sequence. The nucleotide sequence encodes a 2A peptide that mediates separation of the two chains of the DS-TCR encoded by the two nucleic acid sequences. The two separate polypeptides are expressed in the CD8 T cell, and assemble, along with the endogenous CD3 chains, into a DS-TCR which is expressed on the surface of the T cell. Additionally, miRNA sequences against the endogenous TCR are included in the lentivirus. The miRNAs generated from the lentivirus suppress the expression of endogenous TCR in the transfected CD8 T cells. Flow cytometry-based cell sorting is used to enrich for T cells based on their suppressed or lack of expression of endogenous TCR and enhanced expression of DS-TCR against the dominant cancer antigen. The selected DS-TCR-expressing T cell is then administered to the subject via the intravenous route. Follow-up testing is performed on the subject to assess the status of the administered T cells and their effect on the cancer. For example, blood is drawn from the subject at various times following administration of the T cells. Testing is performed to determine whether the administered T cells are activated, for example, by assessing their secretion of the cytokine IL-2. Testing is also performed to determine the half-life of the administered cells, and whether they are able to induce a T cell memory response. Follow-up testing is also performed to assess whether there is a decrease in level of PSA in the serum of the subject suggesting a decrease in cancer load. Additional scans, for example, ultrasound and MRI, are performed to determine whether there is a decrease in cancer prevalence in the subject.

What is claimed is:

1. A method of making a T cell that expresses a domain-swap T cell receptor (DS-TCR), the method comprising contacting a T cell with:

a first nucleic acid that encodes a first domain-swap chain, wherein the first domain-swap chain comprises a first chain transmembrane domain, a second chain variable domain and a second chain constant domain, but does not comprise a first chain variable domain and does not comprise a first chain constant domain; and a second nucleic acid that encodes a second domain-swap chain, wherein the second domain-swap chain comprises a second chain transmembrane domain, a first chain variable domain and a first chain constant domain, but does not comprise a second chain variable domain and does not comprise a second chain constant domain, wherein, the first chain variable domain comprises an alpha chain variable domain, the first chain constant domain comprises an alpha chain constant domain, the first chain transmembrane domain comprises an alpha chain transmembrane domain, the second chain variable domain comprises a beta chain variable domain, the second chain constant domain comprises a beta chain constant domain, and the second chain transmembrane domain comprises a beta chain transmembrane domain, so as to configure the T cell to express a DS-TCR comprising the first domain-swap chain and the second domain-swap chain.

2. The method of claim 1, wherein the first domain-swap chain further comprises a second chain connecting peptide, but does not comprise a first chain connecting peptide, and wherein the second domain-swap chain further comprises a first chain connecting peptide, but does not comprise a second chain connecting peptide, wherein the first chain connecting peptide comprises an alpha chain connecting peptide and the second chain connecting peptide comprises a beta chain connecting peptide.

3. An expression vector or a set of expression vectors comprising:

a first nucleic acid that encodes a first domain-swap chain, wherein the first domain-swap chain comprises a first chain transmembrane domain, a second chain variable domain and a second chain constant domain, but does not comprise a first chain variable domain and does not comprise a first chain constant domain; and a second nucleic acid that encodes a second domain-swap chain, wherein the second domain-swap chain comprises a second chain transmembrane domain, a first chain variable domain and a first chain constant domain, but does not comprise a second chain variable domain and does not comprise a second chain constant domain, wherein, the first chain variable domain comprises an alpha chain variable domain, the first chain constant domain comprises an alpha chain constant domain, the first chain transmembrane domain comprises an alpha chain transmembrane domain, the second chain variable domain comprises a beta chain variable domain, the second chain constant domain comprises a beta chain constant domain, and the second chain transmembrane domain comprises a beta chain transmembrane domain.

4. The expression vector or the set of expression vectors of claim 3, wherein the first domain-swap chain further comprises a second chain connecting peptide, but does not comprise a first chain connecting peptide, and wherein the second domain-swap chain further comprises a first chain connecting peptide, but does not comprise a second chain connecting peptide, and wherein:

the first chain connecting peptide comprises an alpha chain connecting peptide and the second chain connecting peptide comprises a beta chain connecting peptide.

5. The expression vector or the set of expression vectors of claim 3, wherein the first nucleic acid and the second nucleic acid are part of a same polypeptide expression vector, the vector further comprising a 2A peptide-encoding sequence flanked by the first nucleic acid and the second nucleic acid.

6. The expression vector or the set of expression vectors of claim 3, further comprising a promoter configured to drive expression of the first nucleic acid and the second nucleic acid.

7. The expression vector or the set of expression vectors of claim 3, wherein the first nucleic acid and the second nucleic acid are part of separate expression vectors.

8. The expression vector or the set of expression vectors of claim 3, wherein the expression vector or the set of expression vectors comprises a lentiviral vector, retroviral vector, adenoviral vector, or adeno-associated viral vector.

9. A genetically engineered T cell, comprising:

a first nucleic acid that encodes a first domain-swap chain, wherein the first domain-swap chain comprises a first chain transmembrane domain, a second chain variable domain and a second chain constant domain, but does not comprise a first chain variable domain and does not comprise a first chain constant domain; and a second nucleic acid that encodes a second domain-swap chain, wherein the second domain-swap chain comprises a second chain transmembrane domain, a first chain variable domain and a first chain constant domain, but does not comprise a second chain variable domain and does not comprise a second chain constant domain, wherein, the first chain variable domain comprises an alpha chain variable domain, the first chain constant domain comprises an alpha chain constant domain, the first chain transmembrane domain comprises an alpha chain transmembrane domain, the second chain variable domain comprises a beta chain variable domain, the second chain constant domain comprises a beta chain constant domain, and the second chain transmembrane domain comprises a beta chain transmembrane domain, wherein the T cell is configured to express a DS-TCR comprising the first domain-swap chain and the second domain-swap chain.

10. The genetically engineered T cell of claim 9, wherein the first domain-swap chain further comprises a second chain connecting peptide, but does not comprise a first chain connecting peptide, and wherein the second domain-swap chain further comprises a first chain connecting peptide, but does not comprise a second chain connecting peptide, wherein:

the first chain connecting peptide comprises an alpha chain connecting peptide and the second chain connecting peptide comprises a beta chain connecting peptide.

11. The genetically engineered T cell of claim 9, wherein the T genetically engineered T cell is configured to express the first domain-swap chain as a first polypeptide and the second domain-swap chain as second polypeptide, and wherein the first domain-swap chain and second domain-swap chain are separate molecules.

12. The genetically engineered T cell of claim 9, wherein expression of an endogenous TCR is repressed or eliminated.

13. A method of inducing an immune response in a subject, the method comprising:

configuring an isolated T cell to express:

a first domain-swap chain, wherein the first domain-swap chain comprises a first chain transmembrane domain, a second chain variable domain and a second chain constant domain, but does not comprise a first chain variable domain and does not comprise a first chain constant domain; and a second domain-swap chain, wherein the second domain-swap chain comprises a second chain transmembrane domain, a first chain variable domain and a first chain constant domain, but does not comprise a second chain variable domain and does not comprise a second chain constant domain, wherein, the first chain variable domain comprises an alpha chain variable domain, the first chain constant domain comprises an alpha chain constant domain, the first chain transmembrane domain comprises an alpha chain transmembrane domain, the second chain variable domain comprises a beta chain variable domain, the second chain constant domain comprises a beta chain constant domain, and the second chain transmembrane domain comprises a beta chain transmembrane domain, thereby producing a genetically engineered T cell configured to express a domain-swap T cell receptor (DS-TCR) comprising the first domain-swap chain and the second domain-swap chain; and administering the genetically engineered T cell to the subject.

14. The method of claim 13, wherein the first domain-swap chain further comprises a second chain connecting peptide, but does not comprise a first chain connecting peptide, and wherein the second domain-swap chain further comprises a first chain connecting peptide, but does not comprise a second chain connecting peptide, wherein:

the first chain connecting peptide comprises an alpha chain connecting peptide and the second chain connecting peptide comprises a beta chain connecting peptide.

15. The method of claim 13, wherein the T cell comprises an autologous cell of the subject.

16. The method of claim 13, wherein the T cell comprises a donor cell that is allogeneic to the subject.

17. The method of claim 13, wherein the T cell comprises a CD4 T cell, or a CD8 T cell or a regulatory T cell.

18. The method of claim 13, wherein the genetically engineered T cell is co-administered with a second genetically engineered T cell population.

19. The method of claim 13, wherein the subject has at least one of: a tumor or a cancer, an infectious disease, an autoimmune disease, or diminished or ineffective or exhausted T cells, and is in need of treatment therefor.

20. The method of claim 13, wherein the T cell is induced to express a plurality of DS-TCR against an array of antigens.

21. The method of claim 13, wherein administering to the subject comprises at least one of intravenous injection, or intraperitoneal injection.

22. The method of claim 13, further comprising monitoring the administered T cell over time.

23. The method of claim 13, wherein the method is repeated.

24. A domain-swap T cell receptor (DS-TCR) comprising: a first domain-swap chain, wherein the first domain-swap chain comprises a first chain transmembrane domain, a second chain variable domain and a second chain constant domain, but does not comprise a first chain variable domain and does not comprise a first chain constant domain; and a second domain-swap chain, wherein the second domain-swap chain comprises a second chain transmembrane domain, a first chain variable domain and a first chain constant domain, but does not comprise a second chain variable domain and does not comprise a second chain constant domain, wherein, the first chain variable domain comprises an alpha chain variable domain, the first chain constant domain comprises an alpha chain constant domain, the first chain transmembrane domain comprises an alpha chain transmembrane domain, the second chain variable domain comprises a beta chain variable domain, the second chain constant domain comprises a beta chain constant domain, and the second chain transmembrane domain comprises a beta chain transmembrane domain.

25. The domain-swap T cell receptor of claim 24, wherein the first domain-swap chain further comprises a second chain connecting peptide, but does not comprise a first chain connecting peptide, and wherein the second domain-swap chain further comprises a first chain connecting peptide, but does not comprise a second chain connecting peptide, and wherein the first chain connecting peptide comprises an alpha chain connecting peptide and the second chain connecting peptide comprises a beta chain connecting peptide.

26. The domain-swap T cell receptor of claim 24, wherein the first domain-swap chain and the second domain-swap chain are expressed by a single expression vector.

27. The domain-swap T cell receptor of claim 24, wherein the first domain-swap chain and the second domain-swap chain are expressed by separate expression vectors.

* * * * *

UNITED STATES PATENT AND TRADEMARK OFFICE

CERTIFICATE OF CORRECTION

PATENT NO. : 9,884,075 B2
APPLICATION NO. : 14/597908
DATED : February 6, 2018
INVENTOR(S) : Michael T. Bethune, Marvin H. Gee and David Baltimore It is certified that error appears in the above-identified patent and that said Letters Patent is hereby corrected as shown below:

In the Claims

Column 174, Line 54, replace "the T genetically engineered T cell is configured to express" with -- the genetically engineered T cell is configured to express --

Column 174, Line 56, replace "second domain-swap chain as second polypeptide" with -- second domain-swap chain as a second polypeptide --

Signed and Sealed this
Twenty-fifth Day of September, 2018

Andrei Iancu
*Director of the United States Patent and Trademark Office*

SEQUENCE LISTING

```
<160> NUMBER OF SEQ ID NOS: 64

<210> SEQ ID NO 1
<211> LENGTH: 60
<212> TYPE: DNA
<213> ORGANISM: Artificial Sequence
<220> FEATURE:
<223> OTHER INFORMATION: F2A

<400> SEQUENCE: 1

cagctgttga attttgacct tcttaagctt gcgggagacg tcgagtccaa ccccgggccc      60


<210> SEQ ID NO 2
<211> LENGTH: 57
<212> TYPE: DNA
<213> ORGANISM: Artificial sequence
<220> FEATURE:
<223> OTHER INFORMATION: F2A(-I)

<400> SEQUENCE: 2

ctgttgaatt ttgaccttct taagcttgcg ggagacgtcg agtccaaccc cgggccc         57


<210> SEQ ID NO 3
<211> LENGTH: 54
<212> TYPE: DNA
<213> ORGANISM: Artificial Sequence
<220> FEATURE:
<223> OTHER INFORMATION: F2A(-2)

<400> SEQUENCE: 3

ttgaattttg accttcttaa gcttgcggga gacgtcgagt ccaaccccgg gccc            54


<210> SEQ ID NO 4
<211> LENGTH: 51
<212> TYPE: DNA
```

```
<213> ORGANISM: Artificial Sequence
<220> FEATURE:
<223> OTHER INFORMATION: F2A(-3)

<400> SEQUENCE: 4

aattttgacc ttcttaagct tgcgggagac gtcgagtcca accccgggcc c              51


<210> SEQ ID NO 5
<211> LENGTH: 48
<212> TYPE: DNA
<213> ORGANISM: Artificial Sequence
<220> FEATURE:
<223> OTHER INFORMATION: F2A(-4)

<400> SEQUENCE: 5

tttgaccttc ttaagcttgc gggagacgtc gagtccaacc ccgggccc                 48


<210> SEQ ID NO 6
<211> LENGTH: 45
<212> TYPE: DNA
<213> ORGANISM: Artificial Sequence
<220> FEATURE:
<223> OTHER INFORMATION: F2A(-5)

<400> SEQUENCE: 6

gaccttctta agcttgcggg agacgtcgag tccaaccccg ggccc                    45


<210> SEQ ID NO 7
<211> LENGTH: 42
<212> TYPE: DNA
<213> ORGANISM: Artificial Sequence
<220> FEATURE:
<223> OTHER INFORMATION: F2A(-6)

<400> SEQUENCE: 7

cttcttaagc ttgcgggaga cgtcgagtcc aaccccgggc cc                       42


<210> SEQ ID NO 8
<211> LENGTH: 39
<212> TYPE: DNA
<213> ORGANISM: Artificial Sequence
<220> FEATURE:
<223> OTHER INFORMATION: F2A(-7)

<400> SEQUENCE: 8

cttaagcttg cgggagacgt cgagtccaac cccgggccc                           39


<210> SEQ ID NO 9
<211> LENGTH: 60
<212> TYPE: DNA
<213> ORGANISM: Artificial Sequence
<220> FEATURE:
<223> OTHER INFORMATION: F2A(3)

<400> SEQUENCE: 9

cagctgttga attttgacct tcttaagctt gcgggagacg tccagtccaa ccccgggccc     60


<210> SEQ ID NO 10
<211> LENGTH: 60
<212> TYPE: DNA
<213> ORGANISM: Artificial Sequence
<220> FEATURE:
<223> OTHER INFORMATION: F2A(11)

<400> SEQUENCE: 10

cagctgttga attttgacct tcttaagctt gcgggagacg tcgagattaa ccccgggccc     60
```

<210> SEQ ID NO 11
<211> LENGTH: 60
<212> TYPE: DNA
<213> ORGANISM: Artificial Sequence
<220> FEATURE:
<223> OTHER INFORMATION: F2A(14)

<400> SEQUENCE: 11
cagctgttga attttgacct tcttaagctt gcgggagacg tcgagtccga gcccgggccc 60

<210> SEQ ID NO 12
<211> LENGTH: 60
<212> TYPE: DNA
<213> ORGANISM: Artificial Sequence
<220> FEATURE:
<223> OTHER INFORMATION: F2A(19)

<400> SEQUENCE: 12
cagctgttga attttgacct tcttaagctt gcgggagacg tcgagtccaa ccccgcgccc 60

<210> SEQ ID NO 13
<211> LENGTH: 60
<212> TYPE: DNA
<213> ORGANISM: Artificial Sequence
<220> FEATURE:
<223> OTHER INFORMATION: I2A(0)

<400> SEQUENCE: 13
acgagggcgg agattgagga tgaattgatt cgtcgaggaa ttgaatcaaa tcctgggccc 60

<210> SEQ ID NO 14
<211> LENGTH: 60
<212> TYPE: DNA
<213> ORGANISM: Artificial Sequence
<220> FEATURE:
<223> OTHER INFORMATION: I2A(I)

<400> SEQUENCE: 14
acgagggcgg agattgagga tgaattgatt cgtgcaggaa ttgaatcaaa tcctggaccc 60

<210> SEQ ID NO 15
<211> LENGTH: 60
<212> TYPE: DNA
<213> ORGANISM: Artificial Sequence
<220> FEATURE:
<223> OTHER INFORMATION: I2A(2)

<400> SEQUENCE: 15
acgagggcgg agattgagga tgaattgatt cgtcgaggaa ttgaatcaaa tcctggaccc 60

<210> SEQ ID NO 16
<211> LENGTH: 60
<212> TYPE: DNA
<213> ORGANISM: Artificial Sequence
<220> FEATURE:
<223> OTHER INFORMATION: I2A(3)

<400> SEQUENCE: 16
acgagggcgg agattgagga tgaattgatt cgtcgaggaa ttgaatcaaa tcctgcgccc 60

<210> SEQ ID NO 17
<211> LENGTH: 96
<212> TYPE: DNA
<213> ORGANISM: Artificial Sequence
<220> FEATURE:

<223> OTHER INFORMATION: Furin-GSG-F2A

<400> SEQUENCE: 17
agggcaaaac gttcgggttc gggtgcgcca gtaaagcaga cattaaactt tgatttgctg 60
aaacttgcag gtgatgtaga gtcaaatcca ggtcca 96

<210> SEQ ID NO 18
<211> LENGTH: 78
<212> TYPE: DNA
<213> ORGANISM: Artificial Sequence
<220> FEATURE:
<223> OTHER INFORMATION: Furin-GSG-P2A

<400> SEQUENCE: 18
agagccaaaa gaggctccgg agccactaac ttctccctgt tgaaacaggc tggcgatgtt 60
gaagaaaacc ccggtcct 78

<210> SEQ ID NO 19
<211> LENGTH: 20
<212> TYPE: PRT
<213> ORGANISM: Artificial Sequence
<220> FEATURE:
<223> OTHER INFORMATION: F2A wild-type

<400> SEQUENCE: 19

Gln Leu Leu Asn Phe Asp Leu Leu Lys Leu Ala Gly Asp Val Glu Ser
1 5 10 15

Asn Pro Gly Pro
20

<210> SEQ ID NO 20
<211> LENGTH: 19
<212> TYPE: PRT
<213> ORGANISM: Artificial Sequence
<220> FEATURE:
<223> OTHER INFORMATION: F2A(-I) 1aa N-terminal deletion

<400> SEQUENCE: 20

Leu Leu Asn Phe Asp Leu Leu Lys Leu Ala Gly Asp Val Glu Ser Asn
1 5 10 15

Pro Gly Pro

<210> SEQ ID NO 21
<211> LENGTH: 18
<212> TYPE: PRT
<213> ORGANISM: Artificial Sequence
<220> FEATURE:
<223> OTHER INFORMATION: F2A(-2) 2aa N-terminal deletion

<400> SEQUENCE: 21

Leu Asn Phe Asp Leu Leu Lys Leu Ala Gly Asp Val Glu Ser Asn Pro
1 5 10 15

Gly Pro

<210> SEQ ID NO 22
<211> LENGTH: 17
<212> TYPE: PRT
<213> ORGANISM: Artificial Sequence
<220> FEATURE:
<223> OTHER INFORMATION: F2A(-3) 3aa N-terminal deletion

<400> SEQUENCE: 22

Asn Phe Asp Leu Leu Lys Leu Ala Gly Asp Val Glu Ser Asn Pro Gly 1 5 10 15

Pro

<210> SEQ ID NO 23
<211> LENGTH: 16
<212> TYPE: PRT
<213> ORGANISM: Artificial Sequence
<220> FEATURE:
<223> OTHER INFORMATION: F2A(-4) 4aa N-terminal deletion

<400> SEQUENCE: 23

Phe Asp Leu Leu Lys Leu Ala Gly Asp Val Glu Ser Asn Pro Gly Pro
1 5 10 15

<210> SEQ ID NO 24
<211> LENGTH: 15
<212> TYPE: PRT
<213> ORGANISM: Artificial Sequence
<220> FEATURE:
<223> OTHER INFORMATION: F2A(-5) 5aa N-terminal deletion

<400> SEQUENCE: 24

Asp Leu Leu Lys Leu Ala Gly Asp Val Glu Ser Asn Pro Gly Pro
1 5 10 15

<210> SEQ ID NO 25
<211> LENGTH: 14
<212> TYPE: PRT
<213> ORGANISM: Artificial Sequence
<220> FEATURE:
<223> OTHER INFORMATION: F2A(-6) 6aa N-terminal deletion

<400> SEQUENCE: 25

Leu Leu Lys Leu Ala Gly Asp Val Glu Ser Asn Pro Gly Pro
1 5 10

<210> SEQ ID NO 26
<211> LENGTH: 13
<212> TYPE: PRT
<213> ORGANISM: Artificial Sequence
<220> FEATURE:
<223> OTHER INFORMATION: F2A(-7) 7aa N-terminal deletion

<400> SEQUENCE: 26

Leu Lys Leu Ala Gly Asp Val Glu Ser Asn Pro Gly Pro
1 5 10

<210> SEQ ID NO 27
<211> LENGTH: 20
<212> TYPE: PRT
<213> ORGANISM: Artificial Sequence
<220> FEATURE:
<223> OTHER INFORMATION: F2A(3) Point mutation

<400> SEQUENCE: 27

Gln Leu Leu Asn Phe Asp Leu Leu Lys Leu Ala Gly Asp Val Gln Ser
1 5 10 15

Asn Pro Gly Pro
20

<210> SEQ ID NO 28
<211> LENGTH: 20
<212> TYPE: PRT
<213> ORGANISM: Artificial Sequence
<220> FEATURE:
<223> OTHER INFORMATION: F2A(11) Point mutation -continued

<400> SEQUENCE: 28

```
Gln Leu Leu Asn Phe Asp Leu Leu Lys Leu Ala Gly Asp Val Glu Ile
1               5                   10                  15

Asn Pro Gly Pro
            20
```

<210> SEQ ID NO 29
<211> LENGTH: 20
<212> TYPE: PRT
<213> ORGANISM: Artificial Sequence
<220> FEATURE:
<223> OTHER INFORMATION: F2A(14) Point mutation

<400> SEQUENCE: 29

```
Gln Leu Leu Asn Phe Asp Leu Leu Lys Leu Ala Gly Asp Val Glu Ser
1               5                   10                  15

Glu Pro Gly Pro
            20
```

<210> SEQ ID NO 30
<211> LENGTH: 20
<212> TYPE: PRT
<213> ORGANISM: Artificial Sequence
<220> FEATURE:
<223> OTHER INFORMATION: F2A(19) Point mutation

<400> SEQUENCE: 30

```
Gln Leu Leu Asn Phe Asp Leu Leu Lys Leu Ala Gly Asp Val Glu Ser
1               5                   10                  15

Asn Pro Ala Pro
            20
```

<210> SEQ ID NO 31
<211> LENGTH: 20
<212> TYPE: PRT
<213> ORGANISM: Artificial Sequence
<220> FEATURE:
<223> OTHER INFORMATION: I2A(0) wild type

<400> SEQUENCE: 31

```
Thr Arg Ala Glu Ile Glu Asp Glu Leu Ile Arg Arg Gly Ile Glu Ser
1               5                   10                  15

Asn Pro Gly Pro
            20
```

<210> SEQ ID NO 32
<211> LENGTH: 20
<212> TYPE: PRT
<213> ORGANISM: Artificial Sequence
<220> FEATURE:
<223> OTHER INFORMATION: I2A(I) Point mutation

<400> SEQUENCE: 32

```
Thr Arg Ala Glu Ile Glu Asp Glu Leu Ile Arg Ala Gly Ile Glu Ser
1               5                   10                  15

Asn Pro Gly Pro
            20
```

<210> SEQ ID NO 33
<211> LENGTH: 20
<212> TYPE: PRT
<213> ORGANISM: Artificial Sequence
<220> FEATURE:

<223> OTHER INFORMATION: I2A(2) Alternative codon

<400> SEQUENCE: 33

Thr Arg Ala Glu Ile Glu Asp Glu Leu Ile Arg Arg Gly Ile Glu Ser
1               5                   10                  15

Asn Pro Gly Pro
            20

<210> SEQ ID NO 34
<211> LENGTH: 20
<212> TYPE: PRT
<213> ORGANISM: Artificial Sequence
<220> FEATURE:
<223> OTHER INFORMATION: I2A(3) Point mutation

<400> SEQUENCE: 34

Thr Arg Ala Glu Ile Glu Asp Glu Leu Ile Arg Arg Gly Ile Glu Ser
1               5                   10                  15

Asn Pro Ala Pro
            20

<210> SEQ ID NO 35
<211> LENGTH: 32
<212> TYPE: PRT
<213> ORGANISM: Artificial Sequence
<220> FEATURE:
<223> OTHER INFORMATION: Furin-GSG-F2A PRT

<400> SEQUENCE: 35

Arg Ala Lys Arg Ser Gly Ser Gly Ala Pro Val Lys Gln Thr Leu Asn
1               5                   10                  15

Phe Asp Leu Leu Lys Leu Ala Gly Asp Val Glu Ser Asn Pro Gly Pro
            20                  25                  30

<210> SEQ ID NO 36
<211> LENGTH: 26
<212> TYPE: PRT
<213> ORGANISM: Artificial Sequence
<220> FEATURE:
<223> OTHER INFORMATION: Furin-GSG-P2A PRT

<400> SEQUENCE: 36

Arg Ala Lys Arg Gly Ser Gly Ala Thr Asn Phe Ser Leu Leu Lys Gln
1               5                   10                  15

Ala Gly Asp Val Glu Glu Asn Pro Gly Pro
            20                  25

<210> SEQ ID NO 37
<211> LENGTH: 6335
<212> TYPE: DNA
<213> ORGANISM: Artificial Sequence
<220> FEATURE:
<223> OTHER INFORMATION: pMTB1184 vector

<400> SEQUENCE: 37
ctgcataatg aaagacccca cctgtaggtt tggcaagcta gcttaagtaa cgccattttg 60
caaggcatgg aaaaatacat aactgagaat agaaaagttc agatcaaggt caggaacaga 120
tggaacagct gaatatgggc caaagcggat atctgtggta agcagttcct gccccggctc 180
agggccaaga acagatggaa cagctgaata tgggccaaac aggatatctg tggtaagcag 240
ttcctgcccc ggctcagggc caagaacaga tggtccccag atgcggtcca gccctcagca 300
gtttctagag aaccatcaga tgtttccagg gtgccccaag gacctgaaat gaccctgtgc 360

-continued

```
cttatttgaa ctaaccaatc agttcgcttc tcgcttctgt tcgcgcgctt ctgctccccg    420
agctcaataa aagagcccac aacccctcac tcggggcgcc agtcctccga ttgactgagt    480
cgcccgggta cccgtgtatc caataaaccc tcttgcagtt gcatccgact tgtggtctcg    540
ctgttccttg ggagggtctc ctctgagtga ttgactaccc gtcagcgggg gtctttcatt    600
tgggggctcg tccgggatcg ggagacccct gcccagggac caccgaccca ccaccgggag    660
gtaagctggc cagcaactta tctgtgtctg tccgattgtc tagtgtctat gactgatttt    720
atgcgcctgc gtcggtacta gttagctaac tagctctgta tctggcggac ccgtggtgga    780
actgacgagt tcggaacacc cggccgcaac cctgggagac gtcccaggtc gggggccgtt    840
tttgtggccc gacctgagtc caaaaatccc gatcgttttg gactctttgg tgcacccccc    900
ttagaggagg gatatgtggt tctggtagga gacgagaacc taaaacagtt cccgcctccg    960
tctgaatttt tgctttcggt ttgggaccga agccgcgccg cgcgtcttgt ctgctgcagc   1020
atcgttctgt gttgtctctg tctgactgtg tttctgtatt tgtctgaaaa tatgggcccg   1080
ggccagactg ttaccactcc cttaagtttg accttaggtc actggaaaga tgtcgagcgg   1140
atcgctcaca accagtcggt agatgtcaag aagagacgtt gggttacctt ctgctctgca   1200
gaatggccaa cctttaacgt cggatggccg cgagacggca cctttaaccg agacctcatc   1260
acccaggtta agatcaaggt cttttcacct ggcccgcatg gacacccaga ccaggtcccc   1320
tacatcgtga cctgggaagc cttggctttt gacccccctc cctgggtcaa gccctttgta   1380
caccctaagc ctccgcctcc tcttcctcca tccgccccgt ctctccccct tgaacctcct   1440
cgttcgaccc cgcctcgatc ctccctttat ccagccctca ctccttctct aggcgccccc   1500
atatggccat atgagatctt atatggggca cccccgcccc ttgtaaactt ccctgaccct   1560
gacatgacaa gagttactaa cagcccctct ctccaagctc acttacaggc tctctactta   1620
gtccagcacg aagtctggag acctctggcg gcagcctacc aagaacaact ggaccgaccg   1680
gtggtacctc acccttaccg agtcggcgac acagtgtggg tccgccgaca ccagactaag   1740
aacctagaac ctcgctggaa aggaccttac acagtcctgc tgaccacccc caccgccctc   1800
aaagtagacg gcatcgcagc ttggatacac gccgcccacg tgaaggctgc cgaccccggg   1860
ggtggaccat cctctagact gccggatccg ccaccatggc cccgcgggtg ctggccgata   1920
gcgcctgggg catcacactg ctgtcctggg tgaccgtgtt cctgctgggc accagcagcg   1980
ccgacagcgg cgtggtgcag agccccaggc acatcatcaa ggagaagggc ggcagaagcg   2040
tgctgacctg catccccatc agcggccaca gcaacgtggt gtggtatcag cagaccctgg   2100
gcaaggagct gaagttcctg atccagcact acgagaaggt ggagagggac aagggcttcc   2160
tgcccagcag gttcagcgtg cagcagttcg acgactacca cagcgagatg aacatgagcg   2220
ccctggagct ggaggacagc gccatgtact tttgcgccag cagcagggcc aactacgagc   2280
agtacttcgg ccctggcacc aggctgaccg tgctggagga cctgaggaac gtgacccccc   2340
ccaaggtgtc cctgttcgag cccagcaagg ccgagatcgc caacaagcag aaggccaccc   2400
tggtgtgcct ggccaggggc ttcttccccg accacgtgga gctgtcttgg tgggtgaacg   2460
gcaaggaggt gcacagcggc gtgagcaccg acccccaggc ctacaaggag agcaactaca   2520
gctactgcct gagcagcagg ctgagagtga gcgccacctt ctggcacaac cccaggaacc   2580
acttccgctg tcaggtgcag ttccacggcc tgagcgagga ggacaagtgg cccgagggca   2640
gccccaagcc cgtgacccag aacatcagcg ccgaggcctg gggcagagcc gactgcggca   2700
```

-continued tcaccagcgc cagctaccac cagggcgtgc tgtccgccac catcctgtac gagatcctgc 2760
tgggcaaggc cacactgtac gccgtgctgg tgtccggcct ggtgctgatg gccatggtga 2820
agaagaagaa cagcagcggc agcggcgcca ccaacttcag cctgctgaag caggccggcg 2880
acgtggagga aaaccctggg cccatggaca agatcctgac cgccaccttt ctgctgctgg 2940
gcctgcacct ggccggcgtg aacggacagc agcaggagaa gagggatcag cagcaggtgc 3000
ggcagagccc ccagagcctg accgtgtggg agggcgagac cgccatcctg aactgcagct 3060
acgaggacag caccttcaac tacttccctt ggtatcagca gttccccggc gagggccctg 3120
ctctgctgat ctccatcaga agcgtgagcg acaagaagga ggacggcagg ttcaccatct 3180
ttttcaacaa gcgggagaag aagctgtccc tgcacatcac cgacagccag cccggcgaca 3240
gcgccaccta cttttgcgcc gccagcgaca actaccagct gatctggggc agcggcacca 3300
agctgatcat caagcccgac atccagaacc ccgagcccgc cgtgtaccag ctgaaggacc 3360
ccagaagcca ggacagcacc ctgtgcctgt tcaccgactt cgacagccag atcaacgtgc 3420
ccaagaccat ggagagcggc accttcatca ccgacaagac cgtgctggac atgaaggcca 3480
tggacagcaa gagcaacggc gccatcgcct ggtccaacca gaccagcttc acatgccagg 3540
acatcttcaa ggagaccaac gccacctacc ccagcagcga cgtgccctgc gacgccaccc 3600
tgaccgagaa gagcttcgag accgacatga acctgaactt ccagaacctg agcgtgatgg 3660
gcctgagaat cctgctgctg aaggtggccg gcttcaacct gctgatgacc ctgaggctgt 3720
ggagcagctg agtcgacgat aaaataaaag attttattta gtctccagaa aaagggggga 3780
atgaaagacc ccacctgtag gtttggcaag ctagcttaag taacgccatt ttggaaggca 3840
tggaaaaata cataactgag aatagagaag ttcagatcaa ggtcaggaac agatggaaca 3900
gctgaatatg ggccaaacag gatatctgtg gtaagcagtt cctgccccgg ctcagggcca 3960
agaacagatg gaacagctga atatgggcca aacaggatat ctgtggtaag cagttcctgc 4020
cccggctcag ggccaagaac agatggtccc cagatgcggt ccagccctca gcagtttcta 4080
gagaaccatc agatgtttcc agggtgcccc aaggacctga aatgaccctg tgccttattt 4140
gaactaacca atcagttcgc ttctcgcttc tgttcgcgcg cttctgctcc ccgagctcaa 4200
taaaagagcc cacaacccct cactcggggc gccagtcctc cgattgactg agtcgcccgg 4260
gtacccgtgt atccaataaa ccctcttgca gttgcatccg acttgtggtc tcgctgttcc 4320
ttgggagggt ctcctctgag tgattgacta cccgtcagcg ggggtctttc attctgcatt 4380
aatgaatcgg ccaacgcgcg gggagaggcg gtttgcgtat tgggcgctct tccgcttcct 4440
cgctcactga ctcgctgcgc tcggtcgttc ggctgcggcg agcggtatca gctcactcaa 4500
aggcggtaat acggttatcc acagaatcag gggataacgc aggaaagaac atgtgagcaa 4560
aaggccagca aaaggccagg aaccgtaaaa aggccgcgtt gctggcgttt ttccataggc 4620
tccgcccccc tgacgagcat cacaaaaatc gacgctcaag tcagaggtgg cgaaacccga 4680
caggactata aagataccag gcgtttcccc ctggaagctc cctcgtgcgc tctcctgttc 4740
cgaccctgcc gcttaccgga tacctgtccg cctttctccc ttcgggaagc gtggcgcttt 4800
ctcatagctc acgctgtagg tatctcagtt cggtgtaggt cgttcgctcc aagctgggct 4860
gtgtgcacga accccccgtt cagcccgacc gctgcgcctt atccggtaac tatcgtcttg 4920
agtccaaccc ggtaagacac gacttatcgc cactggcagc agccactggt aacaggatta 4980
gcagagcgag gtatgtaggc ggtgctacag agttcttgaa gtggtggcct aactacggct 5040
acactagaag gacagtattt ggtatctgcg ctctgctgaa gccagttacc ttcggaaaaa 5100

```
gagttggtag ctcttgatcc ggcaaacaaa ccaccgctgg tagcggtggt ttttttgttt   5160

gcaagcagca gattacgcgc agaaaaaaag gatctcaaga agatcctttg atcttttcta   5220

cggggtctga cgctcagtgg aacgaaaact cacgttaagg gattttggtc atgagattat   5280

caaaaaggat cttcacctag atccttttgc ggccggccgc aaatcaatct aaagtatata   5340

tgagtaaact tggtctgaca gttaccaatg cttaatcagt gaggcaccta tctcagcgat   5400

ctgtctattt cgttcatcca tagttgcctg actccccgtc gtgtagataa ctacgatacg   5460

ggagggctta ccatctggcc ccagtgctgc aatgataccg cgagacccac gctcaccggc   5520

tccagattta tcagcaataa accagccagc cggaagggcc gagcgcagaa gtggtcctgc   5580

aactttatcc gcctccatcc agtctattaa ttgttgccgg gaagctagag taagtagttc   5640

gccagttaat agtttgcgca acgttgttgc cattgctaca ggcatcgtgg tgtcacgctc   5700

gtcgtttggt atggcttcat tcagctccgg ttcccaacga tcaaggcgag ttacatgatc   5760

ccccatgttg tgcaaaaaag cggttagctc cttcggtcct ccgatcgttg tcagaagtaa   5820

gttggccgca gtgttatcac tcatggttat ggcagcactg cataattctc ttactgtcat   5880

gccatccgta agatgctttt ctgtgactgg tgagtactca accaagtcat tctgagaata   5940

gtgtatgcgg cgaccgagtt gctcttgccc ggcgtcaaca cgggataata ccgcgccaca   6000

tagcagaact ttaaaagtgc tcatcattgg aaaacgttct tcggggcgaa aactctcaag   6060

gatcttaccg ctgttgagat ccagttcgat gtaacccact cgtgcaccca actgatcttc   6120

agcatctttt actttcacca gcgtttctgg gtgagcaaaa acaggaaggc aaaatgccgc   6180

aaaaaaggga ataagggcga cacggaaatg ttgaatactc atactcttcc tttttcaata   6240

ttattgaagc atttatcagg gttattgtct catgagcgga tacatatttg aatgtattta   6300

gaaaaataaa caaatagggg ttccgcgcac atttc                              6335
```

<210> SEQ ID NO 38
<211> LENGTH: 6335
<212> TYPE: DNA
<213> ORGANISM: Artificial Sequence
<220> FEATURE:
<223> OTHER INFORMATION: pMTB1185 vector

<400> SEQUENCE: 38

```
ctgcataatg aaagacccca cctgtaggtt tggcaagcta gcttaagtaa cgccattttg     60

caaggcatgg aaaaatacat aactgagaat agaaaagttc agatcaaggt caggaacaga    120

tggaacagct gaatatgggc caaagcggat atctgtggta agcagttcct gccccggctc    180

agggccaaga acagatggaa cagctgaata tgggccaaac aggatatctg tggtaagcag    240

ttcctgcccc ggctcagggc caagaacaga tggtccccag atgcggtcca gccctcagca    300

gtttctagag aaccatcaga tgtttccagg gtgccccaag gacctgaaat gaccctgtgc    360

cttatttgaa ctaaccaatc agttcgcttc tcgcttctgt tcgcgcgctt ctgctccccg    420

agctcaataa aagagcccac aacccctcac tcggggcgcc agtcctccga ttgactgagt    480

cgcccgggta cccgtgtatc caataaaccc tcttgcagtt gcatccgact tgtggtctcg    540

ctgttccttg ggagggtctc ctctgagtga ttgactaccc gtcagcgggg gtctttcatt    600

tgggggctcg tccgggatcg ggagacccct gcccagggac caccgaccca ccaccgggag    660

gtaagctggc cagcaactta tctgtgtctg tccgattgtc tagtgtctat gactgatttt    720

atgcgcctgc gtcggtacta gttagctaac tagctctgta tctggcggac ccgtggtgga    780
```

-continued

```
actgacgagt tcggaacacc cggccgcaac cctgggagac gtcccaggtc gggggccgtt    840
tttgtggccc gacctgagtc caaaaatccc gatcgttttg gactctttgg tgcacccccc    900
ttagaggagg gatatgtggt tctggtagga gacgagaacc taaaacagtt cccgcctccg    960
tctgaatttt tgctttcggt ttgggaccga agccgcgccg cgcgtcttgt ctgctgcagc   1020
atcgttctgt gttgtctctg tctgactgtg tttctgtatt tgtctgaaaa tatgggcccg   1080
ggccagactg ttaccactcc cttaagtttg accttaggtc actggaaaga tgtcgagcgg   1140
atcgctcaca accagtcggt agatgtcaag aagagacgtt gggttacctt ctgctctgca   1200
gaatggccaa cctttaacgt cggatggccg cgagacggca cctttaaccg agacctcatc   1260
acccaggtta agatcaaggt cttttcacct ggcccgcatg gacacccaga ccaggtcccc   1320
tacatcgtga cctgggaagc cttggctttt gacccccctc cctgggtcaa gccctttgta   1380
caccctaagc ctccgcctcc tcttcctcca tccgccccgt ctctcccccct tgaacctcct   1440
cgttcgaccc cgcctcgatc ctccctttat ccagccctca ctccttctct aggcgccccc   1500
atatggccat atgagatctt atatggggca cccccgcccc ttgtaaactt ccctgaccct   1560
gacatgacaa gagttactaa cagcccctct ctccaagctc acttacaggc tctctactta   1620
gtccagcacg aagtctggag acctctggcg gcagcctacc aagaacaact ggaccgaccg   1680
gtggtacctc acccttaccg agtcggcgac acagtgtggg tccgccgaca ccagactaag   1740
aacctagaac ctcgctggaa aggaccttac acagtcctgc tgaccacccc caccgccctc   1800
aaagtagacg gcatcgcagc ttggatacac gccgcccacg tgaaggctgc cgaccccggg   1860
ggtggaccat cctctagact gccggatccg ccaccatggc cccgcgggtg ctggccgata   1920
gcgcctgggg catcacactg ctgtcctggg tgaccgtgtt cctgctgggc accagcagcg   1980
ccgacagcgg cgtggtgcag agccccaggc acatcatcaa ggagaagggc ggcagaagcg   2040
tgctgacctg catccccatc agcggccaca gcaacgtggt gtggtatcag cagaccctgg   2100
gcaaggagct gaagttcctg atccagcact acgagaaggt ggagagggac aagggcttcc   2160
tgcccagcag gttcagcgtg cagcagttcg acgactacca cagcgagatg aacatgagcg   2220
ccctggagct ggaggacagc gccatgtact tttgcgccag cagcagggcc aactacgagc   2280
agtacttcgg ccctggcacc aggctgaccg tgctggagga cctgaggaac gtgacccccc   2340
ccaaggtgtc cctgttcgag cccagcaagg ccgagatcgc caacaagcag aaggccaccc   2400
tggtgtgcct ggccaggggc ttcttccccg accacgtgga gctgtcttgg tgggtgaacg   2460
gcaaggaggt gcacagcggc gtgagcaccg acccccaggc ctacaaggag agcaactaca   2520
gctactgcct gagcagcagg ctgagagtga gcgccacctt ctggcacaac cccaggaacc   2580
acttccgctg tcaggtgcag ttccacggcc tgagcgagga ggacaagtgg cccgagggca   2640
gccccaagcc cgtgacccag aacatcagcg ccgaggcctg gggcagagcc gactgcgacg   2700
ccaccctgac cgagaagagc ttcgagaccg acatgaacct gaacttccag aacctgagcg   2760
tgatgggcct gagaatcctg ctgctgaagg tggccggctt caacctgctg atgaccctga   2820
ggctgtggag cagcagcggc agcggcgcca ccaacttcag cctgctgaag caggccggcg   2880
acgtggagga aaaccctggg cccatggaca agatcctgac cgccaccttt ctgctgctgg   2940
gcctgcacct ggccggcgtg aacggacagc agcaggagaa gagggatcag cagcaggtgc   3000
ggcagagccc ccagagcctg accgtgtggg agggcgagac cgccatcctg aactgcagct   3060
acgaggacag caccttcaac tacttccctt ggtatcagca gttccccggc gagggccctg   3120
ctctgctgat ctccatcaga agcgtgagcg acaagaagga ggacggcagg ttcaccatct   3180
```

```
ttttcaacaa gcgggagaag aagctgtccc tgcacatcac cgacagccag cccggcgaca   3240
gcgccaccta cttttgcgcc gccagcgaca actaccagct gatctggggc agcggcacca   3300
agctgatcat caagcccgac atccagaacc ccgagcccgc cgtgtaccag ctgaaggacc   3360
ccagaagcca ggacagcacc ctgtgcctgt tcaccgactt cgacagccag atcaacgtgc   3420
ccaagaccat ggagagcggc accttcatca ccgacaagac cgtgctggac atgaaggcca   3480
tggacagcaa gagcaacggc gccatcgcct ggtccaacca gaccagcttc acatgccagg   3540
acatcttcaa ggagaccaac gccacctacc ccagcagcga cgtgccctgc ggcatcacca   3600
gcgccagcta ccaccagggc gtgctgtccg ccaccatcct gtacgagatc ctgctgggca   3660
aggccacact gtacgccgtg ctggtgtccg gcctggtgct gatggccatg gtgaagaaga   3720
agaacagctg agtcgacgat aaaataaaag attttattta gtctccagaa aaagggggga   3780
atgaaagacc ccacctgtag gtttggcaag ctagcttaag taacgccatt ttggaaggca   3840
tggaaaaata cataactgag aatagagaag ttcagatcaa ggtcaggaac agatggaaca   3900
gctgaatatg ggccaaacag gatatctgtg gtaagcagtt cctgccccgg ctcagggcca   3960
agaacagatg gaacagctga atatgggcca aacaggatat ctgtggtaag cagttcctgc   4020
cccggctcag ggccaagaac agatggtccc cagatgcggt ccagccctca gcagtttcta   4080
gagaaccatc agatgtttcc agggtgcccc aaggacctga aatgaccctg tgccttattt   4140
gaactaacca atcagttcgc ttctcgcttc tgttcgcgcg cttctgctcc ccgagctcaa   4200
taaaagagcc cacaacccct cactcggggc gccagtcctc cgattgactg agtcgcccgg   4260
gtacccgtgt atccaataaa ccctcttgca gttgcatccg acttgtggtc tcgctgttcc   4320
ttgggagggt ctcctctgag tgattgacta cccgtcagcg ggggtctttc attctgcatt   4380
aatgaatcgg ccaacgcgcg gggagaggcg gtttgcgtat tgggcgctct tccgcttcct   4440
cgctcactga ctcgctgcgc tcggtcgttc ggctgcggcg agcggtatca gctcactcaa   4500
aggcggtaat acggttatcc acagaatcag gggataacgc aggaaagaac atgtgagcaa   4560
aaggccagca aaaggccagg aaccgtaaaa aggccgcgtt gctggcgttt ttccataggc   4620
tccgcccccc tgacgagcat cacaaaaatc gacgctcaag tcagaggtgg cgaaacccga   4680
caggactata aagataccag gcgtttcccc ctggaagctc cctcgtgcgc tctcctgttc   4740
cgaccctgcc gcttaccgga tacctgtccg cctttctccc ttcgggaagc gtggcgcttt   4800
ctcatagctc acgctgtagg tatctcagtt cggtgtaggt cgttcgctcc aagctgggct   4860
gtgtgcacga accccccgtt cagcccgacc gctgcgcctt atccggtaac tatcgtcttg   4920
agtccaaccc ggtaagacac gacttatcgc cactggcagc agccactggt aacaggatta   4980
gcagagcgag gtatgtaggc ggtgctacag agttcttgaa gtggtggcct aactacggct   5040
acactagaag gacagtattt ggtatctgcg ctctgctgaa gccagttacc ttcggaaaaa   5100
gagttggtag ctcttgatcc ggcaaacaaa ccaccgctgg tagcggtggt ttttttgttt   5160
gcaagcagca gattacgcgc agaaaaaaag gatctcaaga agatcctttg atcttttcta   5220
cggggtctga cgctcagtgg aacgaaaact cacgttaagg gattttggtc atgagattat   5280
caaaaaggat cttcacctag atccttttgc ggccggccgc aaatcaatct aaagtatata   5340
tgagtaaact tggtctgaca gttaccaatg cttaatcagt gaggcaccta tctcagcgat   5400
ctgtctattt cgttcatcca tagttgcctg actccccgtc gtgtagataa ctacgatacg   5460
ggagggctta ccatctggcc ccagtgctgc aatgataccg cgagacccac gctcaccggc   5520
```

tccagattta tcagcaataa accagccagc cggaagggcc gagcgcagaa gtggtcctgc 5580
aactttatcc gcctccatcc agtctattaa ttgttgccgg gaagctagag taagtagttc 5640
gccagttaat agtttgcgca acgttgttgc cattgctaca ggcatcgtgg tgtcacgctc 5700
gtcgtttggt atggcttcat tcagctccgg ttcccaacga tcaaggcgag ttacatgatc 5760
ccccatgttg tgcaaaaaag cggttagctc cttcggtcct ccgatcgttg tcagaagtaa 5820
gttggccgca gtgttatcac tcatggttat ggcagcactg cataattctc ttactgtcat 5880
gccatccgta agatgctttt ctgtgactgg tgagtactca accaagtcat tctgagaata 5940
gtgtatgcgg cgaccgagtt gctcttgccc ggcgtcaaca cgggataata ccgcgccaca 6000
tagcagaact ttaaaagtgc tcatcattgg aaaacgttct tcggggcgaa aactctcaag 6060
gatcttaccg ctgttgagat ccagttcgat gtaacccact cgtgcaccca actgatcttc 6120
agcatctttt actttcacca gcgtttctgg gtgagcaaaa acaggaaggc aaaatgccgc 6180
aaaaaaggga ataagggcga cacggaaatg ttgaatactc atactcttcc tttttcaata 6240
ttattgaagc atttatcagg gttattgtct catgagcgga tacatatttg aatgtattta 6300
gaaaaataaa caaatagggg ttccgcgcac atttc 6335

<210> SEQ ID NO 39
<211> LENGTH: 6335
<212> TYPE: DNA
<213> ORGANISM: Artificial Sequence
<220> FEATURE:
<223> OTHER INFORMATION: pMTB1186 vector

<400> SEQUENCE: 39
ctgcataatg aaagacccca cctgtaggtt tggcaagcta gcttaagtaa cgccattttg 60
caaggcatgg aaaaatacat aactgagaat agaaaagttc agatcaaggt caggaacaga 120
tggaacagct gaatatgggc caaagcggat atctgtggta agcagttcct gccccggctc 180
agggccaaga acagatggaa cagctgaata tgggccaaac aggatatctg tggtaagcag 240
ttcctgcccc ggctcagggc caagaacaga tggtccccag atgcggtcca gccctcagca 300
gtttctagag aaccatcaga tgtttccagg gtgccccaag gacctgaaat gaccctgtgc 360
cttatttgaa ctaaccaatc agttcgcttc tcgcttctgt tcgcgcgctt ctgctccccg 420
agctcaataa aagagcccac aacccctcac tcggggcgcc agtcctccga ttgactgagt 480
cgcccgggta cccgtgtatc caataaaccc tcttgcagtt gcatccgact tgtggtctcg 540
ctgttccttg ggagggtctc ctctgagtga ttgactaccc gtcagcgggg gtctttcatt 600
tgggggctcg tccgggatcg ggagacccct gcccagggac caccgaccca ccaccgggag 660
gtaagctggc cagcaactta tctgtgtctg tccgattgtc tagtgtctat gactgatttt 720
atgcgcctgc gtcggtacta gttagctaac tagctctgta tctggcggac ccgtggtgga 780
actgacgagt tcggaacacc cggccgcaac cctgggagac gtcccaggtc gggggccgtt 840
tttgtggccc gacctgagtc caaaaatccc gatcgttttg gactctttgg tgcacccccc 900
ttagaggagg gatatgtggt tctggtagga gacgagaacc taaaacagtt cccgcctccg 960
tctgaatttt tgctttcggt ttgggaccga agccgcgccg cgcgtcttgt ctgctgcagc 1020
atcgttctgt gttgtctctg tctgactgtg tttctgtatt tgtctgaaaa tatgggcccg 1080
ggccagactg ttaccactcc cttaagtttg accttaggtc actggaaaga tgtcgagcgg 1140
atcgctcaca accagtcggt agatgtcaag aagagacgtt gggttacctt ctgctctgca 1200
gaatggccaa cctttaacgt cggatggccg cgagacggca cctttaaccg agacctcatc 1260

```
acccaggtta agatcaaggt cttttcacct ggcccgcatg gacacccaga ccaggtcccc   1320

tacatcgtga cctgggaagc cttggctttt gacccccctc cctgggtcaa gccctttgta   1380

caccctaagc ctccgcctcc tcttcctcca tccgccccgt ctctccccct tgaacctcct   1440

cgttcgaccc cgcctcgatc ctccctttat ccagccctca ctccttctct aggcgccccc   1500

atatggccat atgagatctt atatggggca cccccgcccc ttgtaaactt ccctgaccct   1560

gacatgacaa gagttactaa cagcccctct ctccaagctc acttacaggc tctctactta   1620

gtccagcacg aagtctggag acctctggcg gcagcctacc aagaacaact ggaccgaccg   1680

gtggtacctc acccttaccg agtcggcgac acagtgtggg tccgccgaca ccagactaag   1740

aacctagaac ctcgctggaa aggaccttac acagtcctgc tgaccacccc caccgccctc   1800

aaagtagacg gcatcgcagc ttggatacac gccgcccacg tgaaggctgc cgaccccggg   1860

ggtggaccat cctctagact gccggatccg ccaccatgga caagatcctg accgccacct   1920

ttctgctgct gggcctgcac ctggccggcg tgaacggaca gcagcaggag aagagggatc   1980

agcagcaggt gcggcagagc cccccagagcc tgaccgtgtg ggagggcgag accgccatcc   2040

tgaactgcag ctacgaggac agcaccttca actacttccc ttggtatcag cagttccccg   2100

gcgagggccc tgctctgctg atctccatca gaagcgtgag cgacaagaag gaggacggca   2160

ggttcaccat ctttttcaac aagcgggaga agaagctgtc cctgcacatc accgacagcc   2220

agcccggcga cagcgccacc tacttttgcg ccgccagcga caactaccag ctgatctggg   2280

gcagcggcac caagctgatc atcaagcccg acatccagaa ccccgagccc gccgtgtacc   2340

agctgaagga ccccagaagc caggacagca ccctgtgcct gttcaccgac ttcgacagcc   2400

agatcaacgt gcccaagacc atggagagcg gcaccttcat caccgacaag accgtgctgg   2460

acatgaaggc catggacagc aagagcaacg gcgccatcgc ctggtccaac cagaccagct   2520

tcacatgcca ggacatcttc aaggagacca acgccaccta ccccagcagc gacgtgccct   2580

gcggcatcac cagcgccagc taccaccagg gcgtgctgtc cgccaccatc ctgtacgaga   2640

tcctgctggg caaggccaca ctgtacgccg tgctggtgtc cggcctggtg ctgatggcca   2700

tggtgaagaa gaagaacagc agcggcagcg gcgccaccaa cttcagcctg ctgaagcagg   2760

ccggcgacgt ggaggaaaac cctgggccca tggccccgcg ggtgctggcc gatagcgcct   2820

ggggcatcac actgctgtcc tgggtgaccg tgttcctgct gggcaccagc agcgccgaca   2880

gcggcgtggt gcagagcccc aggcacatca tcaaggagaa gggcggcaga agcgtgctga   2940

cctgcatccc catcagcggc cacagcaacg tggtgtggta tcagcagacc ctgggcaagg   3000

agctgaagtt cctgatccag cactacgaga aggtggagag ggacaagggc ttcctgccca   3060

gcaggttcag cgtgcagcag ttcgacgact accacagcga gatgaacatg agcgccctgg   3120

agctggagga cagcgccatg tacttttgcg ccagcagcag ggccaactac gagcagtact   3180

tcggccctgg caccaggctg accgtgctgg aggacctgag gaacgtgacc ccccccaagg   3240

tgtccctgtt cgagcccagc aaggccgaga tcgccaacaa gcagaaggcc accctggtgt   3300

gcctggccag gggcttcttc cccgaccacg tggagctgtc ttggtgggtg aacggcaagg   3360

aggtgcacag cggcgtgagc accgaccccc aggcctacaa ggagagcaac tacagctact   3420

gcctgagcag caggctgaga gtgagcgcca ccttctggca caaccccagg aaccacttcc   3480

gctgtcaggt gcagttccac ggcctgagcg aggaggacaa gtggcccgag ggcagcccca   3540

agcccgtgac ccagaacatc agcgccgagg cctggggcag agccgactgc gacgccaccc   3600
```

-continued

```
tgaccgagaa gagcttcgag accgacatga acctgaactt ccagaacctg agcgtgatgg   3660
gcctgagaat cctgctgctg aaggtggccg gcttcaacct gctgatgacc ctgaggctgt   3720
ggagcagctg agtcgacgat aaaataaaag attttattta gtctccagaa aaagggggga   3780
atgaaagacc ccacctgtag gtttggcaag ctagcttaag taacgccatt ttggaaggca   3840
tggaaaaata cataactgag aatagagaag ttcagatcaa ggtcaggaac agatggaaca   3900
gctgaatatg ggccaaacag gatatctgtg gtaagcagtt cctgccccgg ctcagggcca   3960
agaacagatg gaacagctga atatgggcca aacaggatat ctgtggtaag cagttcctgc   4020
cccggctcag ggccaagaac agatggtccc cagatgcggt ccagccctca gcagtttcta   4080
gagaaccatc agatgtttcc agggtgcccc aaggacctga aatgaccctg tgccttattt   4140
gaactaacca atcagttcgc ttctcgcttc tgttcgcgcg cttctgctcc ccgagctcaa   4200
taaaagagcc cacaacccct cactcggggc gccagtcctc cgattgactg agtcgcccgg   4260
gtacccgtgt atccaataaa ccctcttgca gttgcatccg acttgtggtc tcgctgttcc   4320
ttgggagggt ctcctctgag tgattgacta cccgtcagcg ggggtctttc attctgcatt   4380
aatgaatcgg ccaacgcgcg gggagaggcg gtttgcgtat tgggcgctct tccgcttcct   4440
cgctcactga ctcgctgcgc tcggtcgttc ggctgcggcg agcggtatca gctcactcaa   4500
aggcggtaat acggttatcc acagaatcag gggataacgc aggaaagaac atgtgagcaa   4560
aaggccagca aaaggccagg aaccgtaaaa aggccgcgtt gctggcgttt ttccataggc   4620
tccgcccccc tgacgagcat cacaaaaatc gacgctcaag tcagaggtgg cgaaacccga   4680
caggactata aagataccag gcgtttcccc ctggaagctc cctcgtgcgc tctcctgttc   4740
cgaccctgcc gcttaccgga tacctgtccg cctttctccc ttcgggaagc gtggcgcttt   4800
ctcatagctc acgctgtagg tatctcagtt cggtgtaggt cgttcgctcc aagctgggct   4860
gtgtgcacga accccccgtt cagcccgacc gctgcgcctt atccggtaac tatcgtcttg   4920
agtccaaccc ggtaagacac gacttatcgc cactggcagc agccactggt aacaggatta   4980
gcagagcgag gtatgtaggc ggtgctacag agttcttgaa gtggtggcct aactacggct   5040
acactagaag gacagtattt ggtatctgcg ctctgctgaa gccagttacc ttcggaaaaa   5100
gagttggtag ctcttgatcc ggcaaacaaa ccaccgctgg tagcggtggt ttttttgttt   5160
gcaagcagca gattacgcgc agaaaaaaag gatctcaaga agatcctttg atcttttcta   5220
cggggtctga cgctcagtgg aacgaaaact cacgttaagg gattttggtc atgagattat   5280
caaaaaggat cttcacctag atccttttgc ggccggccgc aaatcaatct aaagtatata   5340
tgagtaaact tggtctgaca gttaccaatg cttaatcagt gaggcaccta tctcagcgat   5400
ctgtctattt cgttcatcca tagttgcctg actccccgtc gtgtagataa ctacgatacg   5460
ggagggctta ccatctggcc ccagtgctgc aatgataccg cgagacccac gctcaccggc   5520
tccagattta tcagcaataa accagccagc cggaagggcc gagcgcagaa gtggtcctgc   5580
aactttatcc gcctccatcc agtctattaa ttgttgccgg gaagctagag taagtagttc   5640
gccagttaat agtttgcgca acgttgttgc cattgctaca ggcatcgtgg tgtcacgctc   5700
gtcgtttggt atggcttcat tcagctccgg ttcccaacga tcaaggcgag ttacatgatc   5760
ccccatgttg tgcaaaaaag cggttagctc cttcggtcct ccgatcgttg tcagaagtaa   5820
gttggccgca gtgttatcac tcatggttat ggcagcactg cataattctc ttactgtcat   5880
gccatccgta agatgctttt ctgtgactgg tgagtactca accaagtcat tctgagaata   5940
gtgtatgcgg cgaccgagtt gctcttgccc ggcgtcaaca cgggataata ccgcgccaca   6000
```

```
tagcagaact ttaaaagtgc tcatcattgg aaaacgttct tcggggcgaa aactctcaag   6060

gatcttaccg ctgttgagat ccagttcgat gtaacccact cgtgcaccca actgatcttc   6120

agcatctttt actttcacca gcgtttctgg gtgagcaaaa acaggaaggc aaaatgccgc   6180

aaaaaaggga ataagggcga cacggaaatg ttgaatactc atactcttcc tttttcaata   6240

ttattgaagc atttatcagg gttattgtct catgagcgga tacatatttg aatgtattta   6300

gaaaaataaa caaatagggg ttccgcgcac atttc                              6335
```

```
<210> SEQ ID NO 40
<211> LENGTH: 8941
<212> TYPE: DNA
<213> ORGANISM: Artificial Sequence
<220> FEATURE:
<223> OTHER INFORMATION: pMTB1281 vector

<400> SEQUENCE: 40

caggtggcac ttttcgggga aatgtgcgcg gaacccctat ttgtttattt ttctaaatac     60

attcaaatat gtatccgctc atgagacaat aaccctgata aatgcttcaa taatattgaa    120

aaaggaagag tatgagtatt caacatttcc gtgtcgccct tattcccttt tttgcggcat    180

tttgccttcc tgtttttgct cacccagaaa cgctggtgaa agtaaaagat gctgaagatc    240

agttgggtgc acgagtgggt tacatcgaac tggatctcaa cagcggtaag atccttgaga    300

gttttcgccc cgaagaacgt tttccaatga tgagcacttt taaagttctg ctatgtggcg    360

cggtattatc ccgtattgac gccgggcaag agcaactcgg tcgccgcata cactattctc    420

agaatgactt ggttgagtac tcaccagtca cagaaaagca tcttacggat ggcatgacag    480

taagagaatt atgcagtgct gccataacca tgagtgataa cactgcggcc aacttacttc    540

tgacaacgat cggaggaccg aaggagctaa ccgctttttt gcacaacatg ggggatcatg    600

taactcgcct tgatcgttgg gaaccggagc tgaatgaagc cataccaaac gacgagcgtg    660

acaccacgat gcctgtagca atggcaacaa cgttgcgcaa actattaact ggcgaactac    720

ttactctagc ttcccggcaa caattaatag actggatgga ggcggataaa gttgcaggac    780

cacttctgcg ctcggccctt ccggctggct ggtttattgc tgataaatct ggagccggtg    840

agcgtgggtc tcgcggtatc attgcagcac tggggccaga tggtaagccc tcccgtatcg    900

tagttatcta cacgacgggg agtcaggcaa ctatggatga acgaaataga cagatcgctg    960

agataggtgc ctcactgatt aagcattggt aactgtcaga ccaagtttac tcatatatac   1020

tttagattga tttaaaactt catttttaat ttaaaaggat ctaggtgaag atcctttttg   1080

ataatctcat gaccaaaatc ccttaacgtg agttttcgtt ccactgagcg tcagaccccg   1140

tagaaaagat caaaggatct tcttgagatc ctttttttct gcgcgtaatc tgctgcttgc   1200

aaacaaaaaa accaccgcta ccagcggtgg tttgtttgcc ggatcaagag ctaccaactc   1260

tttttccgaa ggtaactggc ttcagcagag cgcagatacc aaatactgtc cttctagtgt   1320

agccgtagtt aggccaccac ttcaagaact ctgtagcacc gcctacatac ctcgctctgc   1380

taatcctgtt accagtggct gctgccagtg gcgataagtc gtgtcttacc gggttggact   1440

caagacgata gttaccggat aaggcgcagc ggtcgggctg aacggggggt tcgtgcacac   1500

agcccagctt ggagcgaacg acctacaccg aactgagata cctacagcgt gagctatgag   1560

aaagcgccac gcttcccgaa gggagaaagg cggacaggta tccggtaagc ggcagggtcg   1620

gaacaggaga gcgcacgagg gagcttccag ggggaaacgc ctggtatctt tatagtcctg   1680
```

tcgggtttcg ccacctctga cttgagcgtc gatttttgtg atgctcgtca ggggggcgga 1740
gcctatggaa aaacgccagc aacgcggcct ttttacggtt cctggccttt tgctggcctt 1800
ttgctcacat gttctttcct gcgttatccc ctgattctgt ggataaccgt attaccgcct 1860
ttgagtgagc tgataccgct cgccgcagcc gaacgaccga gcgcagcgag tcagtgagcg 1920
aggaagcgga agagcgccca atacgcaaac cgcctctccc cgcgcgttgg ccgattcatt 1980
aatgcagctg gcacgacagg tttcccgact ggaaagcggg cagtgagcgc aacgcaatta 2040
atgtgagtta gctcactcat taggcacccc aggctttaca ctttatgctt ccggctcgta 2100
tgttgtgtgg aattgtgagc ggataacaat ttcacacagg aaacagctat gaccatgatt 2160
acgccaagcg cgcaattaac cctcactaaa gggaacaaaa gctggagctg caagcttggc 2220
cattgcatac gttgtatcca tatcataata tgtacattta tattggctca tgtccaacat 2280
taccgccatg ttgacattga ttattgacta gttattaata gtaatcaatt acggggtcat 2340
tagttcatag cccatatatg gagttccgcg ttacataact tacggtaaat ggcccgcctg 2400
gctgaccgcc caacgacccc cgcccattga cgtcaataat gacgtatgtt cccatagtaa 2460
cgccaatagg gactttccat tgacgtcaat gggtggagta tttacggtaa actgcccact 2520
tggcagtaca tcaagtgtat catatgccaa gtacgccccc tattgacgtc aatgacggta 2580
aatggcccgc ctggcattat gcccagtaca tgaccttatg ggactttcct acttggcagt 2640
acatctacgt attagtcatc gctattacca tggtgatgcg gttttggcag tacatcaatg 2700
ggcgtggata gcggtttgac tcacggggat ttccaagtct ccaccccatt gacgtcaatg 2760
ggagtttgtt ttggcaccaa aatcaacggg actttccaaa atgtcgtaac aactccgccc 2820
cattgacgca aatgggcggt aggcgtgtac ggtgggaggt ctatataagc agagctcgtt 2880
tagtgaaccg gggtctctct ggttagacca gatctgagcc tgggagctct ctggctaact 2940
agggaaccca ctgcttaagc ctcaataaag cttgccttga gtgcttcaag tagtgtgtgc 3000
ccgtctgttg tgtgactctg gtaactagag atccctcaga cccttttagt cagtgtggaa 3060
aatctctagc agtggcgccc gaacagggac ctgaaagcga aagggaaacc agaggagctc 3120
tctcgacgca ggactcggct tgctgaagcg cgcacggcaa gaggcgaggg gcggcgactg 3180
gtgagtacgc caaaaatttt gactagcgga ggctagaagg agagagatgg gtgcgagagc 3240
gtcagtatta agcgggggag aattagatcg cgatgggaaa aaattcggtt aaggccaggg 3300
ggaaagaaaa aatataaatt aaaacatata gtatgggcaa gcagggagct agaacgattc 3360
gcagttaatc ctggcctgtt agaaacatca gaaggctgta gacaaatact gggacagcta 3420
caaccatccc ttcagacagg atcagaagaa cttagatcat tatataatac agtagcaacc 3480
ctctattgtg tgcatcaaag gatagagata aaagacacca aggaagcttt agacaagata 3540
gaggaagagc aaaacaaaag taagaccacc gcacagcaag cggccgctga tcttcagacc 3600
tggaggagga gatatgaggg acaattggag aagtgaatta tataaatata aagtagtaaa 3660
aattgaacca ttaggagtag cacccaccaa ggcaaagaga agagtggtgc agagagaaaa 3720
aagagcagtg ggaataggag ctttgttcct tgggttcttg ggagcagcag gaagcactat 3780
gggcgcagcc tcaatgacgc tgacggtaca ggccagacaa ttattgtctg gtatagtgca 3840
gcagcagaac aatttgctga gggctattga ggcgcaacag catctgttgc aactcacagt 3900
ctggggcatc aagcagctcc aggcaagaat cctggctgtg gaaagatacc taaaggatca 3960
acagctcctg gggatttggg gttgctctgg aaaactcatt tgcaccactg ctgtgccttg 4020
gaatgctagt tggagtaata aatctctgga acagattgga atcacacgac ctggatggag 4080

-continued tgggacagag aaattaacaa ttacacaagc ttaatacact ccttaattga agaatcgcaa 4140
aaccagcaag aaaagaatga acaagaatta ttggaattag ataaatgggc aagtttgtgg 4200
aattggttta acataacaaa ttggctgtgg tatataaaat tattcataat gatagtagga 4260
ggcttggtag gtttaagaat agtttttgct gtactttcta tagtgaatag agttaggcag 4320
ggatattcac cattatcgtt tcagacccac ctcccaaccc cgaggggacc cgacaggccc 4380
gaaggaatag aagaagaagg tggagagaga gacagagaca gatccattcg attagtgaac 4440
ggatctcgac ggtatcgata agctaattca caaatggcag tattcatcca caattttaaa 4500
agaaaagggg ggattggggg gtacagtgca ggggaaagaa tagtagacat aatagcaaca 4560
gacatacaaa ctaaagaatt acaaaaacaa attacaaaaa ttcaaaattt tcgggtttat 4620
tacagggaca gcagagatcc agtttgggaa ttagcttgat cgattagtcc aatttgttaa 4680
agacaggata tcagtggtcc aggctctagt tttgactcaa caatatcacc agctgaagcc 4740
tatagagtac gagccataga tagaataaaa gattttattt agtctccaga aaaagggggg 4800
aatgaaagac cccacctgta ggtttggcaa gctaggatca aggttaggaa cagagagaca 4860
gcagaatatg ggccaaacag gatatctgtg gtaagcagtt cctgccccgg ctcagggcca 4920
agaacagttg gaacagcaga atatgggcca aacaggatat ctgtggtaag cagttcctgc 4980
cccggctcag ggccaagaac agatggtccc cagatgcggt cccgccctca gcagtttcta 5040
gagaaccatc agatgtttcc agggtgcccc aaggacctga aatgaccctg tgccttattt 5100
gaactaacca atcagttcgc ttctcgcttc tgttcgcgcg cttctgctcc ccgagctcaa 5160
taaaagagcc cacaacccct cactcggcgc gatctagatc tcgaatcgaa ttcgttaacc 5220
tcgagggatc catggcgacg ggttcaagaa cttccctact tcttgcattt ggcctgcttt 5280
gtttgccgtg gttacaggaa gcctcagcac aacagaagga ggtggagcag aattctggac 5340
ccctcagtgt tccagaggga gccattgcct ctctcaactg cacttacagt gaccgaggtt 5400
cccagtcctt cttctggtac agacaatatt ctgggaaaag ccctgagttg ataatgttca 5460
tatactccaa tggtgacaaa gaagatggaa ggtttacagc acagctcaat aaagccagcc 5520
agtatgtttc tctgctcatc agagactccc agcccagtga ttcagccacc tacctctgtg 5580
ccgtgaactt cggaggagga aagcttatct tcggacaggg aacggagtta tctgtgaaac 5640
ccaatatcca gaaccctgac cctgccgtgt accagctgag agactctaaa tccagtgaca 5700
agtctgtctg cctattcacc gattttgatt ctcaaacaaa tgtgtcacaa agtaaggatt 5760
ctgatgtgta tatcacagac aaaactgtgc tagacatgag gtctatggac ttcaagagca 5820
acagtgctgt ggcctggagc aacaaatctg actttgcatg tgcaaacgcc ttcaacaaca 5880
gcattattcc agaagacacc ttcttcccca gcccagaaag ttcctgtgat gtcaagctgg 5940
tcgagaaaag ctttgaaaca gatacgaacc taaactttca aaacctgtca gtgattgggt 6000
tccgaatcct cctcctgaaa gtggccgggt ttaatctgct catgacgctg cggctgtggt 6060
ccagcagggc aaaacgttcg ggttcgggtg cgccagtaaa gcagacatta aactttgatt 6120
tgctgaaact tgcaggtgat gtagagtcaa atccaggtcc aatggcaaca gggagccgaa 6180
cctctctgct ccttgctttc gggctccttt gcctaccgtg cctgcaggag ggctcggcag 6240
ggatcaccca ggcaccaaca tctcagatcc tggcagcagg acggcgcatg acactgagat 6300
gtacccagga tatgagacat aatgccatgt actggtatag acaagatcta ggactggggc 6360
taaggctcat ccattattca aatactgcag gtaccactgg caaaggagaa gtccctgatg 6420

-continued

```
gttatagtgt ctccagagca aacacagatg atttccccct cacgttggcg tctgctgtac   6480
cctctcagac atctgtgtac ttctgtgcca gcagcctaag tttcggcact gaagctttct   6540
ttggacaagg caccagactc acagttgtag aggacctgaa caaggtgttc ccacccgagg   6600
tcgctgtgtt tgagccatca gaagcagaga tctcccacac ccaaaaggcc acactggtgt   6660
gcctggccac aggcttcttc cctgaccacg tggagctgag ctggtgggtg aatgggaagg   6720
aggtgcacag tggggtcagc acggacccgc agcccctcaa ggagcagccc gccctcaatg   6780
actccagata ctgcctgagc agccgcctga gggtctcggc caccttctgg cagaaccccc   6840
gcaaccactt ccgctgtcaa gtccagttct acgggctctc ggagaatgac gagtggaccc   6900
aggatagggc caaacccgtc acccagatcg tcagcgccga agcctggggt agagcagact   6960
gtggctttac ctcggtgtcc taccagcaag ggtcctgtc tgccaccatc ctctatgaga   7020
tcctgctagg gaaggccacc ctgtatgctg tgctggtcag cgcccttgtg ttgatggcca   7080
tggtcaagag aaaggatttc agagccaaaa gaggctccgg agccactaac ttctccctgt   7140
tgaaacaggc tggcgatgtt gaagaaaacc ccggtcctat gggggcaggt gccaccggcc   7200
gcgccatgga cgggccgcgc ctgctgctgt tgctgcttct gggggtgtcc cttggaggtg   7260
ccaaggagca gaagctgatc agcgaggagg acctggagat ccctggccgt tggattacac   7320
ggtccacacc cccagagggc tcggacagca cagcccccag cacccaggag cctgaggcac   7380
ctccagaaca agacctcata gccagcacgg tggcaggtgt ggtgaccaca gtgatgggca   7440
gctcccagcc cgtggtgacc cgaggcacca ccgacaacct catccctgtc tattgctcca   7500
tcctggctgc tgtggttgtg ggtcttgtgg cctacatagc cttcaagagg taaaggatcc   7560
cccggggtcg actgatcaaa ttcgagctcg gtacctttaa gaccaatgac ttacaaggca   7620
gctgtagatc ttagccactt tttaaaagaa aaggggggac tggaagggct aattcactcc   7680
caacgaagac aagatctgct ttttgcttgt actgggtctc tctggttaga ccagatctga   7740
gcctgggagc tctctggcta actagggaac ccactgctta agcctcaata aagcttgcct   7800
tgagtgcttc aagtagtgtg tgcccgtctg ttgtgtgact ctggtaacta gagatccctc   7860
agaccctttt agtcagtgtg gaaaatctct agcagtagta gttcatgtca tcttattatt   7920
cagtatttat aacttgcaaa gaaatgaata tcagagagtg agaggaactt gtttattgca   7980
gcttataatg gttacaaata aagcaatagc atcacaaatt tcacaaataa agcatttttt   8040
tcactgcatt ctagttgtgg tttgtccaaa ctcatcaatg tatcttatca tgtctggctc   8100
tagctatccc gcccctaact ccgcccatcc cgcccctaac tccgcccagt tccgcccatt   8160
ctccgcccca tggctgacta atttttttta tttatgcaga ggccgaggcc gcctcggcct   8220
ctgagctatt ccagaagtag tgaggaggct tttttggagg cctaggcttt tgcgtcgaga   8280
cgtacccaat tcgccctata gtgagtcgta ttacgcgcgc tcactggccg tcgttttaca   8340
acgtcgtgac tgggaaaacc ctggcgttac ccaacttaat cgccttgcag cacatccccc   8400
tttcgccagc tggcgtaata gcgaagaggc ccgcaccgat cgcccttccc aacagttgcg   8460
cagcctgaat ggcgaatggc gcgacgcgcc ctgtagcggc gcattaagcg cggcgggtgt   8520
ggtggttacg cgcagcgtga ccgctacact tgccagcgcc ctagcgcccg ctcctttcgc   8580
tttcttccct tcctttctcg ccacgttcgc cggctttccc cgtcaagctc taaatcgggg   8640
gctcccttta gggttccgat ttagtgcttt acggcacctc gaccccaaaa aacttgatta   8700
gggtgatggt tcacgtagtg ggccatcgcc ctgatagacg gtttttcgcc ctttgacgtt   8760
ggagtccacg ttctttaata gtggactctt gttccaaact ggaacaacac tcaaccctat   8820
```

ctcggtctat tcttttgatt tataagggat tttgccgatt tcggcctatt ggttaaaaaa 8880
tgagctgatt taacaaaaat ttaacgcgaa ttttaacaaa atattaacgt ttacaatttc 8940
c 8941

<210> SEQ ID NO 41
<211> LENGTH: 8941
<212> TYPE: DNA
<213> ORGANISM: Artificial Sequence
<220> FEATURE:
<223> OTHER INFORMATION: pMTB1282 vector

<400> SEQUENCE: 41
caggtggcac ttttcgggga aatgtgcgcg gaacccctat ttgtttattt ttctaaatac 60
attcaaatat gtatccgctc atgagacaat aaccctgata aatgcttcaa taatattgaa 120
aaaggaagag tatgagtatt caacatttcc gtgtcgccct tattcccttt tttgcggcat 180
tttgccttcc tgtttttgct cacccagaaa cgctggtgaa agtaaaagat gctgaagatc 240
agttgggtgc acgagtgggt tacatcgaac tggatctcaa cagcggtaag atccttgaga 300
gttttcgccc cgaagaacgt tttccaatga tgagcacttt taaagttctg ctatgtggcg 360
cggtattatc ccgtattgac gccgggcaag agcaactcgg tcgccgcata cactattctc 420
agaatgactt ggttgagtac tcaccagtca cagaaaagca tcttacggat ggcatgacag 480
taagagaatt atgcagtgct gccataacca tgagtgataa cactgcggcc aacttacttc 540
tgacaacgat cggaggaccg aaggagctaa ccgctttttt gcacaacatg ggggatcatg 600
taactcgcct tgatcgttgg gaaccggagc tgaatgaagc cataccaaac gacgagcgtg 660
acaccacgat gcctgtagca atggcaacaa cgttgcgcaa actattaact ggcgaactac 720
ttactctagc ttcccggcaa caattaatag actggatgga ggcggataaa gttgcaggac 780
cacttctgcg ctcggccctt ccggctggct ggtttattgc tgataaatct ggagccggtg 840
agcgtgggtc tcgcggtatc attgcagcac tggggccaga tggtaagccc tcccgtatcg 900
tagttatcta cacgacgggg agtcaggcaa ctatggatga acgaaataga cagatcgctg 960
agataggtgc ctcactgatt aagcattggt aactgtcaga ccaagtttac tcatatatac 1020
tttagattga tttaaaactt catttttaat ttaaaaggat ctaggtgaag atcctttttg 1080
ataatctcat gaccaaaatc ccttaacgtg agttttcgtt ccactgagcg tcagaccccg 1140
tagaaaagat caaaggatct tcttgagatc ctttttttct gcgcgtaatc tgctgcttgc 1200
aaacaaaaaa accaccgcta ccagcggtgg tttgtttgcc ggatcaagag ctaccaactc 1260
tttttccgaa ggtaactggc ttcagcagag cgcagatacc aaatactgtc cttctagtgt 1320
agccgtagtt aggccaccac ttcaagaact ctgtagcacc gcctacatac ctcgctctgc 1380
taatcctgtt accagtggct gctgccagtg gcgataagtc gtgtcttacc gggttggact 1440
caagacgata gttaccggat aaggcgcagc ggtcgggctg aacggggggt tcgtgcacac 1500
agcccagctt ggagcgaacg acctacaccg aactgagata cctacagcgt gagctatgag 1560
aaagcgccac gcttcccgaa gggagaaagg cggacaggta tccggtaagc ggcagggtcg 1620
gaacaggaga gcgcacgagg gagcttccag ggggaaacgc ctggtatctt tatagtcctg 1680
tcgggtttcg ccacctctga cttgagcgtc gatttttgtg atgctcgtca ggggggcgga 1740
gcctatggaa aaacgccagc aacgcggcct ttttacggtt cctggccttt tgctggcctt 1800
ttgctcacat gttctttcct gcgttatccc ctgattctgt ggataaccgt attaccgcct 1860

-continued

```
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttggc   2220
cattgcatac gttgtatcca tatcataata tgtacattta tattggctca tgtccaacat   2280
taccgccatg ttgacattga ttattgacta gttattaata gtaatcaatt acggggtcat   2340
tagttcatag cccatatatg gagttccgcg ttacataact tacggtaaat ggcccgcctg   2400
gctgaccgcc caacgacccc cgcccattga cgtcaataat gacgtatgtt cccatagtaa   2460
cgccaatagg gactttccat tgacgtcaat gggtggagta tttacggtaa actgcccact   2520
tggcagtaca tcaagtgtat catatgccaa gtacgccccc tattgacgtc aatgacggta   2580
aatggcccgc ctggcattat gcccagtaca tgaccttatg ggactttcct acttggcagt   2640
acatctacgt attagtcatc gctattacca tggtgatgcg gttttggcag tacatcaatg   2700
ggcgtggata gcggtttgac tcacggggat ttccaagtct ccaccccatt gacgtcaatg   2760
ggagtttgtt ttggcaccaa aatcaacggg actttccaaa atgtcgtaac aactccgccc   2820
cattgacgca aatgggcggt aggcgtgtac ggtgggaggt ctatataagc agagctcgtt   2880
tagtgaaccg gggtctctct ggttagacca gatctgagcc tgggagctct ctggctaact   2940
agggaaccca ctgcttaagc ctcaataaag cttgccttga gtgcttcaag tagtgtgtgc   3000
ccgtctgttg tgtgactctg gtaactagag atccctcaga cccttttagt cagtgtggaa   3060
aatctctagc agtggcgccc gaacagggac ctgaaagcga aagggaaacc agaggagctc   3120
tctcgacgca ggactcggct tgctgaagcg cgcacggcaa gaggcgaggg gcggcgactg   3180
gtgagtacgc caaaaatttt gactagcgga ggctagaagg agagagatgg gtgcgagagc   3240
gtcagtatta agcgggggag aattagatcg cgatgggaaa aaattcggtt aaggccaggg   3300
ggaaagaaaa aatataaatt aaaacatata gtatgggcaa gcagggagct agaacgattc   3360
gcagttaatc ctggcctgtt agaaacatca gaaggctgta gacaaatact gggacagcta   3420
caaccatccc ttcagacagg atcagaagaa cttagatcat tatataatac agtagcaacc   3480
ctctattgtg tgcatcaaag gatagagata aaagacacca aggaagcttt agacaagata   3540
gaggaagagc aaaacaaaag taagaccacc gcacagcaag cggccgctga tcttcagacc   3600
tggaggagga gatatgaggg acaattggag aagtgaatta tataaatata aagtagtaaa   3660
aattgaacca ttaggagtag cacccaccaa ggcaaagaga agagtggtgc agagagaaaa   3720
aagagcagtg ggaataggag ctttgttcct tgggttcttg ggagcagcag gaagcactat   3780
gggcgcagcc tcaatgacgc tgacggtaca ggccagacaa ttattgtctg gtatagtgca   3840
gcagcagaac aatttgctga gggctattga ggcgcaacag catctgttgc aactcacagt   3900
ctggggcatc aagcagctcc aggcaagaat cctggctgtg gaaagatacc taaaggatca   3960
acagctcctg gggatttggg gttgctctgg aaaactcatt tgcaccactg ctgtgccttg   4020
gaatgctagt tggagtaata aatctctgga acagattgga atcacacgac ctggatggag   4080
tgggacagag aaattaacaa ttacacaagc ttaatacact ccttaattga agaatcgcaa   4140
aaccagcaag aaaagaatga acaagaatta ttggaattag ataaatgggc aagtttgtgg   4200
aattggttta acataacaaa ttggctgtgg tatataaaat tattcataat gatagtagga   4260
```

ggcttggtag gtttaagaat agtttttgct gtactttcta tagtgaatag agttaggcag 4320
ggatattcac cattatcgtt tcagacccac ctcccaaccc cgaggggacc cgacaggccc 4380
gaaggaatag aagaagaagg tggagagaga gacagagaca gatccattcg attagtgaac 4440
ggatctcgac ggtatcgata agctaattca caaatggcag tattcatcca caattttaaa 4500
agaaaagggg ggattggggg gtacagtgca ggggaaagaa tagtagacat aatagcaaca 4560
gacatacaaa ctaaagaatt acaaaaacaa attacaaaaa ttcaaaattt tcgggtttat 4620
tacagggaca gcagagatcc agtttgggaa ttagcttgat cgattagtcc aatttgttaa 4680
agacaggata tcagtggtcc aggctctagt tttgactcaa caatatcacc agctgaagcc 4740
tatagagtac gagccataga tagaataaaa gattttattt agtctccaga aaaagggggg 4800
aatgaaagac cccacctgta ggtttggcaa gctaggatca aggttaggaa cagagagaca 4860
gcagaatatg ggccaaacag gatatctgtg gtaagcagtt cctgccccgg ctcagggcca 4920
agaacagttg gaacagcaga atatgggcca aacaggatat ctgtggtaag cagttcctgc 4980
cccggctcag ggccaagaac agatggtccc cagatgcggt cccgccctca gcagtttcta 5040
gagaaccatc agatgtttcc agggtgcccc aaggacctga aatgaccctg tgccttattt 5100
gaactaacca atcagttcgc ttctcgcttc tgttcgcgcg cttctgctcc ccgagctcaa 5160
taaaagagcc cacaacccct cactcggcgc gatctagatc tcgaatcgaa ttcgttaacc 5220
tcgagggatc catggcgacg ggttcaagaa cttccctact tcttgcattt ggcctgcttt 5280
gtttgccgtg gttacaggaa gcctcagcag ggatcaccca ggcaccaaca tctcagatcc 5340
tggcagcagg acggcgcatg acactgagat gtacccagga tatgagacat aatgccatgt 5400
actggtatag acaagatcta ggactggggc taaggctcat ccattattca aatactgcag 5460
gtaccactgg caaaggagaa gtccctgatg gttatagtgt ctccagagca aacacagatg 5520
atttcccccct cacgttggcg tctgctgtac cctctcagac atctgtgtac ttctgtgcca 5580
gcagcctaag tttcggcact gaagctttct ttggacaagg caccagactc acagttgtag 5640
aggacctgaa caaggtgttc ccacccgagg tcgctgtgtt tgagccatca gaagcagaga 5700
tctcccacac ccaaaaggcc acactggtgt gcctggccac aggcttcttc cctgaccacg 5760
tggagctgag ctggtgggtg aatgggaagg aggtgcacag tggggtcagc acggacccgc 5820
agcccctcaa ggagcagccc gccctcaatg actccagata ctgcctgagc agccgcctga 5880
gggtctcggc caccttctgg cagaaccccc gcaaccactt ccgctgtcaa gtccagttct 5940
acgggctctc ggagaatgac gagtggaccc aggatagggc caaacccgtc acccagatcg 6000
tcagcgccga agcctggggt agagcagact gtgatgtcaa gctggtcgag aaaagctttg 6060
aaacagatac gaacctaaac tttcaaaacc tgtcagtgat tgggttccga atcctcctcc 6120
tgaaagtggc cgggtttaat ctgctcatga cgctgcggct gtggtccagc agggcaaaac 6180
gttcgggttc gggtgcgcca gtaaagcaga cattaaactt tgatttgctg aaacttgcag 6240
gtgatgtaga gtcaaatcca ggtccaatgg caacagggag ccgaacctct ctgctccttg 6300
ctttcgggct cctttgccta ccgtgcctgc aggagggctc ggcacaacag aaggaggtgg 6360
agcagaattc tggacccctc agtgttccag agggagccat tgcctctctc aactgcactt 6420
acagtgaccg aggttcccag tccttcttct ggtacagaca atattctggg aaaagccctg 6480
agttgataat gttcatatac tccaatggtg acaaagaaga tggaaggttt acagcacagc 6540
tcaataaagc cagccagtat gtttctctgc tcatcagaga ctcccagccc agtgattcag 6600

-continued

```
ccacctacct ctgtgccgtg aacttcggag gaggaaagct tatcttcgga cagggaacgg   6660
agttatctgt gaaacccaat atccagaacc ctgaccctgc cgtgtaccag ctgagagact   6720
ctaaatccag tgacaagtct gtctgcctat tcaccgattt tgattctcaa acaaatgtgt   6780
cacaaagtaa ggattctgat gtgtatatca cagacaaaac tgtgctagac atgaggtcta   6840
tggacttcaa gagcaacagt gctgtggcct ggagcaacaa atctgacttt gcatgtgcaa   6900
acgccttcaa caacagcatt attccagaag acaccttctt ccccagccca gaaagttcct   6960
gtggctttac ctcggtgtcc taccagcaag ggtcctgtc tgccaccatc ctctatgaga    7020
tcctgctagg gaaggccacc ctgtatgctg tgctggtcag cgcccttgtg ttgatggcca   7080
tggtcaagag aaaggatttc agagccaaaa gaggctccgg agccactaac ttctccctgt   7140
tgaaacaggc tggcgatgtt gaagaaaacc ccggtcctat gggggcaggt gccaccggcc   7200
gcgccatgga cgggccgcgc ctgctgctgt tgctgcttct gggggtgtcc cttggaggtg   7260
ccaaggagca gaagctgatc agcgaggagg acctggagat ccctggccgt tggattacac   7320
ggtccacacc cccagagggc tcggacagca cagcccccag cacccaggag cctgaggcac   7380
ctccagaaca agacctcata gccagcacgg tggcaggtgt ggtgaccaca gtgatgggca   7440
gctcccagcc cgtggtgacc cgaggcacca ccgacaacct catccctgtc tattgctcca   7500
tcctggctgc tgtggttgtg ggtcttgtgg cctacatagc cttcaagagg taaaggatcc   7560
cccggggtcg actgatcaaa ttcgagctcg gtacctttaa gaccaatgac ttacaaggca   7620
gctgtagatc ttagccactt tttaaaagaa aaggggggac tggaagggct aattcactcc   7680
caacgaagac aagatctgct tttgcttgt actgggtctc tctggttaga ccagatctga    7740
gcctgggagc tctctggcta actagggaac ccactgctta agcctcaata aagcttgcct   7800
tgagtgcttc aagtagtgtg tgcccgtctg ttgtgtgact ctggtaacta gagatccctc   7860
agaccctttt agtcagtgtg gaaaatctct agcagtagta gttcatgtca tcttattatt   7920
cagtatttat aacttgcaaa gaaatgaata tcagagagtg agaggaactt gtttattgca   7980
gcttataatg gttacaaata aagcaatagc atcacaaatt tcacaaataa agcatttttt   8040
tcactgcatt ctagttgtgg tttgtccaaa ctcatcaatg tatcttatca tgtctggctc   8100
tagctatccc gcccctaact ccgcccatcc cgcccctaac tccgcccagt tccgcccatt   8160
ctccgcccca tggctgacta attttttta tttatgcaga ggccgaggcc gcctcggcct     8220
ctgagctatt ccagaagtag tgaggaggct tttttggagg cctaggcttt tgcgtcgaga   8280
cgtacccaat tcgccctata gtgagtcgta ttacgcgcgc tcactggccg tcgttttaca   8340
acgtcgtgac tgggaaaacc ctggcgttac ccaacttaat cgccttgcag cacatccccc   8400
tttcgccagc tggcgtaata gcgaagaggc ccgcaccgat cgcccttccc aacagttgcg   8460
cagcctgaat ggcgaatggc gcgacgcgcc ctgtagcggc gcattaagcg cggcgggtgt   8520
ggtggttacg cgcagcgtga ccgctacact tgccagcgcc ctagcgcccg ctcctttcgc   8580
tttcttccct tcctttctcg ccacgttcgc cggctttccc cgtcaagctc taaatcgggg   8640
gctcccttta gggttccgat ttagtgcttt acggcacctc gaccccaaaa aacttgatta   8700
gggtgatggt tcacgtagtg ggccatcgcc ctgatagacg gtttttcgcc ctttgacgtt   8760
ggagtccacg ttctttaata gtggactctt gttccaaact ggaacaacac tcaaccctat   8820
ctcggtctat tcttttgatt tataagggat tttgccgatt tcggcctatt ggttaaaaaa   8880
tgagctgatt taacaaaaat ttaacgcgaa ttttaacaaa atattaacgt ttacaatttc   8940
c                                                                   8941
```

<210> SEQ ID NO 42
<211> LENGTH: 8941
<212> TYPE: DNA
<213> ORGANISM: Artificial Sequence
<220> FEATURE:
<223> OTHER INFORMATION: pMTB1283 vector

<400> SEQUENCE: 42
caggtggcac ttttcgggga aatgtgcgcg gaacccctat ttgtttattt ttctaaatac 60
attcaaatat gtatccgctc atgagacaat aaccctgata aatgcttcaa taatattgaa 120
aaaggaagag tatgagtatt caacatttcc gtgtcgccct tattcccttt tttgcggcat 180
tttgccttcc tgtttttgct cacccagaaa cgctggtgaa agtaaaagat gctgaagatc 240
agttgggtgc acgagtgggt tacatcgaac tggatctcaa cagcggtaag atccttgaga 300
gttttcgccc cgaagaacgt tttccaatga tgagcacttt taaagttctg ctatgtggcg 360
cggtattatc ccgtattgac gccgggcaag agcaactcgg tcgccgcata cactattctc 420
agaatgactt ggttgagtac tcaccagtca cagaaaagca tcttacggat ggcatgacag 480
taagagaatt atgcagtgct gccataacca tgagtgataa cactgcggcc aacttacttc 540
tgacaacgat cggaggaccg aaggagctaa ccgctttttt gcacaacatg ggggatcatg 600
taactcgcct tgatcgttgg gaaccggagc tgaatgaagc cataccaaac gacgagcgtg 660
acaccacgat gcctgtagca atggcaacaa cgttgcgcaa actattaact ggcgaactac 720
ttactctagc ttcccggcaa caattaatag actggatgga ggcggataaa gttgcaggac 780
cacttctgcg ctcggccctt ccggctggct ggtttattgc tgataaatct ggagccggtg 840
agcgtgggtc tcgcggtatc attgcagcac tggggccaga tggtaagccc tcccgtatcg 900
tagttatcta cacgacgggg agtcaggcaa ctatggatga acgaaataga cagatcgctg 960
agataggtgc ctcactgatt aagcattggt aactgtcaga ccaagtttac tcatatatac 1020
tttagattga tttaaaactt catttttaat ttaaaaggat ctaggtgaag atcctttttg 1080
ataatctcat gaccaaaatc ccttaacgtg agttttcgtt ccactgagcg tcagaccccg 1140
tagaaaagat caaaggatct tcttgagatc cttttttct gcgcgtaatc tgctgcttgc 1200
aaacaaaaaa accaccgcta ccagcggtgg tttgtttgcc ggatcaagag ctaccaactc 1260
tttttccgaa ggtaactggc ttcagcagag cgcagatacc aaatactgtc cttctagtgt 1320
agccgtagtt aggccaccac ttcaagaact ctgtagcacc gcctacatac ctcgctctgc 1380
taatcctgtt accagtggct gctgccagtg gcgataagtc gtgtcttacc gggttggact 1440
caagacgata gttaccggat aaggcgcagc ggtcgggctg aacggggggt tcgtgcacac 1500
agcccagctt ggagcgaacg acctacaccg aactgagata cctacagcgt gagctatgag 1560
aaagcgccac gcttcccgaa gggagaaagg cggacaggta tccggtaagc ggcagggtcg 1620
gaacaggaga gcgcacgagg gagcttccag ggggaaacgc ctggtatctt tatagtcctg 1680
tcgggtttcg ccacctctga cttgagcgtc gatttttgtg atgctcgtca ggggggcgga 1740
gcctatggaa aaacgccagc aacgcggcct ttttacggtt cctggccttt tgctggcctt 1800
ttgctcacat gttctttcct gcgttatccc ctgattctgt ggataaccgt attaccgcct 1860
ttgagtgagc tgataccgct cgccgcagcc gaacgaccga gcgcagcgag tcagtgagcg 1920
aggaagcgga agagcgccca atacgcaaac cgcctctccc cgcgcgttgg ccgattcatt 1980
aatgcagctg gcacgacagg tttcccgact ggaaagcggg cagtgagcgc aacgcaatta 2040

-continued

```
atgtgagtta gctcactcat taggcacccc aggctttaca ctttatgctt ccggctcgta   2100

tgttgtgtgg aattgtgagc ggataacaat ttcacacagg aaacagctat gaccatgatt   2160

acgccaagcg cgcaattaac cctcactaaa gggaacaaaa gctggagctg caagcttggc   2220

cattgcatac gttgtatcca tatcataata tgtacattta tattggctca tgtccaacat   2280

taccgccatg ttgacattga ttattgacta gttattaata gtaatcaatt acggggtcat   2340

tagttcatag cccatatatg gagttccgcg ttacataact tacggtaaat ggcccgcctg   2400

gctgaccgcc caacgacccc cgcccattga cgtcaataat gacgtatgtt cccatagtaa   2460

cgccaatagg gactttccat tgacgtcaat gggtggagta tttacggtaa actgcccact   2520

tggcagtaca tcaagtgtat catatgccaa gtacgccccc tattgacgtc aatgacggta   2580

aatggcccgc ctggcattat gcccagtaca tgaccttatg ggactttcct acttggcagt   2640

acatctacgt attagtcatc gctattacca tggtgatgcg gttttggcag tacatcaatg   2700

ggcgtggata gcggtttgac tcacggggat ttccaagtct ccaccccatt gacgtcaatg   2760

ggagtttgtt ttggcaccaa aatcaacggg actttccaaa atgtcgtaac aactccgccc   2820

cattgacgca aatgggcggt aggcgtgtac ggtgggaggt ctatataagc agagctcgtt   2880

tagtgaaccg gggtctctct ggttagacca gatctgagcc tgggagctct ctggctaact   2940

agggaaccca ctgcttaagc ctcaataaag cttgccttga gtgcttcaag tagtgtgtgc   3000

ccgtctgttg tgtgactctg gtaactagag atccctcaga cccttttagt cagtgtggaa   3060

aatctctagc agtggcgccc gaacagggac ctgaaagcga aagggaaacc agaggagctc   3120

tctcgacgca ggactcggct tgctgaagcg cgcacggcaa gaggcgaggg gcggcgactg   3180

gtgagtacgc caaaaatttt gactagcgga ggctagaagg agagagatgg gtgcgagagc   3240

gtcagtatta agcgggggag aattagatcg cgatgggaaa aaattcggtt aaggccaggg   3300

ggaaagaaaa aatataaatt aaaacatata gtatgggcaa gcagggagct agaacgattc   3360

gcagttaatc ctggcctgtt agaaacatca gaaggctgta gacaaatact gggacagcta   3420

caaccatccc ttcagacagg atcagaagaa cttagatcat tatataatac agtagcaacc   3480

ctctattgtg tgcatcaaag gatagagata aaagacacca aggaagcttt agacaagata   3540

gaggaagagc aaaacaaaag taagaccacc gcacagcaag cggccgctga tcttcagacc   3600

tggaggagga gatatgaggg acaattggag aagtgaatta tataaatata aagtagtaaa   3660

aattgaacca ttaggagtag cacccaccaa ggcaaagaga agagtggtgc agagagaaaa   3720

aagagcagtg ggaataggag ctttgttcct tgggttcttg ggagcagcag gaagcactat   3780

gggcgcagcc tcaatgacgc tgacggtaca ggccagacaa ttattgtctg gtatagtgca   3840

gcagcagaac aatttgctga gggctattga ggcgcaacag catctgttgc aactcacagt   3900

ctggggcatc aagcagctcc aggcaagaat cctggctgtg gaaagatacc taaaggatca   3960

acagctcctg gggatttggg gttgctctgg aaaactcatt tgcaccactg ctgtgccttg   4020

gaatgctagt tggagtaata aatctctgga acagattgga atcacacgac ctggatggag   4080

tgggacagag aaattaacaa ttacacaagc ttaatacact ccttaattga agaatcgcaa   4140

aaccagcaag aaaagaatga acaagaatta ttggaattag ataaatgggc aagtttgtgg   4200

aattggttta acataacaaa ttggctgtgg tatataaaat tattcataat gatagtagga   4260

ggcttggtag gtttaagaat agtttttgct gtactttcta tagtgaatag agttaggcag   4320

ggatattcac cattatcgtt tcagacccac ctcccaaccc cgaggggacc cgacaggccc   4380

gaaggaatag aagaagaagg tggagagaga gacagagaca gatccattcg attagtgaac   4440
```

-continued

```
ggatctcgac ggtatcgata agctaattca caaatggcag tattcatcca caattttaaa   4500
agaaaagggg ggattggggg gtacagtgca ggggaaagaa tagtagacat aatagcaaca   4560
gacatacaaa ctaaagaatt acaaaaacaa attacaaaaa ttcaaaattt tcgggtttat   4620
tacagggaca gcagagatcc agtttgggaa ttagcttgat cgattagtcc aatttgttaa   4680
agacaggata tcagtggtcc aggctctagt tttgactcaa caatatcacc agctgaagcc   4740
tatagagtac gagccataga tagaataaaa gattttattt agtctccaga aaaagggggg   4800
aatgaaagac cccacctgta ggtttggcaa gctaggatca aggttaggaa cagagagaca   4860
gcagaatatg ggccaaacag gatatctgtg gtaagcagtt cctgccccgg ctcagggcca   4920
agaacagttg gaacagcaga atatgggcca aacaggatat ctgtggtaag cagttcctgc   4980
cccggctcag ggccaagaac agatggtccc cagatgcggt cccgccctca gcagtttcta   5040
gagaaccatc agatgtttcc agggtgcccc aaggacctga aatgaccctg tgccttattt   5100
gaactaacca atcagttcgc ttctcgcttc tgttcgcgcg cttctgctcc ccgagctcaa   5160
taaaagagcc cacaacccct cactcggcgc gatctagatc tcgaatcgaa ttcgttaacc   5220
tcgagggatc catggcgacg ggttcaagaa cttccctact tcttgcattt ggcctgcttt   5280
gtttgccgtg gttacaggaa gcctcagcac aacagaagga ggtggagcag aattctggac   5340
ccctcagtgt tccagaggga gccattgcct ctctcaactg cacttacagt gaccgaggtt   5400
cccagtcctt cttctggtac agacaatatt ctgggaaaag ccctgagttg ataatgttca   5460
tatactccaa tggtgacaaa gaagatggaa ggtttacagc acagctcaat aaagccagcc   5520
agtatgtttc tctgctcatc agagactccc agcccagtga ttcagccacc tacctctgtg   5580
ccgtgaactt cggaggagga aagcttatct tcggacaggg aacggagtta tctgtgaaac   5640
ccaatatcca gaaccctgac cctgccgtgt accagctgag agactctaaa tccagtgaca   5700
agtctgtctg cctattcacc gattttgatt ctcaaacaaa tgtgtcacaa agtaaggatt   5760
ctgatgtgta tatcacagac aaaactgtgc tagacatgag gtctatggac ttcaagagca   5820
acagtgctgt ggcctggagc aacaaatctg actttgcatg tgcaaacgcc ttcaacaaca   5880
gcattattcc agaagacacc ttcttcccca gcccagaaag ttcctgtggc tttacctcgg   5940
tgtcctacca gcaaggggtc ctgtctgcca ccatcctcta tgagatcctg ctagggaagg   6000
ccaccctgta tgctgtgctg gtcagcgccc ttgtgttgat ggccatggtc aagagaaagg   6060
atttcagggc aaaacgttcg ggttcgggtg cgccagtaaa gcagacatta aactttgatt   6120
tgctgaaact tgcaggtgat gtagagtcaa atccaggtcc aatggcaaca gggagccgaa   6180
cctctctgct ccttgctttc gggctccttt gcctaccgtg cctgcaggag ggctcggcag   6240
ggatcaccca ggcaccaaca tctcagatcc tggcagcagg acggcgcatg acactgagat   6300
gtacccagga tatgagacat aatgccatgt actggtatag acaagatcta ggactggggc   6360
taaggctcat ccattattca aatactgcag gtaccactgg caaaggagaa gtccctgatg   6420
gttatagtgt ctccagagca aacacagatg atttccccct cacgttggcg tctgctgtac   6480
cctctcagac atctgtgtac ttctgtgcca gcagcctaag tttcggcact gaagctttct   6540
ttggacaagg caccagactc acagttgtag aggacctgaa caaggtgttc ccacccgagg   6600
tcgctgtgtt tgagccatca gaagcagaga tctcccacac ccaaaaggcc acactggtgt   6660
gcctggccac aggcttcttc cctgaccacg tggagctgag ctggtgggtg aatgggaagg   6720
aggtgcacag tggggtcagc acggacccgc agcccctcaa ggagcagccc gccctcaatg   6780
```

```
actccagata ctgcctgagc agccgcctga gggtctcggc caccttctgg cagaaccccc   6840
gcaaccactt ccgctgtcaa gtccagttct acgggctctc ggagaatgac gagtggaccc   6900
aggatagggc caaacccgtc acccagatcg tcagcgccga agcctggggt agagcagact   6960
gtgatgtcaa gctggtcgag aaaagctttg aaacagatac gaacctaaac tttcaaaacc   7020
tgtcagtgat tgggttccga atcctcctcc tgaaagtggc cgggtttaat ctgctcatga   7080
cgctgcggct gtggtccagc agagccaaaa gaggctccgg agccactaac ttctccctgt   7140
tgaaacaggc tggcgatgtt gaagaaaacc ccggtcctat gggggcaggt gccaccggcc   7200
gcgccatgga cgggccgcgc ctgctgctgt tgctgcttct gggggtgtcc cttggaggtg   7260
ccaaggagca gaagctgatc agcgaggagg acctggagat ccctggccgt tggattacac   7320
ggtccacacc cccagagggc tcggacagca cagcccccag cacccaggag cctgaggcac   7380
ctccagaaca agacctcata gccagcacgg tggcaggtgt ggtgaccaca gtgatgggca   7440
gctcccagcc cgtggtgacc cgaggcacca ccgacaacct catccctgtc tattgctcca   7500
tcctggctgc tgtggttgtg ggtcttgtgg cctacatagc cttcaagagg taaaggatcc   7560
cccggggtcg actgatcaaa ttcgagctcg gtacctttaa gaccaatgac ttacaaggca   7620
gctgtagatc ttagccactt tttaaaagaa aaggggggac tggaagggct aattcactcc   7680
caacgaagac aagatctgct ttttgcttgt actgggtctc tctggttaga ccagatctga   7740
gcctgggagc tctctggcta actagggaac ccactgctta agcctcaata aagcttgcct   7800
tgagtgcttc aagtagtgtg tgcccgtctg ttgtgtgact ctggtaacta gagatccctc   7860
agaccctttt agtcagtgtg gaaaatctct agcagtagta gttcatgtca tcttattatt   7920
cagtatttat aacttgcaaa gaaatgaata tcagagagtg agaggaactt gtttattgca   7980
gcttataatg gttacaaata aagcaatagc atcacaaatt tcacaaataa agcatttttt   8040
tcactgcatt ctagttgtgg tttgtccaaa ctcatcaatg tatcttatca tgtctggctc   8100
tagctatccc gcccctaact ccgcccatcc cgcccctaac tccgcccagt tccgcccatt   8160
ctccgcccca tggctgacta attttttta tttatgcaga ggccgaggcc gcctcggcct   8220
ctgagctatt ccagaagtag tgaggaggct tttttggagg cctaggcttt tgcgtcgaga   8280
cgtacccaat tcgccctata gtgagtcgta ttacgcgcgc tcactggccg tcgttttaca   8340
acgtcgtgac tgggaaaacc ctggcgttac ccaacttaat cgccttgcag cacatccccc   8400
tttcgccagc tggcgtaata gcgaagaggc ccgcaccgat cgcccttccc aacagttgcg   8460
cagcctgaat ggcgaatggc gcgacgcgcc ctgtagcggc gcattaagcg cggcgggtgt   8520
ggtggttacg cgcagcgtga ccgctacact tgccagcgcc ctagcgcccg ctcctttcgc   8580
tttcttccct tcctttctcg ccacgttcgc cggctttccc cgtcaagctc taaatcgggg   8640
gctcccttta gggttccgat ttagtgcttt acggcacctc gaccccaaaa aacttgatta   8700
gggtgatggt tcacgtagtg ggccatcgcc ctgatagacg gtttttcgcc ctttgacgtt   8760
ggagtccacg ttctttaata gtggactctt gttccaaact ggaacaacac tcaaccctat   8820
ctcggtctat tcttttgatt tataagggat tttgccgatt tcggcctatt ggttaaaaaa   8880
tgagctgatt taacaaaaat ttaacgcgaa ttttaacaaa atattaacgt ttacaatttc   8940
c                                                                   8941
```

<210> SEQ ID NO 43
<211> LENGTH: 8941
<212> TYPE: DNA
<213> ORGANISM: Artificial Sequence
<220> FEATURE:
<223> OTHER INFORMATION: pMTB1284 vector

<400> SEQUENCE: 43

```
caggtggcac ttttcgggga aatgtgcgcg gaacccctat ttgtttattt ttctaaatac     60
attcaaatat gtatccgctc atgagacaat aaccctgata aatgcttcaa taatattgaa    120
aaaggaagag tatgagtatt caacatttcc gtgtcgccct tattcccttt tttgcggcat    180
tttgccttcc tgtttttgct cacccagaaa cgctggtgaa agtaaaagat gctgaagatc    240
agttgggtgc acgagtgggt tacatcgaac tggatctcaa cagcggtaag atccttgaga    300
gttttcgccc cgaagaacgt tttccaatga tgagcacttt taaagttctg ctatgtggcg    360
cggtattatc ccgtattgac gccgggcaag agcaactcgg tcgccgcata cactattctc    420
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgctttttt gcacaacatg ggggatcatg    600
taactcgcct tgatcgttgg gaaccggagc tgaatgaagc cataccaaac gacgagcgtg    660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac   1020
tttagattga tttaaaactt catttttaat ttaaaaggat ctaggtgaag atcctttttg   1080
ataatctcat gaccaaaatc ccttaacgtg agttttcgtt ccactgagcg tcagaccccg   1140
tagaaaagat caaaggatct tcttgagatc ctttttttct gcgcgtaatc tgctgcttgc   1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca ggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttggc   2220
```

-continued

```
cattgcatac gttgtatcca tatcataata tgtacattta tattggctca tgtccaacat   2280
taccgccatg ttgacattga ttattgacta gttattaata gtaatcaatt acggggtcat   2340
tagttcatag cccatatatg gagttccgcg ttacataact tacggtaaat ggcccgcctg   2400
gctgaccgcc caacgacccc cgcccattga cgtcaataat gacgtatgtt cccatagtaa   2460
cgccaatagg gactttccat tgacgtcaat gggtggagta tttacggtaa actgcccact   2520
tggcagtaca tcaagtgtat catatgccaa gtacgccccc tattgacgtc aatgacggta   2580
aatggcccgc ctggcattat gcccagtaca tgaccttatg ggactttcct acttggcagt   2640
acatctacgt attagtcatc gctattacca tggtgatgcg gttttggcag tacatcaatg   2700
ggcgtggata gcggtttgac tcacggggat ttccaagtct ccaccccatt gacgtcaatg   2760
ggagtttgtt ttggcaccaa aatcaacggg actttccaaa atgtcgtaac aactccgccc   2820
cattgacgca aatgggcggt aggcgtgtac ggtgggaggt ctatataagc agagctcgtt   2880
tagtgaaccg gggtctctct ggttagacca gatctgagcc tgggagctct ctggctaact   2940
agggaaccca ctgcttaagc ctcaataaag cttgccttga gtgcttcaag tagtgtgtgc   3000
ccgtctgttg tgtgactctg gtaactagag atccctcaga cccttttagt cagtgtggaa   3060
aatctctagc agtggcgccc gaacagggac ctgaaagcga aagggaaacc agaggagctc   3120
tctcgacgca ggactcggct tgctgaagcg cgcacggcaa gaggcgaggg gcggcgactg   3180
gtgagtacgc caaaaatttt gactagcgga ggctagaagg agagagatgg gtgcgagagc   3240
gtcagtatta agcgggggag aattagatcg cgatgggaaa aaattcggtt aaggccaggg   3300
ggaaagaaaa aatataaatt aaaacatata gtatgggcaa gcagggagct agaacgattc   3360
gcagttaatc ctggcctgtt agaaacatca gaaggctgta gacaaatact gggacagcta   3420
caaccatccc ttcagacagg atcagaagaa cttagatcat tatataatac agtagcaacc   3480
ctctattgtg tgcatcaaag gatagagata aaagacacca aggaagcttt agacaagata   3540
gaggaagagc aaaacaaaag taagaccacc gcacagcaag cggccgctga tcttcagacc   3600
tggaggagga gatatgaggg acaattggag aagtgaatta tataaatata aagtagtaaa   3660
aattgaacca ttaggagtag cacccaccaa ggcaaagaga agagtggtgc agagagaaaa   3720
aagagcagtg ggaataggag ctttgttcct tgggttcttg ggagcagcag gaagcactat   3780
gggcgcagcc tcaatgacgc tgacggtaca ggccagacaa ttattgtctg gtatagtgca   3840
gcagcagaac aatttgctga gggctattga ggcgcaacag catctgttgc aactcacagt   3900
ctggggcatc aagcagctcc aggcaagaat cctggctgtg gaaagatacc taaaggatca   3960
acagctcctg gggatttggg gttgctctgg aaaactcatt tgcaccactg ctgtgccttg   4020
gaatgctagt tggagtaata aatctctgga acagattgga atcacacgac ctggatggag   4080
tgggacagag aaattaacaa ttacacaagc ttaatacact ccttaattga agaatcgcaa   4140
aaccagcaag aaaagaatga acaagaatta ttggaattag ataaatgggc aagtttgtgg   4200
aattggttta acataacaaa ttggctgtgg tatataaaat tattcataat gatagtagga   4260
ggcttggtag gtttaagaat agtttttgct gtactttcta tagtgaatag agttaggcag   4320
ggatattcac cattatcgtt tcagacccac ctcccaaccc cgaggggacc cgacaggccc   4380
gaaggaatag aagaagaagg tggagagaga gacagagaca gatccattcg attagtgaac   4440
ggatctcgac ggtatcgata agctaattca caaatggcag tattcatcca caattttaaa   4500
agaaaagggg ggattggggg gtacagtgca ggggaaagaa tagtagacat aatagcaaca   4560
gacatacaaa ctaaagaatt acaaaaacaa attacaaaaa ttcaaaattt tcgggtttat   4620
```

-continued tacagggaca gcagagatcc agtttgggaa ttagcttgat cgattagtcc aatttgttaa 4680
agacaggata tcagtggtcc aggctctagt tttgactcaa caatatcacc agctgaagcc 4740
tatagagtac gagccataga tagaataaaa gattttattt agtctccaga aaaagggggg 4800
aatgaaagac cccacctgta ggtttggcaa gctaggatca aggttaggaa cagagagaca 4860
gcagaatatg ggccaaacag gatatctgtg gtaagcagtt cctgccccgg ctcagggcca 4920
agaacagttg gaacagcaga atatgggcca aacaggatat ctgtggtaag cagttcctgc 4980
cccggctcag ggccaagaac agatggtccc cagatgcggt cccgccctca gcagtttcta 5040
gagaaccatc agatgtttcc agggtgcccc aaggacctga aatgaccctg tgccttattt 5100
gaactaacca atcagttcgc ttctcgcttc tgttcgcgcg cttctgctcc ccgagctcaa 5160
taaaagagcc cacaacccct cactcggcgc gatctagatc tcgaatcgaa ttcgttaacc 5220
tcgagggatc catggcgacg ggttcaagaa cttccctact tcttgcattt ggcctgcttt 5280
gtttgccgtg gttacaggaa gcctcagcag ggatcaccca ggcaccaaca tctcagatcc 5340
tggcagcagg acggcgcatg acactgagat gtacccagga tatgagacat aatgccatgt 5400
actggtatag acaagatcta ggactggggc taaggctcat ccattattca aatactgcag 5460
gtaccactgg caaaggagaa gtccctgatg gttatagtgt ctccagagca aacacagatg 5520 atttcccct cacgttggcg tctgctgtac cctctcagac atctgtgtac ttctgtgcca 5580
gcagcctaag tttcggcact gaagctttct ttggacaagg caccagactc acagttgtag 5640
aggacctgaa caaggtgttc ccacccgagg tcgctgtgtt tgagccatca gaagcagaga 5700
tctcccacac ccaaaaggcc acactggtgt gcctggccac aggcttcttc cctgaccacg 5760
tggagctgag ctggtgggtg aatgggaagg aggtgcacag tggggtcagc acggacccgc 5820
agcccctcaa ggagcagccc gccctcaatg actccagata ctgcctgagc agccgcctga 5880
gggtctcggc caccttctgg cagaaccccc gcaaccactt ccgctgtcaa gtccagttct 5940
acgggctctc ggagaatgac gagtggaccc aggatagggc caaacccgtc acccagatcg 6000
tcagcgccga agcctggggt agagcagact gtggctttac ctcggtgtcc taccagcaag 6060
gggtcctgtc tgccaccaac ctgtcagtga ttgggttccg aatcctcctc ctgaaagtgg 6120
ccgggtttaa tctgctcatg acgctgcggc tgtggtccag cagggcaaaa cgttcgggtt 6180
cgggtgcgcc agtaaagcag acattaaact ttgatttgct gaaacttgca ggtgatgtag 6240
agtcaaatcc aggtccaatg gcaacaggga gccgaacctc tctgctcctt gctttcgggc 6300
tcctttgcct accgtgcctg caggagggct cggcacaaca gaaggaggtg gagcagaatt 6360
ctggacccct cagtgttcca gagggagcca ttgcctctct caactgcact tacagtgacc 6420
gaggttccca gtccttcttc tggtacagac aatattctgg gaaaagccct gagttgataa 6480
tgttcatata ctccaatggt gacaaagaag atggaaggtt tacagcacag ctcaataaag 6540
ccagccagta tgtttctctg ctcatcagag actcccagcc cagtgattca gccacctacc 6600
tctgtgccgt gaacttcgga ggaggaaagc ttatcttcgg acagggaacg gagttatctg 6660
tgaaacccaa tatccagaac cctgaccctg ccgtgtacca gctgagagac tctaaatcca 6720
gtgacaagtc tgtctgccta ttcaccgatt ttgattctca aacaaatgtg tcacaaagta 6780
aggattctga tgtgtatatc acagacaaaa ctgtgctaga catgaggtct atggacttca 6840
agagcaacag tgctgtggcc tggagcaaca aatctgactt tgcatgtgca aacgccttca 6900
acaacagcat tattccagaa gacaccttct tccccagccc agaaagttcc tgtgatgtca 6960

-continued

```
agctggtcga gaaaagcttt gaaacagata cgaacctaaa ctttcaaatc ctctatgaga   7020
tcctgctagg gaaggccacc ctgtatgctg tgctggtcag cgcccttgtg ttgatggcca   7080
tggtcaagag aaaggatttc agagccaaaa gaggctccgg agccactaac ttctccctgt   7140
tgaaacaggc tggcgatgtt gaagaaaacc ccggtcctat gggggcaggt gccaccggcc   7200
gcgccatgga cgggccgcgc ctgctgctgt tgctgcttct gggggtgtcc cttggaggtg   7260
ccaaggagca gaagctgatc agcgaggagg acctggagat ccctggccgt tggattacac   7320
ggtccacacc cccagagggc tcggacagca cagcccccag cacccaggag cctgaggcac   7380
ctccagaaca agacctcata gccagcacgg tggcaggtgt ggtgaccaca gtgatgggca   7440
gctcccagcc cgtggtgacc cgaggcacca ccgacaacct catccctgtc tattgctcca   7500
tcctggctgc tgtggttgtg ggtcttgtgg cctacatagc cttcaagagg taaaggatcc   7560
cccggggtcg actgatcaaa ttcgagctcg gtacctttaa gaccaatgac ttacaaggca   7620
gctgtagatc ttagccactt tttaaaagaa aaggggggac tggaagggct aattcactcc   7680
caacgaagac aagatctgct ttttgcttgt actgggtctc tctggttaga ccagatctga   7740
gcctgggagc tctctggcta actagggaac ccactgctta agcctcaata aagcttgcct   7800
tgagtgcttc aagtagtgtg tgcccgtctg ttgtgtgact ctggtaacta gagatccctc   7860
agaccctttt agtcagtgtg gaaaatctct agcagtagta gttcatgtca tcttattatt   7920
cagtatttat aacttgcaaa gaaatgaata tcagagagtg agaggaactt gtttattgca   7980
gcttataatg gttacaaata aagcaatagc atcacaaatt tcacaaataa agcatttttt   8040
tcactgcatt ctagttgtgg tttgtccaaa ctcatcaatg tatcttatca tgtctggctc   8100
tagctatccc gcccctaact ccgcccatcc cgcccctaac tccgcccagt tccgcccatt   8160
ctccgcccca tggctgacta attttttta tttatgcaga ggccgaggcc gcctcggcct   8220
ctgagctatt ccagaagtag tgaggaggct tttttggagg cctaggcttt tgcgtcgaga   8280
cgtacccaat tcgccctata gtgagtcgta ttacgcgcgc tcactggccg tcgttttaca   8340
acgtcgtgac tgggaaaacc ctggcgttac ccaacttaat cgccttgcag cacatccccc   8400
tttcgccagc tggcgtaata gcgaagaggc ccgcaccgat cgcccttccc aacagttgcg   8460
cagcctgaat ggcgaatggc gcgacgcgcc ctgtagcggc gcattaagcg cggcgggtgt   8520
ggtggttacg cgcagcgtga ccgctacact tgccagcgcc ctagcgcccg ctcctttcgc   8580
tttcttccct tcctttctcg ccacgttcgc cggctttccc cgtcaagctc taaatcgggg   8640
gctcccttta gggttccgat ttagtgcttt acggcacctc gaccccaaaa aacttgatta   8700
gggtgatggt tcacgtagtg ggccatcgcc ctgatagacg gtttttcgcc ctttgacgtt   8760
ggagtccacg ttctttaata gtggactctt gttccaaact ggaacaacac tcaaccctat   8820
ctcggtctat tcttttgatt tataagggat tttgccgatt tcggcctatt ggttaaaaaa   8880
tgagctgatt taacaaaaat ttaacgcgaa ttttaacaaa atattaacgt ttacaatttc   8940
c                                                                   8941
```

<210> SEQ ID NO 44
<211> LENGTH: 8941
<212> TYPE: DNA
<213> ORGANISM: Artificial Sequence
<220> FEATURE:
<223> OTHER INFORMATION: pMTB1285 vector

<400> SEQUENCE: 44

```
caggtggcac ttttcgggga aatgtgcgcg gaacccctat ttgtttattt ttctaaatac     60
```

attcaaatat gtatccgctc atgagacaat aaccctgata aatgcttcaa taatattgaa 120
aaaggaagag tatgagtatt caacatttcc gtgtcgccct tattcccttt tttgcggcat 180
tttgccttcc tgtttttgct cacccagaaa cgctggtgaa agtaaaagat gctgaagatc 240
agttgggtgc acgagtgggt tacatcgaac tggatctcaa cagcggtaag atccttgaga 300
gttttcgccc cgaagaacgt tttccaatga tgagcacttt taaagttctg ctatgtggcg 360
cggtattatc ccgtattgac gccgggcaag agcaactcgg tcgccgcata cactattctc 420
agaatgactt ggttgagtac tcaccagtca cagaaaagca tcttacggat ggcatgacag 480
taagagaatt atgcagtgct gccataacca tgagtgataa cactgcggcc aacttacttc 540
tgacaacgat cggaggaccg aaggagctaa ccgctttttt gcacaacatg ggggatcatg 600
taactcgcct tgatcgttgg gaaccggagc tgaatgaagc cataccaaac gacgagcgtg 660
acaccacgat gcctgtagca atggcaacaa cgttgcgcaa actattaact ggcgaactac 720
ttactctagc ttcccggcaa caattaatag actggatgga ggcggataaa gttgcaggac 780
cacttctgcg ctcggccctt ccggctggct ggtttattgc tgataaatct ggagccggtg 840
agcgtgggtc tcgcggtatc attgcagcac tggggccaga tggtaagccc tcccgtatcg 900
tagttatcta cacgacgggg agtcaggcaa ctatggatga acgaaataga cagatcgctg 960
agataggtgc ctcactgatt aagcattggt aactgtcaga ccaagtttac tcatatatac 1020
tttagattga tttaaaactt catttttaat ttaaaaggat ctaggtgaag atcctttttg 1080
ataatctcat gaccaaaatc ccttaacgtg agttttcgtt ccactgagcg tcagaccccg 1140
tagaaaagat caaaggatct tcttgagatc ctttttttct gcgcgtaatc tgctgcttgc 1200
aaacaaaaaa accaccgcta ccagcggtgg tttgtttgcc ggatcaagag ctaccaactc 1260
tttttccgaa ggtaactggc ttcagcagag cgcagatacc aaatactgtc cttctagtgt 1320
agccgtagtt aggccaccac ttcaagaact ctgtagcacc gcctacatac ctcgctctgc 1380
taatcctgtt accagtggct gctgccagtg gcgataagtc gtgtcttacc gggttggact 1440
caagacgata gttaccggat aaggcgcagc ggtcgggctg aacggggggt tcgtgcacac 1500
agcccagctt ggagcgaacg acctacaccg aactgagata cctacagcgt gagctatgag 1560
aaagcgccac gcttcccgaa gggagaaagg cggacaggta tccggtaagc ggcagggtcg 1620
gaacaggaga gcgcacgagg gagcttccag ggggaaacgc ctggtatctt tatagtcctg 1680
tcgggtttcg ccacctctga cttgagcgtc gatttttgtg atgctcgtca ggggggcgga 1740
gcctatggaa aaacgccagc aacgcggcct ttttacggtt cctggccttt tgctggcctt 1800
ttgctcacat gttctttcct gcgttatccc ctgattctgt ggataaccgt attaccgcct 1860
ttgagtgagc tgataccgct cgccgcagcc gaacgaccga gcgcagcgag tcagtgagcg 1920
aggaagcgga agagcgccca atacgcaaac cgcctctccc cgcgcgttgg ccgattcatt 1980
aatgcagctg gcacgacagg tttcccgact ggaaagcggg cagtgagcgc aacgcaatta 2040
atgtgagtta gctcactcat taggcacccc aggctttaca ctttatgctt ccggctcgta 2100
tgttgtgtgg aattgtgagc ggataacaat ttcacacagg aaacagctat gaccatgatt 2160
acgccaagcg cgcaattaac cctcactaaa gggaacaaaa gctggagctg caagcttggc 2220
cattgcatac gttgtatcca tatcataata tgtacattta tattggctca tgtccaacat 2280
taccgccatg ttgacattga ttattgacta gttattaata gtaatcaatt acggggtcat 2340
tagttcatag cccatatatg gagttccgcg ttacataact tacggtaaat ggcccgcctg 2400

-continued

```
gctgaccgcc caacgacccc cgcccattga cgtcaataat gacgtatgtt cccatagtaa   2460
cgccaatagg gactttccat tgacgtcaat gggtggagta tttacggtaa actgcccact   2520
tggcagtaca tcaagtgtat catatgccaa gtacgccccc tattgacgtc aatgacggta   2580
aatggcccgc ctggcattat gcccagtaca tgaccttatg ggactttcct acttggcagt   2640
acatctacgt attagtcatc gctattacca tggtgatgcg gttttggcag tacatcaatg   2700
ggcgtggata gcggtttgac tcacggggat ttccaagtct ccaccccatt gacgtcaatg   2760
ggagtttgtt ttggcaccaa aatcaacggg actttccaaa atgtcgtaac aactccgccc   2820
cattgacgca aatgggcggt aggcgtgtac ggtgggaggt ctatataagc agagctcgtt   2880
tagtgaaccg gggtctctct ggttagacca gatctgagcc tgggagctct ctggctaact   2940
agggaaccca ctgcttaagc ctcaataaag cttgccttga gtgcttcaag tagtgtgtgc   3000
ccgtctgttg tgtgactctg gtaactagag atccctcaga cccttttagt cagtgtggaa   3060
aatctctagc agtggcgccc gaacagggac ctgaaagcga aagggaaacc agaggagctc   3120
tctcgacgca ggactcggct tgctgaagcg cgcacggcaa gaggcgaggg gcggcgactg   3180
gtgagtacgc caaaaatttt gactagcgga ggctagaagg agagagatgg gtgcgagagc   3240
gtcagtatta agcgggggag aattagatcg cgatgggaaa aaattcggtt aaggccaggg   3300
ggaaagaaaa aatataaatt aaaacatata gtatgggcaa gcagggagct agaacgattc   3360
gcagttaatc ctggcctgtt agaaacatca gaaggctgta gacaaatact gggacagcta   3420
caaccatccc ttcagacagg atcagaagaa cttagatcat tatataatac agtagcaacc   3480
ctctattgtg tgcatcaaag gatagagata aaagacacca aggaagcttt agacaagata   3540
gaggaagagc aaaacaaaag taagaccacc gcacagcaag cggccgctga tcttcagacc   3600
tggaggagga gatatgaggg acaattggag aagtgaatta tataaatata aagtagtaaa   3660
aattgaacca ttaggagtag cacccaccaa ggcaaagaga agagtggtgc agagagaaaa   3720
aagagcagtg ggaataggag ctttgttcct tgggttcttg ggagcagcag gaagcactat   3780
gggcgcagcc tcaatgacgc tgacggtaca ggccagacaa ttattgtctg gtatagtgca   3840
gcagcagaac aatttgctga gggctattga ggcgcaacag catctgttgc aactcacagt   3900
ctggggcatc aagcagctcc aggcaagaat cctggctgtg gaaagatacc taaaggatca   3960
acagctcctg gggatttggg gttgctctgg aaaactcatt tgcaccactg ctgtgccttg   4020
gaatgctagt tggagtaata aatctctgga acagattgga atcacacgac ctggatggag   4080
tgggacagag aaattaacaa ttacacaagc ttaatacact ccttaattga agaatcgcaa   4140
aaccagcaag aaaagaatga acaagaatta ttggaattag ataaatgggc aagtttgtgg   4200
aattggttta acataacaaa ttggctgtgg tatataaaat tattcataat gatagtagga   4260
ggcttggtag gtttaagaat agtttttgct gtactttcta tagtgaatag agttaggcag   4320
ggatattcac cattatcgtt tcagacccac ctcccaaccc cgaggggacc cgacaggccc   4380
gaaggaatag aagaagaagg tggagagaga gacagagaca gatccattcg attagtgaac   4440
ggatctcgac ggtatcgata agctaattca caaatggcag tattcatcca caattttaaa   4500
agaaaagggg ggattggggg gtacagtgca ggggaaagaa tagtagacat aatagcaaca   4560
gacatacaaa ctaaagaatt acaaaaacaa attacaaaaa ttcaaaattt tcgggtttat   4620
tacagggaca gcagagatcc agtttgggaa ttagcttgat cgattagtcc aatttgttaa   4680
agacaggata tcagtggtcc aggctctagt tttgactcaa caatatcacc agctgaagcc   4740
tatagagtac gagccataga tagaataaaa gattttattt agtctccaga aaaagggggg   4800
```

-continued aatgaaagac cccacctgta ggtttggcaa gctaggatca aggttaggaa cagagagaca 4860
gcagaatatg ggccaaacag gatatctgtg gtaagcagtt cctgccccgg ctcagggcca 4920
agaacagttg gaacagcaga atatgggcca aacaggatat ctgtggtaag cagttcctgc 4980
cccggctcag ggccaagaac agatggtccc cagatgcggt cccgccctca gcagtttcta 5040
gagaaccatc agatgtttcc agggtgcccc aaggacctga aatgaccctg tgccttattt 5100
gaactaacca atcagttcgc ttctcgcttc tgttcgcgcg cttctgctcc ccgagctcaa 5160
taaaagagcc cacaacccct cactcggcgc gatctagatc tcgaatcgaa ttcgttaacc 5220
tcgagggatc catggcgacg ggttcaagaa cttccctact tcttgcattt ggcctgcttt 5280
gtttgccgtg gttacaggaa gcctcagcac aacagaagga ggtggagcag aattctggac 5340
ccctcagtgt tccagaggga gccattgcct ctctcaactg cacttacagt gaccgaggtt 5400
cccagtcctt cttctggtac agacaatatt ctgggaaaag ccctgagttg ataatgttca 5460
tatactccaa tggtgacaaa gaagatggaa ggtttacagc acagctcaat aaagccagcc 5520
agtatgtttc tctgctcatc agagactccc agcccagtga ttcagccacc tacctctgtg 5580
ccgtgaactt cggaggagga aagcttatct tcggacaggg aacggagtta tctgtgaaac 5640
ccaatatcca gaaccctgac cctgccgtgt accagctgag agactctaaa tccagtgaca 5700
agtctgtctg cctattcacc gattttgatt ctcaaacaaa tgtgtcacaa agtaaggatt 5760
ctgatgtgta tatcacagac aaaactgtgc tagacatgag gtctatggac ttcaagagca 5820
acagtgctgt ggcctggagc aacaaatctg actttgcatg tgcaaacgcc ttcaacaaca 5880
gcattattcc agaagacacc ttcttcccca gcccagaaag ttcctgtgat gtcaagctgg 5940
tcgagaaaag ctttgaaaca gatacgaacc taaactttca aatcctctat gagatcctgc 6000
tagggaaggc caccctgtat gctgtgctgg tcagcgccct tgtgttgatg gccatggtca 6060
agagaaagga tttcagggca aaacgttcgg gttcgggtgc gccagtaaag cagacattaa 6120
actttgattt gctgaaactt gcaggtgatg tagagtcaaa tccaggtcca atggcaacag 6180
ggagccgaac ctctctgctc cttgctttcg ggctcctttg cctaccgtgc ctgcaggagg 6240
gctcggcagg gatcacccag gcaccaacat ctcagatcct ggcagcagga cggcgcatga 6300
cactgagatg tacccaggat atgagacata atgccatgta ctggtataga caagatctag 6360
gactggggct aaggctcatc cattattcaa atactgcagg taccactggc aaaggagaag 6420
tccctgatgg ttatagtgtc tccagagcaa acacagatga tttcccccctc acgttggcgt 6480 ctgctgtacc ctctcagaca tctgtgtact tctgtgccag cagcctaagt ttcggcactg 6540
aagctttctt tggacaaggc accagactca cagttgtaga ggacctgaac aaggtgttcc 6600
cacccgaggt cgctgtgttt gagccatcag aagcagagat ctcccacacc caaaaggcca 6660
cactggtgtg cctggccaca ggcttcttcc ctgaccacgt ggagctgagc tggtgggtga 6720
atgggaagga ggtgcacagt ggggtcagca cggacccgca gcccctcaag gagcagcccg 6780
ccctcaatga ctccagatac tgcctgagca gccgcctgag ggtctcggcc accttctggc 6840
agaacccccg caaccacttc cgctgtcaag tccagttcta cgggctctcg gagaatgacg 6900
agtggaccca ggatagggcc aaacccgtca cccagatcgt cagcgccgaa gcctggggta 6960
gagcagactg tggctttacc tcggtgtcct accagcaagg ggtcctgtct gccaccaacc 7020
tgtcagtgat tgggttccga atcctcctcc tgaaagtggc cgggtttaat ctgctcatga 7080
cgctgcggct gtggtccagc agagccaaaa gaggctccgg agccactaac ttctccctgt 7140

```
tgaaacaggc tggcgatgtt gaagaaaacc ccggtcctat gggggcaggt gccaccggcc   7200

gcgccatgga cgggccgcgc ctgctgctgt tgctgcttct gggggtgtcc cttggaggtg   7260

ccaaggagca gaagctgatc agcgaggagg acctggagat ccctggccgt tggattacac   7320

ggtccacacc cccagagggc tcggacagca cagcccccag cacccaggag cctgaggcac   7380

ctccagaaca agacctcata gccagcacgg tggcaggtgt ggtgaccaca gtgatgggca   7440

gctcccagcc cgtggtgacc cgaggcacca ccgacaacct catccctgtc tattgctcca   7500

tcctggctgc tgtggttgtg ggtcttgtgg cctacatagc cttcaagagg taaaggatcc   7560

cccggggtcg actgatcaaa ttcgagctcg gtacctttaa gaccaatgac ttacaaggca   7620

gctgtagatc ttagccactt tttaaaagaa aaggggggac tggaagggct aattcactcc   7680

caacgaagac aagatctgct ttttgcttgt actgggtctc tctggttaga ccagatctga   7740

gcctgggagc tctctggcta actagggaac ccactgctta agcctcaata aagcttgcct   7800

tgagtgcttc aagtagtgtg tgcccgtctg ttgtgtgact ctggtaacta gagatccctc   7860

agaccctttt agtcagtgtg gaaaatctct agcagtagta gttcatgtca tcttattatt   7920

cagtatttat aacttgcaaa gaaatgaata tcagagagtg agaggaactt gtttattgca   7980

gcttataatg gttacaaata aagcaatagc atcacaaatt tcacaaataa agcatttttt   8040

tcactgcatt ctagttgtgg tttgtccaaa ctcatcaatg tatcttatca tgtctggctc   8100

tagctatccc gcccctaact ccgcccatcc cgcccctaac tccgcccagt tccgcccatt   8160

ctccgcccca tggctgacta attttttta tttatgcaga ggccgaggcc gcctcggcct   8220

ctgagctatt ccagaagtag tgaggaggct tttttggagg cctaggcttt tgcgtcgaga   8280

cgtacccaat tcgccctata gtgagtcgta ttacgcgcgc tcactggccg tcgttttaca   8340

acgtcgtgac tgggaaaacc ctggcgttac ccaacttaat cgccttgcag cacatccccc   8400

tttcgccagc tggcgtaata gcgaagaggc ccgcaccgat cgcccttccc aacagttgcg   8460

cagcctgaat ggcgaatggc gcgacgcgcc ctgtagcggc gcattaagcg cggcgggtgt   8520

ggtggttacg cgcagcgtga ccgctacact tgccagcgcc ctagcgcccg ctcctttcgc   8580

tttcttccct tcctttctcg ccacgttcgc cggctttccc cgtcaagctc taaatcgggg   8640

gctcccttta gggttccgat ttagtgcttt acggcacctc gaccccaaaa aacttgatta   8700

gggtgatggt tcacgtagtg ggccatcgcc ctgatagacg gtttttcgcc ctttgacgtt   8760

ggagtccacg ttctttaata gtggactctt gttccaaact ggaacaacac tcaaccctat   8820

ctcggtctat tcttttgatt tataagggat tttgccgatt tcggcctatt ggttaaaaaa   8880

tgagctgatt taacaaaaat ttaacgcgaa ttttaacaaa atattaacgt ttacaatttc   8940

c                                                                   8941
```

<210> SEQ ID NO 45
<211> LENGTH: 9031
<212> TYPE: DNA
<213> ORGANISM: Artificial Sequence
<220> FEATURE:
<223> OTHER INFORMATION: pMTB1301 vector

<400> SEQUENCE: 45

```
caggtggcac ttttcgggga aatgtgcgcg gaacccctat ttgtttattt ttctaaatac     60

attcaaatat gtatccgctc atgagacaat aaccctgata aatgcttcaa taatattgaa    120

aaaggaagag tatgagtatt caacatttcc gtgtcgccct tattcccttt tttgcggcat    180

tttgccttcc tgtttttgct cacccagaaa cgctggtgaa agtaaaagat gctgaagatc    240
```

agttgggtgc acgagtgggt tacatcgaac tggatctcaa cagcggtaag atccttgaga 300
gttttcgccc cgaagaacgt tttccaatga tgagcacttt taaagttctg ctatgtggcg 360
cggtattatc ccgtattgac gccgggcaag agcaactcgg tcgccgcata cactattctc 420
agaatgactt ggttgagtac tcaccagtca cagaaaagca tcttacggat ggcatgacag 480
taagagaatt atgcagtgct gccataacca tgagtgataa cactgcggcc aacttacttc 540
tgacaacgat cggaggaccg aaggagctaa ccgctttttt gcacaacatg ggggatcatg 600
taactcgcct tgatcgttgg gaaccggagc tgaatgaagc cataccaaac gacgagcgtg 660
acaccacgat gcctgtagca atggcaacaa cgttgcgcaa actattaact ggcgaactac 720
ttactctagc ttcccggcaa caattaatag actggatgga ggcggataaa gttgcaggac 780
cacttctgcg ctcggccctt ccggctggct ggtttattgc tgataaatct ggagccggtg 840
agcgtgggtc tcgcggtatc attgcagcac tggggccaga tggtaagccc tcccgtatcg 900
tagttatcta cacgacgggg agtcaggcaa ctatggatga acgaaataga cagatcgctg 960
agataggtgc ctcactgatt aagcattggt aactgtcaga ccaagtttac tcatatatac 1020
tttagattga tttaaaactt catttttaat ttaaaaggat ctaggtgaag atcctttttg 1080
ataatctcat gaccaaaatc ccttaacgtg agttttcgtt ccactgagcg tcagaccccg 1140
tagaaaagat caaaggatct tcttgagatc ctttttttct gcgcgtaatc tgctgcttgc 1200
aaacaaaaaa accaccgcta ccagcggtgg tttgtttgcc ggatcaagag ctaccaactc 1260
tttttccgaa ggtaactggc ttcagcagag cgcagatacc aaatactgtc cttctagtgt 1320
agccgtagtt aggccaccac ttcaagaact ctgtagcacc gcctacatac ctcgctctgc 1380
taatcctgtt accagtggct gctgccagtg gcgataagtc gtgtcttacc gggttggact 1440
caagacgata gttaccggat aaggcgcagc ggtcgggctg aacggggggt tcgtgcacac 1500
agcccagctt ggagcgaacg acctacaccg aactgagata cctacagcgt gagctatgag 1560
aaagcgccac gcttcccgaa gggagaaagg cggacaggta tccggtaagc ggcagggtcg 1620
gaacaggaga gcgcacgagg gagcttccag ggggaaacgc ctggtatctt tatagtcctg 1680
tcgggtttcg ccacctctga cttgagcgtc gatttttgtg atgctcgtca ggggggcgga 1740
gcctatggaa aaacgccagc aacgcggcct ttttacggtt cctggccttt tgctggcctt 1800
ttgctcacat gttctttcct gcgttatccc ctgattctgt ggataaccgt attaccgcct 1860
ttgagtgagc tgataccgct cgccgcagcc gaacgaccga gcgcagcgag tcagtgagcg 1920
aggaagcgga agagcgccca atacgcaaac cgcctctccc cgcgcgttgg ccgattcatt 1980
aatgcagctg gcacgacagg tttcccgact ggaaagcggg cagtgagcgc aacgcaatta 2040
atgtgagtta gctcactcat taggcacccc aggctttaca ctttatgctt ccggctcgta 2100
tgttgtgtgg aattgtgagc ggataacaat ttcacacagg aaacagctat gaccatgatt 2160
acgccaagcg cgcaattaac cctcactaaa gggaacaaaa gctggagctg caagcttggc 2220
cattgcatac gttgtatcca tatcataata tgtacattta tattggctca tgtccaacat 2280
taccgccatg ttgacattga ttattgacta gttattaata gtaatcaatt acggggtcat 2340
tagttcatag cccatatatg gagttccgcg ttacataact tacggtaaat ggcccgcctg 2400
gctgaccgcc caacgacccc cgcccattga cgtcaataat gacgtatgtt cccatagtaa 2460
cgccaatagg gactttccat tgacgtcaat gggtggagta tttacggtaa actgcccact 2520
tggcagtaca tcaagtgtat catatgccaa gtacgccccc tattgacgtc aatgacggta 2580

-continued

```
aatggcccgc ctggcattat gcccagtaca tgaccttatg ggactttcct acttggcagt   2640
acatctacgt attagtcatc gctattacca tggtgatgcg gttttggcag tacatcaatg   2700
ggcgtggata gcggtttgac tcacggggat ttccaagtct ccaccccatt gacgtcaatg   2760
ggagtttgtt ttggcaccaa aatcaacggg actttccaaa atgtcgtaac aactccgccc   2820
cattgacgca aatgggcggt aggcgtgtac ggtgggaggt ctatataagc agagctcgtt   2880
tagtgaaccg gggtctctct ggttagacca gatctgagcc tgggagctct ctggctaact   2940
agggaaccca ctgcttaagc ctcaataaag cttgccttga gtgcttcaag tagtgtgtgc   3000
ccgtctgttg tgtgactctg gtaactagag atccctcaga cccttttagt cagtgtggaa   3060
aatctctagc agtggcgccc gaacagggac ctgaaagcga aagggaaacc agaggagctc   3120
tctcgacgca ggactcggct tgctgaagcg cgcacggcaa gaggcgaggg gcggcgactg   3180
gtgagtacgc caaaaatttt gactagcgga ggctagaagg agagagatgg gtgcgagagc   3240
gtcagtatta agcgggggag aattagatcg cgatgggaaa aaattcggtt aaggccaggg   3300
ggaaagaaaa aatataaatt aaaacatata gtatgggcaa gcagggagct agaacgattc   3360
gcagttaatc ctggcctgtt agaaacatca gaaggctgta gacaaatact gggacagcta   3420
caaccatccc ttcagacagg atcagaagaa cttagatcat tatataatac agtagcaacc   3480
ctctattgtg tgcatcaaag gatagagata aaagacacca aggaagcttt agacaagata   3540
gaggaagagc aaaacaaaag taagaccacc gcacagcaag cggccgctga tcttcagacc   3600
tggaggagga gatatgaggg acaattggag aagtgaatta tataaatata aagtagtaaa   3660
aattgaacca ttaggagtag cacccaccaa ggcaaagaga agagtggtgc agagagaaaa   3720
aagagcagtg ggaataggag ctttgttcct tgggttcttg ggagcagcag gaagcactat   3780
gggcgcagcc tcaatgacgc tgacggtaca ggccagacaa ttattgtctg gtatagtgca   3840
gcagcagaac aatttgctga gggctattga ggcgcaacag catctgttgc aactcacagt   3900
ctggggcatc aagcagctcc aggcaagaat cctggctgtg gaaagatacc taaaggatca   3960
acagctcctg gggatttggg gttgctctgg aaaactcatt tgcaccactg ctgtgccttg   4020
gaatgctagt tggagtaata aatctctgga acagattgga atcacacgac ctggatggag   4080
tgggacagag aaattaacaa ttacacaagc ttaatacact ccttaattga agaatcgcaa   4140
aaccagcaag aaaagaatga acaagaatta ttggaattag ataaatgggc aagtttgtgg   4200
aattggttta acataacaaa ttggctgtgg tatataaaat tattcataat gatagtagga   4260
ggcttggtag gtttaagaat agtttttgct gtactttcta tagtgaatag agttaggcag   4320
ggatattcac cattatcgtt tcagacccac ctcccaaccc cgaggggacc cgacaggccc   4380
gaaggaatag aagaagaagg tggagagaga gacagagaca gatccattcg attagtgaac   4440
ggatctcgac ggtatcgata agctaattca caaatggcag tattcatcca caattttaaa   4500
agaaaagggg ggattggggg gtacagtgca ggggaaagaa tagtagacat aatagcaaca   4560
gacatacaaa ctaaagaatt acaaaaacaa attacaaaaa ttcaaaattt tcgggtttat   4620
tacagggaca gcagagatcc agtttgggaa ttagcttgat cgattagtcc aatttgttaa   4680
agacaggata tcagtggtcc aggctctagt tttgactcaa caatatcacc agctgaagcc   4740
tatagagtac gagccataga tagaataaaa gattttattt agtctccaga aaaagggggg   4800
aatgaaagac cccacctgta ggtttggcaa gctaggatca aggttaggaa cagagagaca   4860
gcagaatatg ggccaaacag gatatctgtg gtaagcagtt cctgccccgg ctcagggcca   4920
agaacagttg gaacagcaga atatgggcca aacaggatat ctgtggtaag cagttcctgc   4980
```

cccggctcag ggccaagaac agatggtccc cagatgcggt cccgccctca gcagtttcta 5040
gagaaccatc agatgtttcc agggtgcccc aaggacctga aatgaccctg tgccttattt 5100
gaactaacca atcagttcgc ttctcgcttc tgttcgcgcg cttctgctcc ccgagctcaa 5160
taaaagagcc cacaacccct cactcggcgc gatctagatc tcgaatcgaa ttcgttaacc 5220
tcgagggatc catggcgacg ggttcaagaa cttccctact tcttgcattt ggcctgcttt 5280
gtttgccgtg gttacaggaa gcctcagcac aacagaagga ggtggagcag aattctggac 5340
ccctcagtgt tccagaggga gccattgcct ctctcaactg cacttacagt gaccgaggtt 5400
cccagtcctt cttctggtac agacaatatt ctgggaaaag ccctgagttg ataatgttca 5460
tatactccaa tggtgacaaa gaagatggaa ggtttacagc acagctcaat aaagccagcc 5520
agtatgtttc tctgctcatc agagactccc agcccagtga ttcagccacc tacctctgtg 5580
ccgtgaactt cggaggagga aagcttatct tcggacaggg aacggagtta tctgtgaaac 5640
ccaatatcca gaaccctgac cctgccgtgt accagctgag agactctaaa tccagtgaca 5700
agtctgtctg cctattcacc gattttgatt ctcaaacaaa tgtgtcacaa agtaaggatt 5760
ctgatgtgta tatcacagac aaaactgtgc tagacatgag gtctatggac ttcaagagca 5820
acagtgctgt ggcctggagc aacaaatctg actttgcatg tgcaaacgcc ttcaacaaca 5880
gcattattcc agaagacacc ttcttcccca gcccagaaag ttccgactcc acagatcacg 5940
tgaagcccaa agagactgaa aacaccaagc agccatccaa atcttgtcac aagcccaaag 6000
ccattgtgca taccgaaaag gtcaatatga tgtctctgac agtgctgggc ctgagaatgc 6060
tgttcgcaaa aactgtggct gtcaacttcc tgctgactgc tcggctgtgg tccagcaggg 6120
caaaacgttc gggttcgggt gcgccagtaa agcagacatt aaactttgat ttgctgaaac 6180
ttgcaggtga tgtagagtca aatccaggtc caatggcaac agggagccga acctctctgc 6240
tccttgcttt cgggctcctt tgcctaccgt gcctgcagga gggctcggca gggatcaccc 6300
aggcaccaac atctcagatc ctggcagcag gacggcgcat gacactgaga tgtacccagg 6360
atatgagaca taatgccatg tactggtata gacaagatct aggactgggg ctaaggctca 6420
tccattattc aaatactgca ggtaccactg gcaaaggaga agtccctgat ggttatagtg 6480
tctccagagc aaacacagat gatttccccc tcacgttggc gtctgctgta ccctctcaga 6540
catctgtgta cttctgtgcc agcagcctaa gtttcggcac tgaagctttc tttggacaag 6600
gcaccagact cacagttgta gaggacctga acaaggtgtt cccacccgag gtcgctgtgt 6660
ttgagccatc agaagcagag atctcccaca cccaaaaggc cacactggtg tgcctggcca 6720
caggcttctt ccctgaccac gtggagctga gctggtgggt gaatgggaag gaggtgcaca 6780
gtggggtcag cacggacccg cagcccctca aggagcagcc cgccctcaat gactccagat 6840
actgcctgag cagccgcctg agggtctcgg ccaccttctg gcagaacccc cgcaaccact 6900
tccgctgtca agtccagttc tacgggctct cggagaatga cgagtggacc caggataggg 6960
ccaaacccgt cacccagatc gtcagcgccg aagcctgggg tagagcagac gatgtcatta 7020
ccatggaccc caaggataac tgttctaaag acgccaatga tacactgctg ctgcagctga 7080
ccaatacatc agcttactat atgtacctgc tgctgctgct gaagagcgtg gtctatttcg 7140
ccatcatcac ctgttgcctg ctgatggcca tggtcaagag aaaggatttc agagccaaaa 7200
gaggctccgg agccactaac ttctccctgt tgaaacaggc tggcgatgtt gaagaaaacc 7260
ccggtcctat gggggcaggt gccaccggcc gcgccatgga cgggccgcgc ctgctgctgt 7320

-continued

```
tgctgcttct gggggtgtcc cttggaggtg ccaaggagca gaagctgatc agcgaggagg   7380

acctggagat ccctggccgt tggattacac ggtccacacc cccagagggc tcggacagca   7440

cagcccccag cacccaggag cctgaggcac ctccagaaca agacctcata gccagcacgg   7500

tggcaggtgt ggtgaccaca gtgatgggca gctcccagcc cgtggtgacc cgaggcacca   7560

ccgacaacct catccctgtc tattgctcca tcctggctgc tgtggttgtg ggtcttgtgg   7620

cctacatagc cttcaagagg taaaggatcc cccggggtcg actgatcaaa ttcgagctcg   7680

gtacctttaa gaccaatgac ttacaaggca gctgtagatc ttagccactt tttaaaagaa   7740

aaggggggac tggaagggct aattcactcc caacgaagac aagatctgct ttttgcttgt   7800

actgggtctc tctggttaga ccagatctga gcctgggagc tctctggcta actagggaac   7860

ccactgctta agcctcaata aagcttgcct tgagtgcttc aagtagtgtg tgcccgtctg   7920

ttgtgtgact ctggtaacta gagatccctc agaccctttt agtcagtgtg gaaaatctct   7980

agcagtagta gttcatgtca tcttattatt cagtatttat aacttgcaaa gaaatgaata   8040

tcagagagtg agaggaactt gtttattgca gcttataatg gttacaaata aagcaatagc   8100

atcacaaatt tcacaaataa agcatttttt tcactgcatt ctagttgtgg tttgtccaaa   8160

ctcatcaatg tatcttatca tgtctggctc tagctatccc gcccctaact ccgcccatcc   8220

cgcccctaac tccgcccagt tccgcccatt ctccgcccca tggctgacta atttttttta   8280

tttatgcaga ggccgaggcc gcctcggcct ctgagctatt ccagaagtag tgaggaggct   8340

tttttggagg cctaggcttt tgcgtcgaga cgtacccaat tcgccctata gtgagtcgta   8400

ttacgcgcgc tcactggccg tcgttttaca acgtcgtgac tgggaaaacc ctggcgttac   8460

ccaacttaat cgccttgcag cacatccccc tttcgccagc tggcgtaata gcgaagaggc   8520

ccgcaccgat cgcccttccc aacagttgcg cagcctgaat ggcgaatggc gcgacgcgcc   8580

ctgtagcggc gcattaagcg cggcgggtgt ggtggttacg cgcagcgtga ccgctacact   8640

tgccagcgcc ctagcgcccg ctcctttcgc tttcttccct tcctttctcg ccacgttcgc   8700

cggctttccc cgtcaagctc taaatcgggg gctcccttta gggttccgat ttagtgcttt   8760

acggcacctc gaccccaaaa aacttgatta gggtgatggt tcacgtagtg ggccatcgcc   8820

ctgatagacg gtttttcgcc ctttgacgtt ggagtccacg ttctttaata gtggactctt   8880

gttccaaact ggaacaacac tcaaccctat ctcggtctat tcttttgatt tataagggat   8940

tttgccgatt tcggcctatt ggttaaaaaa tgagctgatt taacaaaaat ttaacgcgaa   9000

ttttaacaaa atattaacgt ttacaatttc c                                  9031


<210> SEQ ID NO 46
<211> LENGTH: 9031
<212> TYPE: DNA
<213> ORGANISM: Artificial Sequence
<220> FEATURE:
<223> OTHER INFORMATION: pMTB1302 vector

<400> SEQUENCE: 46

caggtggcac ttttcgggga aatgtgcgcg gaacccctat ttgtttattt ttctaaatac     60

attcaaatat gtatccgctc atgagacaat aaccctgata aatgcttcaa taatattgaa    120

aaaggaagag tatgagtatt caacatttcc gtgtcgccct tattcccttt tttgcggcat    180

tttgccttcc tgtttttgct cacccagaaa cgctggtgaa agtaaaagat gctgaagatc    240

agttgggtgc acgagtgggt tacatcgaac tggatctcaa cagcggtaag atccttgaga    300

gttttcgccc cgaagaacgt tttccaatga tgagcacttt taaagttctg ctatgtggcg    360
```

-continued

```
cggtattatc ccgtattgac gccgggcaag agcaactcgg tcgccgcata cactattctc    420
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgctttttt gcacaacatg ggggatcatg    600
taactcgcct tgatcgttgg gaaccggagc tgaatgaagc cataccaaac gacgagcgtg    660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac   1020
tttagattga tttaaaactt catttttaat ttaaaaggat ctaggtgaag atcctttttg   1080
ataatctcat gaccaaaatc ccttaacgtg agttttcgtt ccactgagcg tcagaccccg   1140
tagaaaagat caaaggatct tcttgagatc cttttttct gcgcgtaatc tgctgcttgc    1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca ggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttggc   2220
cattgcatac gttgtatcca tatcataata tgtacattta tattggctca tgtccaacat   2280
taccgccatg ttgacattga ttattgacta gttattaata gtaatcaatt acggggtcat   2340
tagttcatag cccatatatg gagttccgcg ttacataact tacggtaaat ggcccgcctg   2400
gctgaccgcc caacgacccc cgcccattga cgtcaataat gacgtatgtt cccatagtaa   2460
cgccaatagg gactttccat tgacgtcaat gggtggagta tttacggtaa actgcccact   2520
tggcagtaca tcaagtgtat catatgccaa gtacgccccc tattgacgtc aatgacggta   2580
aatggcccgc ctggcattat gcccagtaca tgaccttatg ggactttcct acttggcagt   2640
acatctacgt attagtcatc gctattacca tggtgatgcg gttttggcag tacatcaatg   2700
```

-continued

```
ggcgtggata gcggtttgac tcacggggat ttccaagtct ccaccccatt gacgtcaatg   2760
ggagtttgtt ttggcaccaa aatcaacggg actttccaaa atgtcgtaac aactccgccc   2820
cattgacgca aatgggcggt aggcgtgtac ggtgggaggt ctatataagc agagctcgtt   2880
tagtgaaccg gggtctctct ggttagacca gatctgagcc tgggagctct ctggctaact   2940
agggaaccca ctgcttaagc ctcaataaag cttgccttga gtgcttcaag tagtgtgtgc   3000
ccgtctgttg tgtgactctg gtaactagag atccctcaga cccttttagt cagtgtggaa   3060
aatctctagc agtggcgccc gaacagggac ctgaaagcga aagggaaacc agaggagctc   3120
tctcgacgca ggactcggct tgctgaagcg cgcacggcaa gaggcgaggg gcggcgactg   3180
gtgagtacgc caaaaatttt gactagcgga ggctagaagg agagagatgg gtgcgagagc   3240
gtcagtatta agcgggggag aattagatcg cgatgggaaa aaattcggtt aaggccaggg   3300
ggaaagaaaa aatataaatt aaaacatata gtatgggcaa gcagggagct agaacgattc   3360
gcagttaatc ctggcctgtt agaaacatca gaaggctgta gacaaatact gggacagcta   3420
caaccatccc ttcagacagg atcagaagaa cttagatcat tatataatac agtagcaacc   3480
ctctattgtg tgcatcaaag gatagagata aaagacacca aggaagcttt agacaagata   3540
gaggaagagc aaaacaaaag taagaccacc gcacagcaag cggccgctga tcttcagacc   3600
tggaggagga gatatgaggg acaattggag aagtgaatta tataaatata aagtagtaaa   3660
aattgaacca ttaggagtag cacccaccaa ggcaaagaga agagtggtgc agagagaaaa   3720
aagagcagtg ggaataggag ctttgttcct tgggttcttg ggagcagcag gaagcactat   3780
gggcgcagcc tcaatgacgc tgacggtaca ggccagacaa ttattgtctg gtatagtgca   3840
gcagcagaac aatttgctga gggctattga ggcgcaacag catctgttgc aactcacagt   3900
ctggggcatc aagcagctcc aggcaagaat cctggctgtg gaaagatacc taaaggatca   3960
acagctcctg gggatttggg gttgctctgg aaaactcatt tgcaccactg ctgtgccttg   4020
gaatgctagt tggagtaata aatctctgga acagattgga atcacacgac ctggatggag   4080
tgggacagag aaattaacaa ttacacaagc ttaatacact ccttaattga agaatcgcaa   4140
aaccagcaag aaaagaatga acaagaatta ttggaattag ataaatgggc aagtttgtgg   4200
aattggttta acataacaaa ttggctgtgg tatataaaat tattcataat gatagtagga   4260
ggcttggtag gtttaagaat agtttttgct gtactttcta tagtgaatag agttaggcag   4320
ggatattcac cattatcgtt tcagacccac ctcccaaccc cgaggggacc cgacaggccc   4380
gaaggaatag aagaagaagg tggagagaga gacagagaca gatccattcg attagtgaac   4440
ggatctcgac ggtatcgata agctaattca caaatggcag tattcatcca caattttaaa   4500
agaaaagggg ggattggggg gtacagtgca ggggaaagaa tagtagacat aatagcaaca   4560
gacatacaaa ctaaagaatt acaaaaacaa attacaaaaa ttcaaaattt tcgggtttat   4620
tacagggaca gcagagatcc agtttgggaa ttagcttgat cgattagtcc aatttgttaa   4680
agacaggata tcagtggtcc aggctctagt tttgactcaa caatatcacc agctgaagcc   4740
tatagagtac gagccataga tagaataaaa gattttattt agtctccaga aaaagggggg   4800
aatgaaagac cccacctgta ggtttggcaa gctaggatca aggttaggaa cagagagaca   4860
gcagaatatg ggccaaacag gatatctgtg gtaagcagtt cctgccccgg ctcagggcca   4920
agaacagttg gaacagcaga atatgggcca aacaggatat ctgtggtaag cagttcctgc   4980
cccggctcag ggccaagaac agatggtccc cagatgcggt cccgccctca gcagtttcta   5040
gagaaccatc agatgtttcc agggtgcccc aaggacctga aatgaccctg tgccttattt   5100
```

-continued

```
gaactaacca atcagttcgc ttctcgcttc tgttcgcgcg cttctgctcc ccgagctcaa   5160
taaaagagcc cacaacccct cactcggcgc gatctagatc tcgaatcgaa ttcgttaacc   5220
tcgagggatc catggcgacg ggttcaagaa cttccctact tcttgcattt ggcctgcttt   5280
gtttgccgtg gttacaggaa gcctcagcac aacagaagga ggtggagcag aattctggac   5340
ccctcagtgt tccagaggga gccattgcct ctctcaactg cacttacagt gaccgaggtt   5400
cccagtcctt cttctggtac agacaatatt ctgggaaaag ccctgagttg ataatgttca   5460
tatactccaa tggtgacaaa gaagatggaa ggtttacagc acagctcaat aaagccagcc   5520
agtatgtttc tctgctcatc agagactccc agcccagtga ttcagccacc tacctctgtg   5580
ccgtgaactt cggaggagga aagcttatct tcggacaggg aacggagtta tctgtgaaac   5640
ccaatatcca gaaccctgac cctgccgtgt accagctgag agactctaaa tccagtgaca   5700
agtctgtctg cctattcacc gattttgatt ctcaaacaaa tgtgtcacaa agtaaggatt   5760
ctgatgtgta tatcacagac aaaactgtgc tagacatgag gtctatggac ttcaagagca   5820
acagtgctgt ggcctggagc aacaaatctg actttgcatg tgcaaacgcc ttcaacaaca   5880
gcattattcc agaagacacc ttcttcccca gcccagaaag ttccgatgtc attaccatgg   5940
accccaagga taactgttct aaagacgcca atgatacact gctgctgcag ctgaccaata   6000
catcagctta ctatatgtac ctgctgctgc tgctgaagag cgtggtctat ttcgccatca   6060
tcacctgttg cctgctgcgg ctgtggtcca gcagggcaaa acgttcgggt tcgggtgcgc   6120
cagtaaagca gacattaaac tttgatttgc tgaaacttgc aggtgatgta gagtcaaatc   6180
caggtccaat ggcaacaggg agccgaacct ctctgctcct tgctttcggg ctcctttgcc   6240
taccgtgcct gcaggagggc tcggcaggga tcacccaggc accaacatct cagatcctgg   6300
cagcaggacg gcgcatgaca ctgagatgta cccaggatat gagacataat gccatgtact   6360
ggtatagaca agatctagga ctggggctaa ggctcatcca ttattcaaat actgcaggta   6420
ccactggcaa aggagaagtc cctgatggtt atagtgtctc cagagcaaac acagatgatt   6480
tcccccctcac gttggcgtct gctgtaccct ctcagacatc tgtgtacttc tgtgccagca   6540
gcctaagttt cggcactgaa gctttctttg gacaaggcac cagactcaca gttgtagagg   6600
acctgaacaa ggtgttccca cccgaggtcg ctgtgtttga gccatcagaa gcagagatct   6660
cccacaccca aaaggccaca ctggtgtgcc tggccacagg cttcttccct gaccacgtgg   6720
agctgagctg gtgggtgaat gggaaggagg tgcacagtgg ggtcagcacg gacccgcagc   6780
ccctcaagga gcagcccgcc ctcaatgact ccagatactg cctgagcagc cgcctgaggg   6840
tctcggccac cttctggcag aacccccgca accacttccg ctgtcaagtc cagttctacg   6900
ggctctcgga gaatgacgag tggacccagg atagggccaa acccgtcacc cagatcgtca   6960
gcgccgaagc ctggggtaga gcagacgact ccacagatca cgtgaagccc aaagagactg   7020
aaaacaccaa gcagccatcc aaatcttgtc acaagcccaa agccattgtg cataccgaaa   7080
aggtcaatat gatgtctctg acagtgctgg gcctgagaat gctgttcgca aaaactgtgg   7140
ctgtcaactt cctgctgact gctatggcca tggtcaagag aaaggatttc agagccaaaa   7200
gaggctccgg agccactaac ttctccctgt tgaaacaggc tggcgatgtt gaagaaaacc   7260
ccggtcctat gggggcaggt gccaccggcc gcgccatgga cgggccgcgc ctgctgctgt   7320
tgctgcttct gggggtgtcc cttggaggtg ccaaggagca gaagctgatc agcgaggagg   7380
acctggagat ccctggccgt tggattacac ggtccacacc cccagagggc tcggacagca   7440
```

cagcccccag cacccaggag cctgaggcac ctccagaaca agacctcata gccagcacgg 7500
tggcaggtgt ggtgaccaca gtgatgggca gctcccagcc cgtggtgacc cgaggcacca 7560
ccgacaacct catccctgtc tattgctcca tcctggctgc tgtggttgtg ggtcttgtgg 7620
cctacatagc cttcaagagg taaaggatcc cccggggtcg actgatcaaa ttcgagctcg 7680
gtacctttaa gaccaatgac ttacaaggca gctgtagatc ttagccactt tttaaaagaa 7740
aaggggggac tggaagggct aattcactcc caacgaagac aagatctgct ttttgcttgt 7800
actgggtctc tctggttaga ccagatctga gcctgggagc tctctggcta actagggaac 7860
ccactgctta agcctcaata aagcttgcct tgagtgcttc aagtagtgtg tgcccgtctg 7920
ttgtgtgact ctggtaacta gagatccctc agaccctttt agtcagtgtg gaaaatctct 7980
agcagtagta gttcatgtca tcttattatt cagtatttat aacttgcaaa gaaatgaata 8040
tcagagagtg agaggaactt gtttattgca gcttataatg gttacaaata aagcaatagc 8100
atcacaaatt tcacaaataa agcatttttt tcactgcatt ctagttgtgg tttgtccaaa 8160
ctcatcaatg tatcttatca tgtctggctc tagctatccc gcccctaact ccgcccatcc 8220
cgcccctaac tccgcccagt tccgcccatt ctccgcccca tggctgacta atttttttta 8280
tttatgcaga ggccgaggcc gcctcggcct ctgagctatt ccagaagtag tgaggaggct 8340
tttttggagg cctaggcttt tgcgtcgaga cgtacccaat tcgccctata gtgagtcgta 8400
ttacgcgcgc tcactggccg tcgttttaca acgtcgtgac tgggaaaacc ctggcgttac 8460
ccaacttaat cgccttgcag cacatccccc tttcgccagc tggcgtaata gcgaagaggc 8520
ccgcaccgat cgcccttccc aacagttgcg cagcctgaat ggcgaatggc gcgacgcgcc 8580
ctgtagcggc gcattaagcg cggcgggtgt ggtggttacg cgcagcgtga ccgctacact 8640
tgccagcgcc ctagcgcccg ctcctttcgc tttcttccct tcctttctcg ccacgttcgc 8700
cggctttccc cgtcaagctc taaatcgggg gctcccttta gggttccgat ttagtgcttt 8760
acggcacctc gaccccaaaa aacttgatta gggtgatggt tcacgtagtg ggccatcgcc 8820
ctgatagacg gtttttcgcc ctttgacgtt ggagtccacg ttctttaata gtggactctt 8880
gttccaaact ggaacaacac tcaaccctat ctcggtctat tcttttgatt tataagggat 8940
tttgccgatt tcggcctatt ggttaaaaaa tgagctgatt taacaaaaat ttaacgcgaa 9000
ttttaacaaa atattaacgt ttacaatttc c 9031

<210> SEQ ID NO 47
<211> LENGTH: 2322
<212> TYPE: DNA
<213> ORGANISM: Artificial Sequence
<220> FEATURE:
<223> OTHER INFORMATION: wild-type F5 TCR (pMTB1281)

<400> SEQUENCE: 47
atggcgacgg gttcaagaac ttccctactt cttgcatttg gcctgctttg tttgccgtgg 60
ttacaggaag cctcagcaca acagaaggag gtggagcaga attctggacc cctcagtgtt 120
ccagagggag ccattgcctc tctcaactgc acttacagtg accgaggttc ccagtccttc 180
ttctggtaca gacaatattc tgggaaaagc cctgagttga taatgttcat atactccaat 240
ggtgacaaag aagatggaag gtttacagca cagctcaata aagccagcca gtatgtttct 300
ctgctcatca gagactccca gcccagtgat tcagccacct acctctgtgc cgtgaacttc 360
ggaggaggaa agcttatctt cggacaggga acggagttat ctgtgaaacc caatatccag 420
aaccctgacc ctgccgtgta ccagctgaga gactctaaat ccagtgacaa gtctgtctgc 480

```
ctattcaccg attttgattc tcaaacaaat gtgtcacaaa gtaaggattc tgatgtgtat    540

atcacagaca aaactgtgct agacatgagg tctatggact tcaagagcaa cagtgctgtg    600

gcctggagca acaaatctga ctttgcatgt gcaaacgcct tcaacaacag cattattcca    660

gaagacacct tcttccccag cccagaaagt tcctgtgatg tcaagctggt cgagaaaagc    720

tttgaaacag atacgaacct aaactttcaa aacctgtcag tgattgggtt ccgaatcctc    780

ctcctgaaag tggccgggtt taatctgctc atgacgctgc ggctgtggtc cagcagggca    840

aaacgttcgg gttcgggtgc gccagtaaag cagacattaa actttgattt gctgaaactt    900

gcaggtgatg tagagtcaaa tccaggtcca atggcaacag gagccgaac ctctctgctc    960

cttgctttcg ggctcctttg cctaccgtgc ctgcaggagg gctcggcagg gatcacccag   1020

gcaccaacat ctcagatcct ggcagcagga cggcgcatga cactgagatg tacccaggat   1080

atgagacata atgccatgta ctggtataga caagatctag gactggggct aaggctcatc   1140

cattattcaa atactgcagg taccactggc aaaggagaag tccctgatgg ttatagtgtc   1200

tccagagcaa acacagatga tttcccccctc acgttggcgt ctgctgtacc ctctcagaca   1260

tctgtgtact tctgtgccag cagcctaagt ttcggcactg aagctttctt tggacaaggc   1320

accagactca cagttgtaga ggacctgaac aaggtgttcc cacccgaggt cgctgtgttt   1380

gagccatcag aagcagagat ctcccacacc caaaaggcca cactggtgtg cctggccaca   1440

ggcttcttcc ctgaccacgt ggagctgagc tggtgggtga atgggaagga ggtgcacagt   1500

ggggtcagca cggacccgca gcccctcaag gagcagcccg ccctcaatga ctccagatac   1560

tgcctgagca gccgcctgag ggtctcggcc accttctggc agaacccccg caaccacttc   1620

cgctgtcaag tccagttcta cgggctctcg gagaatgacg agtggaccca ggatagggcc   1680

aaacccgtca cccagatcgt cagcgccgaa gcctggggta gagcagactg tggctttacc   1740

tcggtgtcct accagcaagg ggtcctgtct gccaccatcc tctatgagat cctgctaggg   1800

aaggccaccc tgtatgctgt gctggtcagc gcccttgtgt tgatggccat ggtcaagaga   1860

aaggatttca gagccaaaag aggctccgga gccactaact tctccctgtt gaaacaggct   1920

ggcgatgttg aagaaaaccc cggtcctatg gggggcaggtg ccaccggccg cgccatggac   1980

gggccgcgcc tgctgctgtt gctgcttctg ggggtgtccc ttggaggtgc caaggagcag   2040

aagctgatca gcgaggagga cctggagatc cctggccgtt ggattacacg gtccacaccc   2100

ccagagggct cggacagcac agcccccagc acccaggagc ctgaggcacc tccagaacaa   2160

gacctcatag ccagcacggt ggcaggtgtg gtgaccacag tgatgggcag ctcccagccc   2220

gtggtgaccc gaggcaccac cgacaacctc atccctgtct attgctccat cctggctgct   2280

gtggttgtgg gtcttgtggc ctacatagcc ttcaagaggt aa                      2322
```

```
<210> SEQ ID NO 48
<211> LENGTH: 2322
<212> TYPE: DNA
<213> ORGANISM: Artificial Sequence
<220> FEATURE:
<223> OTHER INFORMATION: domain-swapped F5 TCR VC-swap, BA orientation
      (pMTB1282)

<400> SEQUENCE: 48

atggcgacgg gttcaagaac ttccctactt cttgcatttg gcctgctttg tttgccgtgg     60

ttacaggaag cctcagcagg gatcacccag gcaccaacat ctcagatcct ggcagcagga    120

cggcgcatga cactgagatg tacccaggat atgagacata atgccatgta ctggtataga    180
```

```
caagatctag gactggggct aaggctcatc cattattcaa atactgcagg taccactggc    240
aaaggagaag tccctgatgg ttatagtgtc tccagagcaa acacagatga tttccccctc    300
acgttggcgt ctgctgtacc ctctcagaca tctgtgtact tctgtgccag cagcctaagt    360
ttcggcactg aagctttctt tggacaaggc accagactca cagttgtaga ggacctgaac    420
aaggtgttcc cacccgaggt cgctgtgttt gagccatcag aagcagagat ctcccacacc    480
caaaaggcca cactggtgtg cctggccaca ggcttcttcc ctgaccacgt ggagctgagc    540
tggtgggtga atgggaagga ggtgcacagt ggggtcagca cggacccgca gcccctcaag    600
gagcagcccg ccctcaatga ctccagatac tgcctgagca gccgcctgag ggtctcggcc    660
accttctggc agaacccccg caaccacttc cgctgtcaag tccagttcta cgggctctcg    720
gagaatgacg agtggaccca ggatagggcc aaacccgtca cccagatcgt cagcgccgaa    780
gcctggggta gagcagactg tgatgtcaag ctggtcgaga aaagctttga aacagatacg    840
aacctaaact ttcaaaacct gtcagtgatt gggttccgaa tcctcctcct gaaagtggcc    900
gggtttaatc tgctcatgac gctgcggctg tggtccagca gggcaaaacg ttcgggttcg    960
ggtgcgccag taaagcagac attaaacttt gatttgctga aacttgcagg tgatgtagag   1020
tcaaatccag gtccaatggc aacagggagc cgaacctctc tgctccttgc tttcgggctc   1080
ctttgcctac cgtgcctgca ggagggctcg gcacaacaga aggaggtgga gcagaattct   1140
ggacccctca gtgttccaga gggagccatt gcctctctca actgcactta cagtgaccga   1200
ggttcccagt ccttcttctg gtacagacaa tattctggga aaagccctga gttgataatg   1260
ttcatatact ccaatggtga caaagaagat ggaaggttta cagcacagct caataaagcc   1320
agccagtatg tttctctgct catcagagac tcccagccca gtgattcagc cacctacctc   1380
tgtgccgtga acttcggagg aggaaagctt atcttcggac agggaacgga gttatctgtg   1440
aaacccaata tccagaaccc tgaccctgcc gtgtaccagc tgagagactc taaatccagt   1500
gacaagtctg tctgcctatt caccgatttt gattctcaaa caaatgtgtc acaaagtaag   1560
gattctgatg tgtatatcac agacaaaact gtgctagaca tgaggtctat ggacttcaag   1620
agcaacagtg ctgtggcctg gagcaacaaa tctgactttg catgtgcaaa cgccttcaac   1680
aacagcatta ttccagaaga caccttcttc cccagcccag aaagttcctg tggctttacc   1740
tcggtgtcct accagcaagg ggtcctgtct gccaccatcc tctatgagat cctgctaggg   1800
aaggccaccc tgtatgctgt gctggtcagc gcccttgtgt tgatggccat ggtcaagaga   1860
aaggatttca gagccaaaag aggctccgga gccactaact tctccctgtt gaaacaggct   1920
ggcgatgttg aagaaaaccc cggtcctatg gggcaggtg ccaccggccg cgccatggac   1980
gggccgcgcc tgctgctgtt gctgcttctg gggtgtccc ttggaggtgc caaggagcag   2040
aagctgatca gcgaggagga cctggagatc cctggccgtt ggattacacg gtccacaccc   2100
ccagagggct cggacagcac agcccccagc acccaggagc ctgaggcacc tccagaacaa   2160
gacctcatag ccagcacggt ggcaggtgtg gtgaccacag tgatgggcag ctcccagccc   2220
gtggtgaccc gaggcaccac cgacaacctc atccctgtct attgctccat cctggctgct   2280
gtggttgtgg gtcttgtggc ctacatagcc ttcaagaggt aa                      2322
```

<210> SEQ ID NO 49
<211> LENGTH: 2322
<212> TYPE: DNA
<213> ORGANISM: Artificial Sequence
<220> FEATURE:

<223> OTHER INFORMATION: domain-swapped F5 TCR VC-swap, AB orientation
(pMTB1283)

<400> SEQUENCE: 49
atggcgacgg gttcaagaac ttccctactt cttgcatttg gcctgctttg tttgccgtgg 60
ttacaggaag cctcagcaca acagaaggag gtggagcaga attctggacc cctcagtgtt 120
ccagagggag ccattgcctc tctcaactgc acttacagtg accgaggttc ccagtccttc 180
ttctggtaca gacaatattc tgggaaaagc cctgagttga taatgttcat atactccaat 240
ggtgacaaag aagatggaag gtttacagca cagctcaata aagccagcca gtatgtttct 300
ctgctcatca gagactccca gcccagtgat tcagccacct acctctgtgc cgtgaacttc 360
ggaggaggaa agcttatctt cggacaggga acggagttat ctgtgaaacc caatatccag 420
aaccctgacc ctgccgtgta ccagctgaga gactctaaat ccagtgacaa gtctgtctgc 480
ctattcaccg attttgattc tcaaacaaat gtgtcacaaa gtaaggattc tgatgtgtat 540
atcacagaca aaactgtgct agacatgagg tctatggact tcaagagcaa cagtgctgtg 600
gcctggagca acaaatctga ctttgcatgt gcaaacgcct tcaacaacag cattattcca 660
gaagacacct tcttccccag cccagaaagt tcctgtggct ttacctcggt gtcctaccag 720
caaggggtcc tgtctgccac catcctctat gagatcctgc tagggaaggc caccctgtat 780
gctgtgctgg tcagcgccct tgtgttgatg gccatggtca agagaaagga tttcagggca 840
aaacgttcgg gttcgggtgc gccagtaaag cagacattaa actttgattt gctgaaactt 900
gcaggtgatg tagagtcaaa tccaggtcca atggcaacag ggagccgaac ctctctgctc 960
cttgctttcg ggctcctttg cctaccgtgc ctgcaggagg gctcggcagg gatcacccag 1020
gcaccaacat ctcagatcct ggcagcagga cggcgcatga cactgagatg tacccaggat 1080
atgagacata atgccatgta ctggtataga caagatctag gactggggct aaggctcatc 1140
cattattcaa atactgcagg taccactggc aaaggagaag tccctgatgg ttatagtgtc 1200
tccagagcaa acacagatga tttcccccctc acgttggcgt ctgctgtacc ctctcagaca 1260
tctgtgtact tctgtgccag cagcctaagt ttcggcactg aagctttctt tggacaaggc 1320
accagactca cagttgtaga ggacctgaac aaggtgttcc cacccgaggt cgctgtgttt 1380
gagccatcag aagcagagat ctcccacacc caaaaggcca cactggtgtg cctggccaca 1440
ggcttcttcc ctgaccacgt ggagctgagc tggtgggtga atgggaagga ggtgcacagt 1500
ggggtcagca cggacccgca gcccctcaag gagcagcccg ccctcaatga ctccagatac 1560
tgcctgagca gccgcctgag ggtctcggcc accttctggc agaacccccg caaccacttc 1620
cgctgtcaag tccagttcta cgggctctcg gagaatgacg agtggaccca ggatagggcc 1680
aaacccgtca cccagatcgt cagcgccgaa gcctggggta gagcagactg tgatgtcaag 1740
ctggtcgaga aaagctttga aacagatacg aacctaaact ttcaaaacct gtcagtgatt 1800
gggttccgaa tcctcctcct gaaagtggcc gggtttaatc tgctcatgac gctgcggctg 1860
tggtccagca gagccaaaag aggctccgga gccactaact tctccctgtt gaaacaggct 1920
ggcgatgttg aagaaaaccc cggtcctatg gggggcaggtg ccaccggccg cgccatggac 1980
gggccgcgcc tgctgctgtt gctgcttctg ggggtgtccc ttggaggtgc caaggagcag 2040
aagctgatca gcgaggagga cctggagatc cctggccgtt ggattacacg gtccacaccc 2100
ccagagggct cggacagcac agccccccagc acccaggagc ctgaggcacc tccagaacaa 2160
gacctcatag ccagcacggt ggcaggtgtg gtgaccacag tgatgggcag ctcccagccc 2220
gtggtgaccc gaggcaccac cgacaacctc atccctgtct attgctccat cctggctgct 2280
gtggttgtgg gtcttgtggc ctacatagcc ttcaagaggt aa 2322

<210> SEQ ID NO 50
<211> LENGTH: 2322
<212> TYPE: DNA
<213> ORGANISM: Artificial Sequence
<220> FEATURE:
<223> OTHER INFORMATION: domain-swapped F5 TCR VCcp-swap, BA orientation
(pMTB1284)

<400> SEQUENCE: 50
atggcgacgg gttcaagaac ttccctactt cttgcatttg gcctgctttg tttgccgtgg 60
ttacaggaag cctcagcagg gatcacccag gcaccaacat ctcagatcct ggcagcagga 120
cggcgcatga cactgagatg tacccaggat atgagacata atgccatgta ctggtataga 180
caagatctag gactggggct aaggctcatc cattattcaa atactgcagg taccactggc 240
aaaggagaag tccctgatgg ttatagtgtc tccagagcaa acacagatga tttcccccctc 300 acgttggcgt ctgctgtacc ctctcagaca tctgtgtact tctgtgccag cagcctaagt 360
ttcggcactg aagctttctt tggacaaggc accagactca cagttgtaga ggacctgaac 420
aaggtgttcc cacccgaggt cgctgtgttt gagccatcag aagcagagat ctcccacacc 480
caaaaggcca cactggtgtg cctggccaca ggcttcttcc ctgaccacgt ggagctgagc 540
tggtgggtga atgggaagga ggtgcacagt ggggtcagca cggacccgca gcccctcaag 600
gagcagcccg ccctcaatga ctccagatac tgcctgagca gccgcctgag ggtctcggcc 660
accttctggc agaacccccg caaccacttc cgctgtcaag tccagttcta cgggctctcg 720
gagaatgacg agtggaccca ggatagggcc aaacccgtca cccagatcgt cagcgccgaa 780
gcctggggta gagcagactg tggctttacc tcggtgtcct accagcaagg ggtcctgtct 840
gccaccaacc tgtcagtgat tgggttccga atcctcctcc tgaaagtggc cgggtttaat 900
ctgctcatga cgctgcggct gtggtccagc agggcaaaac gttcgggttc gggtgcgcca 960
gtaaagcaga cattaaactt tgatttgctg aaacttgcag gtgatgtaga gtcaaatcca 1020
ggtccaatgg caacagggag ccgaacctct ctgctccttg ctttcgggct cctttgccta 1080
ccgtgcctgc aggagggctc ggcacaacag aaggaggtgg agcagaattc tggacccctc 1140
agtgttccag agggagccat tgcctctctc aactgcactt acagtgaccg aggttcccag 1200
tccttcttct ggtacagaca atattctggg aaaagccctg agttgataat gttcatatac 1260
tccaatggtg acaaagaaga tggaaggttt acagcacagc tcaataaagc cagccagtat 1320
gtttctctgc tcatcagaga ctcccagccc agtgattcag ccacctacct ctgtgccgtg 1380
aacttcggag gaggaaagct tatcttcgga cagggaacgg agttatctgt gaaacccaat 1440
atccagaacc ctgaccctgc cgtgtaccag ctgagagact ctaaatccag tgacaagtct 1500
gtctgcctat tcaccgattt tgattctcaa acaaatgtgt cacaaagtaa ggattctgat 1560
gtgtatatca cagacaaaac tgtgctagac atgaggtcta tggacttcaa gagcaacagt 1620
gctgtggcct ggagcaacaa atctgacttt gcatgtgcaa acgccttcaa caacagcatt 1680
attccagaag acaccttctt ccccagccca gaaagttcct gtgatgtcaa gctggtcgag 1740
aaaagctttg aaacagatac gaacctaaac tttcaaatcc tctatgagat cctgctaggg 1800
aaggccaccc tgtatgctgt gctggtcagc gcccttgtgt tgatggccat ggtcaagaga 1860
aaggatttca gagccaaaag aggctccgga gccactaact tctccctgtt gaaacaggct 1920

```
ggcgatgttg aagaaaaccc cggtcctatg ggggcaggtg ccaccggccg cgccatggac   1980

gggccgcgcc tgctgctgtt gctgcttctg ggggtgtccc ttggaggtgc caaggagcag   2040

aagctgatca gcgaggagga cctggagatc cctggccgtt ggattacacg gtccacaccc   2100

ccagagggct cggacagcac agcccccagc acccaggagc ctgaggcacc tccagaacaa   2160

gacctcatag ccagcacggt ggcaggtgtg gtgaccacag tgatgggcag ctcccagccc   2220

gtggtgaccc gaggcaccac cgacaacctc atccctgtct attgctccat cctggctgct   2280

gtggttgtgg gtcttgtggc ctacatagcc ttcaagaggt aa                      2322
```

<210> SEQ ID NO 51
<211> LENGTH: 2322
<212> TYPE: DNA
<213> ORGANISM: Artificial Sequence
<220> FEATURE:
<223> OTHER INFORMATION: domain-swapped F5 TCR VCcp-swap, AB orientation
(pMTB1285)

<400> SEQUENCE: 51

```
atggcgacgg gttcaagaac ttccctactt cttgcatttg gcctgctttg tttgccgtgg     60

ttacaggaag cctcagcaca acagaaggag gtggagcaga attctggacc cctcagtgtt    120

ccagagggag ccattgcctc tctcaactgc acttacagtg accgaggttc ccagtccttc    180

ttctggtaca gacaatattc tgggaaaagc cctgagttga taatgttcat atactccaat    240

ggtgacaaag aagatggaag gtttacagca cagctcaata aagccagcca gtatgtttct    300

ctgctcatca gagactccca gcccagtgat tcagccacct acctctgtgc cgtgaacttc    360

ggaggaggaa agcttatctt cggacaggga acggagttat ctgtgaaacc caatatccag    420

aaccctgacc ctgccgtgta ccagctgaga gactctaaat ccagtgacaa gtctgtctgc    480

ctattcaccg attttgattc tcaaacaaat gtgtcacaaa gtaaggattc tgatgtgtat    540

atcacagaca aaactgtgct agacatgagg tctatggact tcaagagcaa cagtgctgtg    600

gcctggagca acaaatctga ctttgcatgt gcaaacgcct tcaacaacag cattattcca    660

gaagacacct tcttccccag cccagaaagt tcctgtgatg tcaagctggt cgagaaaagc    720

tttgaaacag atacgaacct aaactttcaa atcctctatg agatcctgct agggaaggcc    780

accctgtatg ctgtgctggt cagcgccctt gtgttgatgg ccatggtcaa gagaaaggat    840

ttcagggcaa aacgttcggg ttcgggtgcg ccagtaaagc agacattaaa ctttgatttg    900

ctgaaacttg caggtgatgt agagtcaaat ccaggtccaa tggcaacagg gagccgaacc    960

tctctgctcc ttgctttcgg gctcctttgc ctaccgtgcc tgcaggaggg ctcggcaggg   1020

atcacccagg caccaacatc tcagatcctg gcagcaggac ggcgcatgac actgagatgt   1080

acccaggata tgagacataa tgccatgtac tggtatagac aagatctagg actggggcta   1140

aggctcatcc attattcaaa tactgcaggt accactggca aaggagaagt ccctgatggt   1200

tatagtgtct ccagagcaaa cacagatgat ttccccctca cgttggcgtc tgctgtaccc   1260

tctcagacat ctgtgtactt ctgtgccagc agcctaagtt tcggcactga agctttcttt   1320

ggacaaggca ccagactcac agttgtagag gacctgaaca aggtgttccc acccgaggtc   1380

gctgtgtttg agccatcaga agcagagatc tcccacaccc aaaaggccac actggtgtgc   1440

ctggccacag gcttcttccc tgaccacgtg gagctgagct ggtgggtgaa tgggaaggag   1500

gtgcacagtg ggtcagcac ggacccgcag cccctcaagg agcagcccgc cctcaatgac    1560

tccagatact gcctgagcag ccgcctgagg gtctcggcca ccttctggca gaacccccgc   1620
```

aaccacttcc gctgtcaagt ccagttctac gggctctcgg agaatgacga gtggacccag 1680
gatagggcca aacccgtcac ccagatcgtc agcgccgaag cctggggtag agcagactgt 1740
ggctttacct cggtgtccta ccagcaaggg gtcctgtctg ccaccaacct gtcagtgatt 1800
gggttccgaa tcctcctcct gaaagtggcc gggtttaatc tgctcatgac gctgcggctg 1860
tggtccagca gagccaaaag aggctccgga gccactaact tctccctgtt gaaacaggct 1920
ggcgatgttg aagaaaaccc cggtcctatg ggggcaggtg ccaccggccg cgccatggac 1980
gggccgcgcc tgctgctgtt gctgcttctg ggggtgtccc ttggaggtgc caaggagcag 2040
aagctgatca gcgaggagga cctggagatc cctggccgtt ggattacacg gtccacaccc 2100
ccagagggct cggacagcac agcccccagc acccaggagc ctgaggcacc tccagaacaa 2160
gacctcatag ccagcacggt ggcaggtgtg gtgaccacag tgatgggcag ctcccagccc 2220
gtggtgaccc gaggcaccac cgacaacctc atccctgtct attgctccat cctggctgct 2280
gtggttgtgg gtcttgtggc ctacatagcc ttcaagaggt aa 2322

<210> SEQ ID NO 52
<211> LENGTH: 2412
<212> TYPE: DNA
<213> ORGANISM: Artificial Sequence
<220> FEATURE:
<223> OTHER INFORMATION: domain-swapped F5 TCR AlphaDelta+BetaGamma chimera (pMTB1301)

<400> SEQUENCE: 52
atggcgacgg gttcaagaac ttccctactt cttgcatttg gcctgctttg tttgccgtgg 60
ttacaggaag cctcagcaca acagaaggag gtggagcaga attctggacc cctcagtgtt 120
ccagagggag ccattgcctc tctcaactgc acttacagtg accgaggttc ccagtccttc 180
ttctggtaca gacaatattc tgggaaaagc cctgagttga taatgttcat atactccaat 240
ggtgacaaag aagatggaag gtttacagca cagctcaata aagccagcca gtatgtttct 300
ctgctcatca gagactccca gcccagtgat tcagccacct acctctgtgc cgtgaacttc 360
ggaggaggaa agcttatctt cggacaggga acggagttat ctgtgaaacc caatatccag 420
aaccctgacc ctgccgtgta ccagctgaga gactctaaat ccagtgacaa gtctgtctgc 480
ctattcaccg attttgattc tcaaacaaat gtgtcacaaa gtaaggattc tgatgtgtat 540
atcacagaca aaactgtgct agacatgagg tctatggact tcaagagcaa cagtgctgtg 600
gcctggagca acaaatctga ctttgcatgt gcaaacgcct tcaacaacag cattattcca 660
gaagacacct tcttccccag cccagaaagt tccgactcca cagatcacgt gaagcccaaa 720
gagactgaaa acaccaagca gccatccaaa tcttgtcaca agcccaaagc cattgtgcat 780
accgaaaagg tcaatatgat gtctctgaca gtgctgggcc tgagaatgct gttcgcaaaa 840
actgtggctg tcaacttcct gctgactgct cggctgtggt ccagcagggc aaaacgttcg 900
ggttcgggtg cgccagtaaa gcagacatta aactttgatt tgctgaaact tgcaggtgat 960
gtagagtcaa atccaggtcc aatggcaaca gggagccgaa cctctctgct ccttgctttc 1020
gggctccttt gcctaccgtg cctgcaggag ggctcggcag ggatcaccca ggcaccaaca 1080
tctcagatcc tggcagcagg acggcgcatg acactgagat gtacccagga tatgagacat 1140
aatgccatgt actggtatag acaagatcta ggactggggc taaggctcat ccattattca 1200
aatactgcag gtaccactgg caaaggagaa gtccctgatg gttatagtgt ctccagagca 1260
aacacagatg atttcccccct cacgttggcg tctgctgtac cctctcagac atctgtgtac 1320
ttctgtgcca gcagcctaag tttcggcact gaagctttct ttggacaagg caccagactc 1380
acagttgtag aggacctgaa caaggtgttc ccacccgagg tcgctgtgtt tgagccatca 1440
gaagcagaga tctcccacac ccaaaaggcc acactggtgt gcctggccac aggcttcttc 1500
cctgaccacg tggagctgag ctggtgggtg aatgggaagg aggtgcacag tggggtcagc 1560
acggacccgc agcccctcaa ggagcagccc gccctcaatg actccagata ctgcctgagc 1620
agccgcctga gggtctcggc caccttctgg cagaaccccc gcaaccactt ccgctgtcaa 1680
gtccagttct acgggctctc ggagaatgac gagtggaccc aggatagggc caaacccgtc 1740
acccagatcg tcagcgccga agcctggggt agagcagacg atgtcattac catggacccc 1800
aaggataact gttctaaaga cgccaatgat acactgctgc tgcagctgac caatacatca 1860
gcttactata tgtacctgct gctgctgctg aagagcgtgg tctatttcgc catcatcacc 1920
tgttgcctgc tgatggccat ggtcaagaga aaggatttca gagccaaaag aggctccgga 1980
gccactaact tctccctgtt gaaacaggct ggcgatgttg aagaaaaccc cggtcctatg 2040
ggggcaggtg ccaccggccg cgccatggac gggccgcgcc tgctgctgtt gctgcttctg 2100
ggggtgtccc ttggaggtgc caaggagcag aagctgatca gcgaggagga cctggagatc 2160
cctggccgtt ggattacacg gtccacaccc ccagagggct cggacagcac agccccccagc 2220 acccaggagc ctgaggcacc tccagaacaa gacctcatag ccagcacggt ggcaggtgtg 2280
gtgaccacag tgatgggcag ctcccagccc gtggtgaccc gaggcaccac cgacaacctc 2340
atccctgtct attgctccat cctggctgct gtggttgtgg gtcttgtggc ctacatagcc 2400
ttcaagaggt aa 2412

<210> SEQ ID NO 53
<211> LENGTH: 2412
<212> TYPE: DNA
<213> ORGANISM: Artificial Sequence
<220> FEATURE:
<223> OTHER INFORMATION: domain-swapped F5 TCR AlphaGamma+BetaDelta
chimera (pMTB1302)

<400> SEQUENCE: 53
atggcgacgg gttcaagaac ttccctactt cttgcatttg gcctgctttg tttgccgtgg 60
ttacaggaag cctcagcaca acagaaggag gtggagcaga attctggacc cctcagtgtt 120
ccagagggag ccattgcctc tctcaactgc acttacagtg accgaggttc ccagtccttc 180
ttctggtaca gacaatattc tgggaaaagc cctgagttga taatgttcat atactccaat 240
ggtgacaaag aagatggaag gtttacagca cagctcaata aagccagcca gtatgtttct 300
ctgctcatca gagactccca gcccagtgat tcagccacct acctctgtgc cgtgaacttc 360
ggaggaggaa agcttatctt cggacaggga acggagttat ctgtgaaacc caatatccag 420
aaccctgacc ctgccgtgta ccagctgaga gactctaaat ccagtgacaa gtctgtctgc 480
ctattcaccg attttgattc tcaaacaaat gtgtcacaaa gtaaggattc tgatgtgtat 540
atcacagaca aaactgtgct agacatgagg tctatggact tcaagagcaa cagtgctgtg 600
gcctggagca acaaatctga ctttgcatgt gcaaacgcct tcaacaacag cattattcca 660
gaagacacct tcttccccag cccagaaagt tccgatgtca ttaccatgga ccccaaggat 720
aactgttcta aagacgccaa tgatacactg ctgctgcagc tgaccaatac atcagcttac 780
tatatgtacc tgctgctgct gctgaagagc gtggtctatt tcgccatcat cacctgttgc 840
ctgctgcggc tgtggtccag cagggcaaaa cgttcgggtt cgggtgcgcc agtaaagcag 900

```
acattaaact ttgatttgct gaaacttgca ggtgatgtag agtcaaatcc aggtccaatg    960

gcaacaggga gccgaacctc tctgctcctt gctttcgggc tcctttgcct accgtgcctg   1020

caggagggct cggcagggat cacccaggca ccaacatctc agatcctggc agcaggacgg   1080

cgcatgacac tgagatgtac ccaggatatg agacataatg ccatgtactg gtatagacaa   1140

gatctaggac tggggctaag gctcatccat tattcaaata ctgcaggtac cactggcaaa   1200

ggagaagtcc ctgatggtta tagtgtctcc agagcaaaca cagatgattt cccccctcacg   1260

ttggcgtctg ctgtaccctc tcagacatct gtgtacttct gtgccagcag cctaagtttc   1320

ggcactgaag ctttctttgg acaaggcacc agactcacag ttgtagagga cctgaacaag   1380

gtgttcccac ccgaggtcgc tgtgtttgag ccatcagaag cagagatctc ccacacccaa   1440

aaggccacac tggtgtgcct ggccacaggc ttcttccctg accacgtgga gctgagctgg   1500

tgggtgaatg ggaaggaggt gcacagtggg gtcagcacgg acccgcagcc cctcaaggag   1560

cagcccgccc tcaatgactc cagatactgc ctgagcagcc gcctgagggt ctcggccacc   1620

ttctggcaga acccccgcaa ccacttccgc tgtcaagtcc agttctacgg gctctcggag   1680

aatgacgagt ggacccagga tagggccaaa cccgtcaccc agatcgtcag cgccgaagcc   1740

tggggtagag cagacgactc cacagatcac gtgaagccca aagagactga aaacaccaag   1800

cagccatcca aatcttgtca caagcccaaa gccattgtgc ataccgaaaa ggtcaatatg   1860

atgtctctga cagtgctggg cctgagaatg ctgttcgcaa aaactgtggc tgtcaacttc   1920

ctgctgactg ctatggccat ggtcaagaga aaggatttca gagccaaaag aggctccgga   1980

gccactaact tctccctgtt gaaacaggct ggcgatgttg aagaaaaccc cggtcctatg   2040

ggggcaggtg ccaccggccg cgccatggac gggccgcgcc tgctgctgtt gctgcttctg   2100

ggggtgtccc ttggaggtgc caaggagcag aagctgatca gcgaggagga cctggagatc   2160

cctggccgtt ggattacacg gtccacaccc ccagagggct cggacagcac agcccccagc   2220

acccaggagc ctgaggcacc tccagaacaa gacctcatag ccagcacggt ggcaggtgtg   2280

gtgaccacag tgatgggcag ctcccagccc gtggtgaccc gaggcaccac cgacaacctc   2340

atccctgtct attgctccat cctggctgct gtggttgtgg gtcttgtggc ctacatagcc   2400

ttcaagaggt aa                                                       2412
```

<210> SEQ ID NO 54
<211> LENGTH: 1836
<212> TYPE: DNA
<213> ORGANISM: Artificial Sequence
<220> FEATURE:
<223> OTHER INFORMATION: domain-swapped OTI mouse TCR VC-swap, BA orientation (pMTB1185)

<400> SEQUENCE: 54

```
atggccccgc gggtgctggc cgatagcgcc tggggcatca cactgctgtc ctgggtgacc     60

gtgttcctgc tgggcaccag cagcgccgac agcggcgtgg tgcagagccc caggcacatc    120

atcaaggaga agggcggcag aagcgtgctg acctgcatcc ccatcagcgg ccacagcaac    180

gtggtgtggt atcagcagac cctgggcaag gagctgaagt tcctgatcca gcactacgag    240

aaggtggaga gggacaaggg cttcctgccc agcaggttca gcgtgcagca gttcgacgac    300

taccacagcg agatgaacat gagcgccctg gagctggagg acagcgccat gtacttttgc    360

gccagcagca gggccaacta cgagcagtac ttcggccctg gcaccaggct gaccgtgctg    420

gaggacctga ggaacgtgac cccccccaag gtgtccctgt tcgagcccag caaggccgag    480
```

```
atcgccaaca agcagaaggc caccctggtg tgcctggcca ggggcttctt ccccgaccac     540

gtggagctgt cttggtgggt gaacggcaag gaggtgcaca gcggcgtgag caccgacccc     600

caggcctaca aggagagcaa ctacagctac tgcctgagca gcaggctgag agtgagcgcc     660

accttctggc acaaccccag gaaccacttc cgctgtcagg tgcagttcca cggcctgagc     720

gaggaggaca agtggcccga gggcagcccc aagcccgtga cccagaacat cagcgccgag     780

gcctggggca gagccgactg cgacgccacc ctgaccgaga agagcttcga gaccgacatg     840

aacctgaact tccagaacct gagcgtgatg ggcctgagaa tcctgctgct gaaggtggcc     900

ggcttcaacc tgctgatgac cctgaggctg tggagcagca gcggcagcgg cgccaccaac     960

ttcagcctgc tgaagcaggc cggcgacgtg gaggaaaacc ctgggcccat ggacaagatc    1020

ctgaccgcca cctttctgct gctgggcctg cacctggccg gcgtgaacgg acagcagcag    1080

gagaagaggg atcagcagca ggtgcggcag agcccccaga gcctgaccgt gtgggagggc    1140

gagaccgcca tcctgaactg cagctacgag gacagcacct tcaactactt cccttggtat    1200

cagcagttcc ccggcgaggg ccctgctctg ctgatctcca tcagaagcgt gagcgacaag    1260

aaggaggacg gcaggttcac catctttttc aacaagcggg agaagaagct gtccctgcac    1320

atcaccgaca gccagcccgg cgacagcgcc acctactttt gcgccgccag cgacaactac    1380

cagctgatct ggggcagcgg caccaagctg atcatcaagc ccgacatcca gaacccccgag   1440

cccgccgtgt accagctgaa ggaccccaga agccaggaca gcaccctgtg cctgttcacc    1500

gacttcgaca gccagatcaa cgtgcccaag accatggaga gcggcacctt catcaccgac    1560

aagaccgtgc tggacatgaa ggccatggac agcaagagca acggcgccat cgcctggtcc    1620

aaccagacca gcttcacatg ccaggacatc ttcaaggaga ccaacgccac ctaccccagc    1680

agcgacgtgc cctgcggcat caccagcgcc agctaccacc agggcgtgct gtccgccacc    1740

atcctgtacg agatcctgct gggcaaggcc acactgtacg ccgtgctggt gtccggcctg    1800

gtgctgatgg ccatggtgaa gaagaagaac agctga                              1836
```

<210> SEQ ID NO 55
<211> LENGTH: 1836
<212> TYPE: DNA
<213> ORGANISM: Artificial Sequence
<220> FEATURE:
<223> OTHER INFORMATION: domain-swapped OTI mouse TCR VC-swap, AB orientation (pMTB1186)

<400> SEQUENCE: 55

```
atggacaaga tcctgaccgc cacctttctg ctgctgggcc tgcacctggc cggcgtgaac      60

ggacagcagc aggagaagag ggatcagcag caggtgcggc agagccccca gagcctgacc     120

gtgtgggagg gcgagaccgc catcctgaac tgcagctacg aggacagcac cttcaactac     180

ttcccttggt atcagcagtt ccccggcgag ggccctgctc tgctgatctc catcagaagc     240

gtgagcgaca agaaggagga cggcaggttc accatctttt tcaacaagcg ggagaagaag     300

ctgtccctgc acatcaccga cagccagccc ggcgacagcg ccacctactt ttgcgccgcc     360

agcgacaact accagctgat ctggggcagc ggcaccaagc tgatcatcaa gcccgacatc     420

cagaaccccg agcccgccgt gtaccagctg aaggacccca gaagccagga cagcaccctg     480

tgcctgttca ccgacttcga cagccagatc aacgtgccca agaccatgga gagcggcacc     540

ttcatcaccg acaagaccgt gctggacatg aaggccatgg acagcaagag caacggcgcc     600

atcgcctggt ccaaccagac cagcttcaca tgccaggaca tcttcaagga gaccaacgcc     660
```

-continued acctacccca gcagcgacgt gccctgcggc atcaccagcg ccagctacca ccagggcgtg 720
ctgtccgcca ccatcctgta cgagatcctg ctgggcaagg ccacactgta cgccgtgctg 780
gtgtccggcc tggtgctgat ggccatggtg aagaagaaga acagcagcgg cagcggcgcc 840
accaacttca gcctgctgaa gcaggccggc gacgtggagg aaaaccctgg gcccatggcc 900
ccgcgggtgc tggccgatag cgcctggggc atcacactgc tgtcctgggt gaccgtgttc 960
ctgctgggca ccagcagcgc cgacagcggc gtggtgcaga gccccaggca catcatcaag 1020
gagaagggcg gcagaagcgt gctgacctgc atccccatca gcggccacag caacgtggtg 1080
tggtatcagc agaccctggg caaggagctg aagttcctga tccagcacta cgagaaggtg 1140
gagagggaca agggcttcct gcccagcagg ttcagcgtgc agcagttcga cgactaccac 1200
agcgagatga acatgagcgc cctggagctg gaggacagcg ccatgtactt ttgcgccagc 1260
agcagggcca actacgagca gtacttcggc cctggcacca ggctgaccgt gctggaggac 1320
ctgaggaacg tgaccccccc caaggtgtcc ctgttcgagc ccagcaaggc cgagatcgcc 1380
aacaagcaga aggccaccct ggtgtgcctg gccaggggct tcttccccga ccacgtggag 1440
ctgtcttggt gggtgaacgg caaggaggtg cacagcggcg tgagcaccga cccccaggcc 1500
tacaaggaga gcaactacag ctactgcctg agcagcaggc tgagagtgag cgccaccttc 1560
tggcacaacc ccaggaacca cttccgctgt caggtgcagt tccacggcct gagcgaggag 1620
gacaagtggc ccgagggcag ccccaagccc gtgacccaga acatcagcgc cgaggcctgg 1680
ggcagagccg actgcgacgc caccctgacc gagaagagct tcgagaccga catgaacctg 1740
aacttccaga acctgagcgt gatgggcctg agaatcctgc tgctgaaggt ggccggcttc 1800
aacctgctga tgaccctgag gctgtggagc agctga 1836

<210> SEQ ID NO 56
<211> LENGTH: 773
<212> TYPE: PRT
<213> ORGANISM: Artificial Sequence
<220> FEATURE:
<223> OTHER INFORMATION: wild-type F5 TCR (pMTB1281) PRT

<400> SEQUENCE: 56

Met Ala Thr Gly Ser Arg Thr Ser Leu Leu Leu Ala Phe Gly Leu Leu
1 5 10 15

Cys Leu Pro Trp Leu Gln Glu Ala Ser Ala Gln Gln Lys Glu Val Glu
20 25 30

Gln Asn Ser Gly Pro Leu Ser Val Pro Glu Gly Ala Ile Ala Ser Leu
35 40 45

Asn Cys Thr Tyr Ser Asp Arg Gly Ser Gln Ser Phe Phe Trp Tyr Arg
50 55 60

Gln Tyr Ser Gly Lys Ser Pro Glu Leu Ile Met Phe Ile Tyr Ser Asn
65 70 75 80

Gly Asp Lys Glu Asp Gly Arg Phe Thr Ala Gln Leu Asn Lys Ala Ser
85 90 95

Gln Tyr Val Ser Leu Leu Ile Arg Asp Ser Gln Pro Ser Asp Ser Ala
100 105 110

Thr Tyr Leu Cys Ala Val Asn Phe Gly Gly Gly Lys Leu Ile Phe Gly
115 120 125

Gln Gly Thr Glu Leu Ser Val Lys Pro Asn Ile Gln Asn Pro Asp Pro
130 135 140

Ala Val Tyr Gln Leu Arg Asp Ser Lys Ser Ser Asp Lys Ser Val Cys
145 150 155 160

```
Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
        195                 200                 205

Ala Cys Ala Asn Ala Phe Asn Asn Ser Ile Ile Pro Glu Asp Thr Phe
    210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
            260                 265                 270

Leu Arg Leu Trp Ser Ser Arg Ala Lys Arg Ser Gly Ser Gly Ala Pro
        275                 280                 285

Val Lys Gln Thr Leu Asn Phe Asp Leu Leu Lys Leu Ala Gly Asp Val
    290                 295                 300

Glu Ser Asn Pro Gly Pro Met Ala Thr Gly Ser Arg Thr Ser Leu Leu
305                 310                 315                 320

Leu Ala Phe Gly Leu Leu Cys Leu Pro Cys Leu Gln Glu Gly Ser Ala
                325                 330                 335

Gly Ile Thr Gln Ala Pro Thr Ser Gln Ile Leu Ala Ala Gly Arg Arg
            340                 345                 350

Met Thr Leu Arg Cys Thr Gln Asp Met Arg His Asn Ala Met Tyr Trp
        355                 360                 365

Tyr Arg Gln Asp Leu Gly Leu Gly Leu Arg Leu Ile His Tyr Ser Asn
    370                 375                 380

Thr Ala Gly Thr Thr Gly Lys Gly Glu Val Pro Asp Gly Tyr Ser Val
385                 390                 395                 400

Ser Arg Ala Asn Thr Asp Asp Phe Pro Leu Thr Leu Ala Ser Ala Val
                405                 410                 415

Pro Ser Gln Thr Ser Val Tyr Phe Cys Ala Ser Ser Leu Ser Phe Gly
            420                 425                 430

Thr Glu Ala Phe Phe Gly Gln Gly Thr Arg Leu Thr Val Val Glu Asp
        435                 440                 445

Leu Asn Lys Val Phe Pro Pro Glu Val Ala Val Phe Glu Pro Ser Glu
    450                 455                 460

Ala Glu Ile Ser His Thr Gln Lys Ala Thr Leu Val Cys Leu Ala Thr
465                 470                 475                 480

Gly Phe Phe Pro Asp His Val Glu Leu Ser Trp Trp Val Asn Gly Lys
                485                 490                 495

Glu Val His Ser Gly Val Ser Thr Asp Pro Gln Pro Leu Lys Glu Gln
            500                 505                 510

Pro Ala Leu Asn Asp Ser Arg Tyr Cys Leu Ser Ser Arg Leu Arg Val
        515                 520                 525

Ser Ala Thr Phe Trp Gln Asn Pro Arg Asn His Phe Arg Cys Gln Val
    530                 535                 540

Gln Phe Tyr Gly Leu Ser Glu Asn Asp Glu Trp Thr Gln Asp Arg Ala
545                 550                 555                 560

Lys Pro Val Thr Gln Ile Val Ser Ala Glu Ala Trp Gly Arg Ala Asp
                565                 570                 575
```

```
Cys Gly Phe Thr Ser Val Ser Tyr Gln Gln Gly Val Leu Ser Ala Thr
            580                 585                 590

Ile Leu Tyr Glu Ile Leu Leu Gly Lys Ala Thr Leu Tyr Ala Val Leu
        595                 600                 605

Val Ser Ala Leu Val Leu Met Ala Met Val Lys Arg Lys Asp Phe Arg
    610                 615                 620

Ala Lys Arg Gly Ser Gly Ala Thr Asn Phe Ser Leu Leu Lys Gln Ala
625                 630                 635                 640

Gly Asp Val Glu Glu Asn Pro Gly Pro Met Gly Ala Gly Ala Thr Gly
                645                 650                 655

Arg Ala Met Asp Gly Pro Arg Leu Leu Leu Leu Leu Leu Leu Gly Val
            660                 665                 670

Ser Leu Gly Gly Ala Lys Glu Gln Lys Leu Ile Ser Glu Glu Asp Leu
        675                 680                 685

Glu Ile Pro Gly Arg Trp Ile Thr Arg Ser Thr Pro Pro Glu Gly Ser
    690                 695                 700

Asp Ser Thr Ala Pro Ser Thr Gln Glu Pro Glu Ala Pro Pro Glu Gln
705                 710                 715                 720

Asp Leu Ile Ala Ser Thr Val Ala Gly Val Val Thr Thr Val Met Gly
                725                 730                 735

Ser Ser Gln Pro Val Val Thr Arg Gly Thr Thr Asp Asn Leu Ile Pro
            740                 745                 750

Val Tyr Cys Ser Ile Leu Ala Ala Val Val Val Gly Leu Val Ala Tyr
        755                 760                 765

Ile Ala Phe Lys Arg
    770


<210> SEQ ID NO 57
<211> LENGTH: 773
<212> TYPE: PRT
<213> ORGANISM: Artificial Sequence
<220> FEATURE:
<223> OTHER INFORMATION: domain-swapped F5 TCR VC-swap, BA orientation
      (pMTB1282) PRT

<400> SEQUENCE: 57

Met Ala Thr Gly Ser Arg Thr Ser Leu Leu Leu Ala Phe Gly Leu Leu
1               5                   10                  15

Cys Leu Pro Trp Leu Gln Glu Ala Ser Ala Gly Ile Thr Gln Ala Pro
            20                  25                  30

Thr Ser Gln Ile Leu Ala Ala Gly Arg Arg Met Thr Leu Arg Cys Thr
        35                  40                  45

Gln Asp Met Arg His Asn Ala Met Tyr Trp Tyr Arg Gln Asp Leu Gly
    50                  55                  60

Leu Gly Leu Arg Leu Ile His Tyr Ser Asn Thr Ala Gly Thr Thr Gly
65                  70                  75                  80

Lys Gly Glu Val Pro Asp Gly Tyr Ser Val Ser Arg Ala Asn Thr Asp
                85                  90                  95

Asp Phe Pro Leu Thr Leu Ala Ser Ala Val Pro Ser Gln Thr Ser Val
            100                 105                 110

Tyr Phe Cys Ala Ser Ser Leu Ser Phe Gly Thr Glu Ala Phe Phe Gly
        115                 120                 125

Gln Gly Thr Arg Leu Thr Val Val Glu Asp Leu Asn Lys Val Phe Pro
    130                 135                 140

Pro Glu Val Ala Val Phe Glu Pro Ser Glu Ala Glu Ile Ser His Thr
145                 150                 155                 160
```

```
Gln Lys Ala Thr Leu Val Cys Leu Ala Thr Gly Phe Phe Pro Asp His
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
        195                 200                 205

Arg Tyr Cys Leu Ser Ser Arg Leu Arg Val Ser Ala Thr Phe Trp Gln
    210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Asp Val Lys Leu Val
            260                 265                 270

Glu Lys Ser Phe Glu Thr Asp Thr Asn Leu Asn Phe Gln Asn Leu Ser
        275                 280                 285

Val Ile Gly Phe Arg Ile Leu Leu Leu Lys Val Ala Gly Phe Asn Leu
    290                 295                 300

Leu Met Thr Leu Arg Leu Trp Ser Ser Arg Ala Lys Arg Ser Gly Ser
305                 310                 315                 320

Gly Ala Pro Val Lys Gln Thr Leu Asn Phe Asp Leu Leu Lys Leu Ala
                325                 330                 335

Gly Asp Val Glu Ser Asn Pro Gly Pro Met Ala Thr Gly Ser Arg Thr
            340                 345                 350

Ser Leu Leu Leu Ala Phe Gly Leu Leu Cys Leu Pro Cys Leu Gln Glu
        355                 360                 365

Gly Ser Ala Gln Gln Lys Glu Val Glu Gln Asn Ser Gly Pro Leu Ser
    370                 375                 380

Val Pro Glu Gly Ala Ile Ala Ser Leu Asn Cys Thr Tyr Ser Asp Arg
385                 390                 395                 400

Gly Ser Gln Ser Phe Phe Trp Tyr Arg Gln Tyr Ser Gly Lys Ser Pro
                405                 410                 415

Glu Leu Ile Met Phe Ile Tyr Ser Asn Gly Asp Lys Glu Asp Gly Arg
            420                 425                 430

Phe Thr Ala Gln Leu Asn Lys Ala Ser Gln Tyr Val Ser Leu Leu Ile
        435                 440                 445

Arg Asp Ser Gln Pro Ser Asp Ser Ala Thr Tyr Leu Cys Ala Val Asn
    450                 455                 460

Phe Gly Gly Gly Lys Leu Ile Phe Gly Gln Gly Thr Glu Leu Ser Val
465                 470                 475                 480

Lys Pro Asn Ile Gln Asn Pro Asp Pro Ala Val Tyr Gln Leu Arg Asp
                485                 490                 495

Ser Lys Ser Ser Asp Lys Ser Val Cys Leu Phe Thr Asp Phe Asp Ser
            500                 505                 510

Gln Thr Asn Val Ser Gln Ser Lys Asp Ser Asp Val Tyr Ile Thr Asp
        515                 520                 525

Lys Thr Val Leu Asp Met Arg Ser Met Asp Phe Lys Ser Asn Ser Ala
    530                 535                 540

Val Ala Trp Ser Asn Lys Ser Asp Phe Ala Cys Ala Asn Ala Phe Asn
545                 550                 555                 560

Asn Ser Ile Ile Pro Glu Asp Thr Phe Phe Pro Ser Pro Glu Ser Ser
                565                 570                 575
```

Cys Gly Phe Thr Ser Val Ser Tyr Gln Gln Gly Val Leu Ser Ala Thr
580 585 590

Ile Leu Tyr Glu Ile Leu Leu Gly Lys Ala Thr Leu Tyr Ala Val Leu
595 600 605

Val Ser Ala Leu Val Leu Met Ala Met Val Lys Arg Lys Asp Phe Arg
610 615 620

Ala Lys Arg Gly Ser Gly Ala Thr Asn Phe Ser Leu Leu Lys Gln Ala
625 630 635 640

Gly Asp Val Glu Glu Asn Pro Gly Pro Met Gly Ala Gly Ala Thr Gly
645 650 655

Arg Ala Met Asp Gly Pro Arg Leu Leu Leu Leu Leu Leu Leu Gly Val
660 665 670

Ser Leu Gly Gly Ala Lys Glu Gln Lys Leu Ile Ser Glu Glu Asp Leu
675 680 685

Glu Ile Pro Gly Arg Trp Ile Thr Arg Ser Thr Pro Pro Glu Gly Ser
690 695 700

Asp Ser Thr Ala Pro Ser Thr Gln Glu Pro Glu Ala Pro Pro Glu Gln
705 710 715 720

Asp Leu Ile Ala Ser Thr Val Ala Gly Val Val Thr Thr Val Met Gly
725 730 735

Ser Ser Gln Pro Val Val Thr Arg Gly Thr Thr Asp Asn Leu Ile Pro
740 745 750

Val Tyr Cys Ser Ile Leu Ala Ala Val Val Val Gly Leu Val Ala Tyr
755 760 765

Ile Ala Phe Lys Arg
770

<210> SEQ ID NO 58
<211> LENGTH: 773
<212> TYPE: PRT
<213> ORGANISM: Artificial Sequence
<220> FEATURE:
<223> OTHER INFORMATION: domain-swapped F5 TCR VC-swap, AB orientation
(pMTB1283) PRT

<400> SEQUENCE: 58

Met Ala Thr Gly Ser Arg Thr Ser Leu Leu Leu Ala Phe Gly Leu Leu
1 5 10 15

Cys Leu Pro Trp Leu Gln Glu Ala Ser Ala Gln Gln Lys Glu Val Glu
20 25 30

Gln Asn Ser Gly Pro Leu Ser Val Pro Glu Gly Ala Ile Ala Ser Leu
35 40 45

Asn Cys Thr Tyr Ser Asp Arg Gly Ser Gln Ser Phe Phe Trp Tyr Arg
50 55 60

Gln Tyr Ser Gly Lys Ser Pro Glu Leu Ile Met Phe Ile Tyr Ser Asn
65 70 75 80

Gly Asp Lys Glu Asp Gly Arg Phe Thr Ala Gln Leu Asn Lys Ala Ser
85 90 95

Gln Tyr Val Ser Leu Leu Ile Arg Asp Ser Gln Pro Ser Asp Ser Ala
100 105 110

Thr Tyr Leu Cys Ala Val Asn Phe Gly Gly Gly Lys Leu Ile Phe Gly
115 120 125

Gln Gly Thr Glu Leu Ser Val Lys Pro Asn Ile Gln Asn Pro Asp Pro
130 135 140

Ala Val Tyr Gln Leu Arg Asp Ser Lys Ser Ser Asp Lys Ser Val Cys
145 150 155 160

-continued

```
Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
        195                 200                 205

Ala Cys Ala Asn Ala Phe Asn Asn Ser Ile Ile Pro Glu Asp Thr Phe
    210                 215                 220

Phe Pro Ser Pro Glu Ser Ser Cys Gly Phe Thr Ser Val Ser Tyr Gln
225                 230                 235                 240

Gln Gly Val Leu Ser Ala Thr Ile Leu Tyr Glu Ile Leu Leu Gly Lys
                245                 250                 255

Ala Thr Leu Tyr Ala Val Leu Val Ser Ala Leu Val Leu Met Ala Met
            260                 265                 270

Val Lys Arg Lys Asp Phe Arg Ala Lys Arg Ser Gly Ser Gly Ala Pro
        275                 280                 285

Val Lys Gln Thr Leu Asn Phe Asp Leu Leu Lys Leu Ala Gly Asp Val
    290                 295                 300

Glu Ser Asn Pro Gly Pro Met Ala Thr Gly Ser Arg Thr Ser Leu Leu
305                 310                 315                 320

Leu Ala Phe Gly Leu Leu Cys Leu Pro Cys Leu Gln Glu Gly Ser Ala
                325                 330                 335

Gly Ile Thr Gln Ala Pro Thr Ser Gln Ile Leu Ala Ala Gly Arg Arg
            340                 345                 350

Met Thr Leu Arg Cys Thr Gln Asp Met Arg His Asn Ala Met Tyr Trp
        355                 360                 365

Tyr Arg Gln Asp Leu Gly Leu Gly Leu Arg Leu Ile His Tyr Ser Asn
    370                 375                 380

Thr Ala Gly Thr Thr Gly Lys Gly Glu Val Pro Asp Gly Tyr Ser Val
385                 390                 395                 400

Ser Arg Ala Asn Thr Asp Asp Phe Pro Leu Thr Leu Ala Ser Ala Val
                405                 410                 415

Pro Ser Gln Thr Ser Val Tyr Phe Cys Ala Ser Ser Leu Ser Phe Gly
            420                 425                 430

Thr Glu Ala Phe Phe Gly Gln Gly Thr Arg Leu Thr Val Val Glu Asp
        435                 440                 445

Leu Asn Lys Val Phe Pro Pro Glu Val Ala Val Phe Glu Pro Ser Glu
    450                 455                 460

Ala Glu Ile Ser His Thr Gln Lys Ala Thr Leu Val Cys Leu Ala Thr
465                 470                 475                 480

Gly Phe Phe Pro Asp His Val Glu Leu Ser Trp Trp Val Asn Gly Lys
                485                 490                 495

Glu Val His Ser Gly Val Ser Thr Asp Pro Gln Pro Leu Lys Glu Gln
            500                 505                 510

Pro Ala Leu Asn Asp Ser Arg Tyr Cys Leu Ser Ser Arg Leu Arg Val
        515                 520                 525

Ser Ala Thr Phe Trp Gln Asn Pro Arg Asn His Phe Arg Cys Gln Val
    530                 535                 540

Gln Phe Tyr Gly Leu Ser Glu Asn Asp Glu Trp Thr Gln Asp Arg Ala
545                 550                 555                 560

Lys Pro Val Thr Gln Ile Val Ser Ala Glu Ala Trp Gly Arg Ala Asp
                565                 570                 575
```

```
Cys Asp Val Lys Leu Val Glu Lys Ser Phe Glu Thr Asp Thr Asn Leu
            580                 585                 590

Asn Phe Gln Asn Leu Ser Val Ile Gly Phe Arg Ile Leu Leu Leu Lys
        595                 600                 605

Val Ala Gly Phe Asn Leu Leu Met Thr Leu Arg Leu Trp Ser Ser Arg
    610                 615                 620

Ala Lys Arg Gly Ser Gly Ala Thr Asn Phe Ser Leu Leu Lys Gln Ala
625                 630                 635                 640

Gly Asp Val Glu Glu Asn Pro Gly Pro Met Gly Ala Gly Ala Thr Gly
                645                 650                 655

Arg Ala Met Asp Gly Pro Arg Leu Leu Leu Leu Leu Leu Leu Gly Val
            660                 665                 670

Ser Leu Gly Gly Ala Lys Glu Gln Lys Leu Ile Ser Glu Glu Asp Leu
        675                 680                 685

Glu Ile Pro Gly Arg Trp Ile Thr Arg Ser Thr Pro Pro Glu Gly Ser
    690                 695                 700

Asp Ser Thr Ala Pro Ser Thr Gln Glu Pro Glu Ala Pro Pro Glu Gln
705                 710                 715                 720

Asp Leu Ile Ala Ser Thr Val Ala Gly Val Val Thr Thr Val Met Gly
                725                 730                 735

Ser Ser Gln Pro Val Val Thr Arg Gly Thr Thr Asp Asn Leu Ile Pro
            740                 745                 750

Val Tyr Cys Ser Ile Leu Ala Ala Val Val Val Gly Leu Val Ala Tyr
        755                 760                 765

Ile Ala Phe Lys Arg
    770


<210> SEQ ID NO 59
<211> LENGTH: 773
<212> TYPE: PRT
<213> ORGANISM: Artificial Sequence
<220> FEATURE:
<223> OTHER INFORMATION: domain-swapped F5 TCR VCcp-swap, BA orientation
      (pMTB1284) PRT

<400> SEQUENCE: 59

Met Ala Thr Gly Ser Arg Thr Ser Leu Leu Leu Ala Phe Gly Leu Leu
1               5                   10                  15

Cys Leu Pro Trp Leu Gln Glu Ala Ser Ala Gly Ile Thr Gln Ala Pro
            20                  25                  30

Thr Ser Gln Ile Leu Ala Ala Gly Arg Arg Met Thr Leu Arg Cys Thr
        35                  40                  45

Gln Asp Met Arg His Asn Ala Met Tyr Trp Tyr Arg Gln Asp Leu Gly
    50                  55                  60

Leu Gly Leu Arg Leu Ile His Tyr Ser Asn Thr Ala Gly Thr Thr Gly
65                  70                  75                  80

Lys Gly Glu Val Pro Asp Gly Tyr Ser Val Ser Arg Ala Asn Thr Asp
                85                  90                  95

Asp Phe Pro Leu Thr Leu Ala Ser Ala Val Pro Ser Gln Thr Ser Val
            100                 105                 110

Tyr Phe Cys Ala Ser Ser Leu Ser Phe Gly Thr Glu Ala Phe Phe Gly
        115                 120                 125

Gln Gly Thr Arg Leu Thr Val Val Glu Asp Leu Asn Lys Val Phe Pro
    130                 135                 140

Pro Glu Val Ala Val Phe Glu Pro Ser Glu Ala Glu Ile Ser His Thr
145                 150                 155                 160
```

-continued

```
Gln Lys Ala Thr Leu Val Cys Leu Ala Thr Gly Phe Phe Pro Asp His
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
        195                 200                 205

Arg Tyr Cys Leu Ser Ser Arg Leu Arg Val Ser Ala Thr Phe Trp Gln
    210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Val
            260                 265                 270

Ser Tyr Gln Gln Gly Val Leu Ser Ala Thr Asn Leu Ser Val Ile Gly
        275                 280                 285

Phe Arg Ile Leu Leu Leu Lys Val Ala Gly Phe Asn Leu Leu Met Thr
    290                 295                 300

Leu Arg Leu Trp Ser Ser Arg Ala Lys Arg Ser Gly Ser Gly Ala Pro
305                 310                 315                 320

Val Lys Gln Thr Leu Asn Phe Asp Leu Leu Lys Leu Ala Gly Asp Val
                325                 330                 335

Glu Ser Asn Pro Gly Pro Met Ala Thr Gly Ser Arg Thr Ser Leu Leu
            340                 345                 350

Leu Ala Phe Gly Leu Leu Cys Leu Pro Cys Leu Gln Glu Gly Ser Ala
        355                 360                 365

Gln Gln Lys Glu Val Glu Gln Asn Ser Gly Pro Leu Ser Val Pro Glu
    370                 375                 380

Gly Ala Ile Ala Ser Leu Asn Cys Thr Tyr Ser Asp Arg Gly Ser Gln
385                 390                 395                 400

Ser Phe Phe Trp Tyr Arg Gln Tyr Ser Gly Lys Ser Pro Glu Leu Ile
                405                 410                 415

Met Phe Ile Tyr Ser Asn Gly Asp Lys Glu Asp Gly Arg Phe Thr Ala
            420                 425                 430

Gln Leu Asn Lys Ala Ser Gln Tyr Val Ser Leu Leu Ile Arg Asp Ser
        435                 440                 445

Gln Pro Ser Asp Ser Ala Thr Tyr Leu Cys Ala Val Asn Phe Gly Gly
    450                 455                 460

Gly Lys Leu Ile Phe Gly Gln Gly Thr Glu Leu Ser Val Lys Pro Asn
465                 470                 475                 480

Ile Gln Asn Pro Asp Pro Ala Val Tyr Gln Leu Arg Asp Ser Lys Ser
                485                 490                 495

Ser Asp Lys Ser Val Cys Leu Phe Thr Asp Phe Asp Ser Gln Thr Asn
            500                 505                 510

Val Ser Gln Ser Lys Asp Ser Asp Val Tyr Ile Thr Asp Lys Thr Val
        515                 520                 525

Leu Asp Met Arg Ser Met Asp Phe Lys Ser Asn Ser Ala Val Ala Trp
    530                 535                 540

Ser Asn Lys Ser Asp Phe Ala Cys Ala Asn Ala Phe Asn Asn Ser Ile
545                 550                 555                 560

Ile Pro Glu Asp Thr Phe Phe Pro Ser Pro Glu Ser Ser Cys Asp Val
                565                 570                 575
```

Lys Leu Val Glu Lys Ser Phe Glu Thr Asp Thr Asn Leu Asn Phe Gln
580 585 590

Ile Leu Tyr Glu Ile Leu Leu Gly Lys Ala Thr Leu Tyr Ala Val Leu
595 600 605

Val Ser Ala Leu Val Leu Met Ala Met Val Lys Arg Lys Asp Phe Arg
610 615 620

Ala Lys Arg Gly Ser Gly Ala Thr Asn Phe Ser Leu Leu Lys Gln Ala
625 630 635 640

Gly Asp Val Glu Glu Asn Pro Gly Pro Met Gly Ala Gly Ala Thr Gly
645 650 655

Arg Ala Met Asp Gly Pro Arg Leu Leu Leu Leu Leu Leu Leu Gly Val
660 665 670

Ser Leu Gly Gly Ala Lys Glu Gln Lys Leu Ile Ser Glu Glu Asp Leu
675 680 685

Glu Ile Pro Gly Arg Trp Ile Thr Arg Ser Thr Pro Pro Glu Gly Ser
690 695 700

Asp Ser Thr Ala Pro Ser Thr Gln Glu Pro Glu Ala Pro Pro Glu Gln
705 710 715 720

Asp Leu Ile Ala Ser Thr Val Ala Gly Val Val Thr Thr Val Met Gly
725 730 735

Ser Ser Gln Pro Val Val Thr Arg Gly Thr Thr Asp Asn Leu Ile Pro
740 745 750

Val Tyr Cys Ser Ile Leu Ala Ala Val Val Val Gly Leu Val Ala Tyr
755 760 765

Ile Ala Phe Lys Arg
770

<210> SEQ ID NO 60
<211> LENGTH: 773
<212> TYPE: PRT
<213> ORGANISM: Artificial Sequence
<220> FEATURE:
<223> OTHER INFORMATION: domain-swapped F5 TCR VCcp-swap, AB orientation
(pMTB1285)

<400> SEQUENCE: 60

Met Ala Thr Gly Ser Arg Thr Ser Leu Leu Leu Ala Phe Gly Leu Leu
1 5 10 15

Cys Leu Pro Trp Leu Gln Glu Ala Ser Ala Gln Gln Lys Glu Val Glu
20 25 30

Gln Asn Ser Gly Pro Leu Ser Val Pro Glu Gly Ala Ile Ala Ser Leu
35 40 45

Asn Cys Thr Tyr Ser Asp Arg Gly Ser Gln Ser Phe Phe Trp Tyr Arg
50 55 60

Gln Tyr Ser Gly Lys Ser Pro Glu Leu Ile Met Phe Ile Tyr Ser Asn
65 70 75 80

Gly Asp Lys Glu Asp Gly Arg Phe Thr Ala Gln Leu Asn Lys Ala Ser
85 90 95

Gln Tyr Val Ser Leu Leu Ile Arg Asp Ser Gln Pro Ser Asp Ser Ala
100 105 110

Thr Tyr Leu Cys Ala Val Asn Phe Gly Gly Gly Lys Leu Ile Phe Gly
115 120 125

Gln Gly Thr Glu Leu Ser Val Lys Pro Asn Ile Gln Asn Pro Asp Pro
130 135 140

Ala Val Tyr Gln Leu Arg Asp Ser Lys Ser Ser Asp Lys Ser Val Cys
145 150 155 160

-continued

```
Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
        195                 200                 205

Ala Cys Ala Asn Ala Phe Asn Asn Ser Ile Ile Pro Glu Asp Thr Phe
    210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Ile Leu Tyr Glu Ile Leu
                245                 250                 255

Leu Gly Lys Ala Thr Leu Tyr Ala Val Leu Val Ser Ala Leu Val Leu
            260                 265                 270

Met Ala Met Val Lys Arg Lys Asp Phe Arg Ala Lys Arg Ser Gly Ser
        275                 280                 285

Gly Ala Pro Val Lys Gln Thr Leu Asn Phe Asp Leu Leu Lys Leu Ala
    290                 295                 300

Gly Asp Val Glu Ser Asn Pro Gly Pro Met Ala Thr Gly Ser Arg Thr
305                 310                 315                 320

Ser Leu Leu Leu Ala Phe Gly Leu Leu Cys Leu Pro Cys Leu Gln Glu
                325                 330                 335

Gly Ser Ala Gly Ile Thr Gln Ala Pro Thr Ser Gln Ile Leu Ala Ala
            340                 345                 350

Gly Arg Arg Met Thr Leu Arg Cys Thr Gln Asp Met Arg His Asn Ala
        355                 360                 365

Met Tyr Trp Tyr Arg Gln Asp Leu Gly Leu Gly Leu Arg Leu Ile His
    370                 375                 380

Tyr Ser Asn Thr Ala Gly Thr Thr Gly Lys Gly Glu Val Pro Asp Gly
385                 390                 395                 400

Tyr Ser Val Ser Arg Ala Asn Thr Asp Asp Phe Pro Leu Thr Leu Ala
                405                 410                 415

Ser Ala Val Pro Ser Gln Thr Ser Val Tyr Phe Cys Ala Ser Ser Leu
            420                 425                 430

Ser Phe Gly Thr Glu Ala Phe Phe Gly Gln Gly Thr Arg Leu Thr Val
        435                 440                 445

Val Glu Asp Leu Asn Lys Val Phe Pro Pro Glu Val Ala Val Phe Glu
    450                 455                 460

Pro Ser Glu Ala Glu Ile Ser His Thr Gln Lys Ala Thr Leu Val Cys
465                 470                 475                 480

Leu Ala Thr Gly Phe Phe Pro Asp His Val Glu Leu Ser Trp Trp Val
                485                 490                 495

Asn Gly Lys Glu Val His Ser Gly Val Ser Thr Asp Pro Gln Pro Leu
            500                 505                 510

Lys Glu Gln Pro Ala Leu Asn Asp Ser Arg Tyr Cys Leu Ser Ser Arg
        515                 520                 525

Leu Arg Val Ser Ala Thr Phe Trp Gln Asn Pro Arg Asn His Phe Arg
    530                 535                 540

Cys Gln Val Gln Phe Tyr Gly Leu Ser Glu Asn Asp Glu Trp Thr Gln
545                 550                 555                 560

Asp Arg Ala Lys Pro Val Thr Gln Ile Val Ser Ala Glu Ala Trp Gly
                565                 570                 575
```

-continued

```
Arg Ala Asp Cys Gly Phe Thr Ser Val Ser Tyr Gln Gln Gly Val Leu
            580                 585                 590

Ser Ala Thr Asn Leu Ser Val Ile Gly Phe Arg Ile Leu Leu Leu Lys
        595                 600                 605

Val Ala Gly Phe Asn Leu Leu Met Thr Leu Arg Leu Trp Ser Ser Arg
    610                 615                 620

Ala Lys Arg Gly Ser Gly Ala Thr Asn Phe Ser Leu Leu Lys Gln Ala
625                 630                 635                 640

Gly Asp Val Glu Glu Asn Pro Gly Pro Met Gly Ala Gly Ala Thr Gly
                645                 650                 655

Arg Ala Met Asp Gly Pro Arg Leu Leu Leu Leu Leu Leu Leu Gly Val
            660                 665                 670

Ser Leu Gly Gly Ala Lys Glu Gln Lys Leu Ile Ser Glu Glu Asp Leu
        675                 680                 685

Glu Ile Pro Gly Arg Trp Ile Thr Arg Ser Thr Pro Pro Glu Gly Ser
    690                 695                 700

Asp Ser Thr Ala Pro Ser Thr Gln Glu Pro Glu Ala Pro Pro Glu Gln
705                 710                 715                 720

Asp Leu Ile Ala Ser Thr Val Ala Gly Val Val Thr Thr Val Met Gly
                725                 730                 735

Ser Ser Gln Pro Val Val Thr Arg Gly Thr Thr Asp Asn Leu Ile Pro
            740                 745                 750

Val Tyr Cys Ser Ile Leu Ala Ala Val Val Val Gly Leu Val Ala Tyr
        755                 760                 765

Ile Ala Phe Lys Arg
    770
```

<210> SEQ ID NO 61
<211> LENGTH: 803
<212> TYPE: PRT
<213> ORGANISM: Artificial Sequence
<220> FEATURE:
<223> OTHER INFORMATION: domain-swapped F5 TCR AlphaDelta+BetaGamma
      chimera (pMTB1301) PRT

<400> SEQUENCE: 61

```
Met Ala Thr Gly Ser Arg Thr Ser Leu Leu Leu Ala Phe Gly Leu Leu
1               5                   10                  15

Cys Leu Pro Trp Leu Gln Glu Ala Ser Ala Gln Gln Lys Glu Val Glu
            20                  25                  30

Gln Asn Ser Gly Pro Leu Ser Val Pro Glu Gly Ala Ile Ala Ser Leu
        35                  40                  45

Asn Cys Thr Tyr Ser Asp Arg Gly Ser Gln Ser Phe Phe Trp Tyr Arg
    50                  55                  60

Gln Tyr Ser Gly Lys Ser Pro Glu Leu Ile Met Phe Ile Tyr Ser Asn
65                  70                  75                  80

Gly Asp Lys Glu Asp Gly Arg Phe Thr Ala Gln Leu Asn Lys Ala Ser
                85                  90                  95

Gln Tyr Val Ser Leu Leu Ile Arg Asp Ser Gln Pro Ser Asp Ser Ala
            100                 105                 110

Thr Tyr Leu Cys Ala Val Asn Phe Gly Gly Gly Lys Leu Ile Phe Gly
        115                 120                 125

Gln Gly Thr Glu Leu Ser Val Lys Pro Asn Ile Gln Asn Pro Asp Pro
    130                 135                 140

Ala Val Tyr Gln Leu Arg Asp Ser Lys Ser Ser Asp Lys Ser Val Cys
145                 150                 155                 160
```

-continued

Leu Phe Thr Asp Phe Asp Ser Gln Thr Asn Val Ser Gln Ser Lys Asp
165 170 175

Ser Asp Val Tyr Ile Thr Asp Lys Thr Val Leu Asp Met Arg Ser Met
180 185 190

Asp Phe Lys Ser Asn Ser Ala Val Ala Trp Ser Asn Lys Ser Asp Phe
195 200 205

Ala Cys Ala Asn Ala Phe Asn Asn Ser Ile Ile Pro Glu Asp Thr Phe
210 215 220

Phe Pro Ser Pro Glu Ser Ser Asp Ser Thr Asp His Val Lys Pro Lys
225 230 235 240

Glu Thr Glu Asn Thr Lys Gln Pro Ser Lys Ser Cys His Lys Pro Lys
245 250 255

Ala Ile Val His Thr Glu Lys Val Asn Met Met Ser Leu Thr Val Leu
260 265 270

Gly Leu Arg Met Leu Phe Ala Lys Thr Val Ala Val Asn Phe Leu Leu
275 280 285

Thr Ala Arg Leu Trp Ser Ser Arg Ala Lys Arg Ser Gly Ser Gly Ala
290 295 300

Pro Val Lys Gln Thr Leu Asn Phe Asp Leu Leu Lys Leu Ala Gly Asp
305 310 315 320

Val Glu Ser Asn Pro Gly Pro Met Ala Thr Gly Ser Arg Thr Ser Leu
325 330 335

Leu Leu Ala Phe Gly Leu Leu Cys Leu Pro Cys Leu Gln Glu Gly Ser
340 345 350

Ala Gly Ile Thr Gln Ala Pro Thr Ser Gln Ile Leu Ala Ala Gly Arg
355 360 365

Arg Met Thr Leu Arg Cys Thr Gln Asp Met Arg His Asn Ala Met Tyr
370 375 380

Trp Tyr Arg Gln Asp Leu Gly Leu Gly Leu Arg Leu Ile His Tyr Ser
385 390 395 400

Asn Thr Ala Gly Thr Thr Gly Lys Gly Glu Val Pro Asp Gly Tyr Ser
405 410 415

Val Ser Arg Ala Asn Thr Asp Asp Phe Pro Leu Thr Leu Ala Ser Ala
420 425 430

Val Pro Ser Gln Thr Ser Val Tyr Phe Cys Ala Ser Ser Leu Ser Phe
435 440 445

Gly Thr Glu Ala Phe Phe Gly Gln Gly Thr Arg Leu Thr Val Val Glu
450 455 460

Asp Leu Asn Lys Val Phe Pro Pro Glu Val Ala Val Phe Glu Pro Ser
465 470 475 480

Glu Ala Glu Ile Ser His Thr Gln Lys Ala Thr Leu Val Cys Leu Ala
485 490 495

Thr Gly Phe Phe Pro Asp His Val Glu Leu Ser Trp Trp Val Asn Gly
500 505 510

Lys Glu Val His Ser Gly Val Ser Thr Asp Pro Gln Pro Leu Lys Glu
515 520 525

Gln Pro Ala Leu Asn Asp Ser Arg Tyr Cys Leu Ser Ser Arg Leu Arg
530 535 540

Val Ser Ala Thr Phe Trp Gln Asn Pro Arg Asn His Phe Arg Cys Gln
545 550 555 560

Val Gln Phe Tyr Gly Leu Ser Glu Asn Asp Glu Trp Thr Gln Asp Arg
565 570 575

```
Ala Lys Pro Val Thr Gln Ile Val Ser Ala Glu Ala Trp Gly Arg Ala
            580                 585                 590

Asp Asp Val Ile Thr Met Asp Pro Lys Asp Asn Cys Ser Lys Asp Ala
        595                 600                 605

Asn Asp Thr Leu Leu Leu Gln Leu Thr Asn Thr Ser Ala Tyr Tyr Met
    610                 615                 620

Tyr Leu Leu Leu Leu Leu Lys Ser Val Val Tyr Phe Ala Ile Ile Thr
625                 630                 635                 640

Cys Cys Leu Leu Met Ala Met Val Lys Arg Lys Asp Phe Arg Ala Lys
                645                 650                 655

Arg Gly Ser Gly Ala Thr Asn Phe Ser Leu Leu Lys Gln Ala Gly Asp
            660                 665                 670

Val Glu Glu Asn Pro Gly Pro Met Gly Ala Gly Ala Thr Gly Arg Ala
        675                 680                 685

Met Asp Gly Pro Arg Leu Leu Leu Leu Leu Leu Leu Gly Val Ser Leu
    690                 695                 700

Gly Gly Ala Lys Glu Gln Lys Leu Ile Ser Glu Glu Asp Leu Glu Ile
705                 710                 715                 720

Pro Gly Arg Trp Ile Thr Arg Ser Thr Pro Pro Glu Gly Ser Asp Ser
                725                 730                 735

Thr Ala Pro Ser Thr Gln Glu Pro Glu Ala Pro Pro Glu Gln Asp Leu
            740                 745                 750

Ile Ala Ser Thr Val Ala Gly Val Val Thr Thr Val Met Gly Ser Ser
        755                 760                 765

Gln Pro Val Val Thr Arg Gly Thr Thr Asp Asn Leu Ile Pro Val Tyr
    770                 775                 780

Cys Ser Ile Leu Ala Ala Val Val Val Gly Leu Val Ala Tyr Ile Ala
785                 790                 795                 800

Phe Lys Arg


<210> SEQ ID NO 62
<211> LENGTH: 803
<212> TYPE: PRT
<213> ORGANISM: Artificial Sequence
<220> FEATURE:
<223> OTHER INFORMATION: domain-swapped F5 TCR AlphaGamma+BetaDelta
      chimera (pMTB1302) PRT

<400> SEQUENCE: 62

Met Ala Thr Gly Ser Arg Thr Ser Leu Leu Leu Ala Phe Gly Leu Leu
1               5                   10                  15

Cys Leu Pro Trp Leu Gln Glu Ala Ser Ala Gln Gln Lys Glu Val Glu
            20                  25                  30

Gln Asn Ser Gly Pro Leu Ser Val Pro Glu Gly Ala Ile Ala Ser Leu
        35                  40                  45

Asn Cys Thr Tyr Ser Asp Arg Gly Ser Gln Ser Phe Phe Trp Tyr Arg
    50                  55                  60

Gln Tyr Ser Gly Lys Ser Pro Glu Leu Ile Met Phe Ile Tyr Ser Asn
65                  70                  75                  80

Gly Asp Lys Glu Asp Gly Arg Phe Thr Ala Gln Leu Asn Lys Ala Ser
                85                  90                  95

Gln Tyr Val Ser Leu Leu Ile Arg Asp Ser Gln Pro Ser Asp Ser Ala
            100                 105                 110

Thr Tyr Leu Cys Ala Val Asn Phe Gly Gly Gly Lys Leu Ile Phe Gly
        115                 120                 125
```

-continued

```
Gln Gly Thr Glu Leu Ser Val Lys Pro Asn Ile Gln Asn Pro Asp Pro
    130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
        195                 200                 205

Ala Cys Ala Asn Ala Phe Asn Asn Ser Ile Ile Pro Glu Asp Thr Phe
    210                 215                 220

Phe Pro Ser Pro Glu Ser Ser Asp Val Ile Thr Met Asp Pro Lys Asp
225                 230                 235                 240

Asn Cys Ser Lys Asp Ala Asn Asp Thr Leu Leu Leu Gln Leu Thr Asn
                245                 250                 255

Thr Ser Ala Tyr Tyr Met Tyr Leu Leu Leu Leu Leu Lys Ser Val Val
            260                 265                 270

Tyr Phe Ala Ile Ile Thr Cys Cys Leu Leu Arg Leu Trp Ser Ser Arg
        275                 280                 285

Ala Lys Arg Ser Gly Ser Gly Ala Pro Val Lys Gln Thr Leu Asn Phe
    290                 295                 300

Asp Leu Leu Lys Leu Ala Gly Asp Val Glu Ser Asn Pro Gly Pro Met
305                 310                 315                 320

Ala Thr Gly Ser Arg Thr Ser Leu Leu Leu Ala Phe Gly Leu Leu Cys
                325                 330                 335

Leu Pro Cys Leu Gln Glu Gly Ser Ala Gly Ile Thr Gln Ala Pro Thr
            340                 345                 350

Ser Gln Ile Leu Ala Ala Gly Arg Arg Met Thr Leu Arg Cys Thr Gln
        355                 360                 365

Asp Met Arg His Asn Ala Met Tyr Trp Tyr Arg Gln Asp Leu Gly Leu
    370                 375                 380

Gly Leu Arg Leu Ile His Tyr Ser Asn Thr Ala Gly Thr Thr Gly Lys
385                 390                 395                 400

Gly Glu Val Pro Asp Gly Tyr Ser Val Ser Arg Ala Asn Thr Asp Asp
                405                 410                 415

Phe Pro Leu Thr Leu Ala Ser Ala Val Pro Ser Gln Thr Ser Val Tyr
            420                 425                 430

Phe Cys Ala Ser Ser Leu Ser Phe Gly Thr Glu Ala Phe Phe Gly Gln
        435                 440                 445

Gly Thr Arg Leu Thr Val Val Glu Asp Leu Asn Lys Val Phe Pro Pro
    450                 455                 460

Glu Val Ala Val Phe Glu Pro Ser Glu Ala Glu Ile Ser His Thr Gln
465                 470                 475                 480

Lys Ala Thr Leu Val Cys Leu Ala Thr Gly Phe Phe Pro Asp His Val
                485                 490                 495

Glu Leu Ser Trp Trp Val Asn Gly Lys Glu Val His Ser Gly Val Ser
            500                 505                 510

Thr Asp Pro Gln Pro Leu Lys Glu Gln Pro Ala Leu Asn Asp Ser Arg
        515                 520                 525

Tyr Cys Leu Ser Ser Arg Leu Arg Val Ser Ala Thr Phe Trp Gln Asn
    530                 535                 540

Pro Arg Asn His Phe Arg Cys Gln Val Gln Phe Tyr Gly Leu Ser Glu
```

-continued

```
545                 550                 555                 560

Asn Asp Glu Trp Thr Gln Asp Arg Ala Lys Pro Val Thr Gln Ile Val
                565                 570                 575

Ser Ala Glu Ala Trp Gly Arg Ala Asp Asp Ser Thr Asp His Val Lys
            580                 585                 590

Pro Lys Glu Thr Glu Asn Thr Lys Gln Pro Ser Lys Ser Cys His Lys
        595                 600                 605

Pro Lys Ala Ile Val His Thr Glu Lys Val Asn Met Met Ser Leu Thr
    610                 615                 620

Val Leu Gly Leu Arg Met Leu Phe Ala Lys Thr Val Ala Val Asn Phe
625                 630                 635                 640

Leu Leu Thr Ala Met Ala Met Val Lys Arg Lys Asp Phe Arg Ala Lys
                645                 650                 655

Arg Gly Ser Gly Ala Thr Asn Phe Ser Leu Leu Lys Gln Ala Gly Asp
            660                 665                 670

Val Glu Glu Asn Pro Gly Pro Met Gly Ala Gly Ala Thr Gly Arg Ala
        675                 680                 685

Met Asp Gly Pro Arg Leu Leu Leu Leu Leu Leu Leu Gly Val Ser Leu
    690                 695                 700

Gly Gly Ala Lys Glu Gln Lys Leu Ile Ser Glu Glu Asp Leu Glu Ile
705                 710                 715                 720

Pro Gly Arg Trp Ile Thr Arg Ser Thr Pro Pro Glu Gly Ser Asp Ser
                725                 730                 735

Thr Ala Pro Ser Thr Gln Glu Pro Glu Ala Pro Pro Glu Gln Asp Leu
            740                 745                 750

Ile Ala Ser Thr Val Ala Gly Val Val Thr Thr Val Met Gly Ser Ser
        755                 760                 765

Gln Pro Val Val Thr Arg Gly Thr Thr Asp Asn Leu Ile Pro Val Tyr
    770                 775                 780

Cys Ser Ile Leu Ala Ala Val Val Val Gly Leu Val Ala Tyr Ile Ala
785                 790                 795                 800

Phe Lys Arg


<210> SEQ ID NO 63
<211> LENGTH: 611
<212> TYPE: PRT
<213> ORGANISM: Artificial Sequence
<220> FEATURE:
<223> OTHER INFORMATION: domain-swapped OTI mouse TCR VC-swap, BA
      orientation (pMTB1185)

<400> SEQUENCE: 63

Met Ala Pro Arg Val Leu Ala Asp Ser Ala Trp Gly Ile Thr Leu Leu
1               5                   10                  15

Ser Trp Val Thr Val Phe Leu Leu Gly Thr Ser Ser Ala Asp Ser Gly
            20                  25                  30

Val Val Gln Ser Pro Arg His Ile Ile Lys Glu Lys Gly Gly Arg Ser
        35                  40                  45

Val Leu Thr Cys Ile Pro Ile Ser Gly His Ser Asn Val Val Trp Tyr
    50                  55                  60

Gln Gln Thr Leu Gly Lys Glu Leu Lys Phe Leu Ile Gln His Tyr Glu
65                  70                  75                  80

Lys Val Glu Arg Asp Lys Gly Phe Leu Pro Ser Arg Phe Ser Val Gln
                85                  90                  95

Gln Phe Asp Asp Tyr His Ser Glu Met Asn Met Ser Ala Leu Glu Leu
```

-continued

```
            100                 105                 110

Glu Asp Ser Ala Met Tyr Phe Cys Ala Ser Ser Arg Ala Asn Tyr Glu
        115                 120                 125

Gln Tyr Phe Gly Pro Gly Thr Arg Leu Thr Val Leu Glu Asp Leu Arg
    130                 135                 140

Asn Val Thr Pro Pro Lys Val Ser Leu Phe Glu Pro Ser Lys Ala Glu
145                 150                 155                 160

Ile Ala Asn Lys Gln Lys Ala Thr Leu Val Cys Leu Ala Arg Gly Phe
                165                 170                 175

Phe Pro Asp His Val Glu Leu Ser Trp Trp Val Asn Gly Lys Glu Val
            180                 185                 190

His Ser Gly Val Ser Thr Asp Pro Gln Ala Tyr Lys Glu Ser Asn Tyr
        195                 200                 205

Ser Tyr Cys Leu Ser Ser Arg Leu Arg Val Ser Ala Thr Phe Trp His
    210                 215                 220

Asn Pro Arg Asn His Phe Arg Cys Gln Val Gln Phe His Gly Leu Ser
225                 230                 235                 240

Glu Glu Asp Lys Trp Pro Glu Gly Ser Pro Lys Pro Val Thr Gln Asn
                245                 250                 255

Ile Ser Ala Glu Ala Trp Gly Arg Ala Asp Cys Asp Ala Thr Leu Thr
            260                 265                 270

Glu Lys Ser Phe Glu Thr Asp Met Asn Leu Asn Phe Gln Asn Leu Ser
        275                 280                 285

Val Met Gly Leu Arg Ile Leu Leu Leu Lys Val Ala Gly Phe Asn Leu
    290                 295                 300

Leu Met Thr Leu Arg Leu Trp Ser Ser Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Asp Lys Ile Leu Thr Ala Thr Phe Leu Leu Leu Gly Leu His Leu
            340                 345                 350

Ala Gly Val Asn Gly Gln Gln Gln Glu Lys Arg Asp Gln Gln Gln Val
        355                 360                 365

Arg Gln Ser Pro Gln Ser Leu Thr Val Trp Glu Gly Glu Thr Ala Ile
    370                 375                 380

Leu Asn Cys Ser Tyr Glu Asp Ser Thr Phe Asn Tyr Phe Pro Trp Tyr
385                 390                 395                 400

Gln Gln Phe Pro Gly Glu Gly Pro Ala Leu Leu Ile Ser Ile Arg Ser
                405                 410                 415

Val Ser Asp Lys Lys Glu Asp Gly Arg Phe Thr Ile Phe Phe Asn Lys
            420                 425                 430

Arg Glu Lys Lys Leu Ser Leu His Ile Thr Asp Ser Gln Pro Gly Asp
        435                 440                 445

Ser Ala Thr Tyr Phe Cys Ala Ala Ser Asp Asn Tyr Gln Leu Ile Trp
    450                 455                 460

Gly Ser Gly Thr Lys Leu Ile Ile Lys Pro Asp Ile Gln Asn Pro Glu
465                 470                 475                 480

Pro Ala Val Tyr Gln Leu Lys Asp Pro Arg Ser Gln Asp Ser Thr Leu
                485                 490                 495

Cys Leu Phe Thr Asp Phe Asp Ser Gln Ile Asn Val Pro Lys Thr Met
            500                 505                 510

Glu Ser Gly Thr Phe Ile Thr Asp Lys Thr Val Leu Asp Met Lys Ala
        515                 520                 525
```

Met Asp Ser Lys Ser Asn Gly Ala Ile Ala Trp Ser Asn Gln Thr Ser
    530                 535                 540

Phe Thr Cys Gln Asp Ile Phe Lys Glu Thr Asn Ala Thr Tyr Pro Ser
545                 550                 555                 560

Ser Asp Val Pro Cys Gly Ile Thr Ser Ala Ser Tyr His Gln Gly Val
                565                 570                 575

Leu Ser Ala Thr Ile Leu Tyr Glu Ile Leu Leu Gly Lys Ala Thr Leu
            580                 585                 590

Tyr Ala Val Leu Val Ser Gly Leu Val Leu Met Ala Met Val Lys Lys
        595                 600                 605

Lys Asn Ser
    610

<210> SEQ ID NO 64
<211> LENGTH: 611
<212> TYPE: PRT
<213> ORGANISM: Artificial Sequence
<220> FEATURE:
<223> OTHER INFORMATION: domain-swapped OTI mouse TCR VC-swap, AB
      orientation (pMTB1186) PRT

<400> SEQUENCE: 64

Met Asp Lys Ile Leu Thr Ala Thr Phe Leu Leu Leu Gly Leu His Leu
1               5                   10                  15

Ala Gly Val Asn Gly Gln Gln Gln Glu Lys Arg Asp Gln Gln Gln Val
            20                  25                  30

Arg Gln Ser Pro Gln Ser Leu Thr Val Trp Glu Gly Glu Thr Ala Ile
        35                  40                  45

Leu Asn Cys Ser Tyr Glu Asp Ser Thr Phe Asn Tyr Phe Pro Trp Tyr
    50                  55                  60

Gln Gln Phe Pro Gly Glu Gly Pro Ala Leu Leu Ile Ser Ile Arg Ser
65                  70                  75                  80

Val Ser Asp Lys Lys Glu Asp Gly Arg Phe Thr Ile Phe Phe Asn Lys
                85                  90                  95

Arg Glu Lys Lys Leu Ser Leu His Ile Thr Asp Ser Gln Pro Gly Asp
            100                 105                 110

Ser Ala Thr Tyr Phe Cys Ala Ala Ser Asp Asn Tyr Gln Leu Ile Trp
        115                 120                 125

Gly Ser Gly Thr Lys Leu Ile Ile Lys Pro Asp Ile Gln Asn Pro Glu
    130                 135                 140

Pro Ala Val Tyr Gln Leu Lys Asp Pro Arg Ser Gln Asp Ser Thr Leu
145                 150                 155                 160

Cys Leu Phe Thr Asp Phe Asp Ser Gln Ile Asn Val Pro Lys Thr Met
                165                 170                 175

Glu Ser Gly Thr Phe Ile Thr Asp Lys Thr Val Leu Asp Met Lys Ala
            180                 185                 190

Met Asp Ser Lys Ser Asn Gly Ala Ile Ala Trp Ser Asn Gln Thr Ser
        195                 200                 205

Phe Thr Cys Gln Asp Ile Phe Lys Glu Thr Asn Ala Thr Tyr Pro Ser
    210                 215                 220

Ser Asp Val Pro Cys Gly Ile Thr Ser Ala Ser Tyr His Gln Gly Val
225                 230                 235                 240

Leu Ser Ala Thr Ile Leu Tyr Glu Ile Leu Leu Gly Lys Ala Thr Leu
                245                 250                 255

Tyr Ala Val Leu Val Ser Gly Leu Val Leu Met Ala Met Val Lys Lys

-continued

```
            260                 265                 270

Lys Asn Ser Ser Gly Ser Gly Ala Thr Asn Phe Ser Leu Leu Lys Gln
        275                 280                 285

Ala Gly Asp Val Glu Glu Asn Pro Gly Pro Met Ala Pro Arg Val Leu
    290                 295                 300

Ala Asp Ser Ala Trp Gly Ile Thr Leu Leu Ser Trp Val Thr Val Phe
305                 310                 315                 320

Leu Leu Gly Thr Ser Ser Ala Asp Ser Gly Val Val Gln Ser Pro Arg
                325                 330                 335

His Ile Ile Lys Glu Lys Gly Gly Arg Ser Val Leu Thr Cys Ile Pro
            340                 345                 350

Ile Ser Gly His Ser Asn Val Val Trp Tyr Gln Gln Thr Leu Gly Lys
        355                 360                 365

Glu Leu Lys Phe Leu Ile Gln His Tyr Glu Lys Val Glu Arg Asp Lys
    370                 375                 380

Gly Phe Leu Pro Ser Arg Phe Ser Val Gln Gln Phe Asp Asp Tyr His
385                 390                 395                 400

Ser Glu Met Asn Met Ser Ala Leu Glu Leu Glu Asp Ser Ala Met Tyr
                405                 410                 415

Phe Cys Ala Ser Ser Arg Ala Asn Tyr Glu Gln Tyr Phe Gly Pro Gly
            420                 425                 430

Thr Arg Leu Thr Val Leu Glu Asp Leu Arg Asn Val Thr Pro Pro Lys
        435                 440                 445

Val Ser Leu Phe Glu Pro Ser Lys Ala Glu Ile Ala Asn Lys Gln Lys
    450                 455                 460

Ala Thr Leu Val Cys Leu Ala Arg Gly Phe Phe Pro Asp His Val Glu
465                 470                 475                 480

Leu Ser Trp Trp Val Asn Gly Lys Glu Val His Ser Gly Val Ser Thr
                485                 490                 495

Asp Pro Gln Ala Tyr Lys Glu Ser Asn Tyr Ser Tyr Cys Leu Ser Ser
            500                 505                 510

Arg Leu Arg Val Ser Ala Thr Phe Trp His Asn Pro Arg Asn His Phe
        515                 520                 525

Arg Cys Gln Val Gln Phe His Gly Leu Ser Glu Glu Asp Lys Trp Pro
    530                 535                 540

Glu Gly Ser Pro Lys Pro Val Thr Gln Asn Ile Ser Ala Glu Ala Trp
545                 550                 555                 560

Gly Arg Ala Asp Cys Asp Ala Thr Leu Thr Glu Lys Ser Phe Glu Thr
                565                 570                 575

Asp Met Asn Leu Asn Phe Gln Asn Leu Ser Val Met Gly Leu Arg Ile
            580                 585                 590

Leu Leu Leu Lys Val Ala Gly Phe Asn Leu Leu Met Thr Leu Arg Leu
        595                 600                 605

Trp Ser Ser
    610
```